United States Patent
Keenan et al.

(10) Patent No.: US 11,649,237 B2
(45) Date of Patent: May 16, 2023

(54) SUBSTITUTED IMIDAZO[1,5-A]PYRAZINES FOR IRE1 INHIBITION

(71) Applicants: Optikira LLC, Cleveland, OH (US); The Regents of the University of California, Oakland, CA (US)

(72) Inventors: Richard M. Keenan, Malvern, PA (US); Bradley J. Backes, San Francisco, CA (US); Dustin J. Maly, Seattle, WA (US); Charles Reynolds, Malvern, PA (US); Ben Whittaker, Malvern, PA (US); Jamie Knight, Malvern, PA (US); Jonathan Mark Sutton, Malvern, PA (US); George Hynd, Malvern, PA (US); Feroz R. Papa, Oakland, CA (US); Scott A. Oakes, Oakland, CA (US)

(73) Assignees: Optikira LLC, Cleveland, OH (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 16/642,208

(22) PCT Filed: Aug. 31, 2018

(86) PCT No.: PCT/US2018/049081
§ 371 (c)(1),
(2) Date: Feb. 26, 2020

(87) PCT Pub. No.: WO2019/046711
PCT Pub. Date: Mar. 7, 2019

(65) Prior Publication Data
US 2020/0354367 A1    Nov. 12, 2020

Related U.S. Application Data

(60) Provisional application No. 62/553,320, filed on Sep. 1, 2017.

(51) Int. Cl.
*A61K 31/4985* (2006.01)
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
CPC ........................ A61K 31/4985; C07D 487/04
USPC ........................................... 514/249; 549/350
See application file for complete search history.

(56) References Cited

U.S. PATENT DOCUMENTS

| | | | |
|---|---|---|---|
| 2009/0286768 A1 | 11/2009 | Crew et al. | |
| 2012/0322814 A1 | 12/2012 | Korennykh et al. | |
| 2013/0116247 A1 | 5/2013 | Zeng | |
| 2016/0024094 A1* | 1/2016 | Backes | A61P 1/16 514/249 |
| 2017/0165259 A1 | 6/2017 | Maly | |
| 2017/0252350 A1 | 9/2017 | Glimcher | |

FOREIGN PATENT DOCUMENTS

| | | |
|---|---|---|
| CN | 103917545 A | 7/2014 |
| JP | 2011-520970 A | 7/2011 |
| JP | 2015-532287 A | 11/2015 |
| RU | 2015115631 A | 11/2016 |
| WO | 2007064993 | 6/2007 |
| WO | 2009-143051 A1 | 11/2009 |
| WO | 2014052669 | 4/2014 |
| WO | 2016004254 | 1/2016 |
| WO | 2018102751 A1 | 6/2018 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Vippagunta, et al. Advanced Drug Delivery Reviews, 48, 2001, 18.*
Hannah C. Feldman et al, "Structural and Functional Analysis of the Allosteric Inhibition of IRE1[alpha] with ATP-Competitive Ligands", Acs Chemical Biology, (Jun. 9, 2016), vol. 11, No. 8, doi:10.1021/acschembio.5b00940, ISSN 1554-8929, pp. 2195-2205, XP055490667.
"1-Phenylimidazo[1,5-a]pyrazine', U.S. National Library of Medicine", Pubmed, (Aug. 19, 2012), Database accession No. 58761369.

(Continued)

*Primary Examiner* — Douglas M Willis
(74) *Attorney, Agent, or Firm* — Saul Ewing LLP

(57) ABSTRACT

Provided herein, inter alia, are substituted imidazo[1,5-α] pyrazine compounds, compositions and methods for treating or preventing an IRE1α-related disease or disorder. In certain embodiments, the disease or disorder is selected from the group consisting of a neurodegenerative disease, a demyelinating disease, cancer, an eye disease, a fibrotic disease, and diabetes.

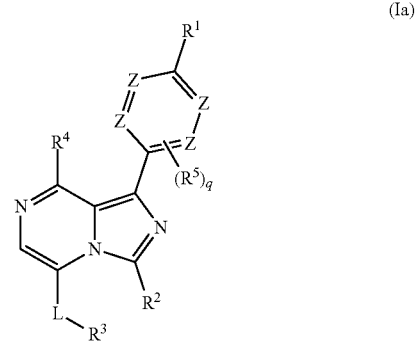

(Ia)

18 Claims, No Drawings

(56) References Cited

OTHER PUBLICATIONS

Jordan, V.C. "Tamoxifen: A most Unlikely Pioneering Medicine." Nature Reviews: Drug Discovery, 2, 2003, 205.
Wang, et al., "Divergent allosteric control of the IRE1-alpha endoribonuclease using kinase inhibitors", 2012 Nature Chemical Biology 8:982-989.
Vippagunta, et al. "Crystalline solids." 2001, Advanced Drug Delivery Reviews, 48:3-26.
Ghosh Rajarshi et al, "Allosteric Inhibition of the IRE1[alpha] RNase Preserves Cell Viability and Function during Endoplasmic Reticulum St", Cell, Elsevier, Amsterdam NL, (Jul. 10, 2014), vol. 158, No. 3, doi:10.1016/J.CELL.2014.07.002, ISSN 0092-8674, pp. 534-548, XP029012888.

\* cited by examiner

SUBSTITUTED IMIDAZO[1,5-A]PYRAZINES FOR IRE1 INHIBITION

CROSS-REFERENCE TO RELATED APPLICATIONS

The present application is a 35 U.S.C. § 371 national phase application from, and claims priority to, International Application No. PCT/US2018/049081, filed Aug. 31, 2018, and published under PCT Article 21(2) in English, which claims priority under 35 U.S.C. § 119(e) to U.S. Provisional Application No. 62/553,320, filed Sep. 1, 2017, all of which applications are incorporated herein by reference in their entireties.

STATEMENT REGARDING FEDERALLY SPONSORED RESEARCH OR DEVELOPMENT

This invention was made with government support under grant numbers R41 DK108377 and R41 EY026370 awarded by the National Institutes of Health. The government has certain rights in the invention.

BACKGROUND OF THE INVENTION

Cells often experience conditions during which the workload on the endoplasmic reticulum ("ER") protein folding machinery exceeds its capability, causing ER stress. ER stress can result from secretory work overload, expression of folding-defective secretory proteins, deprivation of nutrients or oxygen, changes in luminal calcium concentration, and deviation from resting redox state. Under ER stress, secretory proteins accumulate in unfolded forms within the organelle to trigger a set of intracellular signaling pathways called the unfolded protein response (UPR). UPR signaling increases transcription of genes encoding chaperones, oxidoreductases, lipid-biosynthetic enzymes, and ER-associated degradation (ERAD) components.

In some instances, the ER stressed state remains too great, and cannot be remedied through the UPR's homeostatic outputs. In these situations, the UPR switches strategies and actively triggers apoptosis. Apoptosis of irremediably stressed cells is a quality control strategy that protects multicellular organisms from exposure to immature and damaged secretory proteins. Many deadly human diseases occur if too many cells die through this process. Conversely, many human diseases such as diabetes mellitus and retinopathies proceed from unchecked cell degeneration under ER stress.

IRE1α and IRE1β are ER-transmembrane proteins that become activated when unfolded proteins accumulate within the organelle. IRE1α is the more widely expressed family member. The bifunctional kinase/endoribonuclease IRE1α controls entry into the terminal UPR. IRE1α senses unfolded proteins through an ER lumenal domain that becomes oligomerized during stress.

Under irremediable ER stress, positive feedback signals emanate from the UPR and become integrated and amplified at key nodes to trigger apoptosis. IRE1α is a key initiator of these pro-apoptotic signals. IRE1α employs auto-phosphorylation as a timer. Remediable ER stress causes low-level, transient auto-phosphorylation that confines RNase activity to XBP1 mRNA splicing. However, sustained kinase auto-phosphorylation causes IRE1a's RNase to acquire relaxed specificity, causing it to endonucleolytically degrade thousands of ER-localized mRNAs in close proximity to IRE1α. These mRNAs encode secretory proteins being co-translationally translocated (e.g., insulin in Rcells). As mRNA degradation continues, transcripts encoding ER-resident enzymes also become depleted, thus destabilizing the entire ER protein-folding machinery. Once IRE1a's RNase becomes hyperactive, adaptive signaling through XBP1 splicing becomes eclipsed by ER mRNA destruction, which pushes cells into apoptosis.

A terminal UPR signature tightly controlled by IRE1α's hyperactive RNase activity causes (1) widespread mRNA degradation at the ER membrane that leads to mitochondrial apoptosis, (2) induction of the pro-oxidant thioredoxin-interacting protein (TXNIP), which activates the NLRP3 inflammasome to produce maturation and secretion of interleukin-1β, and consequent sterile inflammation in pancreatic islets leading to diabetes, and (3) degradation of pre-miRNA 17, leading to translational upregulation and cleavage of pre-mitochondrial caspase 2 and stabilization of the mRNA encoding TXNIP.

Retinitis pigmentosa (RP) is a clinically and genetically heterogeneous group of inherited retinal disorders characterized by diffuse progressive dysfunction and loss of rod and cone photoreceptors, and retinal pigment epithelium. There are no approved therapies to treat RP patients, who suffer irreversible vision loss. Accumulation of misfolded proteins within the ER appears to be a central causative mechanism in many forms of RP. Mutations in rhodopsin lead to a defective rhodopsin protein that misfolds and accumulates in the ER, causing ER stress.

There is a need in the art for novel small molecule compounds that are capable of treating ER stress without resorting to UPR based apoptosis, thereby treating a wide range of disorders and diseases tied to ER stress. Such diseases include, for example, neurodegenerative diseases, demyelinating diseases, cancers, eye diseases, fibrotic diseases, and/or diabetes. The present invention meets these needs.

BRIEF SUMMARY OF THE INVENTION

The invention provides certain compounds, as well as pharmaceutical composition comprising at least one compound of the invention and at least one pharmaceutically acceptable carrier. The invention further provides a method of treating a IRE1α-related disease in a subject. The invention further provides a method of inhibiting the activity of an IRE1 protein.

In certain embodiments, the compound is a compound of formula (Ia), formula (Ib), or formula (Ic), or a salt, solvate, enantiomer, diastereoisomer, isotopologue, or tautomer thereof:

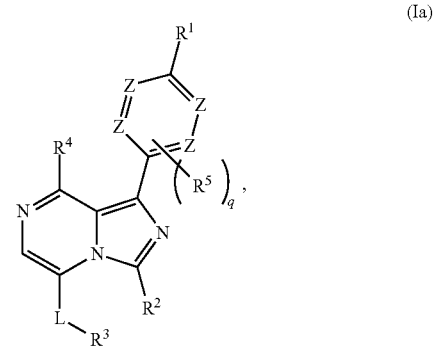

(Ia)

-continued

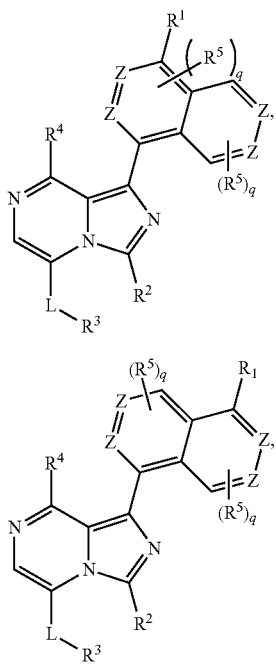

wherein: $R^1$ is selected from the group consisting of

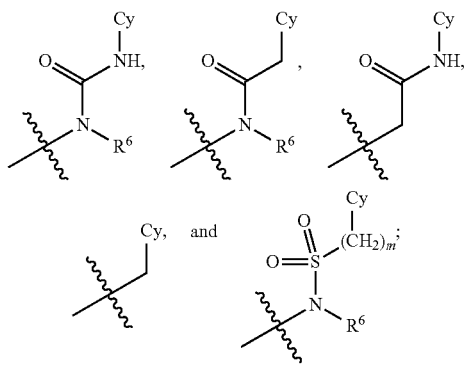

$R^2$ is selected from the group consisting of H, methyl, ethyl, propyl, $CF_3$, $CHF_2$, 1-methylcyclopropyl, isopropyl, tert-butyl, and $C_3$-$C_8$ cycloalkyl, wherein each non-H substituent is independently optionally substituted with a single instance of $R^7$, with the proviso that, if $R^7$ is present, $R^3$ is H; L is selected from the group consisting of a bond, —$CH_2$—, and —C(=O)—; $R^3$ is selected from the group consisting of H, optionally substituted $C_1$-$C_8$ alkyl, optionally substituted $C_3$-$C_8$ cycloalkyl, optionally substituted $C_2$-$C_8$ alkenyl, optionally substituted $C_2$-$C_8$ alkynyl, optionally substituted $C_1$-$C_8$ heteroalkyl, optionally substituted $C_3$-$C_8$ heterocycloalkyl, optionally substituted $C_2$-$C_8$ heteroalkenyl, optionally substituted benzyl, optionally substituted $C_2$-$C_8$ cycloheteroalkyl, optionally substituted heterocyclyl, optionally substituted aryl, and optionally substituted heteroaryl (such as, but not limited to, imidazolyl or pyrazolyl); $R^4$ is selected from the group consisting of —H, —OH, $C_1$-$C_6$ alkoxy, halogen, —$NH_2$, and —$NHR^8$; each instance of $R^5$ is independently selected from the group consisting of halide, —OH, $C_1$-$C_6$ alkoxy, optionally substituted phenyl, optionally substituted $C_1$-$C_6$ alkyl, optionally substituted $C_1$-$C_6$ alkoxy, and optionally substituted heterocycloalkyl; $R^6$ is selected from the group consisting of H and optionally substituted $C_1$-$C_6$ alkyl; $R^7$ is selected from the group consisting of optionally substituted $C_1$-$C_8$ alkyl, optionally substituted $C_3$-$C_8$ cycloalkyl, optionally substituted $C_2$-$C_8$ alkenyl, optionally substituted $C_2$-$C_8$ alkynyl, optionally substituted $C_1$-$C_8$ heteroalkyl, optionally substituted $C_3$-$C_8$ heterocycloalkyl, optionally substituted $C_2$-$C_8$ heteroalkenyl, optionally substituted aryl, optionally substituted heteroaryl (such as, but not limited to, imidazolyl or pyrazolyl), and optionally substituted benzyl; $R^8$ is optionally substituted $C_1$-$C_3$ alkyl; Cy is selected from the group consisting of aryl, heteroaryl, $C_3$-$C_{10}$ cycloalkyl, $C_3$-$C_{10}$ cycloalkenyl, $C_3$-$C_{10}$ heterocycloalkyl, $C_3$-$C_{10}$ heterocycloalkenyl, polycyclic aryl, polycyclic heteroaryl, polycyclic $C_3$-$C_{10}$ cycloalkyl, polycyclic $C_3$-$C_{10}$ cycloalkenyl, polycyclic $C_3$-$C_{10}$ heterocycloalkyl, and polycyclic $C_3$-$C_{10}$ heterocycloalkenyl; wherein Cy is substituted with 0 to 'n' instances of X, each instance of X being independently selected from the group consisting of H, OH, halide, nitrile, optionally substituted $C_1$-$C_6$ alkyl, $C_1$-$C_6$ haloalkyl, optionally substituted $C_1$-$C_6$ alkoxy, optionally substituted aryl, optionally substituted heteroaryl, and

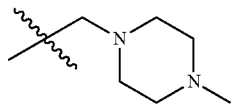

each instance of Z, if present, is independently selected from the group consisting of CH and N; m is an integer selected from the group consisting of 0, 1, 2, 3, and 4; n is an integer selected from the group consisting of 0, 1, 2, 3, 4, and 5; and q is an integer selected from the group consisting of 0, 1, 2, 3, 4, and 5.

In certain embodiments, each occurrence of optionally substituted alkyl, alkenyl, alkynyl, heteroalkyl, heterocycloalkyl, heteroalkenyl, benzyl, heterocyclyl, or cycloalkyl is independently optionally substituted with at least one substituent selected from the group consisting of $C_1$-$C_6$ alkyl, halo, —$OR^a$, optionally substituted phenyl, optionally substituted heteroaryl, optionally substituted heterocyclyl, —$N(R^a)C(=O)R^a$, —$C(=O)NR^aR^a$, and —$N(R^a)(R^a)$, wherein each occurrence of $R^a$ is independently H, optionally substituted $C_1$-$C_6$ alkyl, optionally substituted $C_3$-$C_8$ cycloalkyl, optionally substituted aryl, or optionally substituted heteroaryl, or two $R^a$ groups combine with the N to which they are bound to form a heterocycle.

In certain embodiments, each occurrence of optionally substituted aryl or heteroaryl is independently optionally substituted with at least one substituent selected from the group consisting of $C_1$-$C_6$ alkyl, $C_1$-$C_6$ haloalkyl, $C_1$-$C_6$ haloalkoxy, halo, —CN, —OR, —$N(R^b)(R^b)$, —$NO_2$, —$S(=O)_2N(R^b)(R^b)$, acyl, and $C_1$-$C_6$ alkoxycarbonyl, wherein each occurrence of $R^b$ is independently H, $C_1$-$C_6$ alkyl, or $C_3$-$C_8$ cycloalkyl.

In certain embodiments, each occurrence of optionally substituted aryl or heteroaryl is independently optionally substituted with at least one substituent selected from the group consisting of $C_1$-$C_6$ alkyl, $C_1$-$C_6$ haloalkyl, $C_1$-$C_6$ haloalkoxy, halo, —CN, —OR, —$N(R^c)(R^c)$, and $C_1$-$C_6$ alkoxycarbonyl, wherein each occurrence of $R^c$ is independently H, $C_1$-$C_6$ alkyl, or $C_3$-$C_8$ cycloalkyl.

In certain embodiments, Cy is selected from the group consisting of:
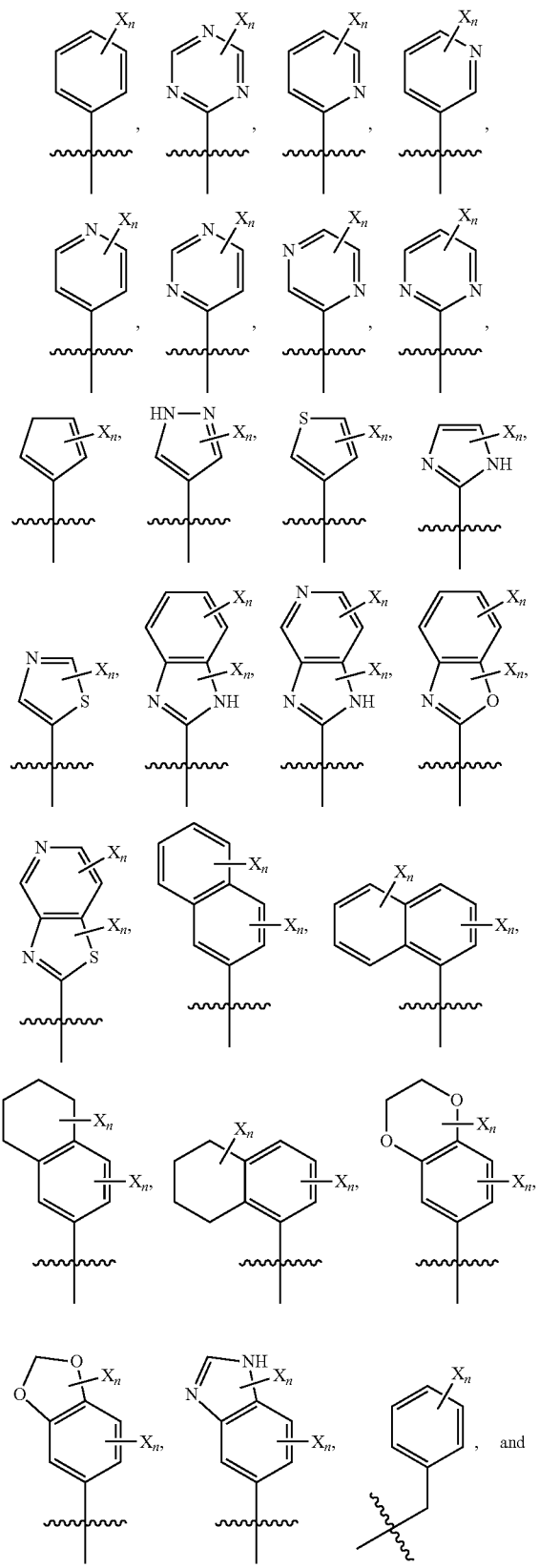
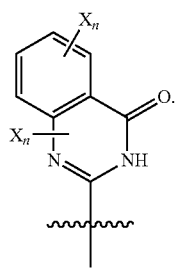
In certain embodiments, R is selected from the group consisting of:
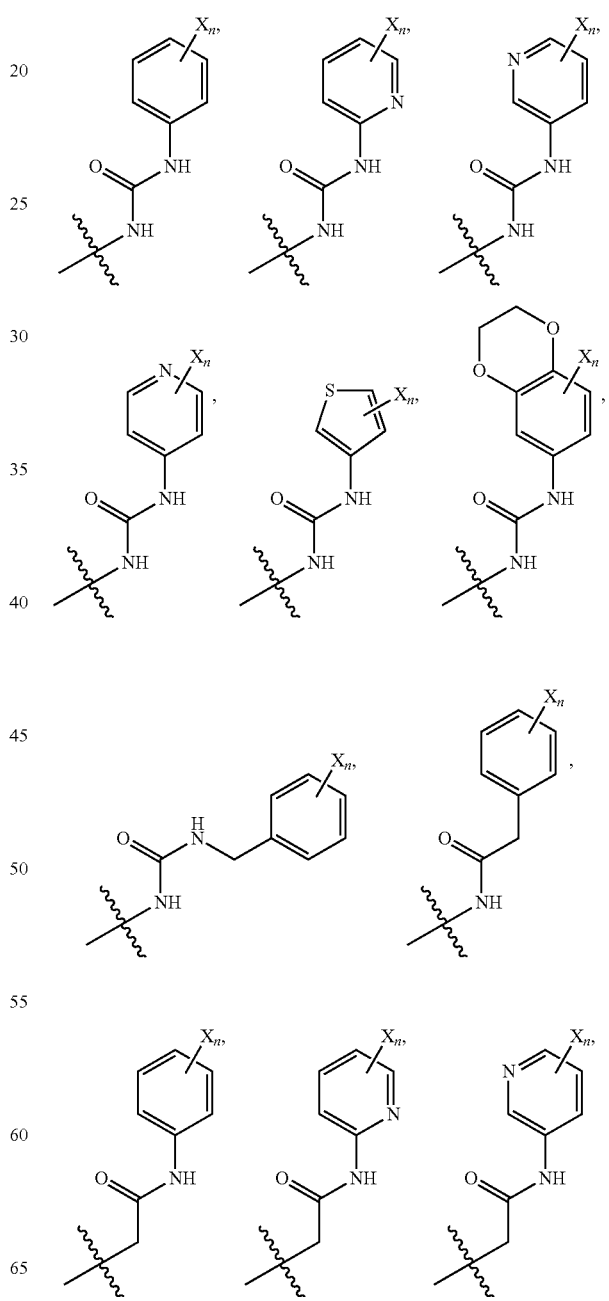

-continued
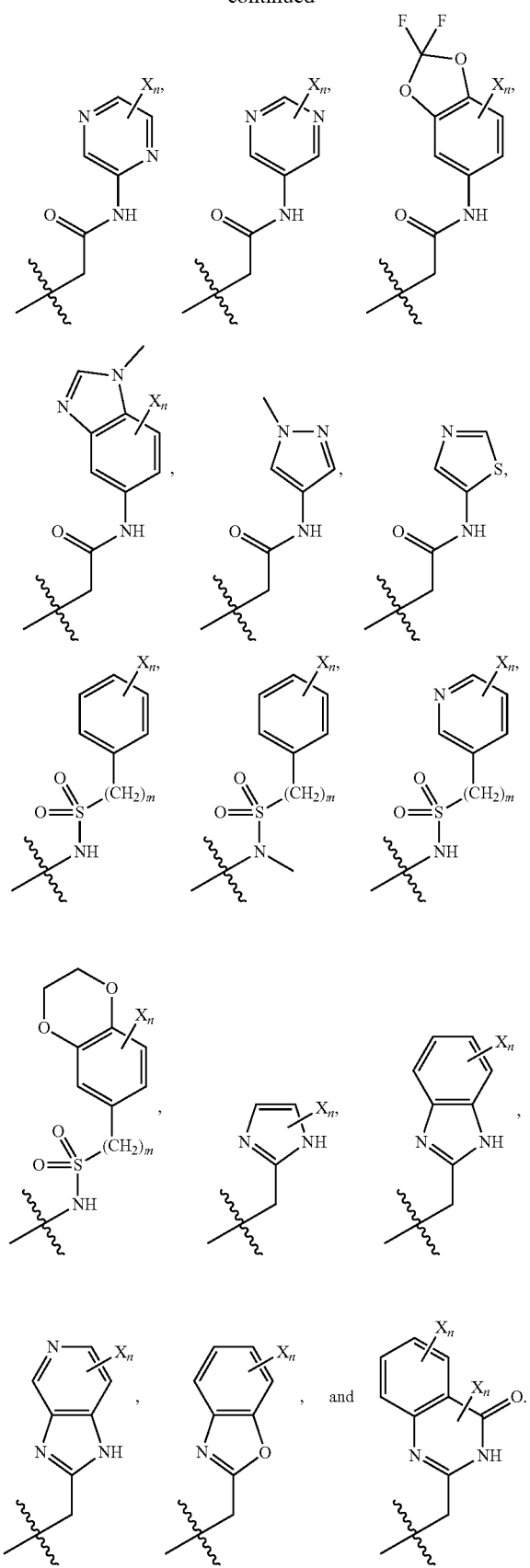
In certain embodiments, R[1] is selected from the group consisting of:
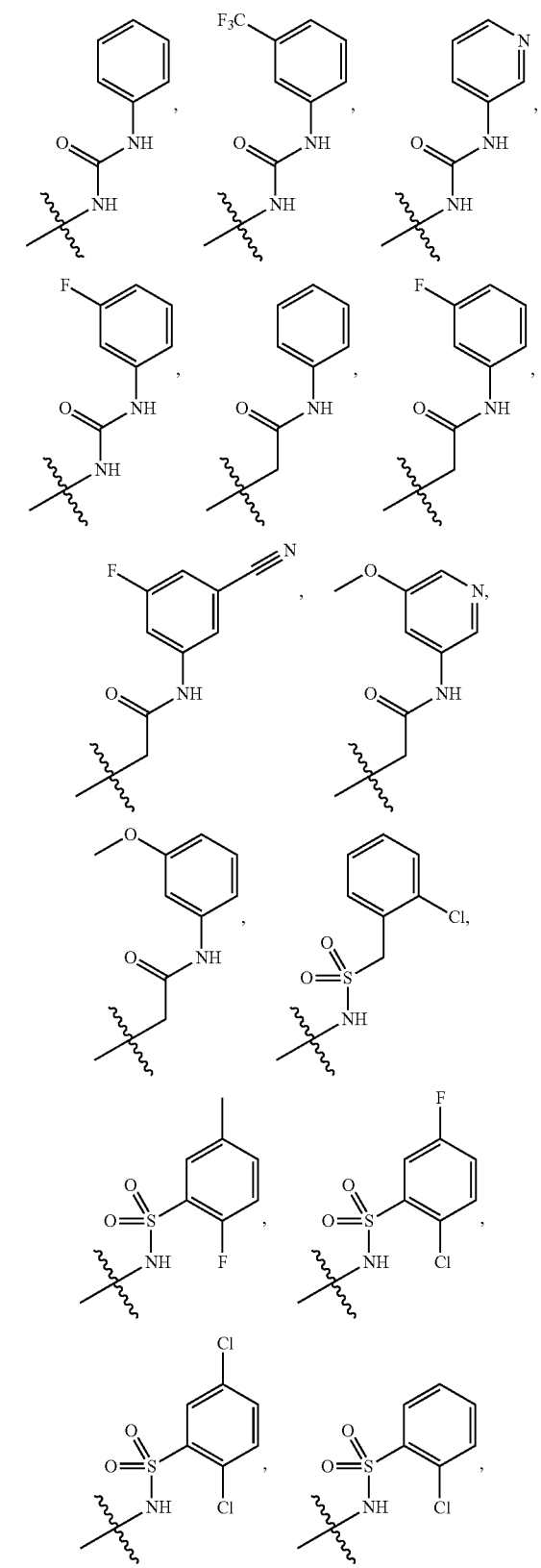

-continued
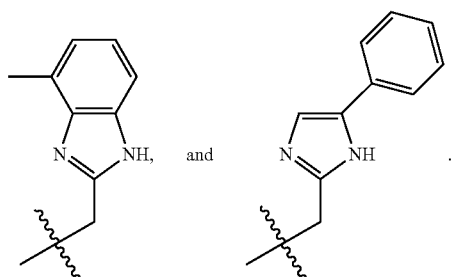 [SMILES: *Cc1nc2c(C)cccc2[nH]1 ; "and" ; *Cc1ncc(-c2ccccc2)[nH]1]
In certain embodiments, R² is selected from the group consisting of methyl, ethyl and isopropyl.
In certain embodiments, R³ is selected from the group consisting of:
H, C₁-C₈ alkyl,
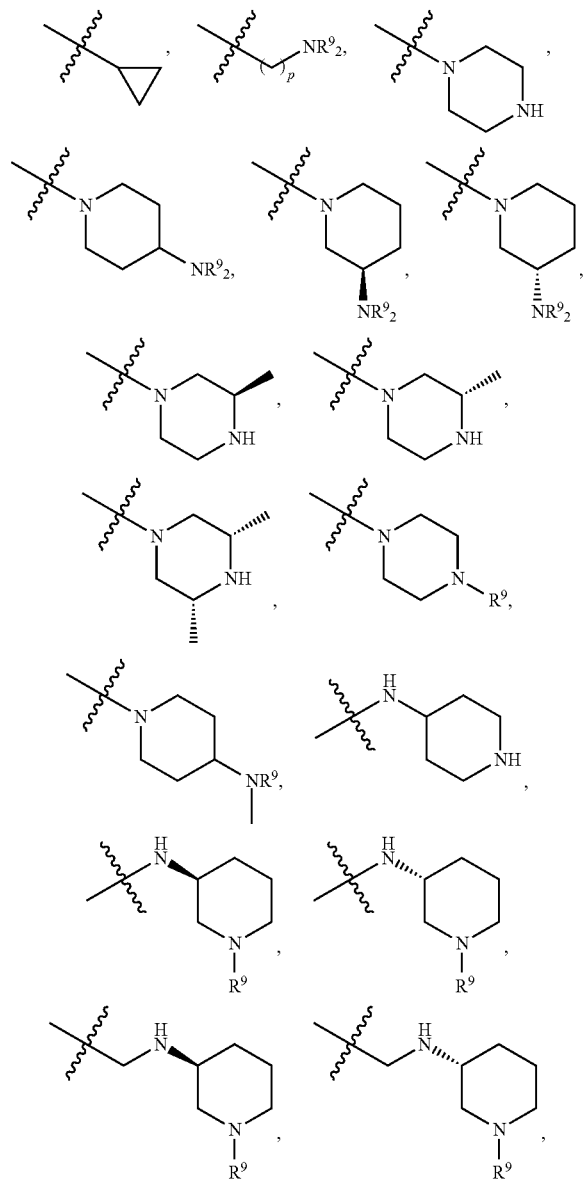
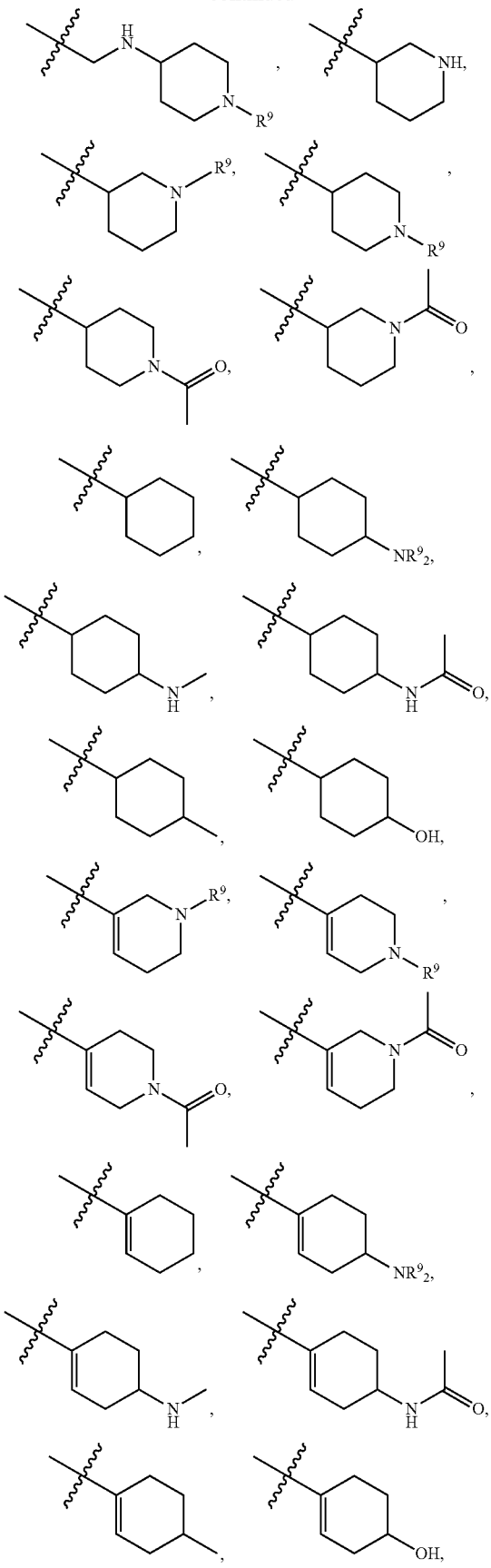

-continued

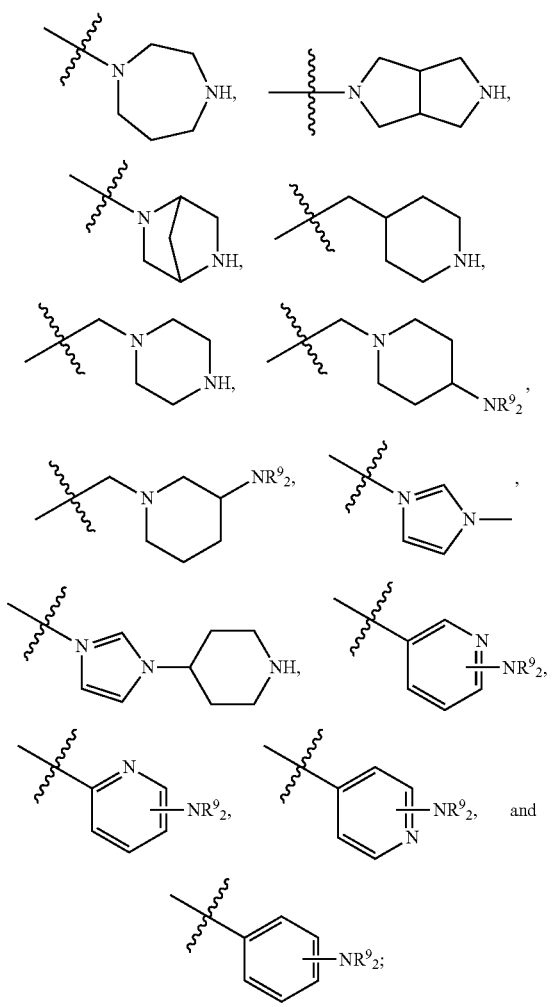

wherein p is an integer from 0-5; and wherein each occurrence of $R^9$ is independently selected from the group consisting of H, oxetanyl, $C_1$-$C_6$ hydroxyalkyl, $C_1$-$C_6$ haloalkyl, $C_1$-$C_6$ carboxamido alkyl, $C_1$-$C_6$ carboxy alkyl, $C_1$-$C_6$ carboxy($C_1$-$C_6$)alkyl alkyl, and $C_1$-$C_6$ cyano alkyl.

In certain embodiments, $R^3$ is selected from the group consisting of:

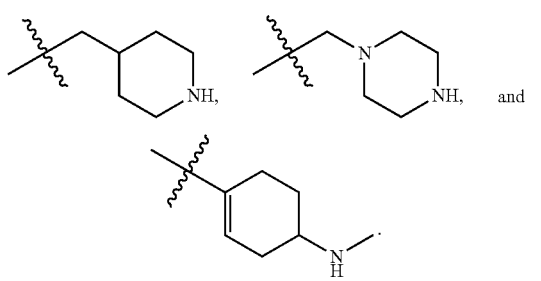

In certain embodiments, $R^4$ is H or —$NH_2$. In certain embodiments, $R^5$, if present, is —F.

In certain embodiments, $R^7$, if present, is selected from the group consisting of.

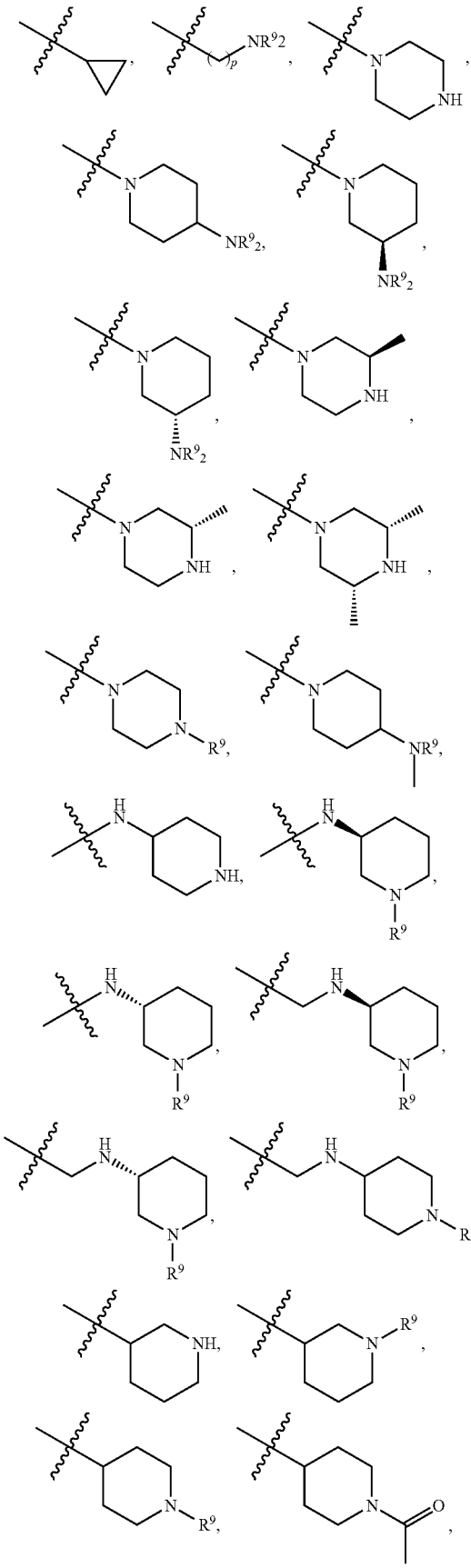

-continued

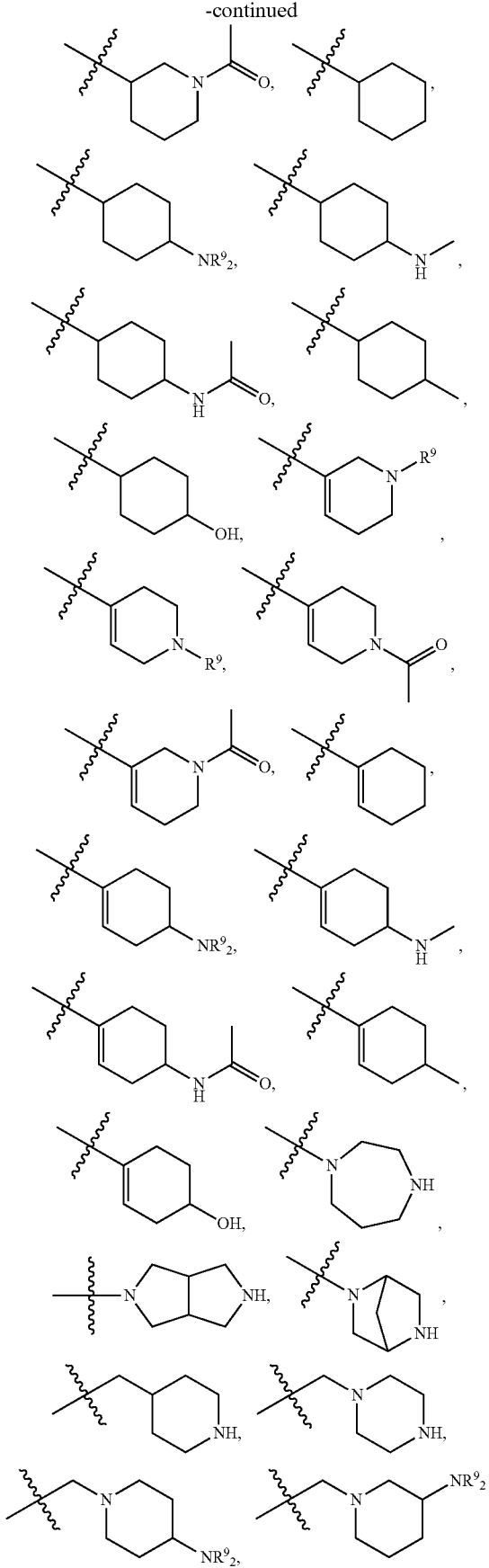

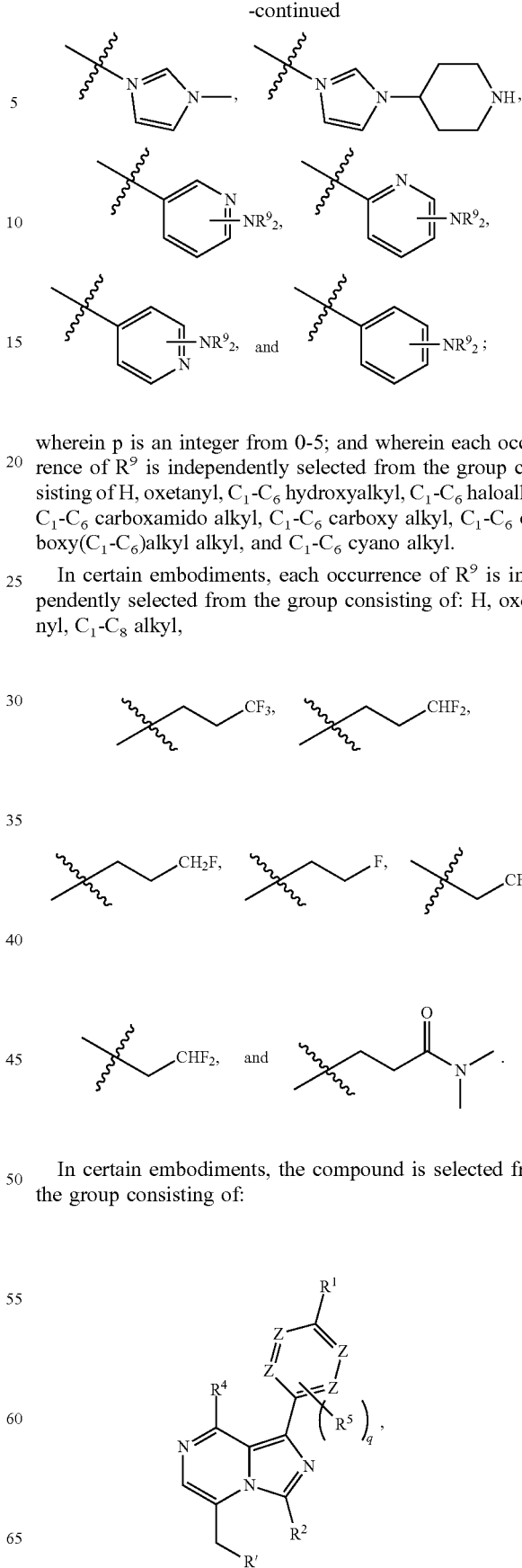

wherein p is an integer from 0-5; and wherein each occurrence of $R^9$ is independently selected from the group consisting of H, oxetanyl, $C_1$-$C_6$ hydroxyalkyl, $C_1$-$C_6$ haloalkyl, $C_1$-$C_6$ carboxamido alkyl, $C_1$-$C_6$ carboxy alkyl, $C_1$-$C_6$ carboxy($C_1$-$C_6$)alkyl alkyl, and $C_1$-$C_6$ cyano alkyl.

In certain embodiments, each occurrence of $R^9$ is independently selected from the group consisting of: H, oxetanyl, $C_1$-$C_8$ alkyl, In certain embodiments, the compound is selected from the group consisting of:

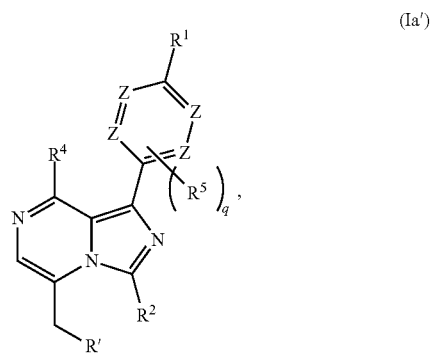

(Ia')

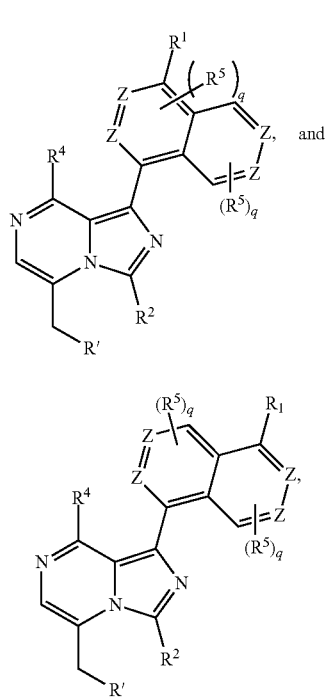
(Ib')
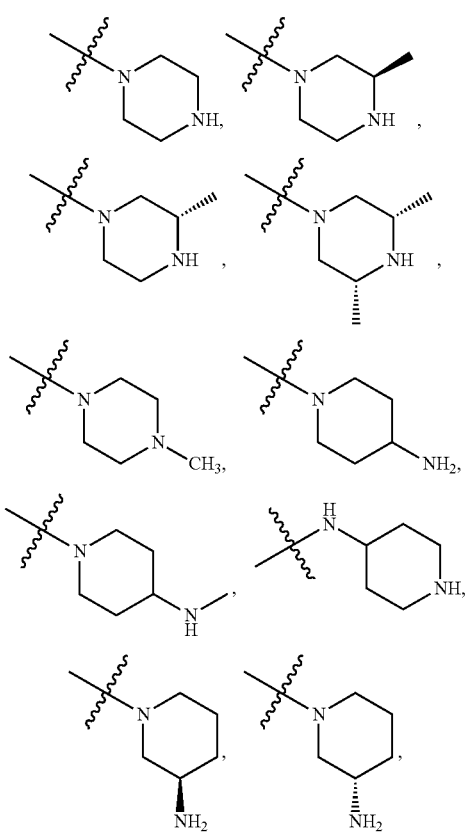
(Ic')
wherein R' is R³.
In certain embodiments, R' is selected from the group consisting of:
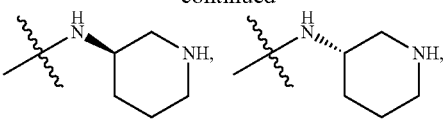
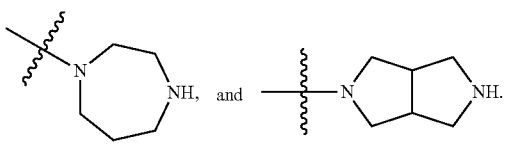
In certain embodiments, the compound is selected from the group consisting of:
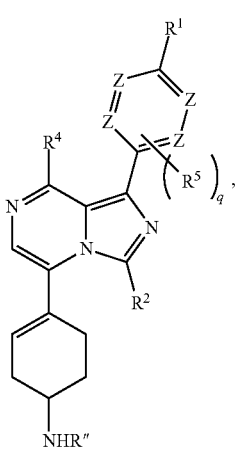
(Ia'')
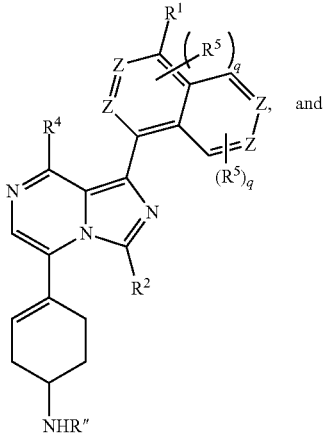
(Ib'')

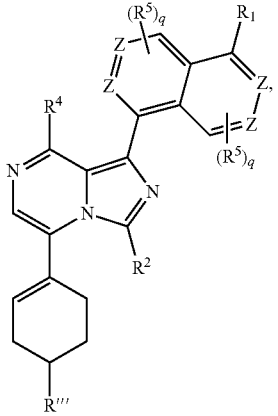
(Ic″)

wherein each occurrence of R″ is independently H or C$_1$-C$_6$ alkyl.

In certain embodiments, the compound is selected from the group consisting of:

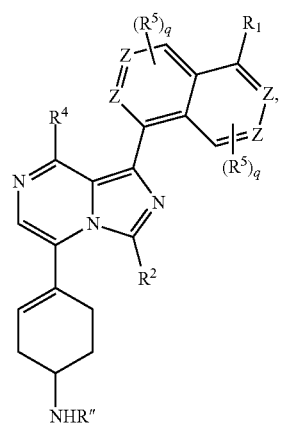
(Ia‴)

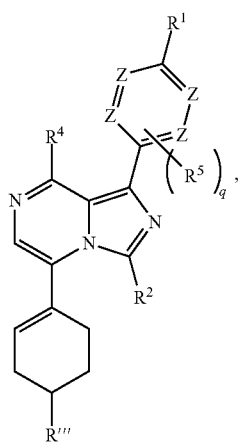
(Ib‴)

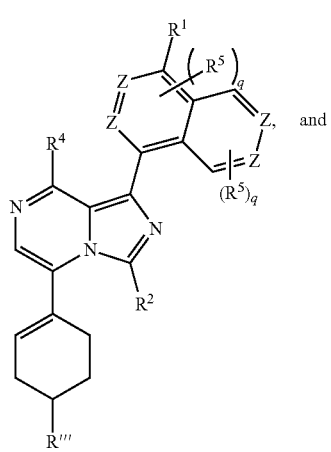
and

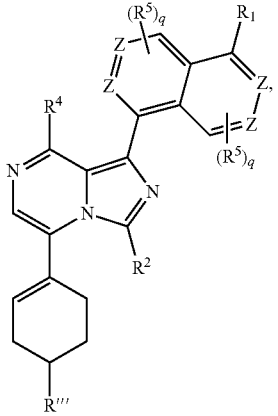
(Ic‴)

wherein each occurrence of R‴ is independently selected from the group consisting of —OH, C$_1$-C$_6$ alkoxy, —NH$_2$, —NH(C$_1$-C$_6$ alkyl), —N(C$_1$-C$_6$ alkyl)(C$_1$-C$_6$ alkyl), and —NH(oxetanyl), wherein each C$_1$-C$_6$ alkyl is optionally substituted with at least one independently selected from the group consisting of halogen, —C(=O)NH$_2$, —C(=O)N (C$_1$-C$_6$ alkyl), —C(=O)N(C$_1$-C$_6$ alkyl)(C$_1$-C$_6$ alkyl), —OH, and —C$_1$-C$_6$ alkoxy.

In certain embodiments, R‴ is selected from the group consisting of —OH, —NH$_2$, —NHCH$_3$, —N(CH$_3$)$_2$, —NHCH$_2$CH$_2$F, —N(Me)CH$_2$CH$_2$F, —NHCH$_2$CHF$_2$, —N(Me)CH$_2$CHF$_2$, —NHCH$_2$CF$_3$, —N(Me)CH$_2$CF$_3$, —NHCH$_2$CH$_2$CF$_3$, —N(Me)CH$_2$CH$_2$CF$_3$, —NHCH$_2$CH$_2$C(=O)NMe$_2$, —N(Me)CH$_2$CH$_2$C(=O) NMe$_2$, —NHCH$_2$CH$_2$C(=O)NH$_2$, —N(Me)CH$_2$CH$_2$C (=O)NH$_2$, —NHCH$_2$CH$_2$C(=O)NHMe, —N(Me) CH$_2$CH$_2$C(=O)NHMe$_2$, and

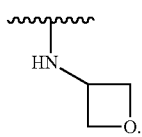

In certain embodiments, the compound is selected from the group consisting of Example 1-Example 232; or a salt, solvate, enantiomer, diastereoisomer, isotopologue, or tautomer thereof.

In certain embodiments, the method comprises administering to the subject a therapeutically effective amount of a compound, or a pharmaceutically acceptable salt, solvate, enantiomer, diastereoisomer, or tautomer thereof, and/or a composition of the invention.

In certain embodiments, the method comprises contacting the IRE1 protein with an effective amount of a compound, or a pharmaceutically acceptable salt thereof, and/or a composition of the invention.

In certain embodiments, the disease is selected from the group consisting of a neurodegenerative disease, a demyelinating disease, cancer, an eye disease, a fibrotic disease, and diabetes.

In certain embodiments, the neurodegenerative disease is selected from the group consisting of retinitis pigmentosa, amyotrophic lateral sclerosis, retinal degeneration, macular degeneration, Parkinson's Disease, Alzheimer's Disease, Huntington's Disease, Prion Disease, Creutzfeldt-Jakob Disease, and Kuru.

In certain embodiments, the demyelinating disease is selected from the group consisting of Wolfram Syndrome, Pelizaeus-Merzbacher Disease, Transverse Myelitis, Charcot-Marie-Tooth Disease, and Multiple Sclerosis.

In certain embodiments, the cancer is multiple myeloma.

In certain embodiments, the diabetes is selected from the group consisting of type I diabetes and type II diabetes.

In certain embodiments, the eye disease is selected from the group consisting of retinitis pigmentosa, retinal degeneration, macular degeneration, and Wolfram Syndrome.

In certain embodiments, the fibrotic disease is selected from the group consisting of idiopathic pulmonary fibrosis (IPF), myocardial infarction, cardiac hypertrophy, heart failure, cirrhosis, acetominophen (TYLENOL®) liver toxicity, hepatitis C liver disease, hepatosteatosis (fatty liver disease), or hepatic fibrosis.

In certain embodiments, the activity is selected from the group consisting of kinase activity, oligomerization activity, and RNase activity.

In certain embodiments, the IRE1 protein is within a cell.

In certain embodiments, apoptosis of the cell is prevented or minimized.

In certain embodiments, the cell is in an organism that has an IRE1α-related disease or disorder.

In certain embodiments, the subject is a subject in need of the treatment.

DETAILED DESCRIPTION OF THE INVENTION

The present invention relates in part to the unexpected discovery that novel inhibitors of IRE1α prevent oligomerization and/or allosterically inhibit its RNase activity. In certain embodiments, the compounds of the invention are compounds of formula (Ia), (Ib) or (Ic):

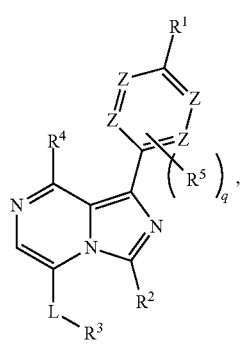

(Ia)

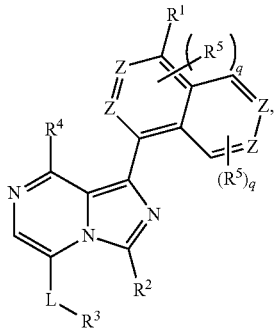

(Ib)

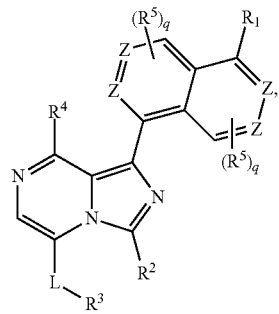

(Ic)

or a salt, solvate, enantiomer, diastereoisomer, isotopologue, or tautomer thereof. These compounds can be used to treat diseases or disorders associated with ER stress, such as those selected from the group consisting of a neurodegenerative disease, demyelinating disease, cancer, eye disease, fibrotic disease, and diabetes. In certain embodiments, the disease or disorder is a neurodegenerative disease. In other embodiments, the disease or disorder is a demyelinating disease. In yet other embodiments, the disease or disorder is cancer. In yet other embodiments, the disease or disorder is eye disease. In yet other embodiments, the disease or disorder is a fibrotic disease. In yet other embodiments, the disease or disorder is diabetes.

Definitions

As used herein, each of the following terms has the meaning associated with it in this section.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

Generally, the nomenclature used herein and the laboratory procedures in pharmaceutical science and organic chemistry are those well-known and commonly employed in the art.

As used herein, the articles "a" and "an" refer to one or to more than one (i.e. to at least one) of the grammatical object of the article. By way of example, "an element" means one element or more than one element.

As used herein, the term "about" is understood by persons of ordinary skill in the art and varies to some extent on the context in which it is used. As used herein when referring to a measurable value such as an amount, a temporal duration, and the like, the term "about" is meant to encompass variations of 20% or 10%, in certain other embodiments 5%, in other embodiments 1%, and in yet other embodiments 0.1% from the specified value, as such variations are appropriate to perform the disclosed methods.

As used herein, the term "cancer" is defined as disease characterized by the rapid and uncontrolled growth of aberrant cells. Cancer cells can spread locally or through the bloodstream and lymphatic system to other parts of the body. Examples of cancers include but are not limited to, bone cancer, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

As used herein, a "disease" is a state of health of a subject wherein the subject cannot maintain homeostasis, and wherein if the disease is not ameliorated then the subject's health continues to deteriorate.

As used herein, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

As used herein, the term "$ED_{50}$" or "ED50" refers to the effective dose of a formulation that produces about 50% of the maximal effect in subjects that are administered that formulation.

As used herein, an "effective amount," "therapeutically effective amount" or "pharmaceutically effective amount" of a compound is that amount of compound that is sufficient to provide a beneficial effect to the subject to which the compound is administered.

"Instructional material," as that term is used herein, includes a publication, a recording, a diagram, or any other medium of expression that can be used to communicate the usefulness of the composition and/or compound of the invention in a kit. The instructional material of the kit may, for example, be affixed to a container that contains the compound and/or composition of the invention or be shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

As used herein, a "patient" or "subject" may be a human or non-human mammal or a bird. Non-human mammals include, for example, livestock and pets, such as ovine, bovine, porcine, canine, feline and murine mammals. In certain other embodiments, the subject is human.

As used herein, the term "pharmaceutical composition" or "composition" refers to a mixture of at least one compound useful within the invention with a pharmaceutically acceptable carrier. The pharmaceutical composition facilitates administration of the compound to a subject.

As used herein, the term "pharmaceutically acceptable" refers to a material, such as a carrier or diluent, which does not abrogate the biological activity or properties of the compound useful within the invention, and is relatively non-toxic, i.e., the material may be administered to a subject without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the subject. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof.

As used herein, the term "pharmaceutical composition" refers to a mixture of at least one compound useful within the invention with other chemical components, such as carriers, stabilizers, diluents, dispersing agents, suspending agents, thickening agents, and/or excipients. The pharmaceutical composition facilitates administration of the compound to an organism. Multiple techniques of administering a compound include, but are not limited to, intravenous, oral, aerosol, parenteral, ophthalmic, pulmonary and topical administration.

The term "prevent," "preventing" or "prevention," as used herein, means avoiding or delaying the onset of symptoms associated with a disease or condition in a subject that has not developed such symptoms at the time the administering of an agent or compound commences. Disease, condition and disorder are used interchangeably herein.

The term "solvate," as used herein, refers to a compound formed by solvation, which is a process of attraction and association of molecules of a solvent with molecules or ions of a solute. As molecules or ions of a solute dissolve in a solvent, they spread out and become surrounded by solvent molecules.

The term "treat," "treating" or "treatment," as used herein, means reducing the frequency or severity with which symptoms of a disease or condition are experienced by a subject by virtue of administering an agent or compound to the subject.

As used herein, the term "alkyl," by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert butyl, pentyl, neopentyl, hexyl, and cyclopropylmethyl. Most preferred is ($C_1$-$C_6$) alkyl, such as, but not limited to, ethyl, methyl, isopropyl, isobutyl, n-pentyl, n-hexyl and cyclopropylmethyl.

As used herein, the term "alkylene" by itself or as part of another substituent means, unless otherwise stated, a straight or branched hydrocarbon group having the number of carbon atoms designated (i.e., $C_1$-$C_{10}$ means one to ten carbon atoms) and includes straight, branched chain, or cyclic substituent groups, wherein the group has two open valencies. Examples include methylene, 1,2-ethylene, 1,1-ethylene, 1,1-propylene, 1,2-propylene and 1,3-propylene.

As used herein, the term "cycloalkyl," by itself or as part of another substituent means, unless otherwise stated, a cyclic chain hydrocarbon having the number of carbon atoms designated (i.e., $C_3$-$C_6$ means a cyclic group comprising a ring group consisting of three to six carbon atoms) and includes straight, branched chain or cyclic substituent groups. Examples include cyclopropyl, cyclobutyl, cyclopentyl, cyclohexyl, cycloheptyl, and cyclooctyl. Most preferred is ($C_3$-$C_6$)cycloalkyl, such as, but not limited to, cyclopropyl, cyclobutyl, cyclopentyl and cyclohexyl.

As used herein, the term "alkenyl," employed alone or in combination with other terms, means, unless otherwise stated, a stable mono-unsaturated or di-unsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by —$CH_2$—CH=$CH_2$.

As used herein, the term "alkynyl," employed alone or in combination with other terms, means, unless otherwise stated, a stable straight chain or branched chain hydrocarbon group with a triple carbon-carbon bond, having the stated number of carbon atoms. Non-limiting examples include ethynyl and propynyl, and the higher homologs and isomers. The term "propargylic" refers to a group exemplified by —$CH_2$—C≡CH. The term "homopropargylic" refers to a group exemplified by —$CH_2CH_2$—C≡CH. The term "substituted propargylic" refers to a group exemplified by —$CR_2$—C≡CR, wherein each occurrence of R is independently H, alkyl, substituted alkyl, alkenyl or substituted alkenyl, with the proviso that at least one R group is not hydrogen. The term "substituted homopropargylic" refers to a group exemplified by —$CR_2CR_2$—C≡CR, wherein each occurrence of R is independently H, alkyl, substituted alkyl, alkenyl or substituted alkenyl, with the proviso that at least one R group is not hydrogen.

As used herein, the term "alkenylene", employed alone or in combination with other terms, means, unless otherwise stated, a stable mono-unsaturated or di-unsaturated straight chain or branched chain hydrocarbon group having the stated number of carbon atoms wherein the group has two open valencies.

As used herein, the term "alkynylene", employed alone or in combination with other terms, means, unless otherwise stated, a stable straight chain or branched chain hydrocarbon group with a triple carbon-carbon bond, having the stated number of carbon atoms wherein the group has two open valencies.

As used herein, the term "substituted alkyl", "substituted cycloalkyl", "substituted alkenyl", "substituted alkynyl", "substituted alkylene", "substituted alkenylene", "substituted alkynylene", "substituted heteroalkyl", "substituted heteroalkenyl", "substituted heteroalkynyl", "substituted aryl", "substituted heteroaryl" or "substituted heterocycloalkyl" means alkyl, cycloalkyl, alkenyl, alkynyl, alkylene, alkenylene, alkynylene, heteroalkyl, heteroalkenyl, heteroalkynyl, aryl, heteroaryl, or heterocycloalkyl as defined above, substituted by one, two or three substituents selected from the group consisting of $C_1$-$C_{10}$ alkyl, halogen, perhaloakyl, =O, —OH, alkoxy, —$NH_2$, —N($CH_3$)$_2$, —NH($CH_3$)$_2$, phenyl, benzyl, (1-methyl-imidazol-2-yl), pyridin-2-yl, pyridin-3-yl, pyridin-4-yl, —C(=O)OH, —OC(=O)($C_1$-$C_4$)alkyl, —C(=O)($C_1$-$C_4$)alkyl, —C≡N, —C(=O)O($C_1$-$C_4$)alkyl, —C(=O)$NH_2$, —C(=O)NH($C_1$-$C_4$)alkyl, —C(=O)N(($C_1$-$C_4$)alkyl)$_2$, —$SO_2NH_2$, —C(=NH)$NH_2$, and —$NO_2$, preferably containing one or two substituents selected from halogen, —OH, alkoxy, —$NH_2$, trifluoromethyl, —N($CH_3$)$_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$) alkoxy, such as, but not limited to, ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$.

As used herein, the term "heteroalkenyl" by itself or in combination with another term means, unless otherwise stated, a stable straight or branched chain monounsaturated or di unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CHO—$CH_3$, —CH=CH—$CH_2$—OH, —$CH_2$—CH=N—$OCH_3$, —CH=CH—N($CH_3$)—$CH_3$, and —$CH_2$—CH=CH—$CH_2$—SH.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. Preferred are phenyl and naphthyl, most preferred is phenyl.

As used herein, the term "aryl-($C_1$-$C_3$)alkyl" means a functional group wherein a one to three carbon alkylene chain is attached to an aryl group, e.g., —$CH_2CH_2$-phenyl or —$CH_2$— phenyl (benzyl). Preferred is aryl-$CH_2$— and aryl-CH($CH_3$)—. The term "substituted aryl-($C_1$-$C_3$)alkyl" means an aryl-($C_1$-$C_3$)alkyl functional group in which the aryl group is substituted. Preferred is substituted aryl ($CH_2$)—. Similarly, the term "heteroaryl-($C_1$-$C_3$)alkyl" means a functional group wherein a one to three carbon alkylene chain is attached to a heteroaryl group, e.g., —$CH_2CH_2$-pyridyl. Preferred is heteroaryl-($CH_2$)—. The term "substituted heteroaryl-($C_1$-$C_3$)alkyl" means a heteroaryl-($C_1$-$C_3$)alkyl functional group in which the heteroaryl group is substituted. Preferred is substituted heteroaryl-($CH_2$)—.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In certain other embodiments, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3 dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "substituted" means that an atom or group of atoms has replaced hydrogen as the substituent attached to another group. Non-limiting examples of "substituted" groups include $C_1$-$C_{10}$ alkyl, halogen, perhaloakyl, =O, —OH, alkoxy, —$NH_2$, —N($CH_3$)$_2$, —NH($CH_3$)$_2$, phenyl, benzyl, (1-methyl-imidazol-2-yl), pyridin-2-yl, pyridin-3-yl, pyridin-4-yl, —C(=O)OH, —OC(=O) ($C_1$-$C_4$)alkyl, —C(=O)($C_1$-$C_4$)alkyl, —C≡N, —C(=O)O($C_1$-$C_4$)alkyl, —C(=O)$NH_2$, —C(=O)NH($C_1$-$C_4$)alkyl, —C(=O)N(($C_1$-$C_4$)alkyl)$_2$, —$SO_2NH_2$, —C(=NH)$NH_2$, and —$NO_2$.

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In certain other embodiments, the substituents vary in number between one and four. In other embodiments, the substituents vary in number between one and three. In yet other embodiments, the substituents vary in number between one and two. In yet other embodiments, the substituents are independently selected from the group consisting of $C_1$-$C_6$ alkyl, —OH, $C_1$-$C_6$ alkoxy, halo, amino, acetamido and nitro. As used herein, where a substituent is an alkyl or alkoxy group, the carbon chain may be branched, straight or cyclic, with straight being preferred. The term "substituted heterocycle" and "substituted heteroaryl" as used herein refers to a heterocycle or heteroaryl group having one or more substituents including halogen, CN, OH, $NO_2$, amino, alkyl, cycloalkyl, carboxyalkyl (C(O)Oalkyl), trifluoroalkyl such as $CF_3$, aryloxy, alkoxy, aryl, or heteroaryl. A substituted heterocycle or heteroaryl group may have 1, 2, 3, or 4 substituents.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following abbreviations are used herein: Boc, tert-Butyloxycarbonyl; $Cs_2CO_3$, Cesium carbonate; DCM, Dichloromethane; DEA, Diethylamine; DIPEA, N,N-Diisopropylethylamine; DMF, Dimethylformamide; DMSO, Dimethyl sulfoxide; EDC.HCl, N-(3-Dimethylaminopropyl)-N'-ethylcarbodiimide hydrochloride; ER, endoplasmic reticulum; ERAD, endoplasmic reticulum-associated degradation; EtOAc, Ethyl acetate; $Et_2O$, Diethyl ether; HATU, 1-[Bis(dimethylamino)methylene]-1H-1,2,3-triazolo[4,5-b]

pyridinium 3-oxide hexafluorophosphate; HOBT, 1-Hydroxybenzotriazole; HPLC, High-performance liquid chromatography; IPA, 2-Propanol; KOAc, Potassium acetate; LC-MS, Liquid chromatography-mass spectrometry; LiOH, Lithium hydroxide; MDAP, Mass-directed automated purification; MeCN, Acetonitrile; MeOH, Methanol; MgSO$_4$, Magnesium sulfate; Na$_2$SO$_4$, Sodium sulfate; NBS, N-bromosuccinimide; Pd(dppf)Cl$_2$.DCM, [1,1'-Bis(diphenylphosphino)ferrocene]-dichloropalladium(II) DCM complex; Ph, phenyl; RP, Retinitis pigmentosa; RT, Room temperature; Rt, Retention time; SCX-2, Biotage Isolute—strong cationic ion-exchange resin; TEA, trimethylamine; TFA, trifluoroacetic acid; THF, tetrahydrofuran; UPLC, Ultra-high performance liquid chromatography; UPR, unfolded protein response.

Compounds and Compositions

The invention includes a compound of formula (Ia), formula (Ib) or formula (Ic), or a salt, solvate, enantiomer, diastereoisomer, isotopologue, or tautomer thereof:

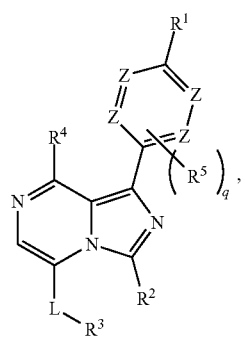

(Ia)

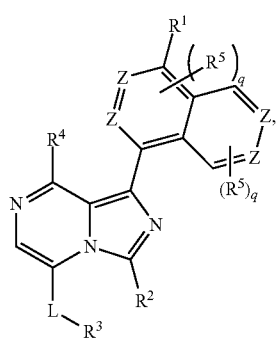

(Ib)

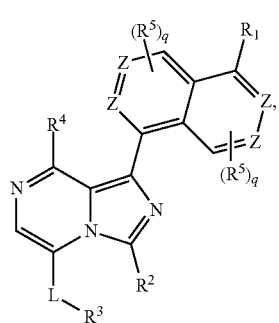

(Ic)

wherein:

R$^1$ is selected from the group consisting of

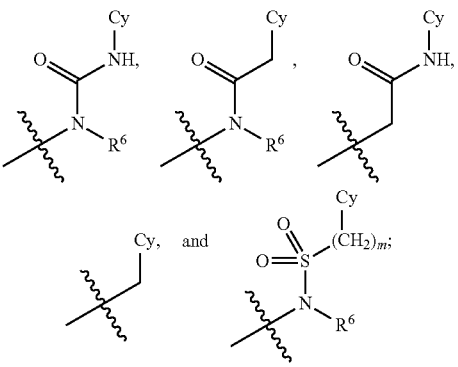

R$^2$ is selected from the group consisting of H, methyl, ethyl, propyl, CF$_3$, CHF$_2$, 1-methylcyclopropyl, isopropyl, tert-butyl, and C$_3$-C$_8$ cycloalkyl, wherein each non-H substituent is independently optionally substituted with a single instance of R$^7$, with the proviso that, if R$^7$ is present, R$^3$ is H;

L is selected from the group consisting of a bond, —CH$_2$—, and —C(=O)—;

R$^3$ is selected from the group consisting of H, optionally substituted C$_1$-C$_8$ alkyl, optionally substituted C$_3$-C$_8$ cycloalkyl, optionally substituted C$_2$-C$_8$ alkenyl, optionally substituted C$_2$-C$_8$ alkynyl, optionally substituted C$_1$-C$_8$ heteroalkyl, optionally substituted C$_3$-C$_8$ heterocycloalkyl, optionally substituted C$_2$-C$_8$ heteroalkenyl, optionally substituted benzyl, optionally substituted C$_2$-C$_8$ cycloheteroalkenyl, optionally substituted heterocyclyl, optionally substituted aryl, and optionally substituted heteroaryl (such as, but not limited to, imidazolyl or pyrazolyl);

R$^4$ is selected from the group consisting of —H, —OH, C$_1$-C$_6$ alkoxy, halogen, —NH$_2$, and —NHR$^8$;

each instance of R$^5$ is independently selected from the group consisting of halide, —OH, C$_1$-C$_6$ alkoxy, optionally substituted phenyl, optionally substituted C$_1$-C$_6$ alkyl, optionally substituted C$_1$-C$_6$ alkoxy, and optionally substituted heterocycloalkyl;

R$^6$ is selected from the group consisting of H and optionally substituted C$_1$-C$_6$ alkyl;

R$^7$ is selected from the group consisting of optionally substituted C$_1$-C$_8$ alkyl, optionally substituted C$_3$-C$_8$ cycloalkyl, optionally substituted C$_2$-C$_8$ alkenyl, optionally substituted C$_2$-C$_8$ alkynyl, optionally substituted C$_1$-C$_8$ heteroalkyl, optionally substituted C$_3$-C$_8$ heterocycloalkyl, optionally substituted C$_2$-C$_8$ heteroalkenyl, optionally substituted aryl, optionally substituted heteroaryl (such as, but not limited to, imidazolyl or pyrazolyl), and benzyl;

R$^8$ is optionally substituted C$_1$-C$_3$ alkyl;

Cy is selected from the group consisting of aryl, heteroaryl, C$_3$-C$_1$ cycloalkyl, C$_3$-C$_{10}$ cycloalkenyl, C$_3$-C$_{10}$ heterocycloalkyl, C$_3$-C$_{10}$ heterocycloalkenyl, polycyclic aryl, polycyclic heteroaryl, polycyclic C$_3$-C$_{10}$ cycloalkyl, polycyclic C$_3$-C$_{10}$ cycloalkenyl, polycyclic C$_3$-C$_{10}$ heterocycloalkyl, and polycyclic C$_3$-C$_{10}$ heterocycloalkenyl;

wherein Cy is substituted with 0 to 'n' instances of X, each instance of X being independently selected from the group consisting of H, OH, halide, nitrile, optionally substituted $C_1$-$C_6$ alkyl, $C_1$-$C_6$ haloalkyl, optionally substituted $C_1$-$C_6$ alkoxy, optionally substituted aryl (such as, but not limited, phenyl), optionally substituted heteroaryl, and

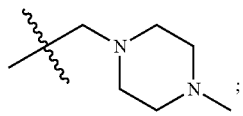 [SMILES: *CN1CCN(C)CC1]

each instance of Z, if present, is independently selected from the group consisting of CH and N;

m is an integer selected from the group consisting of 0, 1, 2, 3, and 4;

n is an integer selected from the group consisting of 0, 1, 2, 3, 4, and 5; and q is an integer selected from the group consisting of 0, 1, 2, 3, 4, and 5.

In certain embodiments, an optionally substituted group is unsubstituted. In other embodiments, an optionally substituted group is substituted with at least substituent contemplated herein.

In certain embodiments, each occurrence of optionally substituted alkyl, alkenyl, alkynyl, heteroalkyl, heterocycloalkyl, heteroalkenyl, benzyl, heterocyclyl, or cycloalkyl is independently optionally substituted with at least one substituent selected from the group consisting of $C_1$-$C_6$ alkyl, halo, —OR$^a$, optionally substituted phenyl, optionally substituted heteroaryl, optionally substituted heterocyclyl, —N(R$^a$)C(=O)R$^a$, —C(=O)NR$^a$R$^a$, and —N(R$^a$)(R$^a$), wherein each occurrence of R$^a$ is independently H, optionally substituted $C_1$-$C_6$ alkyl, optionally substituted $C_3$-$C_8$ cycloalkyl, optionally substituted aryl, or optionally substituted heteroaryl, or two R$^a$ groups combine with the N to which they are bound to form a heterocycle.

In certain embodiments, each occurrence of optionally substituted aryl or heteroaryl is independently optionally substituted with at least one substituent selected from the group consisting of $C_1$-$C_6$ alkyl, $C_1$-$C_6$ haloalkyl, $C_1$-$C_6$ haloalkoxy, halo, —CN, —OR, —N(R$^b$)(R$^b$), —NO$_2$, —S(=O)$_2$N(R$^b$)(R$^b$), acyl, and $C_1$-$C_6$ alkoxycarbonyl, wherein each occurrence of R$^b$ is independently H, $C_1$-$C_6$ alkyl, or $C_3$-$C_8$ cycloalkyl.

In certain embodiments, each occurrence of optionally substituted aryl or heteroaryl is independently optionally substituted with at least one substituent selected from the group consisting of $C_1$-$C_6$ alkyl, $C_1$-$C_6$ haloalkyl, $C_1$-$C_6$ haloalkoxy, halo, —CN, —OR, —N(R$^c$)(R$^c$), and $C_1$-$C_6$ alkoxycarbonyl, wherein each occurrence of R$^c$ is independently H, $C_1$-$C_6$ alkyl, or $C_3$-$C_8$ cycloalkyl.

In certain embodiments, Cy is selected from the group consisting of:

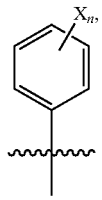 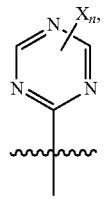 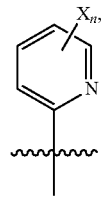 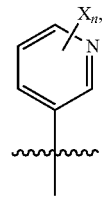

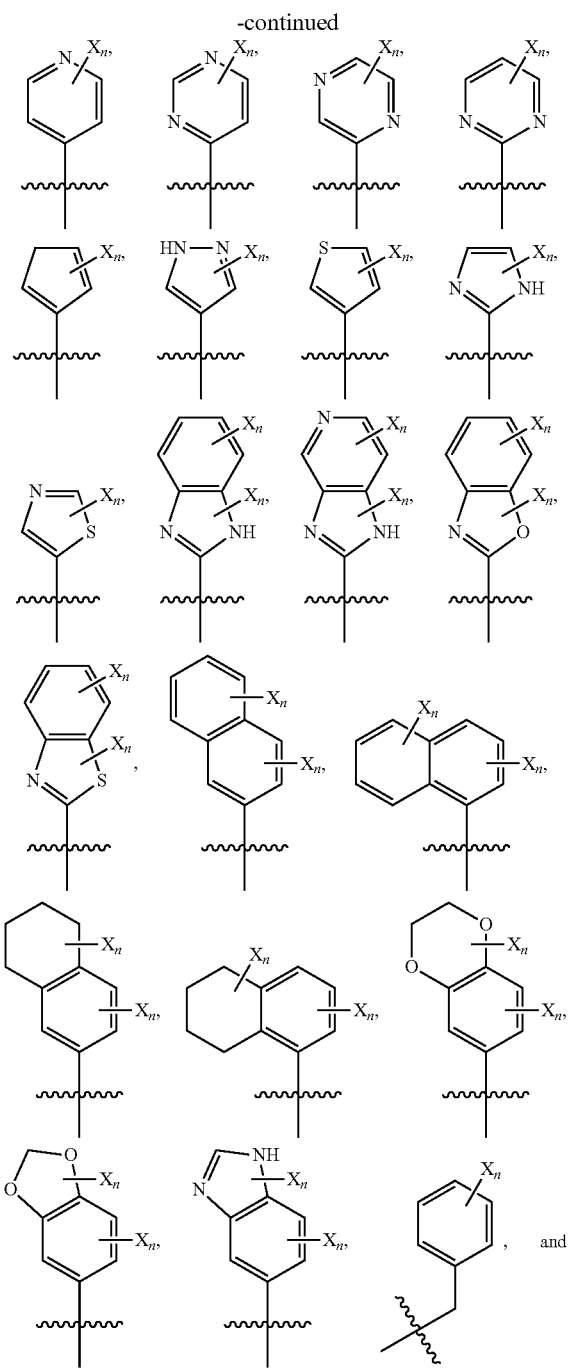

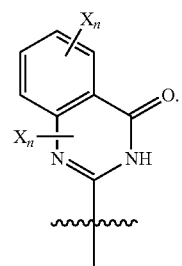

In certain embodiments, R¹ is
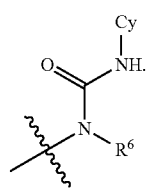
In certain embodiments, R¹ is
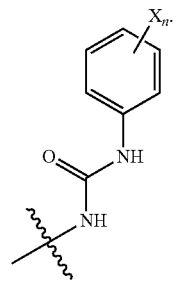
In certain embodiments R¹ is
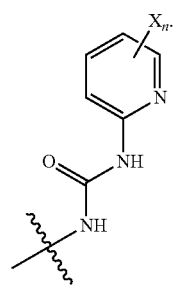
In certain embodiments, R¹ is
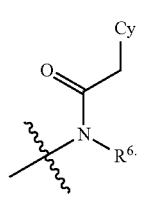
In certain embodiments, R¹ is
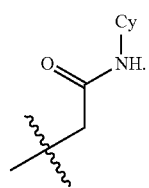
In certain embodiments, R¹ is
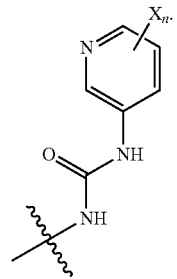
In certain embodiments, R¹ is
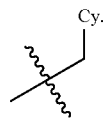
certain embodiments, R¹ is
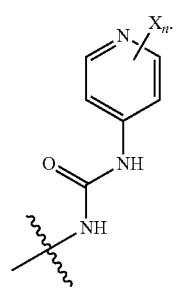
In certain embodiments, R¹ is
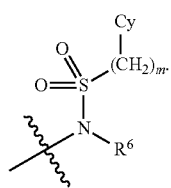

In certain embodiments, R¹ is
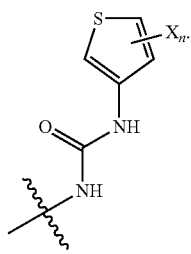
In certain embodiments, R¹ is
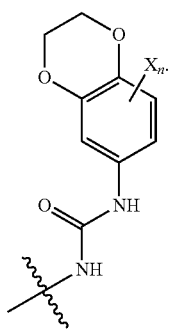
In certain embodiments, R¹ is
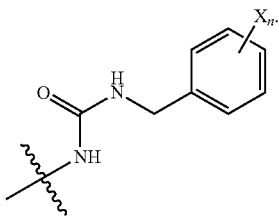
In certain embodiments, R¹ is
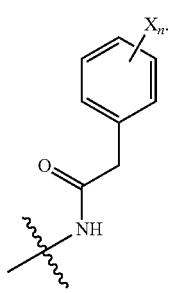
In certain embodiments, R¹ is
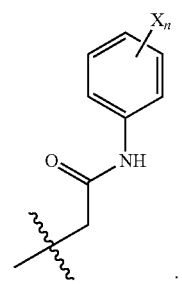
In certain embodiments, R¹ is
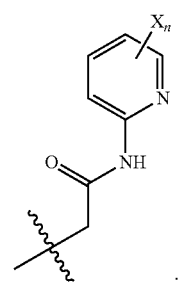
In certain embodiments, R¹ is
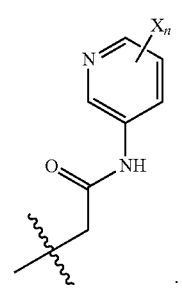
In certain embodiments, R¹ is
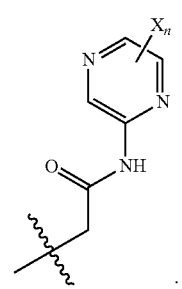

In certain embodiments, $R^1$ is
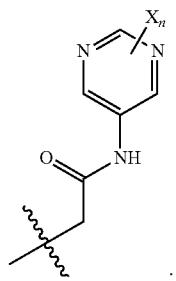
In certain embodiments, $R^1$ is
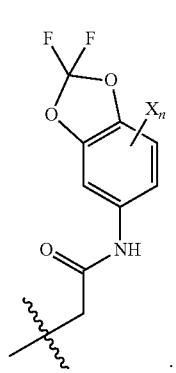
In certain embodiments, $R^1$ is
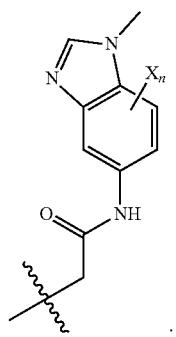
In certain embodiments, $R^1$ is
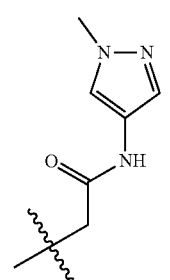
In certain embodiments, $R^1$ is
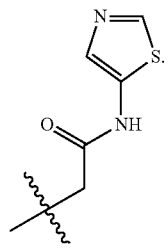 [SMILES: *CC(=O)Nc1cncs1]
In certain embodiments, $R^1$ is
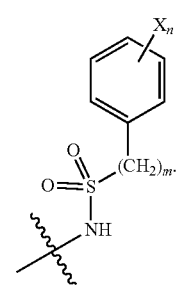
In certain embodiments, $R^1$ is
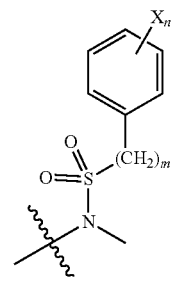
In certain embodiments, $R^1$ is
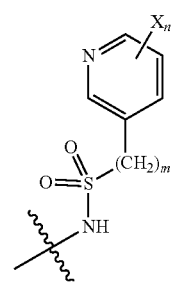

In certain embodiments, $R^1$ is
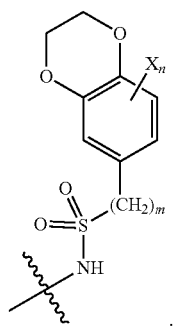
In certain embodiments, $R^1$ is
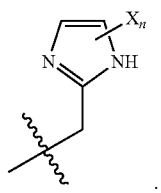
In certain embodiments, $R^1$ is
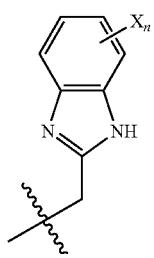
In certain embodiments, $R^1$ is
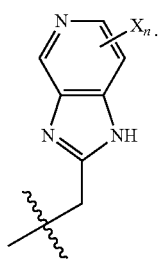
In certain embodiments, $R^1$ is
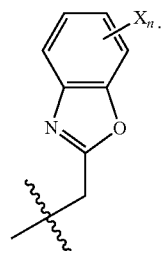
In certain embodiments, $R^1$ is
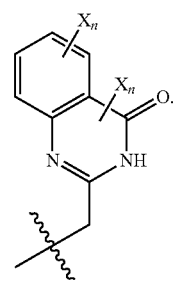
In other embodiments, $R^1$ is
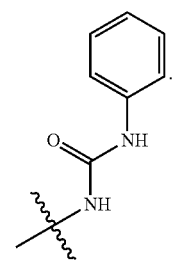 [SMILES: *NC(=O)Nc1ccccc1]
In certain embodiments $R^1$ is
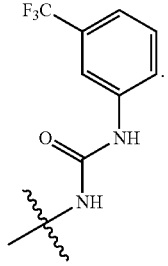 [SMILES: *NC(=O)Nc1cccc(C(F)(F)F)c1]

In certain embodiments, R¹ is
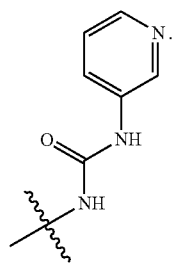
In certain embodiments, R¹ is
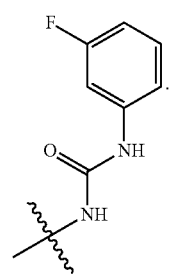 [SMILES: *NC(=O)Nc1cccc(F)c1]
In certain embodiments, R¹ is
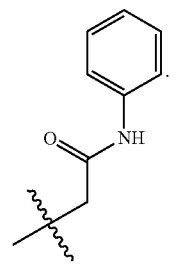 [SMILES: *CC(=O)Nc1ccccc1]
In certain embodiments, R¹ is
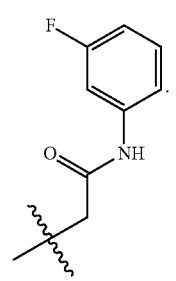 [SMILES: *CC(=O)Nc1cccc(F)c1]
In certain embodiments, R¹ is
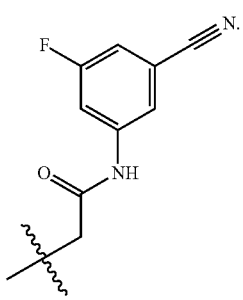 [SMILES: *CC(=O)Nc1cc(F)cc(C#N)c1]
In certain embodiments, R¹ is
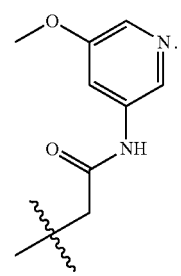 [SMILES: *CC(=O)Nc1cncc(OC)c1]
In certain embodiments, R¹ is
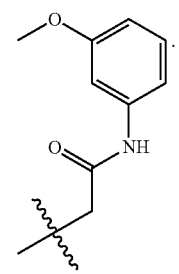 [SMILES: *CC(=O)Nc1cccc(OC)c1]
In certain embodiments, R¹ is
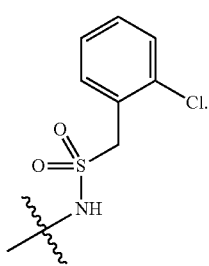 [SMILES: *NS(=O)(=O)Cc1ccccc1Cl]

In certain embodiments, R¹ is

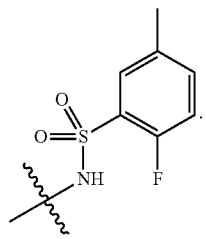 [SMILES: *NS(=O)(=O)c1cc(C)ccc1F]

In certain embodiments, R¹ is

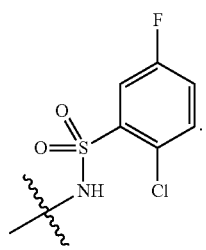 [SMILES: *NS(=O)(=O)c1cc(F)ccc1Cl]

In certain embodiments, R¹ is

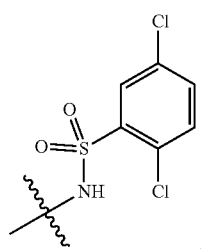

In certain embodiments, R¹ is

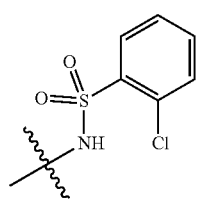

In certain embodiments, R¹ is

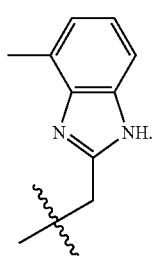 [SMILES: *Cc1nc2c(C)cccc2[nH]1]

In certain embodiments, R¹ is

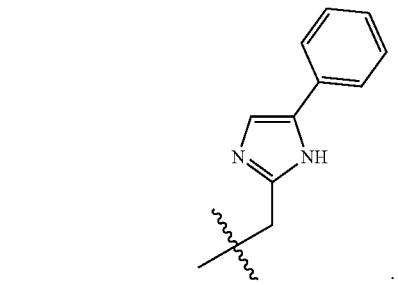 [SMILES: *Cc1ncc(-c2ccccc2)[nH]1]

In certain embodiments, R² is methyl. In certain embodiments, R² is ethyl. In certain embodiments, R² is isopropyl.

In certain embodiments, R³ is H. In certain embodiments, R³ is $C_1$-$C_8$ alkyl. In certain embodiments, R³ is

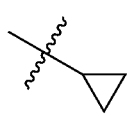

In certain embodiments, R³ is

In certain embodiments, R³ is

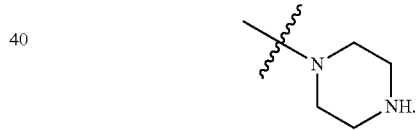

In certain embodiments, R³ is

In certain embodiments, R³ is

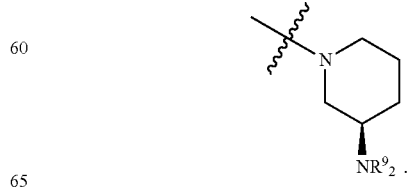

In certain embodiments, R³ is
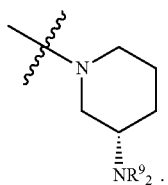
In certain embodiments, R³ is
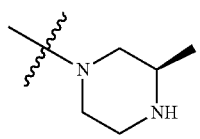
In certain embodiments, R³ is
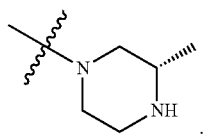 [SMILES: *N1CCN[C@@H](C)C1]
In certain embodiments, R³ is
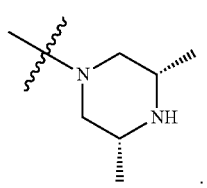 [SMILES: *N1C[C@@H](C)N[C@@H](C)C1]
In certain embodiments, R³ is
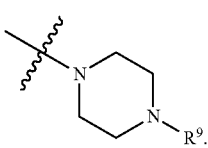
In certain embodiments, R³ is
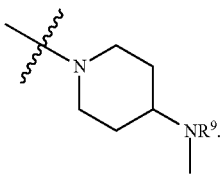
In certain embodiments, R³ is
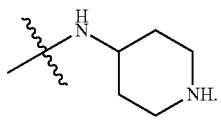 [SMILES: *NC1CCNCC1]
In certain embodiments, R³ is
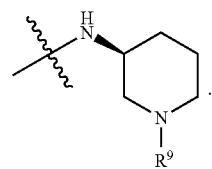
In certain embodiments, R³ is
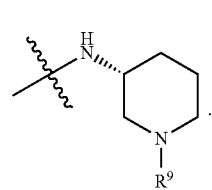
In certain embodiments, R³ is
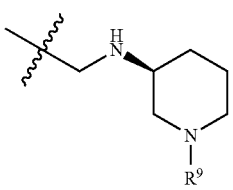
In certain embodiments, R³ is
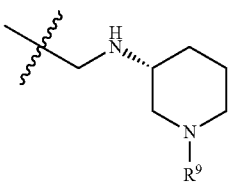
In certain embodiments, R³ is
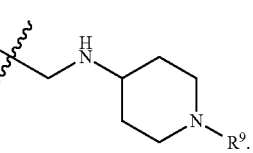

In certain embodiments, $R^3$ is

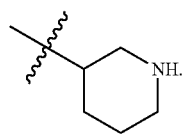 [SMILES: *C1CCCNC1]

In certain embodiments, $R^3$ is

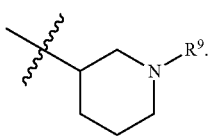

In certain embodiments, $R^3$ is

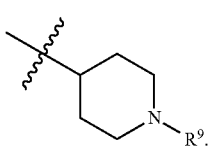

In certain embodiments, $R^3$ is

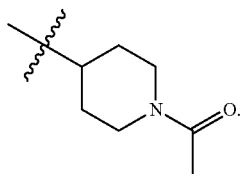 [SMILES: *C1CCN(C(C)=O)CC1]

In certain embodiments, $R^3$ is

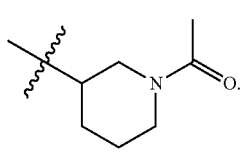

In certain embodiments, $R^3$ is

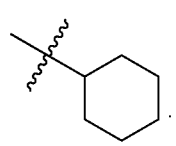 [SMILES: *C1CCCCC1]

In certain embodiments, $R^3$ is

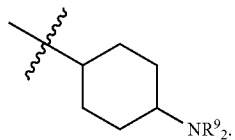

In certain embodiments, $R^3$ is

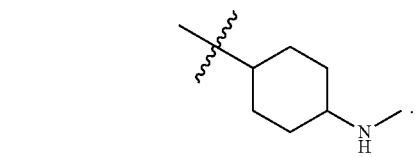 [SMILES: *C1CCC(NC)CC1]

In certain embodiments, $R^3$ is

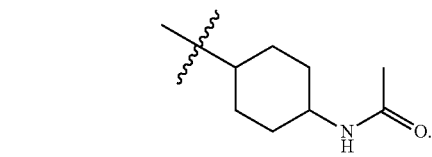 [SMILES: *C1CCC(NC(C)=O)CC1]

In certain embodiments, $R^3$ is

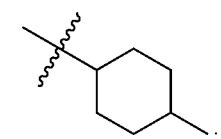 [SMILES: *C1CCC(C)CC1]

In certain embodiments, $R^3$ is

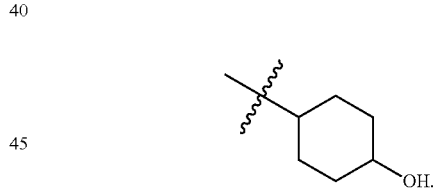

In certain embodiments, $R^3$ is

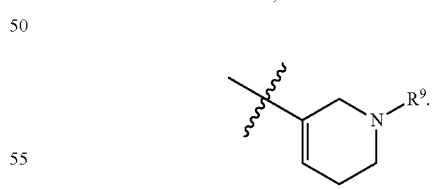

In certain embodiments, $R^3$ is

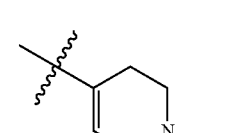

In certain embodiments, R³ is

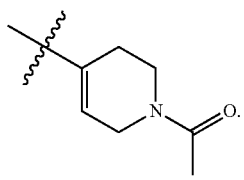 [SMILES: *C1=CCN(C(C)=O)CC1]

In certain embodiments, R³ is

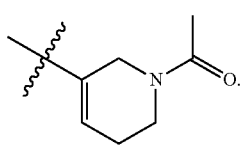 [SMILES: *C1=CCCN(C(C)=O)C1]

In certain embodiments, R³ is

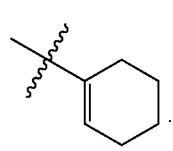

In certain embodiments, R³ is

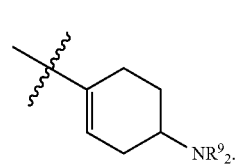

In certain embodiments, R³ is

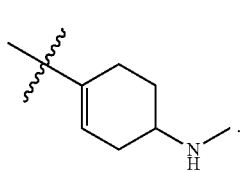 [SMILES: *C1=CCC(NC)CC1]

In certain embodiments, R³ is

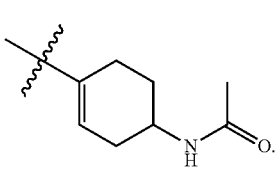 [SMILES: *C1=CCC(NC(C)=O)CC1]

In certain embodiments, R³ is

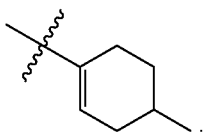 [SMILES: *C1=CCC(C)CC1]

In certain embodiments, R³ is

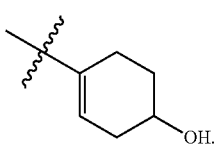

In certain embodiments, R³ is

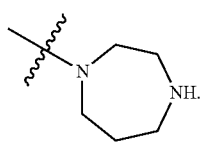 [SMILES: *N1CCCNCC1]

In certain embodiments, R³ is

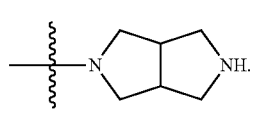

In certain embodiments, R³ is

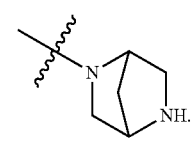 [SMILES: *N1CC2CC1CN2]

In certain embodiments, R³ is

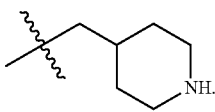 [SMILES: *CC1CCNCC1]

In certain embodiments, R³ is

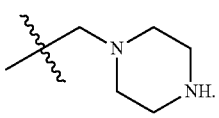 [SMILES: *CN1CCNCC1]

In certain embodiments, $R^3$ is

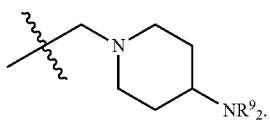

In certain embodiments, $R^3$ is

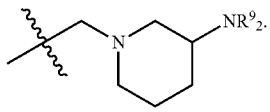

In certain embodiments, $R^3$ is

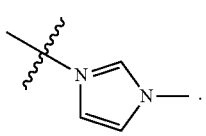

In certain embodiments, $R^3$ is

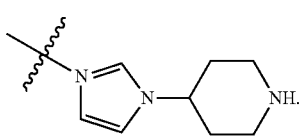

In certain embodiments, $R^3$ is

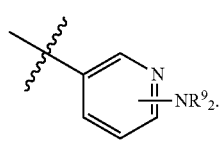

In certain embodiments, $R^3$ is

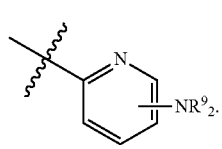

In certain embodiments, $R^3$ is

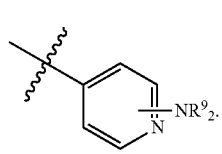

In certain embodiments $R^3$ is

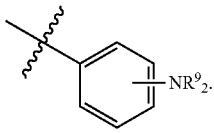

In certain embodiments, p is an integer from 0-5.

In certain embodiments, each occurrence of $R^9$ is independently selected from the group consisting of H, oxetanyl, $C_1$-$C_6$ hydroxyalkyl, $C_1$-$C_6$ haloalkyl, $C_1$-$C_6$ carboxamido alkyl, $C_1$-$C_6$ carboxy alkyl, $C_1$-$C_6$ carboxy($C_1$-$C_6$)alkyl alkyl, and $C_1$-$C_6$ cyano alkyl.

In certain embodiments, L=bond, and $R^3$ is NH

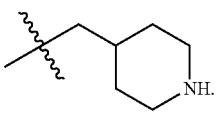 [SMILES: *CC1CCNCC1]

In certain embodiments, L=bond, and $R^3$ is

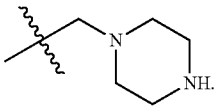

In certain embodiments, L=bond, and $R^3$ is

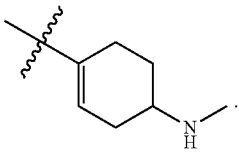 [SMILES: *C1=CCC(NC)CC1]

In certain embodiments, $R^4$ is H. In certain embodiments, $R^4$ is —$NH_2$.

In certain embodiments, $R^5$, if present, is a halogen. In other embodiments, q=1 and $R^5$ is F.

In certain embodiments, $R^7$ is

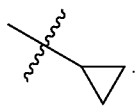 [SMILES: *C1CC1]

In certain embodiments, $R^7$ is

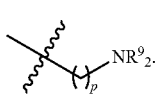

In certain embodiments, R⁷ is

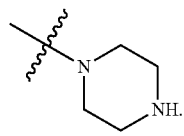 [SMILES: *N1CCNCC1]

In certain embodiments, R⁷ is

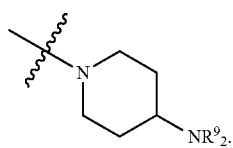

In certain embodiments, R⁷ is

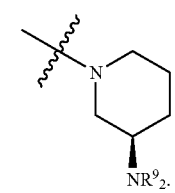

In certain embodiments, R⁷ is

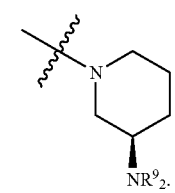

In certain embodiments, R⁷ is

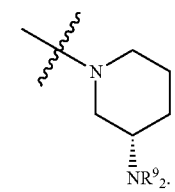

In certain embodiments, R⁷ is

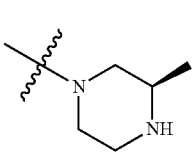

In certain embodiments, R⁷ is

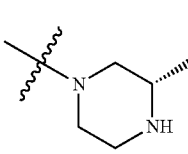

In certain embodiments, R⁷ is

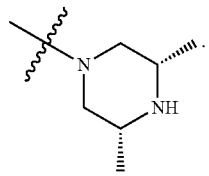 [SMILES: *N1C[C@@H](C)N[C@@H](C)C1]

In certain embodiments, R⁷ is

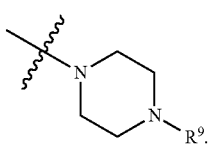

In certain embodiments, R⁷ is

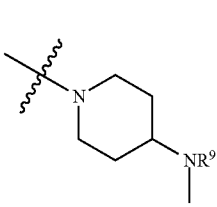

In certain embodiments, R⁷ is

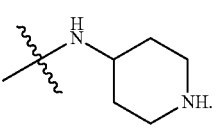 [SMILES: *NC1CCNCC1]

In certain embodiments, R⁷ is

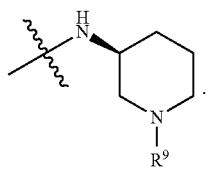

In certain embodiments, R⁷ is

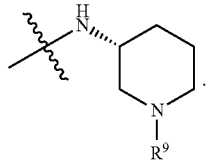

In certain embodiments, R⁷ is
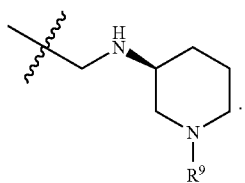
In certain embodiments, R⁷ is
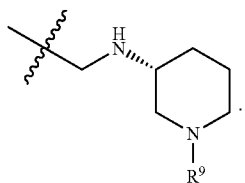
In certain embodiments, R⁷ is
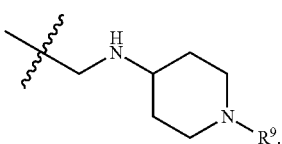
In certain embodiments, R⁷ is
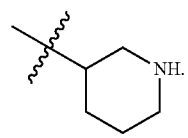 [SMILES: *C1CCCNC1]
In certain embodiments, R⁷ is
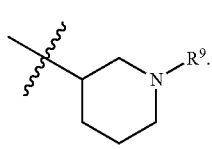
In certain embodiments, R⁷ is
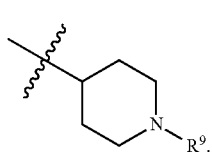
In certain embodiments, R⁷ is
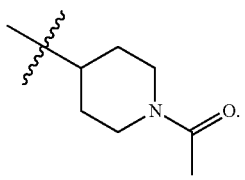 [SMILES: *C1CCN(C(C)=O)CC1]
In certain embodiments, R⁷ is
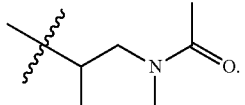
In certain embodiments, R⁷ is
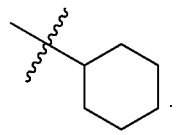
In certain embodiments, R⁷ is
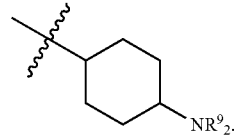
In certain embodiments, R⁷ is
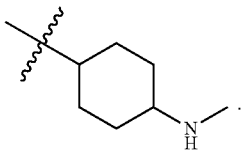 [SMILES: *C1CCC(NC)CC1]
In certain embodiments, R⁷ is
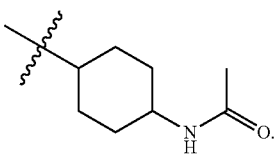 [SMILES: *C1CCC(NC(C)=O)CC1]

In certain embodiments, R⁷ is
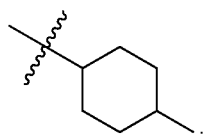 [SMILES: *C1CCC(C)CC1]
In certain embodiments, R⁷ is
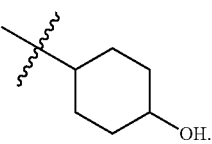 [SMILES: *C1CCC(O)CC1]
In certain embodiments, R⁷ is
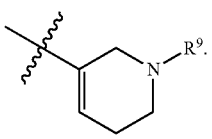
In certain embodiments, R⁷ is
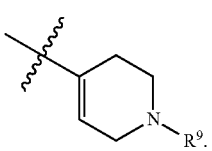
In certain embodiments, R⁷ is
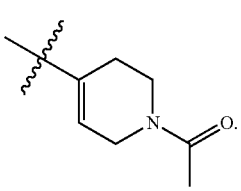 [SMILES: *C1=CCN(C(C)=O)CC1]
In certain embodiments, R⁷ is
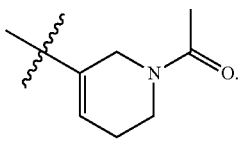 [SMILES: *C1=CCCN(C(C)=O)C1]
In certain embodiments, R⁷ is
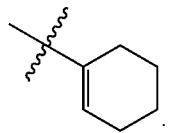
In certain embodiments, R⁷ is
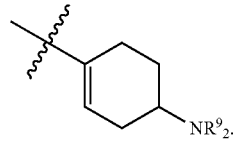
In certain embodiments, R⁷ is
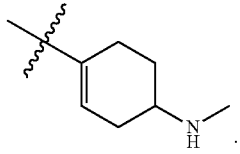 [SMILES: *C1=CCC(NC)CC1]
In certain embodiments, R⁷ is
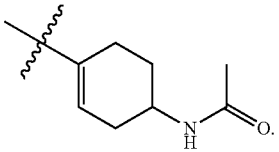 [SMILES: *C1=CCC(NC(C)=O)CC1]
In certain embodiments, R⁷ is
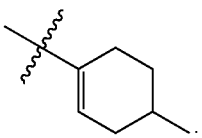 [SMILES: *C1=CCC(C)CC1]
In certain embodiments, R⁷ is
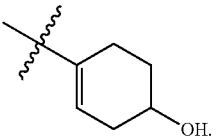 [SMILES: *C1=CCC(O)CC1]

In certain embodiments, R$^7$ is

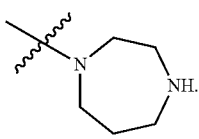 [SMILES: *N1CCCNCC1]

In certain embodiments, R$^7$ is

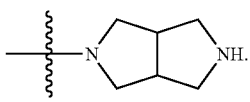

In certain embodiments, R$^7$ is

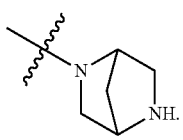

In certain embodiments, R$^7$ is

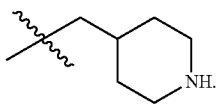 [SMILES: *CC1CCNCC1]

In certain embodiments, R$^7$ is

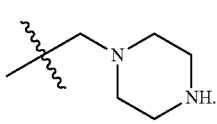 [SMILES: *CN1CCNCC1]

In certain embodiments, R$^7$ is

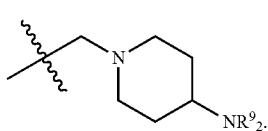

In certain embodiments, R$^7$ is

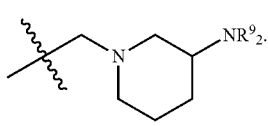

In certain embodiments, R$^7$ is

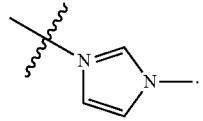

In certain embodiments, R$^7$ is

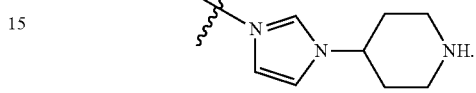

In certain embodiments, R$^7$ is

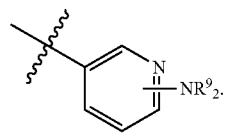

In certain embodiments, R$^7$ is

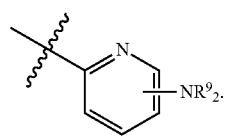

In certain embodiments, R$^7$ is

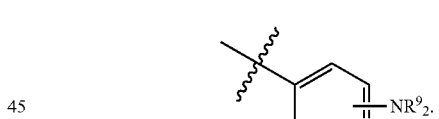

In certain embodiments, R$^7$ is

In certain embodiments, p is an integer from 0-5. In certain embodiments, each occurrence of R$^9$ is independently selected from the group consisting of H, oxetanyl, C$_1$-C$_6$ hydroxyalkyl, C$_1$-C$_6$ haloalkyl, C$_1$-C$_6$ carboxamido alkyl, C$_1$-C$_6$ carboxy alkyl, C$_1$-C$_6$ carboxy(C$_1$-C$_6$)alkyl alkyl, and C$_1$-C$_6$ cyano alkyl.

In certain embodiments, each occurrence of R$^9$ is independently selected from the group consisting of: H, oxetanyl, C$_1$-C$_8$ alkyl,

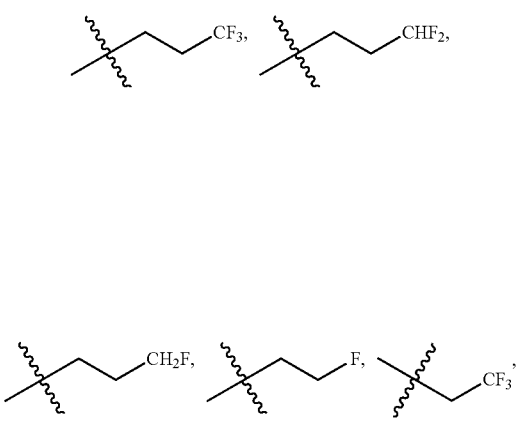

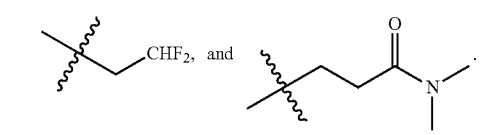

In certain embodiments, the compound is

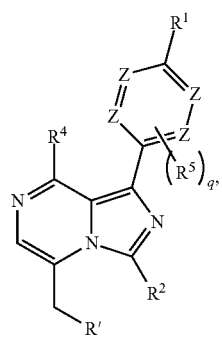

(Ia')

wherein R' is R³ as defined elsewhere herein. In certain embodiments, the compound is

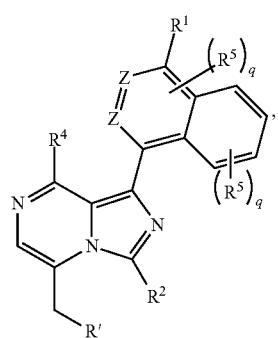

(Ib')

wherein R' is R³ as defined elsewhere herein. In certain embodiments, the compound is

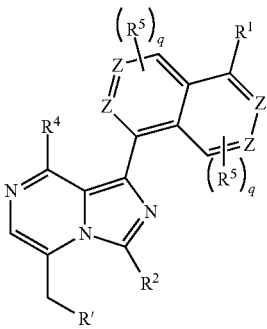

(Ic')

wherein R' is R³ as defined elsewhere herein. In certain embodiments, R' is optionally substituted heterocyclyl. In certain embodiments, R' is optionally substituted —NH-(optionally substituted heterocyclyl). In certain embodiments, R' is optionally substituted —N(C₁-C₆ alkyl)-(optionally substituted heterocyclyl). In certain embodiments, R' is

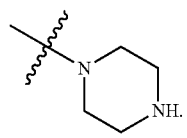

In certain embodiments, R' is

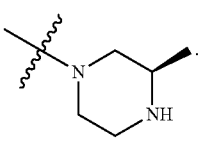 [SMILES: *N1CCN[C@H](C)C1]

In certain embodiments, R' is

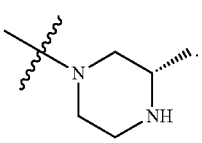

In certain embodiments, R' is.

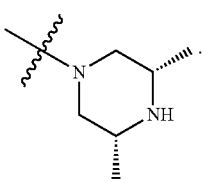 [SMILES: *N1C[C@@H](C)N[C@@H](C)C1]

In certain embodiments, R' is
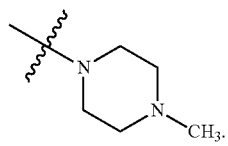
In certain embodiments, R' is
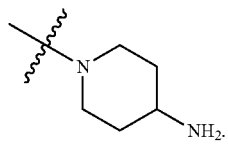
In certain embodiments, R' is
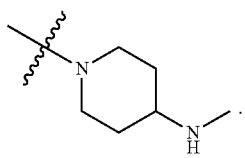 [SMILES: *N1CCC(NC)CC1]
In certain embodiments, R' is
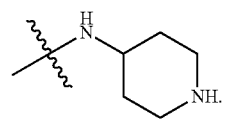 [SMILES: *NC1CCNCC1]
In certain embodiments, R' is
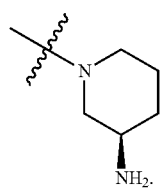
In certain embodiments, R' is
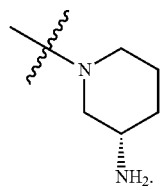
In certain embodiments, R' is
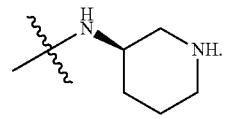
In certain embodiments, R'
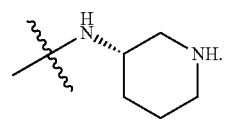 [SMILES: *N[C@H]1CCCNC1]
In certain embodiments, R' is
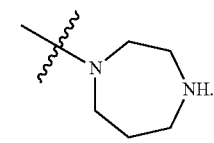 [SMILES: *N1CCCNCC1]
In certain embodiments, R' is
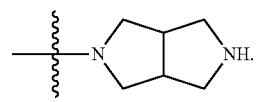 [SMILES: *N1CC2CNCC2C1]
In certain embodiments, the compound is
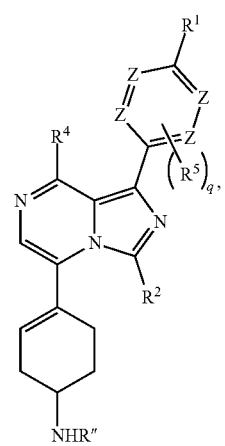
(Ia″)

wherein R″ is H or $C_1$-$C_6$ alkyl. In certain embodiments, the compound is

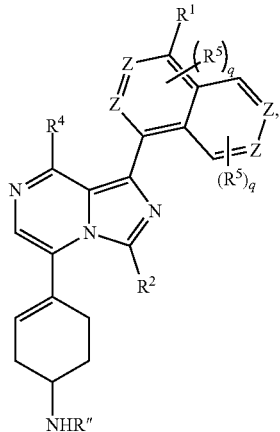
(Ib″)

wherein R″ is H or $C_1$-$C_6$ alkyl. In certain embodiments, the compound is

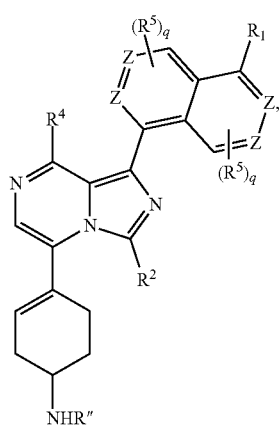
(Ic″)

wherein R″ is H or $C_1$-$C_6$ alkyl. In certain embodiments, R″ is H. In certain embodiments, R″ is $C_1$-$C_6$ alkyl. In certain embodiments, $R^1$ is

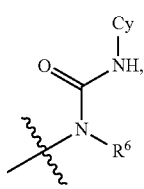

In certain embodiments, $R^1$ is

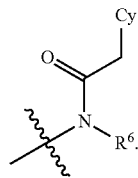

In certain embodiments, $R^1$

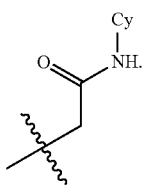

In certain embodiments, $R^1$ is

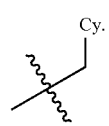

In certain embodiments, $R^1$ is

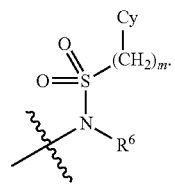

In certain embodiments, the compound is

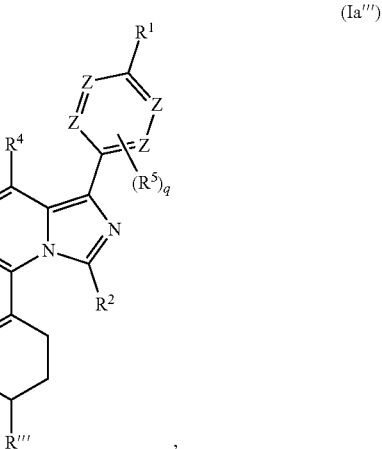
(Ia‴)

wherein R‴ is selected from the group consisting of —OH, $C_1$-$C_6$ alkoxy, —$NH_2$, —NH($C_1$-$C_6$ alkyl), —N($C_1$-$C_6$ alkyl)($C_1$-$C_6$ alkyl), and —NH(oxetanyl), wherein each $C_1$-$C_6$ alkyl is optionally substituted with at least one independently selected from the group consisting of halogen, —C(=O)NH$_2$, —C(=O)N($C_1$-$C_6$ alkyl), —C(=O)N($C_1$-$C_6$ alkyl)($C_1$-$C_6$ alkyl), —OH, and —$C_1$-$C_6$ alkoxy. In certain embodiments, the compound is

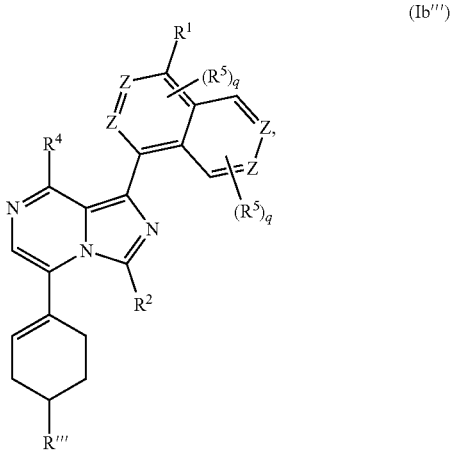

(Ib''')

wherein R''' is selected from the group consisting of —OH, $C_1$-$C_6$ alkoxy, —NH$_2$, —NH($C_1$-$C_6$ alkyl), —N($C_1$-$C_6$ alkyl)($C_1$-$C_6$ alkyl), and —NH(oxetanyl), wherein each $C_1$-$C_6$ alkyl is optionally substituted with at least one independently selected from the group consisting of halogen, —C(=O)NH$_2$, —C(=O)N($C_1$-$C_6$ alkyl), —C(=O)N($C_1$-$C_6$ alkyl)($C_1$-$C_6$ alkyl), —OH, and —$C_1$-$C_6$ alkoxy. In certain embodiments, the compound is

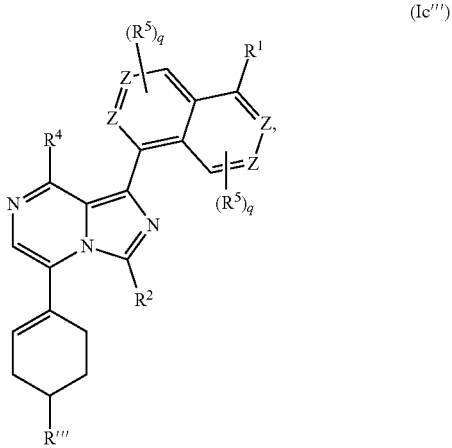

(Ic''')

wherein R''' is selected from the group consisting of —OH, $C_1$-$C_6$ alkoxy, —NH$_2$, —NH($C_1$-$C_6$ alkyl), —N($C_1$-$C_6$ alkyl)($C_1$-$C_6$ alkyl), and —NH(oxetanyl), wherein each $C_1$-$C_6$ alkyl is optionally substituted with at least one independently selected from the group consisting of halogen, —C(=O)NH$_2$, —C(=O)N($C_1$-$C_6$ alkyl), —C(=O)N($C_1$-$C_6$ alkyl)($C_1$-$C_6$ alkyl), —OH, and —$C_1$-$C_6$ alkoxy. In certain embodiments, R''' is H. In certain embodiments, R''' is —OH. In certain embodiments, R''' is —NH$_2$. In certain embodiments, R''' is —NHCH$_3$. In certain embodiments, R' is —N(CH$_3$)$_2$. In certain embodiments, R''' is —NHCH$_2$CH$_2$F. In certain embodiments, R' is —N(Me)CH$_2$CH$_2$F. In certain embodiments, R''' is —NHCH$_2$CHF$_2$.

In certain embodiments, R''' is —N(Me)CH$_2$CHF$_2$. In certain embodiments, R''' is —NHCH$_2$CF$_3$. In certain embodiments, R''' is —N(Me)CH$_2$CF$_3$. In certain embodiments, R''' is —NHCH$_2$CH$_2$CF$_3$. In certain embodiments, R''' is —N(Me)CH$_2$CH$_2$CF$_3$. In certain embodiments, R''' is —NHCH$_2$CH$_2$C(=O)NMe$_2$. In certain embodiments, R''' is —N(Me)CH$_2$CH$_2$C(=O)NMe$_2$. In certain embodiments, R''' is —NHCH$_2$CH$_2$C(=O)NH$_2$. In certain embodiments, R''' is —N(Me)CH$_2$CH$_2$C(=O)NH$_2$. In certain embodiments, R''' is —NHCH$_2$CH$_2$C(=O)NHMe. In certain embodiments, R''' is —N(Me)CH$_2$CH$_2$C(=O)NHMe$_2$. In certain embodiments, R''' is

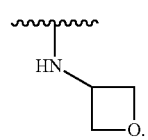

In certain embodiments, the compound is selected from the group consisting of:

Example 1: 3-{4-[8-amino-3-methyl-5-(piperazine-1-carbonyl)imidazo[1,5-a]pyrazin-1-yl]naphthalen-1-yl}-1-[3-(trifluoromethyl)phenyl]urea;

Example 2: 3-{4-[8-amino-5-(4-aminopiperidine-1-carbonyl)-3-methylimidazo[1,5-a]pyrazin-1-yl]naphthalen-1-yl}-1-[3-(trifluoromethyl)phenyl]urea);

Example 3: 8-amino-3-methyl-N-(piperidin-4-yl)-1-[4-({[3-(trifluoromethyl)phenyl]carbamoyl}amino)naphthalen-1-yl]imidazo[1,5-a]pyrazine-5-carboxamide;

Example 4: 3-(4-{8-amino-5-[(3R)-3-aminopiperidine-1-carbonyl]-3-methylimidazo[1,5-a]pyrazin-1-yl}naphthalen-1-yl)-1-[3-(trifluoromethyl)phenyl]urea;

Example 5: 3-(4-{8-amino-5-[(3S)-3-aminopiperidine-1-carbonyl]-3-methylimidazo[1,5-a]pyrazin-1-yl}naphthalen-1-yl)-1-[3-(trifluoromethyl)phenyl]urea);

Example 6: 8-amino-3-methyl-N-[(3R)-piperidin-3-yl]-1-[4-({[3-(trifluoromethyl)phenyl]carbamoyl}amino)naphthalen-1-yl]imidazo[1,5-a]pyrazine-5-carboxamide;

Example 7: 8-amino-3-methyl-N-(piperidin-3-yl)-1-[4-({[3-(trifluoromethyl)phenyl]carbamoyl}amino)naphthalen-1-yl]imidazo[1,5-a]pyrazine-5-carboxamide;

Example 8: 8-amino-3-methyl-N-[(3S)-1-methylpiperidin-3-yl]-1-[4-({[3-(trifluoromethyl)phenyl]carbamoyl}amino)naphthalen-1-yl]imidazo[1,5-a]pyrazine-5-carboxamide;

Example 9:8-amino-3-methyl-N-[(3R)-1-methylpiperidin-3-yl]-1-[4-({[3-(trifluoromethyl)phenyl]carbamoyl}amino)naphthalen-1-yl]imidazo[1,5-a]pyrazine-5-carboxamide;

Example 10:3-{4-[8-amino-3-methyl-5-(4-methylpiperazine-1-carbonyl)imidazo[1,5-a]pyrazin-1-yl]naphthalen-1-yl}-1-[3-(trifluoromethyl)phenyl]urea;

Example 11:3-{4-[8-amino-3-methyl-5-(piperidin-4-ylmethyl)imidazo[1,5-a]pyrazin-1-yl]naphthalen-1-yl}-1-[3-(trifluoromethyl)phenyl]urea;

Example 12:3-{4-[8-amino-3-methyl-5-(piperazin-1-ylmethyl)imidazo[1,5-a]pyrazin-1-yl]naphthalen-1-yl}-1-[3-(trifluoromethyl)phenyl]urea;

Example 13:3-(4-{8-amino-5-[(4-aminopiperidin-1-yl)methyl]-3-methylimidazo[1,5-a]pyrazin-1-yl}naphthalen-1-yl)-1-[3-(trifluoromethyl)phenyl]urea;

Example 14:3-[4-(8-amino-3-methyl-5-{[(piperidin-4-yl)amino]methyl}imidazo[1,5-a]pyrazin-1-yl)naphthalen-1-yl]-1-[3-(trifluoromethyl)phenyl]urea;

Example 15: 3-[4-(8-amino-5-{[(3R)-3-aminopiperidin-1-yl]methyl}-3-methylimidazo[1,5-a]pyrazin-1-yl)naphtalen-1-yl]-1-[3-(trifluoromethyl)phenyl]urea;

Example 16: 3-[4-(8-amino-5-{[(3S)-3-aminopiperidin-1-yl]methyl}-3-methylimidazo[1,5-a]pyrazin-1-yl)naphtalen-1-yl]-1-[3-(trifluoromethyl)phenyl]urea;

Example 17: 3-[4-(8-amino-3-methyl-5-{[(piperidin-3-yl)amino]methyl}imidazo[1,5-a]pyrazin-1-yl)naphtalen-1-yl]-1-[3-(trifluoromethyl)phenyl]urea;

Example 18: 3-{4-[8-amino-3-methyl-5-({[(3S)-piperidin-3-yl]amino}methyl)imidazo[1,5-a]pyrazin-1-yl]naphtalen-1-yl}-1-[3-(trifluoromethyl)phenyl]urea;

Example 19: 3-(4-{8-amino-3-methyl-5-[(4-methylpiperazin-1-yl)methyl]imidazo[1,5-a]pyrazin-1-yl}naphthalen-1-yl)-1-[3-(trifluoromethyl)phenyl]urea;

Example 20: 3-{4-[8-amino-3-ethyl-5-(piperazin-1-ylmethyl)imidazo[1,5-a]pyrazin-1-yl]naphthalen-1-yl}-1-[3-(trifluoromethyl)phenyl]urea;

Example 21: 3-{4-[8-amino-5-(piperazin-1-ylmethyl)-3-(propan-2-yl)imidazo[1,5-a]pyrazin-1-yl]naphthalen-1-yl}-1-[3-(trifluoromethyl)phenyl]urea;

Example 22: 3-(4-{8-amino-3-ethyl-5-[(4-methylpiperazin-1-yl)methyl]imidazo[1,5-a]pyrazin-1-yl}naphthalen-1-yl)-1-[3-(trifluoromethyl)phenyl]urea;

Example 23: 3-[4-(8-amino-3-methyl-5-{[4-(methylamino)piperidin-1-yl]methyl}imidazo[1,5-a]pyrazin-1-yl)naphthalen-1-yl]-1-[3-(trifluoromethyl)phenyl]urea;

Example 24: 3-[4-(8-amino-3-methyl-5-{[(3R)-3-methylpiperazin-1-yl]methyl}imidazo[1,5-a]pyrazin-1-yl)naphthalen-1-yl]-1-[3-(trifluoromethyl)phenyl]urea;

Example 25: 3-[4-(8-amino-3-methyl-5-{[(3S)-3-methylpiperazin-1-yl]methyl}imidazo[1,5-a]pyrazin-1-yl)naphthalen-1-yl]-1-[3-(trifluoromethyl)phenyl]urea;

Example 26: 3-[4-(8-amino-5-{[(3R,5S)-3,5-dimethylpiperazin-1-yl]methyl}-3-methylimidazo[1,5-a]pyrazin-1-yl)naphthalen-1-yl]-1-[3-(trifluoromethyl)phenyl]urea;

Example 27: 3-[4-(8-amino-3-ethyl-5-{[(3R)-3-methylpiperazin-1-yl]methyl}imidazo[1,5-a]pyrazin-1-yl)naphtalen-1-yl]-1-[3-(trifluoromethyl)phenyl]urea;

Example 28: 3-[4-(8-amino-3-ethyl-5-{[(3S)-3-methylpiperazin-1-yl]methyl}imidazo[1,5-a]pyrazin-1-yl)naphtalen-1-yl]-1-[3-(trifluoromethyl)phenyl]urea;

Example 29: 3-{4-[8-amino-5-(1,4-diazepan-1-ylmethyl)-3-methylimidazo[1,5-a]pyrazin-1-yl]naphthalen-1-yl}-1-[3-(trifluoromethyl)phenyl]urea;

Example 30: 3-[4-(8-amino-5-{2,5-diazabicyclo[2.2.1]heptan-2-ylmethyl}-3-methylimidazo[1,5-a]pyrazin-1-yl)naphthalen-1-yl]-1-[3-(trifluoromethyl)phenyl]urea;

Example 31: 3-[4-(8-amino-3-methyl-5-{octahydropyrrolo[3,4-c]pyrrol-2-ylmethyl}imidazo[1,5-a]pyrazin-1-yl)naphthalen-1-yl]-1-[3-(trifluoromethyl)phenyl]urea;

Example 32: 3-{4-[8-amino-3-methyl-5-(piperazin-1-ylmethyl)imidazo[1,5-a]pyrazin-1-yl]naphthalen-1-yl}-1-(3-fluorophenyl)urea;

Example 33: 3-{4-[8-amino-3-methyl-5-(piperazin-1-ylmethyl)imidazo[1,5-a]pyrazin-1-yl]naphthalen-1-yl}-1-(3-methylphenyl)urea;

Example 34: 3-{4-[8-amino-3-methyl-5-(piperazin-1-ylmethyl)imidazo[1,5-a]pyrazin-1-yl]-3-fluorophenyl}-1-[3-(trifluoromethyl)phenyl]urea;

Example 35: 3-{4-[8-amino-3-ethyl-5-(piperazin-1-ylmethyl)imidazo[1,5-a]pyrazin-1-yl]-3-fluorophenyl}-1-[3-(trifluoromethyl)phenyl]urea;

Example 36: N-(4-(8-amino-3-isopropyl-5-(piperazin-1-ylmethyl)imidazo[1,5-a]pyrazin-1-yl)-2-fluorophenyl)-1-(2-chlorophenyl)methanesulfonamide;

Example 37: 3-isopropyl-1-(4-((7-methyl-1H-benzo[d]imidazol-2-yl)methyl)naphthalen-1-yl)-5-(piperazin-1-ylmethyl)imidazo[1,5-a]pyrazin-8-amine;

Example 38: 2-{4-[8-amino-3-methyl-5-(piperazin-1-ylmethyl)imidazo[1,5-a]pyrazin-1-yl]naphthalen-1-yl}-N-[3-(trifluoromethyl)phenyl]acetamide;

Example 39: 3-{4-[8-amino-3-methyl-5-(1,2,5,6-tetrahydropyridin-3-yl)imidazo[1,5-a]pyrazin-1-yl]naphthalen-1-yl}-1-[3-(trifluoromethyl)phenyl]urea;

Example 40: 3-{4-[8-amino-3-methyl-5-(piperidin-3-yl)imidazo[1,5-a]pyrazin-1-yl]naphthalen-1-yl}-1-[3-(trifluoromethyl)phenyl]urea;

Example 41: 3-{4-[8-amino-3-methyl-5-(1,2,3,6-tetrahydropyridin-4-yl)imidazo[1,5-a]pyrazin-1-yl]naphthalen-1-yl}-1-[3-(trifluoromethyl)phenyl]urea;

Example 42: 3-{4-[8-amino-3-methyl-5-(1,2,3,6-tetrahydropyridin-4-yl)imidazo[1,5-a]pyrazin-1-yl]-3-fluorophenyl}-1-[3-(trifluoromethyl)phenyl]urea;

Example 43: 3-{4-[5-(1-acetyl-1,2,5,6-tetrahydropyridin-3-yl)-8-amino-3-methylimidazo[1,5-a]pyrazin-1-yl]naphthalen-1-yl}-1-[3-(trifluoromethyl)phenyl]urea;

Example 44: 3-{4-[5-(1-acetylpiperidin-3-yl)-8-amino-3-methylimidazo[1,5-a]pyrazin-1-yl]naphthalen-1-yl}-1-[3-(trifluoromethyl)phenyl]urea;

Example 45: 3-{4-[5-(1-acetyl-1,2,3,6-tetrahydropyridin-4-yl)-8-amino-3-methylimidazo[1,5-a]pyrazin-1-yl]-3-fluorophenyl}-1-[3-(trifluoromethyl)phenyl]urea;

Example 46: 3-{4-[8-amino-5-(cyclohex-1-en-1-yl)-3-methylimidazo[1,5-a]pyrazin-1-yl]naphthalen-1-yl}-1-[3-(trifluoromethyl)phenyl]urea;

Example 47: 3-{4-[8-amino-3-methyl-5-(1-methyl-1,2,3,6-tetrahydropyridin-4-yl)imidazo[1,5-a]pyrazin-1-yl]naphthalen-1-yl}-1-[3-(trifluoromethyl)phenyl]urea;

Example 48: 3-{4-[8-amino-3-methyl-5-(pyridin-3-yl)imidazo[1,5-a]pyrazin-1-yl]naphthalen-1-yl}-1-[3-(trifluoromethyl)phenyl]urea;

Example 49: 3-(4-{8-amino-3-methyl-5-[1-(prop-2-enoyl)-1,2,3,6-tetrahydropyridin-4-yl]imidazo[1,5-a]pyrazin-1-yl}naphthalen-1-yl)-1-[3-(trifluoromethyl)phenyl]urea;

Example 50: 3-{4-[8-amino-5-(4-aminophenyl)-3-methylimidazo[1,5-a]pyrazin-1-yl]naphthalen-1-yl}-1-[3-(trifluoromethyl)phenyl]urea;

Example 51: 3-{4-[8-amino-3-methyl-5-(1-methyl-1H-pyrazol-4-yl)imidazo[1,5-a]pyrazin-1-yl]naphthalen-1-yl}-1-[3-(trifluoromethyl)phenyl]urea;

Example 52: 3-{4-[8-amino-5-(1,5-dimethyl-1H-pyrazol-4-yl)-3-methylimidazo[1,5-a]pyrazin-1-yl]naphthalen-1-yl}-1-[3-(trifluoromethyl)phenyl]urea;

Example 53: 3-{4-[8-amino-5-(1,3-dimethyl-1H-pyrazol-4-yl)-3-methylimidazo[1,5-a]pyrazin-1-yl]naphthalen-1-yl}-1-[3-(trifluoromethyl)phenyl]urea;

Example 54: 3-(4-{8-amino-3-methyl-5-[1-(piperidin-4-yl)-1H-pyrazol-4-yl]imidazo[1,5-a]pyrazin-1-yl}naphthalen-1-yl)-1-[3-(trifluoromethyl)phenyl]urea;

Example 55: 3-{4-[8-amino-3-methyl-5-(1,2,3,4-tetrahydroisoquinolin-5-yl)imidazo[1,5-a]pyrazin-1-yl]naphtalen-1-yl}-1-[3-(trifluoromethyl)phenyl]urea;

Example 56: 3-{4-[8-amino-5-(2-aminopyridin-4-yl)-3-methylimidazo[1,5-a]pyrazin-1-yl]naphthalen-1-yl}-1-[3-(trifluoromethyl)phenyl]urea;

Example 57: 2-(4-(8-amino-5-(4-aminocyclohex-1-en-1-yl)-3-methylimidazo[1,5-a]pyrazin-1-yl)naphthalen-1-yl)-N-(3-(trifluoromethyl)phenyl)acetamide;

Example 58: 2-(4-{8-amino-3-ethyl-5-[4-(methylamino)cyclohex-1-en-1-yl]imidazo[1,5-a]pyrazin-1-yl}naphthalen-1-yl)-N-[3-(trifluoromethyl)phenyl]acetamide;

Example 59: 2-(4-{8-amino-5-[4-(methylamino)cyclohex-1-en-1-yl]-3-(propan-2-yl)imidazo[1,5-a]pyrazin-1-yl}naphthalen-1-yl)-N-[3-(trifluoromethyl)phenyl]acetamide;

Example 60: 2-(4-{8-amino-3-methyl-5-[4-(methylamino)cyclohex-1-en-1-yl]imidazo[1,5-a]pyrazin-1-yl}naphthalen-1-yl)-N-[3-(trifluoromethyl)phenyl]acetamide;

Example 61: 2-(4-{8-amino-3-methyl-5-[4-(methylamino)cyclohex-1-en-1-yl]imidazo[1,5-a]pyrazin-1-yl}-3-fluorophenyl)-N-[3-(trifluoromethyl)phenyl]acetamide;

Example 62: 2-(4-(8-amino-3-isopropyl-5-(4-(methylamino)cyclohex-1-en-1-yl)imidazo[1,5-a]pyrazin-1-yl)naphthalen-1-yl)-N-phenylacetamide;

Example 63: 2-(4-(8-amino-3-isopropyl-5-(4-(methylamino)cyclohex-1-en-1-yl)imidazo[1,5-a]pyrazin-1-yl)-3-fluorophenyl)-N-(3-fluorophenyl)acetamide;

Example 64: 2-(4-(8-amino-3-isopropyl-5-(4-(methylamino)cyclohex-1-en-1-yl)imidazo[1,5-a]pyrazin-1-yl)naphthalen-1-yl)-N-(3-fluorophenyl)acetamide;

Example 65: 2-(4-(8-amino-3-isopropyl-5-(4-(methylamino)cyclohex-1-en-1-yl)imidazo[1,5-a]pyrazin-1-yl)naphthalen-1-yl)-N-(3-fluoro-5-methoxyphenyl)acetamide;

Example 66: 2-(4-(8-amino-3-isopropyl-5-(4-(methylamino)cyclohex-1-en-1-yl)imidazo[1,5-a]pyrazin-1-yl)-3-fluorophenyl)-N-phenylacetamide;

Example 67: 2-(4-(8-amino-3-isopropyl-5-(4-(methylamino)cyclohex-1-en-1-yl)imidazo[1,5-a]pyrazin-1-yl)naphthalen-1-yl)-N-(3-cyano-5-fluorophenyl)acetamide;

Example 68: 2-(4-(8-amino-3-isopropyl-5-(4-(methylamino)cyclohex-1-en-1-yl)imidazo[1,5-a]pyrazin-1-yl)naphthalen-1-yl)-N-(pyridin-2-yl)acetamide;

Example 69: 2-(4-(8-amino-3-isopropyl-5-(4-(methylamino)cyclohex-1-en-1-yl)imidazo[1,5-a]pyrazin-1-yl)naphthalen-1-yl)-N-(5-methoxypyridin-3-yl)acetamide;

Example 70: 2-(4-(8-amino-3-isopropyl-5-(4-(methylamino)cyclohex-1-en-1-yl)imidazo[1,5-a]pyrazin-1-yl)naphthalen-1-yl)-N-(3-cyanophenyl)acetamide;

Example 71: 2-(4-(8-amino-3-isopropyl-5-(4-(methylamino)cyclohex-1-en-1-yl)imidazo[1,5-a]pyrazin-1-yl)naphthalen-1-yl)-N-(3-methoxyphenyl)acetamide;

Example 72: 2-(4-(8-amino-3-isopropyl-5-(4-(methylamino)cyclohex-1-en-1-yl)imidazo[1,5-a]pyrazin-1-yl)naphthalen-1-yl)-N-(pyridin-3-yl)acetamide;

Example 73: 2-(4-(8-amino-3-isopropyl-5-(4-(methylamino)cyclohex-1-en-1-yl)imidazo[1,5-a]pyrazin-1-yl)naphthalen-1-yl)-N-(pyrazin-2-yl)acetamide;

Example 74: 2-(4-(8-amino-3-isopropyl-5-(4-(methylamino)cyclohex-1-en-1-yl)imidazo[1,5-a]pyrazin-1-yl)naphthalen-1-yl)-N-(thiazol-5-yl)acetamide;

Example 75: 2-(4-(8-amino-3-isopropyl-5-(4-(methylamino)cyclohex-1-en-1-yl)imidazo[1,5-a]pyrazin-1-yl)naphthalen-1-yl)-N-(1-methyl-1H-benzo[d]imidazol-5-yl)acetamide;

Example 76: 2-(4-(8-amino-3-isopropyl-5-(4-(methylamino)cyclohex-1-en-1-yl)imidazo[1,5-a]pyrazin-1-yl)naphthalen-1-yl)-N-(2,2-difluorobenzo[d][1,3]dioxol-5-yl)acetamide;

Example 77: 2-(4-(8-amino-3-isopropyl-5-(4-(methylamino)cyclohex-1-en-1-yl)imidazo[1,5-a]pyrazin-1-yl)naphthalen-1-yl)-N-(1-methyl-1H-pyrazol-4-yl)acetamide;

Example 78: 2-(4-(8-amino-3-isopropyl-5-(4-(methylamino)cyclohex-1-en-1-yl)imidazo[1,5-a]pyrazin-1-yl)naphthalen-1-yl)-N-(3,4-dimethoxyphenyl)acetamide;

Example 79: 2-(4-(8-amino-3-isopropyl-5-(4-(methylamino)cyclohex-1-en-1-yl)imidazo[1,5-a]pyrazin-1-yl)naphthalen-1-yl)-N-(pyrimidin-5-yl)acetamide;

Example 80: 2-(4-(8-amino-3-isopropyl-5-(4-(methylamino)cyclohex-1-en-1-yl)imidazo[1,5-a]pyrazin-1-yl)naphthalen-1-yl)-N-(5-fluoropyridin-3-yl)acetamide;

Example 81: 2-(5-(8-amino-3-isopropyl-5-(4-(methylamino)cyclohex-1-en-1-yl)imidazo[1,5-a]pyrazin-1-yl)naphthalen-1-yl)-N-(3-fluorophenyl)acetamide;

Example 82: 2-(5-(8-amino-3-isopropyl-5-(4-(methylamino)cyclohex-1-en-1-yl)imidazo[1,5-a]pyrazin-1-yl)naphthalen-1-yl)-N-phenylacetamide;

Example 83: 3-{4-[8-amino-5-(4-aminocyclohex-1-en-1-yl)-3-methylimidazo[1,5-a]pyrazin-1-yl]naphthalen-1-yl}-1-[3-(trifluoromethyl)phenyl]urea;

Example 84: 3-(4-{8-amino-3-methyl-5-[4-(methylamino)cyclohex-1-en-1-yl]imidazo[1,5-a]pyrazin-1-yl}naphthalen-1-yl)-1-[3-(trifluoromethyl)phenyl]urea;

Example 85: 1-(4-(8-amino-5-(4-aminocyclohex-1-en-1-yl)-3-ethylimidazo[1,5-a]pyrazin-1-yl)naphthalen-1-yl)-3-(3-(trifluoromethyl)phenyl)urea;

Example 86: 3-{4-[8-amino-5-(4-aminocyclohex-1-en-1-yl)-3-(propan-2-yl)imidazo[1,5-a]pyrazin-1-yl]naphtha-len-1-yl}-1-[3-(trifluoromethyl)phenyl]urea;

Example 87: 1-(4-(8-amino-5-(4-aminocyclohex-1-en-1-yl)-3-methylimidazo[1,5-a]pyrazin-1-yl)naphthalen-1-yl)-3-phenylurea;

Example 88: 3-{4-[8-amino-5-(4-aminocyclohex-1-en-1-yl)-3-methylimidazo[1,5-a]pyrazin-1-yl]naphthalen-1-yl}-1-[3,5-bis(trifluoromethyl)phenyl]urea;

Example 89: 3-{4-[8-amino-5-(4-aminocyclohex-1-en-1-yl)-3-methylimidazo[1,5-a]pyrazin-1-yl]naphthalen-1-yl}-1-(3,5-dimethylphenyl)urea;

Example 90: 3-{4-[8-amino-5-(4-aminocyclohex-1-en-1-yl)-3-methylimidazo[1,5-a]pyrazin-1-yl]naphthalen-1-yl}-1-[4-chloro-3-(trifluoromethyl)phenyl]urea;

Example 91: 1-(4-(8-amino-5-(4-aminocyclohex-1-en-1-yl)-3-methylimidazo[1,5-a]pyrazin-1-yl)naphthalen-1-yl)-3-benzylurea;

Example 92: 3-{4-[8-amino-5-(4-aminocyclohex-1-en-1-yl)-3-methylimidazo[1,5-a]pyrazin-1-yl]naphthalen-1-yl}-1-[(4-methylphenyl)methyl]urea;

Example 93: 1-(4-(8-amino-5-(4-aminocyclohex-1-en-1-yl)-3-methylimidazo[1,5-a]pyrazin-1-yl)naphthalen-1-yl)-3-(2-chloro-5-(trifluoromethyl)phenyl)urea;

Example 94: 1-{4-[8-amino-5-(4-aminocyclohex-1-en-1-yl)-3-methylimidazo[1,5-a]pyrazin-1-yl]naphthalen-1-yl}-3-(5-chloro-2-methoxyphenyl)urea;

Example 95: 1-{4-[8-amino-5-(4-aminocyclohex-1-en-1-yl)-3-methylimidazo[1,5-a]pyrazin-1-yl]naphthalen-1-yl}-3-(2-methoxy-5-methylphenyl)urea;

Example 96: 3-{4-[8-amino-5-(4-aminocyclohex-1-en-1-yl)-3-methylimidazo[1,5-a]pyrazin-1-yl]naphthalen-1-yl}-1-(5-chloro-2-methylphenyl)urea;

Example 97: 3-{4-[8-amino-5-(4-aminocyclohex-1-en-1-yl)-3-methylimidazo[1,5-a]pyrazin-1-yl]naphthalen-1-yl}-1-(3-fluorophenyl)urea;

Example 98: 1-(4-(8-amino-5-(4-aminocyclohex-1-en-1-yl)-3-methylimidazo[1,5-a]pyrazin-1-yl)naphthalen-1-yl)-3-(m-tolyl)urea;

Example 99: 1-{4-[8-amino-5-(4-aminocyclohex-1-en-1-yl)-3-methylimidazo[1,5-a]pyrazin-1-yl]naphthalen-1-yl}-3-(2-methoxyphenyl)urea;

Example 100: 3-{4-[8-amino-5-(4-aminocyclohex-1-en-1-yl)-3-methylimidazo[1,5-a]pyrazin-1-yl]naphthalen-1-yl}-1-[4-(trifluoromethyl)phenyl]urea;

Example 101: N-(4-{8-amino-3-methyl-1-[4-({[3-(trifluoromethyl)phenyl]carbamoyl}amino)naphthalen-1-yl]imidazo[1,5-a]pyrazin-5-yl}cyclohex-3-en-1-yl)acetamide;

Example 102: 1-{4-[8-amino-5-(4-aminocyclohex-1-en-1-yl)-3-methylimidazo[1,5-a]pyrazin-1-yl]naphthalen-1-yl}-3-{4-[(4-methylpiperazin-1-yl)methyl]phenyl}urea;

Example 103: 3-{4-[8-amino-5-(4-aminocyclohex-1-en-1-yl)-3-methylimidazo[1,5-a]pyrazin-1-yl]naphthalen-1-yl}-1-(2,3-dihydro-1,4-benzodioxin-6-yl)urea;

Example 104: 3-{4-[8-amino-5-(4-aminocyclohex-1-en-1-yl)-3-methylimidazo[1,5-a]pyrazin-1-yl]-3-fluorophenyl}-1-(2,3-dihydro-1,4-benzodioxin-6-yl)urea;

Example 105: 1-{4-[8-amino-5-(4-aminocyclohex-1-en-1-yl)-3-methylimidazo[1,5-a]pyrazin-1-yl]-3-fluorophenyl}-3-{4-[(4-methylpiperazin-1-yl)methyl]phenyl}urea;

Example 106: 3-(4-{8-amino-3-ethyl-5-[4-(methylamino)cyclohex-1-en-1-yl]imidazo[1,5-a]pyrazin-1-yl}naphthalen-1-yl)-1-[3-(trifluoromethyl)phenyl]urea;

Example 107: 1-(4-(8-amino-3-isopropyl-5-(4-(methylamino)cyclohex-1-en-1-yl)imidazo[1,5-a]pyrazin-1-yl)naphthalen-1-yl)-3-(3-(trifluoromethyl)phenyl)urea;

Example 108: 3-(4-{8-amino-3-ethyl-5-[4-(methylamino)cyclohex-1-en-1-yl]imidazo[1,5-a]pyrazin-1-yl}-3-fluorophenyl)-1-[3-(trifluoromethyl)phenyl]urea;

Example 109: 3-(4-{8-amino-5-[4-(methylamino)cyclohex-1-en-1-yl]-3-(propan-2-yl)imidazo[1,5-a]pyrazin-1-yl}-3-fluorophenyl)-1-[3-(trifluoromethyl)phenyl]urea;

Example 110: 3-(4-{8-amino-3-methyl-5-[4-(methylamino)cyclohex-1-en-1-yl]imidazo[1,5-a]pyrazin-1-yl}-3-fluorophenyl)-1-[3-(trifluoromethyl)phenyl]urea;

Example 111: 3-(4-{8-amino-3-methyl-5-[4-(methylamino)cyclohex-1-en-1-yl]imidazo[1,5-a]pyrazin-1-yl}-3-methylphenyl)-1-[3-(trifluoromethyl)phenyl]urea;

Example 112: 3-(4-{8-amino-3-methyl-5-[4-(methylamino)cyclohex-1-en-1-yl]imidazo[1,5-a]pyrazin-1-yl}-2-methylphenyl)-1-[3-(trifluoromethyl)phenyl]urea;

Example 113: 3-(4-{8-amino-3-methyl-5-[4-(methylamino)cyclohex-1-en-1-yl]imidazo[1,5-a]pyrazin-1-yl}-5-fluoro-2-methylphenyl)-1-[3-(trifluoromethyl)phenyl]urea;

Example 114: 3-(4-{8-amino-3-methyl-5-[4-(methylamino)cyclohex-1-en-1-yl]imidazo[1,5-a]pyrazin-1-yl}-5-fluoro-2-methoxyphenyl)-1-[3-(trifluoromethyl)phenyl]urea;

Example 115: 3-(4-{8-amino-3-methyl-5-[4-(methylamino)cyclohex-1-en-1-yl]imidazo[1,5-a]pyrazin-1-yl}naphthalen-1-yl)-1-(3-methylphenyl)urea;

Example 116: 3-(4-{8-amino-3-methyl-5-[4-(methylamino)cyclohex-1-en-1-yl]imidazo[1,5-a]pyrazin-1-yl}naphthalen-1-yl)-1-(3-fluorophenyl)urea;

Example 117: 3-(4-{8-amino-3-ethyl-5-[4-(methylamino)cyclohex-1-en-1-yl]imidazo[1,5-a]pyrazin-1-yl}naphthalen-1-yl)-1-(3-fluorophenyl)urea;

Example 118: 3-(4-{8-amino-3-ethyl-5-[4-(methylamino)cyclohex-1-en-1-yl]imidazo[1,5-a]pyrazin-1-yl}naphthalen-1-yl)-1-(3-methylphenyl)urea;

Example 119: 3-(4-{8-amino-5-[4-(methylamino)cyclohex-1-en-1-yl]-3-(propan-2-yl)imidazo[1,5-a]pyrazin-1-yl}naphthalen-1-yl)-1-(3-methylphenyl)urea;

Example 120: 3-(4-{8-amino-5-[4-(methylamino)cyclohex-1-en-1-yl]-3-(propan-2-yl)imidazo[1,5-a]pyrazin-1-yl}naphthalen-1-yl)-1-(3-fluorophenyl)urea;

Example 121: 1-(4-(8-Amino-3-isopropyl-5-(4-(methylamino)cyclohex-1-en-1-yl)imidazo[1,5-a] pyrazin-1-yl)naphthalen-1-yl)-3-phenylurea;

Example 122: 1-(4-(8-amino-3-isopropyl-5-(4-(methylamino)cyclohex-1-en-1-yl)imidazo[1,5-a]pyrazin-1-yl)naphthalen-1-yl)-3-(pyridin-3-yl)urea;

Example 123: 1-(5-(8-amino-3-isopropyl-5-(4-(methylamino)cyclohex-1-en-1-yl)imidazo[1,5-a]pyrazin-1-yl)naphthalen-1-yl)-3-(3-fluorophenyl)urea;

Example 124: 1-(5-(8-amino-3-isopropyl-5-(4-(methylamino)cyclohex-1-en-1-yl)imidazo[1,5-a]pyrazin-1-yl)naphthalen-1-yl)-3-(3-(trifluoromethyl)phenyl)urea;

Example 125: 1-(4-(8-amino-3-isopropyl-5-(4-(methylamino)cyclohex-1-en-1-yl)imidazo[1,5-a]pyrazin-1-yl)-3-fluorophenyl)-3-(2,3-dihydrobenzo[b][1,4]dioxin-6-yl)urea;

Example 126: 1-(4-(8-amino-3-ethyl-5-(4-(methylamino)cyclohex-1-en-1-yl)imidazo[1,5-a]pyrazin-1-yl)-3-fluorophenyl)-3-(3-fluorophenyl)urea;

Example 127: 1-(5-(8-amino-3-isopropyl-5-(4-(methylamino)cyclohex-1-en-1-yl)imidazo[1,5-a]pyrazin-1-yl)naphthalen-1-yl)-3-phenylurea;

Example 128: 1-(5-(8-amino-3-isopropyl-5-(4-(methylamino)cyclohex-1-en-1-yl)imidazo[1,5-a]pyrazin-1-yl)naphthalen-1-yl)-3-(2,3-dihydrobenzo[b][1,4]dioxin-6-yl)urea;

Example 129: 1-(4-(8-amino-3-isopropyl-5-(4-(methylamino)cyclohex-1-en-1-yl)imidazo[1,5-a]pyrazin-1-yl)-3-fluorophenyl)-3-(3-fluorophenyl)urea;

Example 130: 1-(4-(8-amino-3-isopropyl-5-(4-(methylamino)cyclohex-1-en-1-yl)imidazo[1,5-a]pyrazin-1-yl)-3-fluorophenyl)-3-phenylurea;

Example 131: 1-(4-(8-amino-3-isopropyl-5-(4-(methylamino)cyclohex-1-en-1-yl)imidazo[1,5-a]pyrazin-1-yl)naphthalen-1-yl)-3-(pyridin-2-yl)urea;

Example 132: 1-(4-(8-amino-3-isopropyl-5-(4-(methylamino)cyclohex-1-en-1-yl)imidazo[1,5-a]pyrazin-1-yl)-3-methoxyphenyl)-3-(3-fluorophenyl)urea;

Example 133: 1-(4-(8-amino-3-isopropyl-5-(4-(methylamino)cyclohex-1-en-1-yl)imidazo[1,5-a]pyrazin-1-yl)-2-fluorophenyl)-3-phenylurea;

Example 134: 1-(4-(8-amino-3-isopropyl-5-(4-(methylamino)cyclohex-1-en-1-yl)imidazo[1,5-a]pyrazin-1-yl)-2-fluorophenyl)-3-(3-fluorophenyl)urea;

Example 135: 1-(4-(8-amino-3-isopropyl-5-(4-(methylamino)cyclohex-1-en-1-yl)imidazo[1,5-a]pyrazin-1-yl)phenyl)-3-(pyridin-3-yl)urea;

Example 136: 1-(4-(8-amino-3-isopropyl-5-(4-(methylamino)cyclohex-1-en-1-yl)imidazo[1,5-a]pyrazin-1-yl)naphthalen-1-yl)-3-(3-cyano-5-fluorophenyl)urea;

Example 137: 1-(5-(8-amino-3-isopropyl-5-(4-(methylamino)cyclohex-1-en-1-yl)imidazo[1,5-a]pyrazin-1-yl)isoquinolin-8-yl)-3-(3-fluorophenyl)urea;

Example 138: 1-(4-(8-amino-3-isopropyl-5-(4-(methylamino)cyclohex-1-en-1-yl)imidazo[1,5-a]pyrazin-1-yl)-3-fluorophenyl)-3-(pyridin-3-yl)urea;

Example 139: 1-(4-(8-amino-3-isopropyl-5-(4-(methylamino)cyclohex-1-en-1-yl)imidazo[1,5-a]pyrazin-1-yl)naphthalen-1-yl)-3-benzylurea;

Example 140: 1-(4-(8-amino-3-isopropyl-5-(4-(methylamino)cyclohex-1-en-1-yl)imidazo[1,5-a]pyrazin-1-yl)naphthalen-1-yl)-3-(2,3-dihydrobenzo[b][1,4]dioxin-6-yl)urea;

Example 141: 1-(4-(8-amino-3-isopropyl-5-(4-(methylamino)cyclohex-1-en-1-yl)imidazo[1,5-a]pyrazin-1-yl)naphthalen-1-yl)-3-(3-methoxyphenyl)urea;

Example 142: 1-(4-(8-amino-3-isopropyl-5-(4-(methylamino)cyclohex-1-en-1-yl)imidazo[1,5-a]pyrazin-1-yl)naphthalen-1-yl)-3-(3-cyanophenyl)urea;

Example 143: 1-(4-(8-amino-3-isopropyl-5-(4-(methylamino)cyclohex-1-en-1-yl)imidazo[1,5-a]pyrazin-1-yl)naphthalen-1-yl)-3-(3,4-dimethoxyphenyl)urea;

Example 144: 1-(4-(8-amino-3-isopropyl-5-(4-(methylamino)cyclohex-1-en-1-yl)imidazo[1,5-a]pyrazin-1-yl)naphthalen-1-yl)-3-(pyridin-4-yl)urea;

Example 145: 1-(4-(8-amino-3-isopropyl-5-(4-(methylamino)cyclohex-1-en-1-yl)imidazo[1,5-a]pyrazin-1-yl)naphthalen-1-yl)-3-(4-fluorophenyl)urea;

Example 146: 1-(4-(8-amino-3-isopropyl-5-(4-(methylamino)cyclohex-1-en-1-yl)imidazo[1,5-a]pyrazin-1-yl)-3-fluorophenyl)-3-(3-fluoro-5-methoxyphenyl)urea;

Example 147: 1-(4-(8-amino-3-methyl-5-(4-(methylamino)cyclohex-1-en-1-yl)imidazo[1,5-a]pyrazin-1-yl)naphthalen-1-yl)-3-(pyridin-3-yl)urea;

Example 148: 1-(4-(8-amino-3-isopropyl-5-(4-(methylamino)cyclohex-1-en-1-yl)imidazo[1,5-a]pyrazin-1-yl)-3-fluorophenyl)-3-(5-methoxypyridin-3-yl)urea;

Example 149: 1-(4-(8-amino-3-isopropyl-5-(4-(methylamino)cyclohex-1-en-1-yl)imidazo[1,5-a]pyrazin-1-yl)-3-fluorophenyl)-3-(5-fluoropyridin-3-yl)urea;

Example 150: 1-(4-(8-amino-3-isopropyl-5-(4-(methylamino)cyclohex-1-en-1-yl)imidazo[1,5-a]pyrazin-1-yl)naphthalen-1-yl)-3-(thiophen-3-yl)urea;

Example 151: 1-(4-(8-amino-3-isopropyl-5-(4-(methylamino)cyclohex-1-en-1-yl)imidazo[1,5-a]pyrazin-1-yl)naphthalen-1-yl)-3-(3,5-difluorophenyl)urea;

Example 152: 1-(4-(8-amino-3-isopropyl-5-(4-(methylamino)cyclohex-1-en-1-yl)imidazo[1,5-a]pyrazin-1-yl)naphthalen-1-yl)-3-(2-fluorophenyl)urea;

Example 153: 1-(4-(8-amino-3-isopropyl-5-(4-(methylamino)cyclohex-1-en-1-yl)imidazo[1,5-a]pyrazin-1-yl)-3-methylphenyl)-3-(pyridin-3-yl)urea;

Example 154: 1-(4-(8-amino-3-isopropyl-5-(4-(methylamino)cyclohex-1-en-1-yl)imidazo[1,5-a]pyrazin-1-yl)-3-chlorophenyl)-3-(pyridin-3-yl)urea;

Example 155: 1-(4-(3-isopropyl-5-(4-(methylamino)cyclohex-1-en-1-yl)imidazo[1,5-a]pyrazin-1-yl)naphthalen-1-yl)-3-phenylurea;

Example 156: 3-Isopropyl-1-(4-((7-methyl-1H-benzo[d]imidazol-2-yl)methyl)naphthalen-1-yl)-5-(4-(methylamino)cyclohex-1-en-1-yl)imidazo[1,5-a]pyrazin-8-amine;

Example 157: 1-(4-((1H-benzo[d]imidazol-2-yl)methyl)naphthalen-1-yl)-3-methyl-5-(4-(methylamino)cyclohex-1-en-1-yl)imidazo[1,5-a]pyrazin-8-amine;

Example 158: 1-(4-((1H-benzo[d]imidazol-2-yl)methyl)-2-fluorophenyl)-3-isopropyl-5-(4-(methylamino)cyclohex-1-en-1-yl)imidazo[1,5-a]pyrazin-8-amine;

Example 159: 1-(4-((1H-benzo[d]imidazol-2-yl)methyl)naphthalen-1-yl)-3-isopropyl-5-(4-(methylamino)cyclohex-1-en-1-yl)imidazo[1,5-a]pyrazin-8-amine;

Example 160: 1-(5-((1H-benzo[d]imidazol-2-yl)methyl)naphthalen-1-yl)-3-isopropyl-5-(4-(methylamino)cyclohex-1-en-1-yl)imidazo[1,5-a]pyrazin-8-amine;

Example 161: 1-(4-((4,6-difluoro-1H-benzo[d]imidazol-2-yl)methyl)naphthalen-1-yl)-3-isopropyl-5-(4-(methylamino)cyclohex-1-en-1-yl)imidazo[1,5-a]pyrazin-8-amine;

Example 162: 1-(4-((4,6-dimethyl-1H-benzo[d]imidazol-2-yl)methyl)naphthalen-1-yl)-3-isopropyl-5-(4-(methylamino)cyclohex-1-en-1-yl)imidazo[1,5-a]pyrazin-8-amine;

Example 163: 3-isopropyl-1-(4-((5-methoxy-1H-benzo[d]imidazol-2-yl)methyl)naphthalen-1-yl)-5-(4-(methylamino)cyclohex-1-en-1-yl)imidazo[1,5-a]pyrazin-8-amine;

Example 164: 2-((4-(8-amino-3-isopropyl-5-(4-(methylamino)cyclohex-1-en-1-yl)imidazo[1,5-a]pyrazin-1-yl)naphthalen-1-yl)methyl)-1H-benzo[d]imidazole-5-carbonitrile;

Example 165: 1-(4-((7-fluoro-1H-benzo[d]imidazol-2-yl)methyl)naphthalen-1-yl)-3-isopropyl-5-(4-(methylamino)cyclohex-1-en-1-yl)imidazo[1,5-a]pyrazin-8-amine;

Example 166: 1-(4-((1H-imidazo[4,5-c]pyridin-2-yl)methyl)naphthalen-1-yl)-3-isopropyl-5-(4-(methylamino)cyclohex-1-en-1-yl)imidazo[1,5-a]pyrazin-8-amine;

Example 167: 1-(4-((7-chloro-1H-benzo[d]imidazol-2-yl)methyl)naphthalen-1-yl)-3-isopropyl-5-(4-(methylamino)cyclohex-1-en-1-yl)imidazo[1,5-a]pyrazin-8-amine;

Example 168: 3-Isopropyl-5-(4-(methylamino)cyclohex-1-en-1-yl)-1-(4-((5-phenyl-1H-imidazol-2-yl)methyl)naphthalen-1-yl)imidazo[1,5-a]pyrazin-8-amine;

Example 169: N-(4-(8-Amino-3-isopropyl-5-(4-(methylamino)cyclohex-1-en-1-yl)imidazo[1,5-a]pyrazin-1-yl)-2-fluorophenyl)-1-(2-chlorophenyl)methanesulfonamide;

Example 170: N-(4-(8-amino-3-methyl-5-(4-(methylamino)cyclohex-1-en-1-yl)imidazo[1,5-a]pyrazin-1-yl)naphthalen-1-yl)-2-chlorobenzenesulfonamide;

Example 171: N-(4-(8-amino-3-isopropyl-5-(4-(methylamino)cyclohex-1-en-1-yl)imidazo[1,5-a]pyrazin-1-yl)-3-fluorophenyl)benzenesulfonamide;

Example 172: N-(4-(8-amino-3-isopropyl-5-(4-(methylamino)cyclohex-1-en-1-yl)imidazo[1,5-a]pyrazin-1-yl)-3-fluorophenyl)-3-fluorobenzenesulfonamide;

Example 173: N-(4-(8-amino-3-isopropyl-5-(4-(methylamino)cyclohex-1-en-1-yl)imidazo[1,5-a]pyrazin-1-yl)naphthalen-1-yl)-1-(2-chlorophenyl)methanesulfonamide;

Example 174: N-(4-(8-amino-3-isopropyl-5-(4-(methylamino)cyclohex-1-en-1-yl)imidazo[1,5-a]pyrazin-1-yl)-3-fluorophenyl)-2-chlorobenzenesulfonamide;

Example 175: N-(5-(8-amino-3-isopropyl-5-(4-(methylamino)cyclohex-1-en-1-yl)imidazo[1,5-a]pyrazin-1-yl)naphthalen-1-yl)-2-chlorobenzenesulfonamide;

Example 176: N-(4-(8-amino-3-isopropyl-5-(4-(methylamino)cyclohex-1-en-1-yl)imidazo[1,5-a]pyrazin-1-yl)naphthalen-1-yl)-3-fluorobenzenesulfonamide;

Example 177: N-(4-(8-amino-3-isopropyl-5-(4-(methylamino)cyclohex-1-en-1-yl)imidazo[1,5-a]pyrazin-1-yl)naphthalen-1-yl)-2,3-dihydrobenzo[b][1,4]dioxine-6-sulfonamide;

Example 178: N-(4-(8-amino-3-isopropyl-5-(4-(methylamino)cyclohex-1-en-1-yl)imidazo[1,5-a]pyrazin-1-yl)-3-fluorophenyl)-2,3-dihydrobenzo[b][1,4]dioxine-6-sulfonamide;

Example 179: N-(4-(8-amino-3-isopropyl-5-(4-(methylamino)cyclohex-1-en-1-yl)imidazo[1,5-a]pyrazin-1-yl)-2-fluorophenyl)-2-chlorobenzenesulfonamide;

Example 180: N-(4-(8-amino-3-isopropyl-5-(4-(methylamino)cyclohex-1-en-1-yl)imidazo[1,5-a]pyrazin-1-yl)-3-fluorophenyl)-1-(2-chlorophenyl)methanesulfonamide;

Example 181: N-(4-(8-amino-3-isopropyl-5-(4-(methylamino)cyclohex-1-en-1-yl)imidazo[1,5-a]pyrazin-1-yl)naphthalen-1-yl)-2-chlorobenzenesulfonamide;

Example 182: N-(4-(8-amino-3-isopropyl-5-(4-(methylamino)cyclohex-1-en-1-yl)imidazo[1,5-a]pyrazin-1-yl)naphthalen-1-yl)-1-(3-fluorophenyl)methanesulfonamide;

Example 183: N-(4-(8-amino-3-isopropyl-5-(4-(methylamino)cyclohex-1-en-1-yl)imidazo[1,5-a]pyrazin-1-yl)-3-fluorophenyl)-1-phenylmethanesulfonamide;

Example 184: N-(4-(8-amino-3-isopropyl-5-(4-(methylamino)cyclohex-1-en-1-yl)imidazo[1,5-a]pyrazin-1-yl)naphthalen-1-yl)-2,5-difluorobenzenesulfonamide;
Example 185: N-(4-(8-amino-3-isopropyl-5-(4-(methylamino)cyclohex-1-en-1-yl)imidazo[1,5-a]pyrazin-1-yl)naphthalen-1-yl)-2-fluoro-5-methylbenzenesulfonamide;
Example 186: N-(4-(8-amino-3-isopropyl-5-(4-(methylamino)cyclohex-1-en-1-yl)imidazo[1,5-a]pyrazin-1-yl)naphthalen-1-yl)-2-chloro-5-fluorobenzenesulfonamide;
Example 187: N-(4-(8-amino-3-isopropyl-5-(4-(methylamino)cyclohex-1-en-1-yl)imidazo[1,5-a]pyrazin-1-yl)naphthalen-1-yl)-1-(2-fluorophenyl)methanesulfonamide;
Example 188: N-(4-(8-amino-3-isopropyl-5-(4-(methylamino)cyclohex-1-en-1-yl)imidazo[1,5-a]pyrazin-1-yl)naphthalen-1-yl)-1-(2,5-difluorophenyl)methanesulfonamide;
Example 189: N-(4-(8-amino-3-isopropyl-5-(4-(methylamino)cyclohex-1-en-1-yl)imidazo[1,5-a]pyrazin-1-yl)-3-fluorophenyl)-1-(2-fluorophenyl)methanesulfonamide;
Example 190: N-(4-(8-amino-3-isopropyl-5-(4-(methylamino)cyclohex-1-en-1-yl)imidazo[1,5-a]pyrazin-1-yl)-3-fluorophenyl)-1-(2,5-difluorophenyl)methanesulfonamide;
Example 191: N-(4-(8-amino-3-isopropyl-5-(4-(methylamino)cyclohex-1-en-1-yl)imidazo[1,5-a]pyrazin-1-yl)-3-fluorophenyl)-1-(3,5-difluorophenyl)methanesulfonamide;
Example 192: N-(4-(8-amino-3-isopropyl-5-(4-(methylamino)cyclohex-1-en-1-yl)imidazo[1,5-a]pyrazin-1-yl)naphthalen-1-yl)-2-fluoro-5-(trifluoromethyl)benzenesulfonamide;
Example 193: N-(4-(8-amino-3-isopropyl-5-(4-(methylamino)cyclohex-1-en-1-yl)imidazo[1,5-a]pyrazin-1-yl)naphthalen-1-yl)-3-(trifluoromethyl)benzenesulfonamide;
Example 194: N-(4-(8-amino-3-isopropyl-5-(4-(methylamino)cyclohex-1-en-1-yl)imidazo[1,5-a]pyrazin-1-yl)-3-fluorophenyl)-3-(trifluoromethyl)benzenesulfonamide;
Example 195: N-(4-(8-amino-3-isopropyl-5-(4-(methylamino)cyclohex-1-en-1-yl)imidazo[1,5-a]pyrazin-1-yl)-3-fluorophenyl)-2,5-dichlorobenzenesulfonamide;
Example 196: N-(4-(8-amino-3-isopropyl-5-(4-(methylamino)cyclohex-1-en-1-yl)imidazo[1,5-a]pyrazin-1-yl)-2,5-difluorophenyl)-1-(2-chlorophenyl)methanesulfonamide;
Example 197: N-(4-(8-amino-3-isopropyl-5-(4-(methylamino)cyclohex-1-en-1-yl)imidazo[1,5-a]pyrazin-1-yl)-2,3-difluorophenyl)-1-(2-chlorophenyl)methanesulfonamide;
Example 198: N-(4-(8-amino-3-isopropyl-5-(4-(methylamino)cyclohex-1-en-1-yl)imidazo[1,5-a]pyrazin-1-yl)-3-fluorophenyl)-1-(pyridin-3-yl)methanesulfonamide;
Example 199: N-(4-(8-amino-3-isopropyl-5-(4-(methylamino)cyclohex-1-en-1-yl)imidazo[1,5-a]pyrazin-1-yl)naphthalen-1-yl)-1-(pyridin-3-yl)methanesulfonamide;
Example 200: N-(4-(8-amino-3-isopropyl-5-(4-(methylamino)cyclohex-1-en-1-yl)imidazo[1,5-a]pyrazin-1-yl)naphthalen-1-yl)-1-(3-methoxyphenyl)methanesulfonamide;
Example 201: N-(4-(8-amino-3-isopropyl-5-(4-(methylamino)cyclohex-1-en-1-yl)imidazo[1,5-a]pyrazin-1-yl)-3-fluorophenyl)-1-(3-methoxyphenyl)methanesulfonamide;
Example 202: N-(4-(8-amino-3-isopropyl-5-(4-(methylamino)cyclohex-1-en-1-yl)imidazo[1,5-a]pyrazin-1-yl)naphthalen-1-yl)-1-(3,5-difluorophenyl)methanesulfonamide;
Example 203: N-(4-(8-amino-3-isopropyl-5-(4-(methylamino)cyclohex-1-en-1-yl)imidazo[1,5-a]pyrazin-1-yl)naphthalen-1-yl)-1-(2-chlorophenyl)-N-methylmethanesulfonamide;
Example 204: 1-[(8-amino-1-{4-[(4-methyl-1H-1,3-benzodiazol-2-yl)methyl]naphthalen-1-yl}-3-(propan-2-yl)imidazo[1,5-a]pyrazin-5-yl)methyl]piperidin-4-amine;
Example 205: (3S)-1-[(8-amino-1-{4-[(4-methyl-1H-1,3-benzodiazol-2-yl)methyl]naphthalen-1-yl}-3-(propan-2-yl)imidazo[1,5-a]pyrazin-5-yl)methyl]piperidin-3-amine;
Example 206: 1-{4-[(1-methyl-1H-1,3-benzodiazol-2-yl)methyl]naphthalen-1-yl}-5-[4-(methylamino)cyclohex-1-en-1-yl]-3-(propan-2-yl)imidazo[1,5-a]pyrazin-8-amine;
Example 207: 4-(8-amino-1-{4-[(4-methyl-1H-1,3-benzodiazol-2-yl)methyl]naphthalen-1-yl}-3-(propan-2-yl)imidazo[1,5-a]pyrazin-5-yl)cyclohex-3-en-1-ol;
Example 208: 5-[4-(dimethylamino)cyclohex-1-en-1-yl]-1-{4-[(1-methyl-1H-1,3-benzodiazol-2-yl)methyl]naphthalen-1-yl}-3-(propan-2-yl)imidazo[1,5-a]pyrazin-8-amine;
Example 209: 5-{4-[(2,2-difluoroethyl)(methyl)amino]cyclohex-1-en-1-yl}-1-{4-[(4-methyl-1H-1,3-benzodiazol-2-yl)methyl]naphthalen-1-yl}-3-(propan-2-yl)imidazo[1,5-a]pyrazin-8-amine;
Example 210: 5-(4-aminocyclohex-1-en-1-yl)-1-{4-[(4-methyl-1H-1,3-benzodiazol-2-yl)methyl]naphthalen-1-yl}-3-(propan-2-yl)imidazo[1,5-a]pyrazin-8-amine;
Example 211: 5-{4-[methyl(2,2,2-trifluoroethyl)amino]cyclohex-1-en-1-yl}-1-{4-[(4-methyl-1H-1,3-benzodiazol-2-yl)methyl]naphthalen-1-yl}-3-(propan-2-yl)imidazo[1,5-a]pyrazin-8-amine;
Example 212: 5-{4-[(2,2-difluoroethyl)amino]cyclohex-1-en-1-yl}-1-{4-[(4-methyl-1H-1,3-benzodiazol-2-yl)methyl]naphthalen-1-yl}-3-(propan-2-yl)imidazo[1,5-a]pyrazin-8-amine;
Example 213: 5-{4-[(2-fluoroethyl)amino]cyclohex-1-en-1-yl}-1-{4-[(4-methyl-1H-1,3-benzodiazol-2-yl)methyl]naphthalen-1-yl}-3-(propan-2-yl)imidazo[1,5-a]pyrazin-8-amine;
Example 214: 1-{4-[(4-methyl-1H-1,3-benzodiazol-2-yl)methyl]naphthalen-1-yl}-3-(propan-2-yl)-5-{4-[(2,2,2-trifluoroethyl)amino]cyclohex-1-en-1-yl}imidazo[1,5-a]pyrazin-8-amine;
Example 215: 5-{4-[(2-fluoroethyl)(methyl)amino]cyclohex-1-en-1-yl}-1-{4-[(4-methyl-1H-1,3-benzodiazol-2-yl)methyl]naphthalen-1-yl}-3-(propan-2-yl)imidazo[1,5-a]pyrazin-8-amine;
Example 216: 5-{4-[methyl(3,3,3-trifluoropropyl)amino]cyclohex-1-en-1-yl}-1-{4-[(4-methyl-1H-1,3-benzodiazol-2-yl)methyl]naphthalen-1-yl}-3-(propan-2-yl)imidazo[1,5-a]pyrazin-8-amine;
Example 217: 3-((4-(8-amino-3-isopropyl-1-(4-((7-methyl-1H-benzo[d]imidazol-2-yl)methyl)naphthalen-1-yl)imidazo[1,5-a]pyrazin-5-yl)cyclohex-3-en-1-yl)amino)-N,N-dimethylpropanamide;
Example 218: N-(4-{8-amino-5-[4-(methylamino)cyclohex-1-en-1-yl]-3-(propan-2-yl)imidazo[1,5-a]pyrazin-1-yl}-2-fluorophenyl)-2-fluoro-5-methylbenzene-1-sulfonamide;
Example 219: N-(4-{8-amino-5-[4-(methylamino)cyclohex-1-en-1-yl]-3-(propan-2-yl)imidazo[1,5-a]pyrazin-1-yl}naphthalen-1-yl)-2-chloro-5-methylbenzene-1-sulfonamide;

Example 220: N-(4-(8-amino-5-(4-((2-fluoroethyl)amino)cyclohex-1-en-1-yl)-3-isopropylimidazo[1,5-a]pyrazin-1-yl)-2-fluorophenyl)-1-(2-chlorophenyl) methanesulfonamide;
Example 221: 1-(4-((1H-Benzo[d]imidazol-2-yl)methyl)naphthalen-1-yl)-8-chloro-3-(piperazin-1-ylmethyl)imidazo[1,5-a]pyrazine;
Example 222: 1-(4-((1H-benzo[d]imidazol-2-yl)methyl)naphthalen-1-yl)-8-chloro-3-((4-methylpiperazin-1-yl)methyl)imidazo[1,5-a]pyrazine;
Example 223: N-(4-(8-amino-5-(4-((2-fluoroethyl)amino)cyclohex-1-en-1-yl)-3-isopropylimidazo[1,5-a]pyrazin-1-yl)-2-fluorophenyl)-2-chlorobenzenesulfonamide;
Example 224: N-(4-(8-amino-5-(4-hydroxycyclohex-1-en-1-yl)-3-isopropylimidazo[1,5-a]pyrazin-1-yl)-2-fluorophenyl)-1-(2-chlorophenyl)methanesulfonamide;
Example 225: N-(4-(8-amino-5-(4-hydroxycyclohex-1-en-1-yl)-3-isopropylimidazo[1,5-a]pyrazin-1-yl)-2-fluorophenyl)-2-chlorobenzenesulfonamide;
Example 226: N-(4-(8-amino-5-(4-((2,2-difluoroethyl)amino)cyclohex-1-en-1-yl)-3-isopropylimidazo[1,5-a]pyrazin-1-yl)-2-fluorophenyl)-2-chlorobenzenesulfonamide;
Example 227: N-(4-(8-amino-3-isopropyl-5-(4-(oxetan-3-ylamino)cyclohex-1-en-1-yl)imidazo[1,5-a]pyrazin-1-yl)-2-fluorophenyl)-1-(2-chlorophenyl)methanesulfonamide;
Example 228: N-(4-(8-amino-5-(4-((2-fluoroethyl)amino)cyclohex-1-en-1-yl)-3-isopropylimidazo[1,5-a]pyrazin-1-yl)-2,5-difluorophenyl)-2-chlorobenzenesulfonamide;
Example 229: N-(4-(8-amino-5-(4-((2-fluoroethyl)amino)cyclohex-1-en-1-yl)-3-isopropylimidazo[1,5-a]pyrazin-1-yl)-2-fluorophenyl)-2-fluorobenzenesulfonamide;
Example 230: N-(4-(8-amino-5-(4-((2-fluoroethyl)(methyl)amino)cyclohex-1-en-1-yl)-3-isopropylimidazo[1,5-a]pyrazin-1-yl)-2-fluorophenyl)-2-chlorobenzenesulfonamide;
Example 231: N-(4-(8-amino-5-(4-((2-fluoroethyl)amino)cyclohex-1-en-1-yl)-3-methylimidazo[1,5-a]pyrazin-1-yl)-2-fluorophenyl)-2-chlorobenzenesulfonamide;
Example 232: N-(4-(8-amino-3-isopropyl-5-(4-(oxetan-3-ylamino)cyclohex-1-en-1-yl)imidazo[1,5-a]pyrazin-1-yl)-2-fluorophenyl)-2-chlorobenzenesulfonamide;

or a salt, solvate, enantiomer, diastereoisomer, isotopologue or tautomer thereof.

In certain embodiments, the compound is an inhibitor of IRE1. In other embodiments, the compound is an inhibitor of IRE1α. In yet other embodiments, the compound is an inhibitor of IRE1α kinase activity. In yet other embodiments, the compound is an inhibitor of IRE1a RNase activity. In yet other embodiments, the compound binds the ATP binding site of IRE1α. In yet other embodiments, the compound binds IRE1α in the DFG-out conformation. In yet other embodiments, the compound binds IRE1α in the DFG-in conformation. In yet other embodiments, the compound induces the DFG-out conformation of IRE1α. In yet other embodiments, the compound is an inhibitor of IRE1α oligomerization. In yet other embodiments, the compound is an inhibitor of IRE1α dimerization. In yet other embodiments, the compound is an inhibitor of IRE1α phosphorylation. In yet other embodiments, the compound is an inhibitor of IRE1α autophosphorylation. In yet other embodiments, the compound is an inhibitor of apoptosis. In yet other embodiments, the compound is an inhibitor of IRE1α induced apoptosis. In yet other embodiments, the compound is an inhibitor of cell death. In yet other embodiments, the compound is an inhibitor of IRE1α induced cell death. In yet other embodiments, the compound is an inhibitor of a pathway induced by IRE1α phosphorylation. In yet other embodiments, the compound is an inhibitor of a pathway induced by IRE1α kinase activity. In yet other embodiments, the compound is an inhibitor of a pathway induced by IRE1α RNase activity. In yet other embodiments, the compound is an inhibitor of neuronal cell death. In yet other embodiments, the compound is a cytotoxic agent. In yet other embodiments, the compound is an anticancer agent. In yet other embodiments, the compound is an inhibitor of demyelination. In yet other embodiments, the compound is an antidiabetic agent. In yet other embodiments, the compound is a neuroprotective agent. In yet other embodiments, the compound protects against loss of photoreceptor cells. In yet other embodiments, the compound is an inhibitor of fibrosis. In yet other embodiments, the compound decreases apoptosis in cells under ER stress. In yet other embodiments, the compound decreases apoptosis in cells under ER stress, but not cells that are under the same conditions but not under ER stress. In yet other embodiments, the compound decreases apoptosis in cells under ER stress more than in cells that are under the same conditions but not under ER stress. In yet other embodiments, the compound decreases cleavage of miR-17. In yet other embodiments, the compound decreases IRE1α associated cleavage of miR-17. In yet other embodiments, the compound decreases cleavage of miR-34a. In yet other embodiments, the compound decreases IRE1a associated cleavage of miR-34a. In yet other embodiments, the compound decreases cleavage of miR-96. In yet other embodiments, the compound decreases IRE1α associated cleavage of miR-96. In yet other embodiments, the compound decreases cleavage of miR-125b. In yet other embodiments, the compound decreases IRE1α associated cleavage of miR-125b. In yet other embodiments, the compound decreases XBP 1 mRNA splicing. In yet other embodiments, the compound decreases IRE1α associated XBP1 mRNA splicing. In yet other embodiments, the compound decreases UPR signaling. In yet other embodiments, the compound decreases IRE1α associated UPR signaling. In yet other embodiments, the compound decreases terminal UPR signaling. In other embodiments, the compound decreases IRE1α associated terminal UPR signaling.

The compounds described herein may form salts with acids and/or bases, and such salts are included in the present invention. In certain other embodiments, the salts are pharmaceutically acceptable salts. The term "salts" embraces addition salts of free acids and/or bases that are useful within the methods of the invention. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include sulfate, hydrogen sulfate, hemisulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric, galacturonic acid, glycerophosphonic acids and saccharin (e.g., saccharinate, saccharate).

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, ammonium, N,N'-dibenzylethylene-diamine, chloroprocaine, choline, diethanolamine, ethylenediamine, meglumine (N-methylglucamine) and procaine.

All of these salts may be prepared from the corresponding compound by reacting, for example, the appropriate acid or base with the compound. Salts may be comprised of a fraction of less than one, one, or more than one molar equivalent of acid or base with respect to any compound of the invention.

In certain other embodiments, the at least one compound of the invention is a component of a pharmaceutical composition further including at least one pharmaceutically acceptable carrier.

The compounds of the invention may possess one or more stereocenters, and each stereocenter may exist independently in either the (R) or (S) configuration. In certain other embodiments, compounds described herein are present in optically active or racemic forms. The compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In certain other embodiments, a mixture of one or more isomer is utilized as the therapeutic compound described herein. In other embodiments, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In certain other embodiments, the compounds described herein exist in solvated forms with pharmaceutically acceptable solvents such as water, and ethanol. In other embodiments, the compounds described herein exist in unsolvated form.

In certain other embodiments, the compounds of the invention exist as tautomers. All tautomers are included within the scope of the compounds recited herein.

In certain other embodiments, compounds described herein are prepared as prodrugs. A "prodrug" is an agent converted into the parent drug in vivo. In certain other embodiments, upon in vivo administration, a prodrug is chemically converted to the biologically, pharmaceutically or therapeutically active form of the compound. In other embodiments, a prodrug is enzymatically metabolized by one or more steps or processes to the biologically, pharmaceutically or therapeutically active form of the compound.

In certain other embodiments, sites on, for example, the aromatic ring portion of compounds of the invention are susceptible to various metabolic reactions. Incorporation of appropriate substituents on the aromatic ring structures may reduce, minimize or eliminate this metabolic pathway. In certain other embodiments, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In certain other embodiments, isotopically-labeled compounds are useful in drug and/or substrate tissue distribution studies. In other embodiments, substitution with heavier isotopes such as deuterium affords greater metabolic stability (for example, increased in vivo half-life or reduced dosage requirements). In yet other embodiments, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In certain other embodiments, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and in the art. General methods for the preparation of compound as described herein are modified by the use of appropriate reagents and conditions, for the introduction of the various moieties found in the formula as provided herein.

Methods

The invention includes methods of treating disorders associated with ER stress. In certain embodiments, the invention provides methods of treating a disease or disorder in a subject, the method comprising administering to the subject a therapeutically effective amount of one or more compounds of the invention, or pharmaceutically acceptable salts, solvates, enantiomers, diastereoisomers, or tautomers thereof. In other embodiments, the subject is in need of the treatment.

In certain embodiments, the disease or disorder is selected from the group consisting of a neurodegenerative disease, a demyelinating disease, cancer, an eye disease, a fibrotic disease, and diabetes.

In certain embodiments, the disease is a neurodegenerative disease selected from the group consisting of retinitis pigmentosa, amyotrophic lateral sclerosis, retinal degeneration, macular degeneration, Parkinson's Disease, Alzheimer's Disease, Huntington's Disease, Prion Disease, Creutzfeldt-Jakob Disease, and Kuru.

In certain embodiments, the disease is a demyelinating disease selected from the group consisting of Wolfram Syndrome, Pelizaeus-Merzbacher Disease, Transverse Myelitis, Charcot-Marie-Tooth Disease, and Multiple Sclerosis.

In certain embodiments, the disease is cancer. In other embodiments, the disease is multiple myeloma.

In certain embodiments, the disease is diabetes. In other embodiments, the disease is selected from the group consisting of type I diabetes and type II diabetes.

In certain embodiments, the disease is an eye disease selected from the group consisting of retinitis pigmentosa, retinal degeneration, macular degeneration, and Wolfram Syndrome.

In certain embodiments, the disease is a fibrotic disease selected from the group consisting of idiopathic pulmonary fibrosis (IPF), myocardial infarction, cardiac hypertrophy, heart failure, cirrhosis, acetominophen (Tylenol) liver toxicity, hepatitis C liver disease, hepatosteatosis (fatty liver disease), and hepatic fibrosis.

Without being limited to any single theory, the compounds of the invention treat the aforementioned diseases and disorders by modulating the activity of an IRE1 protein. In certain embodiments, the compounds inhibit the activity of an IRE1 protein.

In certain embodiments, the compounds of the invention modulate kinase activity of an IRE1 protein. In other embodiments, the compounds of the invention modulate autophosphorylation activity of an IRE1 protein. In yet other embodiments, the compounds of the invention modulate oligomerization activity of an IRE1 protein. In yet other embodiments, the compounds of the invention modulate dimerization activity of an IRE1 protein.

Administration/Dosage/Formulations

The regimen of administration may affect what constitutes an effective amount. The therapeutic formulations may be administered to the subject either prior to or after the onset of a disease or disorder contemplated in the invention. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a disease or disorder contemplated in the invention. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder contemplated in the invention. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. The pharmaceutical compositions useful for practicing the invention may be administered to deliver a dose of from 1 ng/kg/day and 100 mg/kg/day. One of ordinary skill in the art would be able to study the relevant factors and make the determination regarding the effective amount of the therapeutic compound without undue experimentation.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle.

In certain other embodiments, the compositions of the invention are formulated using one or more pharmaceutically acceptable excipients or carriers. In other embodiments, the pharmaceutical compositions of the invention comprise a therapeutically effective amount of a compound of the invention and a pharmaceutically acceptable carrier. In yet other embodiments, the compound of the invention is the only biologically active agent (i.e., capable of treating or preventing diseases and disorders related to IRE1) in the composition. In yet other embodiments, the compound of the invention is the only biologically active agent (i.e., capable of treating or preventing diseases and disorders related to IRE1) in therapeutically effective amounts in the composition.

In certain other embodiments, the compositions of the invention are administered to the patient in dosages that range from one to five times per day or more. In other embodiments, the compositions of the invention are administered to the patient in range of dosages that include, but are not limited to, once every day, every two days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration may be in the range of from about 1 µg to about 10,000 mg, about 20 g to about 9,500 mg, about 40 g to about 9,000 mg, about 75 g to about 8,500 mg, about 150 g to about 7,500 mg, about 200 g to about 7,000 mg, about 300 g to about 6,000 mg, about 500 g to about 5,000 mg, about 750 g to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain other embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder contemplated in the invention.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents.

Routes of administration of any of the compositions of the invention include intravitreal, oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravitreal, intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intravitreal, intraperitoneal, intramuscular, intrasternal injection, and kidney dialytic infusion techniques.

Intravitreal Administration

As used herein, "intravitreal administration" of a pharmaceutical composition includes administration into the vitreous fluid within the eye of a subject. Intravitreal administration includes, but is not limited to, administration of a pharmaceutical composition into the eye of a subject by injection of the composition. In some embodiments, the pharmaceutical composition can be administered through the use of a hypodermic needle or through a surgical incision. Preferably, administration takes place through the sclera of the eye, avoiding damage to the cornea or lens.

In certain embodiments, the pharmaceutical composition of the invention can be formulated for administration to the eye of the subject with sustained release over a period of 3-12 months.

Controlled Release Formulations and Drug Delivery Systems

In certain other embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form. In certain embodiments, the compounds of the invention can be formulated for sustained release over a period of 3-12 months.

For sustained release, the compounds may be formulated with a suitable polymer or hydrophobic material that provides sustained release properties to the compounds. As such, the compounds useful within the methods of the invention may be administered in the form of microparticles, for example by injection, or in the form of wafers or discs by implantation.

In one embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, about 10 minutes, or about 1 minute and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, about 10 minutes, or about 1 minute and any and all whole or partial increments thereof after drug administration.

Dosing

The therapeutically effective amount or dose of a compound of the present invention depends on the age, sex and weight of the patient, the current medical condition of the patient and the progression of a disease or disorder contemplated in the invention. The skilled artisan is able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 5 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the disease or disorder, to a level at which the improved disease is retained. In certain other embodiments, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 5 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods

General Experimental Details

Reactions were not carried out under an inert atmosphere unless specified, and all solvents and commercial reagents were used as received.

Purification by chromatography refers to purification using the COMBIFLASH® Companion purification system or the Biotage SP1 purification system. Where products were purified using an Isolute® SPE Si II cartridge, 'Isolute SPE Si cartridge' refers to a pre-packed polypropylene column containing unbonded activated silica with irregular particles with average size of 50 µm and nominal 60 Å porosity. Fractions containing the required product (identified by TLC and/or LCMS analysis) were pooled, the organic fraction removed by evaporation, and the remaining aqueous fraction lyophilised, to give the final product. Where thin layer chromatography (TLC) has been used, it refers to silica-gel TLC using plates, typically 3×6 cm silica-gel on aluminium foil plates with a fluorescent indicator (254 nm), (e.g. Fluka 60778). Microwave experiments were carried out using a Biotage Initiator 60™ which uses a single-mode resonator and dynamic field tuning. Temperature from 40-250° C. can be achieved, and pressures of up to 30 bar can be reached.

NMR spectra were obtained on a Bruker Avance 400 MHz, 5 mm QNP probe H, C, F, P, single Z gradient, two channel instrument running TopSpin 2.1 or on a Bruker Avance III 400 MHz, 5 mm BBFO Plus probe, single Z gradient, two channel instrument running TopSpin 3.0.

Compound names were standardly generated using the Struct>Name function in ChemDraw Professional 15.1.

Analytical LC-MS Conditions

LC-MS Method 1: Acquity H-Class (quaternary pump/PDA detector)+QDa Mass Spectrometer. Column: Acquity UPLC BEH C18 (1.7 µm, 100×2.1 mm), maintained at 50° C. Conditions: 0.1% aqueous formic acid [eluent A]; MeCN (containing 0.1% formic acid) [eluent B]. Gradient: 3 to 99% B over 1.5 min at 1 m/min QC LC-MS Conditions Any of following methods for LC-MS analysis were typically employed.

QC LC-MS Method 1: Waters SQD2, single quadrapole UPLC-MS. Column: Acquity UPLC HSS C18 (1.8 µm, 100×2.1 mm). Conditions: 0.1% aqueous formic acid [eluent A]; MeCN (containing 0.1% formic acid) [eluent B]. Gradient: 5 to 100% B over 4.9 min at 0.5 mL/min.

QC LC-MS Method 2: Waters SQD2, single quadrapole UPLC-MS. Column: Acquity UPLC BEH Shield RP18 (1.7 µm, 100×2.1 mm). Conditions: 10 mM aqueous ammonium bicarbonate [eluent A]; MeCN [eluent B]. Gradient: 5 to 100% B over 4.9 min at 0.5 mL/min.

QC LC-MS Method 3: Acquity UPLC (binary pump/PDA detector)+Waters Micromass ZQ2000 Mass Spectrometer. Column: Acquity UPLC BEH C18 (1.7 µm, 100×2.1 mm), maintained at 40° C. Conditions: 0.1% aqueous formic acid [eluent A]; MeCN (containing 0.1% formic acid) [eluent B]. Gradient: 5 to 95% B over 6.8 min at 0.4 m/min.

QC LC-MS Method 4: UPLC+Waters DAD+Waters SQD2, single quadrapole UPLC-MS. Column: Acquity UPLC HSS C18 (1.8 µm 100×2.1 mm), maintained at 40° C. Conditions: 0.1% aqueous formic acid [eluent A]; MeCN (containing 0.1% formic acid) [eluent B]. Gradient: 5 to 100% B over 3.5 min at 0.5 mL/min.

QC LC-MS Method 5: UPLC+Waters DAD+Waters SQD2, single quadrapole UPLC-MS. Column: Acquity UPLC BEH Shield RP18 (1.7 µm 100×2.1 mm), maintained at 40° C. Conditions: 10 mM aqueous ammonium bicarbonate [eluent A]; MeCN [eluent B]. Gradient: isocratic at 5% B for 1.2 min then 5 to 100% B over 2.3 min at 0.5 mL/min.

SFC Methods

Preparative SFC: Waters Thar Prep100 preparative SFC system (P200 $CO_2$ pump, 2545 modifier pump, 2998 UV/VIS detector, 2767 liquid handler with Stacked Injection Module). Column: Phenomenex Lux Cellulose-4 or YMC Cellulose-SC (5 µm, 10-21.2×250 mm), maintained at 40° C. Conditions: supercritical fluid $CO_2$ and eluents chosen from MeOH, EtOH, IPA, MeCN, EtOAc, THF with modifiers chosen from $Et_2NH$ or formic acid as specified. Gradient/isocratic as specified at 100 mL/min, 120 bar (or as appropriate).

Analytical SFC was carried out on a similar system using smaller columns and lower flow rates.

Compound Preparation

The compounds of this invention may be made by a variety of methods, including well-known standard synthetic methods. Illustrative general synthetic methods are set out below and then specific compounds of the invention are prepared in the working examples. The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. In all of the schemes described below, protecting groups for sensitive or reactive groups are employed where necessary in accordance with general principles of synthetic chemistry. Protecting groups are manipulated according to standard methods of organic synthesis (T. W. Green and P. G. M. Wuts, (1991) Protecting Groups in Organic Synthesis, John Wiley & Sons, incorporated by reference with regard to protecting groups).

In the procedures that follow, some of the starting materials are identified through a "Step" or "Example" number. This is provided merely for assistance to the skilled chemist. The starting material may not necessarily have been prepared from the batch referred to.

When reference is made to the use of a "similar" or "analogous" procedure, as will be appreciated by those skilled in the art, such a procedure may involve minor variations, for example reaction temperature, reagent/solvent amount, reaction time, work-up conditions or chromatographic purification conditions.

The synthesis of the compounds of the general formula (Ia), (Ib), (Ic) and pharmaceutically acceptable derivatives and salts thereof may be accomplished as outlined below in Schemes 1-8 by those skilled in the art. Starting materials are commercially available or are made from commercially available starting materials using methods known to those skilled in the art.

Examples 1-10 can be made following the general procedure outlined in Scheme 1. Treatment of 8-chloro-3-methyl-imidazo[1,5-a]pyrazine 1A with n-butyllithium affords selective lithiation at C-5. Quenching with carbon dioxide yields the carboxylic acid 1B and amide formation under standard conditions provides an amide such as 1C, which is brominated and then treated with ammonium hydroxide to give 1 D. Palladium-catalyzed coupling with an aryl boronic acid followed by deprotection yields the final product 1E.

Scheme 1

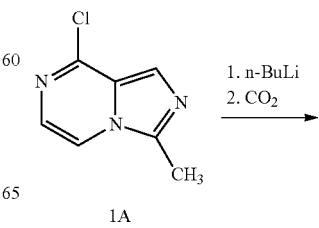

1A

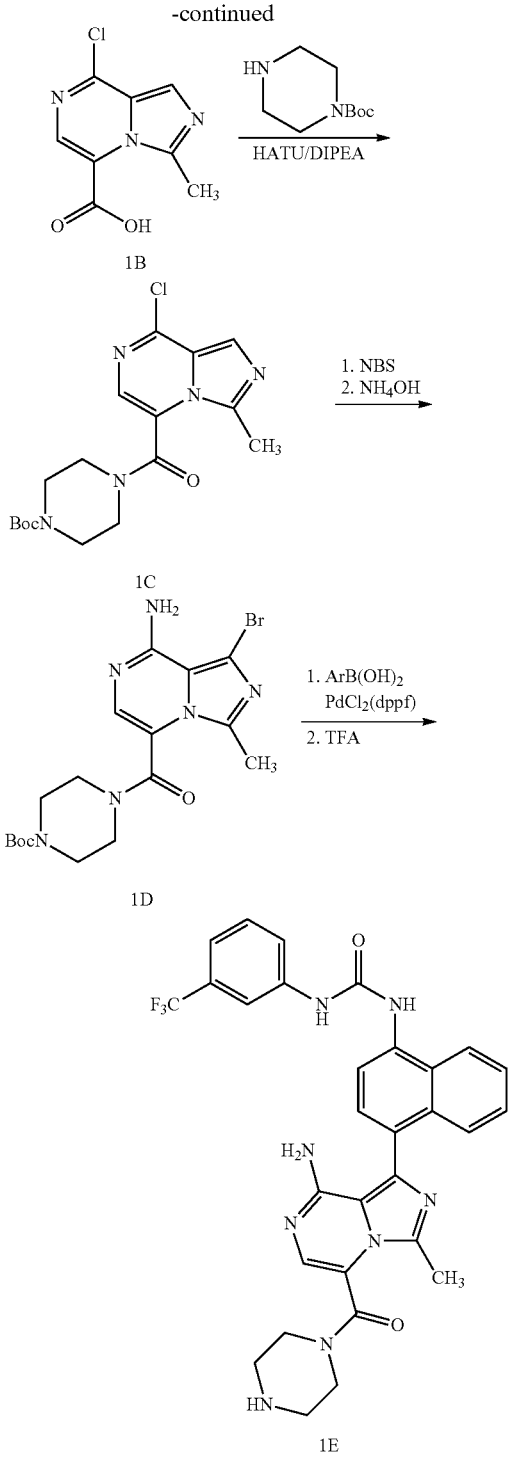

Example 1. 3-{4-[8-amino-3-methyl-5-(piperazine-1-carbonyl)imidazo[1,5-a]pyrazin-1-yl]naphthalen-1-yl}-1-[3-(trifluoromethyl)phenyl]urea 1E Step 1: A solution of n-BuLi (1.2 eq.) was added dropwise to a stirred slurry of 8-chloro-3-methyl-imidazo[1,5-a]pyrazine (6.0 g, 35.8 mmol) at −78° C. in THF (to give 0.2 M solution) and the reaction mixture was stirred for 10 min. $CO_2$ was bubbled into the reaction mixture under stirring for 30 min. After removal of the solvent, the desired compound was purified using flash column chromatography to yield 5.3 g (70%) of 8-chloro-3-methylimidazo[1,5-a]pyrazine-5-carboxylic acid 1B.

Step 2: 8-Chloro-3-methylimidazo[1,5-a]pyrazine-5-carboxylic acid 1B (200 mg, 0.945 mmol) was dissolved in DMF, HATU (1.2 eq.) was added and stirred for 0.5 h, followed by DIPEA (2.0 eq.) and then 1-Boc-piperazine. After extractive workup, the desired compound was purified through flash column chromatography to provide 73 mg (20%) of 8-chloro-3-methylimidazo[1,5-a]pyrazine-5-(N-Boc-piperazine)-1-carboxamide 1C.

Step 3: 8-chloro-3-methylimidazo[1,5-a]pyrazine-5-(N-Boc-piperazine)-1-carboxamide 1C (1.7 g, 4.48 mmol) was dissolved in DMF, and NBS (1.1 eq.) was added into the solution. The reaction mixture was stirred at RT for 2 h. The desired compound was purified through flash column chromatography to give 1.2 g. 900 mg was dissolved in 1,4-dioxane, and ammonium hydroxide was added into the solution. The reaction mixture was irradiated by microwave at 100° C. for 2 h. After removal of solvent and purification via column chromatography, 500 mg (34%) of 8-amino-1-bromo-3-methylimidazo[1,5-a]pyrazine-5-(N-Boc-piperazine)-1-carboxamide 1 D was isolated.

Step 4: 8-amino-1-bromo-3-methylimidazo[1,5-a]pyrazine-5-(N-Boc-piperazine)-1-carboxamide 1 D (500 mg, 1.14 mmol), 1-(4-(4,4,5,5-tetramethyl-1,3,2-dioxaborolan-2-yl)naphthalene-1-yl)-3-(3-(trifluoromethyl)phenyl)urea (1.5 eq.) and $Cs_2CO_3$ (3 eq.) were suspended in DME (12 mL) and $H_2O$ (3 mL). $Pd(PPh_3)_4$ (0.05 eq.) was added. The mixture was heated under reflux for 2 h under $N_2$. After cooled, the mixture was filtered, and the filtrate was concentrated to dryness. The residue was purified by flash column chromatography on silica gel to afford 3-{4-[8-amino-3-methyl-5-(N-Boc-piperazine-1-carbonyl)imidazo[1,5-a]pyrazin-1-yl]naphthalen-1-yl}-1-[3-(trifluoromethyl)phenyl]urea (300 mg) as solid, which was dissolved in DCM and TFA, and the mixture was stirred for 3 h. The solvent was removed and the residue was neutralized with saturated $NaHCO_3$. The desired compound was purified through C-18 column chromatography to provide 91 mg of final product 3-{4-[8-amino-3-methyl-5-(piperazine-1-carbonyl)imidazo[1,5-a]pyrazin-1-yl]naphthalen-1-yl}-1-[3-(trifluoromethyl)phenyl]urea 1E, ES-LCMS m/z 589.4 (M+H). The following examples were made using similar procedures substituting the requisite protected amine intermediate in step 2.

Example 2. 3-{4-[8-amino-5-(4-aminopiperidine-1-carbonyl)-3-methylimidazo[1,5-a]pyrazin-1-yl]naphthalen-1-yl}-1-[3-(trifluoromethyl)phenyl]urea; ES-LCMS m/z 602.4 (M+H).

Example 3. 8-amino-3-methyl-N-(piperidin-4-yl)-1-[4-({[3-(trifluoromethyl)phenyl]carbamoyl}amino)naphthalen-1-yl]imidazo[1,5-a]pyrazine-5-carboxamide; ES-LCMS m/z 603.6 (M+H).

Example 4. 3-(4-{8-amino-5-[(3R)-3-aminopiperidine-1-carbonyl]-3-methylimidazo[1,5-a]pyrazin-1-yl}naphthalen-1-yl)-1-[3-(trifluoromethyl)phenyl]urea; ES-LCMS m/z 603.3 (M+H).

Example 5. 3-(4-{8-amino-5-[(3S)-3-aminopiperidine-1-carbonyl]-3-methylimidazo[1,5-a]pyrazin-1-yl}naphthalen-1-yl)-1-[3-(trifluoromethyl)phenyl]urea; ES-LCMS m/z 603.5 (M+H).

Example 6. 8-amino-3-methyl-N-[(3R)-piperidin-3-yl]-1-[4-({[3-(trifluoromethyl)phenyl]carbamoyl}amino)naphthalen-1-yl]imidazo[1,5-a]pyrazine-5-carboxamide; ES-LCMS m/z 603.5 (M+H).

Example 7. 8-amino-3-methyl-N-(piperidin-3-yl)-1-[4-({[3-(trifluoromethyl)phenyl]carbamoyl}amino)naphthalen-1-yl]imidazo[1,5-a]pyrazine-5-carboxamide; ES-LCMS m/z 603.8 (M+H).

Example 8. 8-amino-3-methyl-N-[(3S)-1-methylpiperidin-3-yl]-1-[4-({[3-(trifluoromethyl)phenyl]carbamoyl}amino)naphthalen-1-yl]imidazo[1,5-a]pyrazine-5-carboxamide; ES-LCMS m/z 617.6 (M+H).

Example 9. 8-amino-3-methyl-N-[(3R)-1-methylpiperidin-3-yl]-1-[4-({[3-(trifluoromethyl)phenyl]carbamoyl}amino)naphthalen-1-yl]imidazo[1,5-a]pyrazine-5-carboxamide; ES-LCMS m/z 617.6 (M+H).

Example 10. 3-{4-[8-amino-3-methyl-5-(4-methylpiperazine-1-carbonyl)imidazo[1,5-a]pyrazin-1-yl]naphthalen-1-yl}-1-[3-(trifluoromethyl)phenyl]urea; ES-LCMS m/z 602.7 (M+H).

In another embodiment, alkyl analogs such as 2E can be made as outlined in Scheme 2. Quenching of lithiated 8-chloro-3-methylimidazo[1,5-a]pyrazine with an aldehyde gives alcohol 2B. Treatment with mesyl chloride followed by sodium borohydride provides the reduced compound 2C which is carried through the bromination, ammoniolysis and Pd(0)-catalyzed coupling reactions as before to yield final product 2E.

Scheme 2

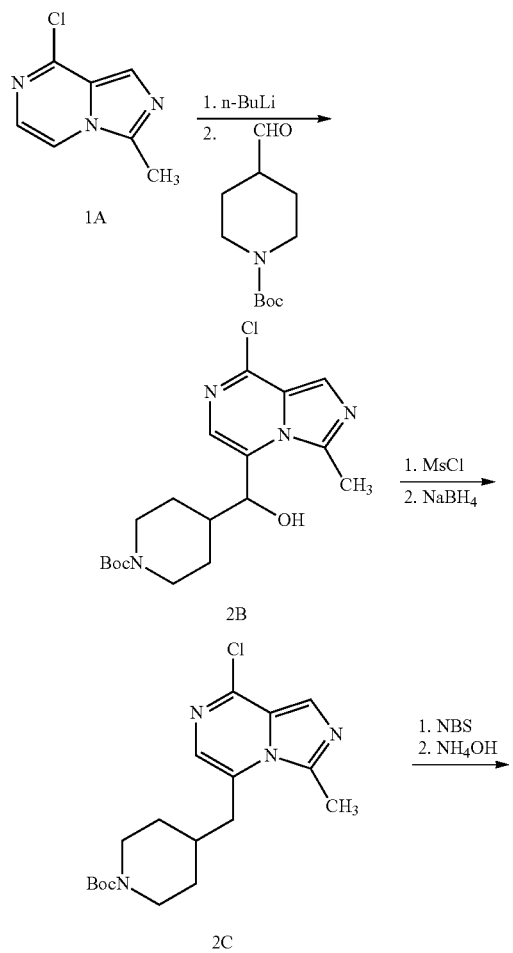

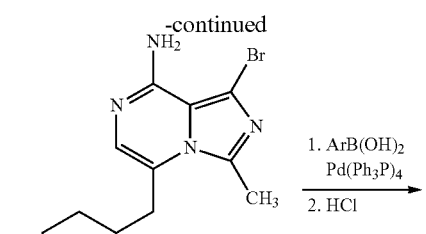

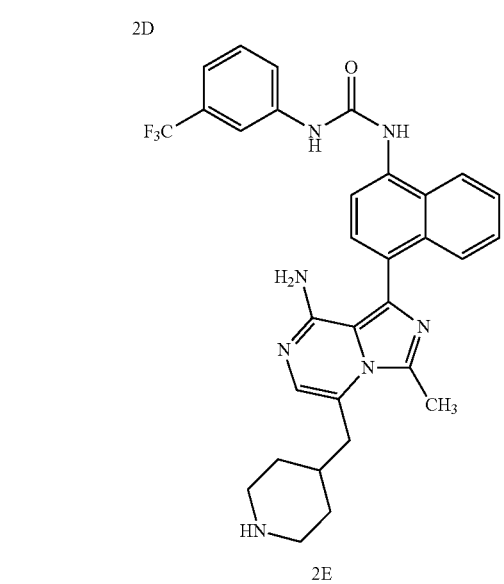

Example 11. 3-{4-[8-amino-3-methyl-5-(piperidin-4-ylmethyl)imidazo[1,5-a]pyrazin-1-yl]naphthalen-1-yl}-1-[3-(trifluoromethyl)phenyl]urea 2E Step 1: A solution of n-BuLi (1.2 eq.) was added dropwise to a stirred slurry of 8-chloro-3-methylimidazo[1,5-a]pyrazine (2.0 g, 11.9 mmol) at −78° C. in THF (to give 0.2 M solution) and the reaction mixture was stirred for 10 min. 1-N-Boc-4-Formylpiperidine (1.3 eq.) was added dropwise and the reaction mixture was stirred for a further 15 min, quenched with NH$_4$Cl (5 mL, sat. aq.) and removed from cooling to warm to room temperature over 15-20 min. Purification using flash column chromatography yielded 3.8 g (83%) of 8-chloro-3-methylimidazo[1,5-a]pyrazine-5-(N-Boc-piperidin-4-ylmethyl)-methanol 2B.

Step 2: 8-chloro-3-methylimidazo[1,5-a]pyrazine-5-(N-Boc-piperidin-4-ylmethyl)-methanol 2B (1.0 g, 2.62 mmol) and TEA (1.3 eq.) were dissolved in DCM. MsCl (1.2 eq.) was added into the solution. The mixture was stirred at RT for 2 h. 8-chloro-3-methylimidazo[1,5-a]pyrazine-5-(N-Boc-piperidin-4-ylmethyl)-methanol mesylate (0.9 g, 75%) was obtained through flash column chromatography.

Step 3: 8-chloro-3-methylimidazo[1,5-a]pyrazine-5-(N-Boc-piperidin-4-ylmethyl)-methanol mesylate (20 mg, 0.044 mmol) was dissolved in DMF, NaBH$_4$ (1.5 eq.) was added to the solution. The mixture was heated to 50° C. overnight. 8-chloro-3-methylimidazo[1,5-a]pyrazine-5-(N-Boc-piperidin-4-ylmethyl) 2C (31%) was observed through LC-MS.

Step 4: 8-chloro-3-methylimidazo[1,5-a]pyrazine-5-(N-Boc-piperidin-4-ylmethyl) 2C (50 mg, 0.137 mmol) was dissolved in DMF (5 mL) and NBS (1.5 eq.) in DMF was added into the solution. The mixture was stirred at RT for 1 h. The desired compound 8-chloro-1-bromo-3-methylimidazo[1,5-a]pyrazine-5-(N-Boc-piperidin-4-ylmethyl) was purified through column chromatography.

Step 5: 8-chloro-1-bromo-3-methylimidazo[1,5-a]pyrazine-5-(N-Boc-piperidin-4-ylmethyl) was dissolved in 1,4-dioxane, ammonium hydroxide was added into the solution. The reaction mixture was irradiated by microwave at 100° C. for 2 h and 8-amino-1-bromo-3-methylimidazo[1,5-a]pyrazine-5-(N-Boc-piperidin-4-ylmethyl) 2D was isolated by column chromatography (35 mg, 60% for the two steps).

Step 6: 8-amino-1-bromo-3-methylimidazo[1,5-a]pyrazine-5-(N-Boc-piperidin-4-ylmethyl) (120 mg, 0.28 mmol) 2D 1-(4-(4,4,5,5-tetramethyl-1,3,2-dioxaborolan-2-yl)naphthalene-1-yl)-3-(3-(trifluoromethyl)phenyl)urea (1.5 eq), and $Cs_2CO_3$ (3 eq) were suspended in DME (12 mL) and $H_2O$ (3 mL). $Pd(PPh_3)_4$ (0.05 eq) was added. The mixture was heated to 90° C. for 2 h in a microwave. 3-{4-[8-amino-3-methyl-5-(N-Boc-piperidin-4-ylmethyl)imidazo[1,5-a]pyrazin-1-yl]naphthalen-1-yl}-1-[3-(trifluoromethyl)phenyl]urea was obtained (100 mg, 54%) through column chromatography.

Step 7: 3-{4-[8-amino-3-methyl-5-(N-Boc-piperidin-4-ylmethyl)imidazo[1,5-a]pyrazin-1-yl]naphthalen-1-yl}-1-[3-(trifluoromethyl)phenyl]urea (100 mg, 0.15 mmol) was dissolved in dioxane, HCl (37%) was dropped into the solution, the mixture was stirred for 3 h. After removal of solvents, the desired compound was purified through C-18 column chromatography and 3-{4-[8-amino-3-methyl-5-(piperidin-4-ylmethyl)imidazo[1,5-a]pyrazin-1-yl]naphthalen-1-yl}-1-[3-(trifluoromethyl)phenyl]urea hydrochloride 2E was isolated (25 mg, 29% yield). $^1$H NMR (400 MHz, $CD_3OD$) δ 8.26 (d, 1H), 8.04 (d, 2H), 7.79 (d, 1H), 7.71-7.51 (m, 5H), 7.36 (d, 1H), 6.81 (s, 1H), 3.50 (d, 2H), 3.09-3.02 (m, 4H), 3.02 (s, 3H), 2.14 (m, 3H), 1.60 (m, 2H); ES-LCMS m/z 573.4 (M+H).

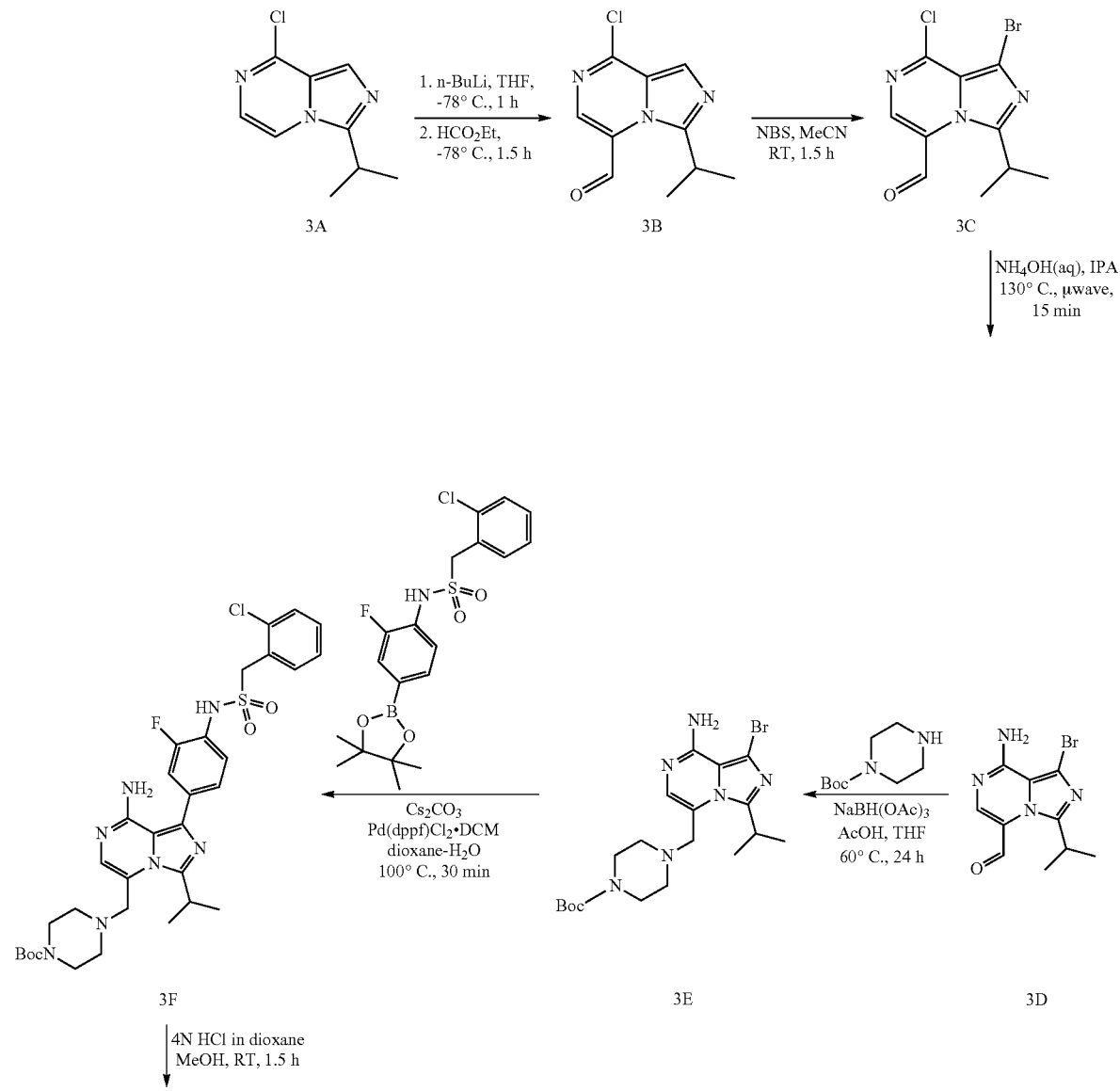

Scheme 3

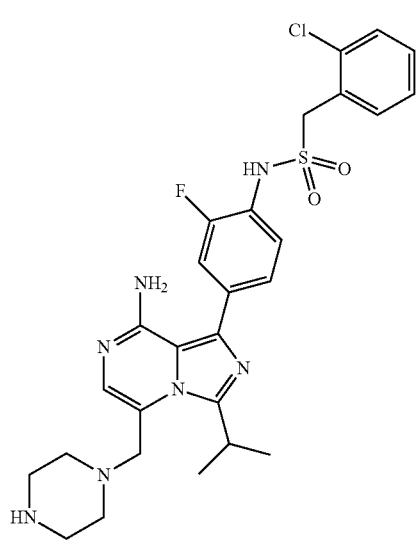

3G

Compounds exemplifying another aspect of this invention can be made according to the chemistry outlined in Scheme 3. Treatment of 8-chloro-3-isopropylimidazo[1,5-a]pyrazine 3A with n-butyllithium followed by ethyl formate gives aldehyde 3B. Bromination and reaction with ammonium hydroxide affords 3D which can be reductively aminated to provide an amine derivative such as 3E. Pd(0)-catalyzed coupling and deprotection provides the final product 3G.

Example 36: N-(4-(8-amino-3-isopropyl-5-(piperazin-1-ylmethyl)imidazo[1,5-a]pyrazin-1-yl)-2-fluorophenyl)-1-(2-chlorophenyl)methanesulfonamide 3G Step 1: 8-Chloro-3-isopropylimidazo[1,5-a]pyrazine-5-carbaldehyde 3B To a solution of 8-chloro-3-isopropylimidazo[1,5-a]pyrazine 3A (1.00 g, 5.11 mmol) in THF at −65° C. was added dropwise a solution of n-butyllithium (2.5 M solution in THF, 2.9 mL, 7.16 mmol), keeping the temperature below −55° C. The resulting dark brown solution was stirred at −78° C. for 1 h then ethyl formate (0.62 mL, 7.67 mmol) was added dropwise and the mixture was stirred at −78° C. for 1.5 h. The mixture was diluted with water and extracted with EtOAc. The combined organic extracts were dried (MgSO$_4$), filtered and concentrated in vacuo. The residue was purified by silica-gel chromatography, eluting with 0-50% EtOAc in isohexane to give the title compound 3B as a yellow oil that crystallised on standing (900 mg, 79%). LC-MS (Method 1): Rt=1.06 min, m/z=224.1 [M($^{35}$Cl)+H]$^+$.

Step 2: 1-Bromo-8-chloro-3-isopropylimidazo[1,5-a]pyrazine-5-carbaldehyde 3C

To a solution of 8-chloro-3-isopropylimidazo[1,5-a]pyrazine-5-carbaldehyde 3B (900 mg, 4.02 mmol) in MeCN (20 mL) was added NBS (788 mg, 4.43 mmol) and the mixture was stirred at RT for 1.5 h. The mixture was diluted with water and extracted with EtOAc. The combined organic extracts were washed with brine, dried (MgSO$_4$), filtered, and concentrated in vacuo to give the title compound 3C as a yellow solid (1.23 g, 100%). LC-MS (Method 1): Rt=1.29 min, m/z=302.0 [M($^{35}$Cl$^{79}$Br)+H]$^+$.

Step 3: 8-Amino-1-bromo-3-isopropylimidazo[1,5-a]pyrazine-5-carbaldehyde 3D

A solution of 1-bromo-8-chloro-3-isopropylimidazo[1,5-a]pyrazine-5-carbaldehyde 3C (1.23 g, 4.07 mmol) in IPA (3 mL) and aqueous ammonium hydroxide solution (33%, 3 mL) was heated in a microwave at 130° C. for 15 min. The mixture was diluted with water and extracted with EtOAc. The combined organic extracts were washed with brine, dried (MgSO$_4$), filtered and concentrated in vacuo. The residue was purified by silica-gel chromatography, eluting with 0-100% EtOAc in isohexane to give the title compound 3D (535 mg, 47%). LC-MS (Method 1): Rt=0.95 min, m/z=283.1 [M($^{79}$Br)+H]$^+$.

Step 4: tert-Butyl 4-((8-amino-1-bromo-3-isopropylimidazo[1,5-a]pyrazin-5-yl)methyl) piperazine-1-carboxylate 3E A solution of 8-amino-1-bromo-3-isopropylimidazo[1,5-a]pyrazine-5-carbaldehyde 3D (468 mg, 1.65 mmol), 1-N-

Boc-piperazine (770 mg, 4.13 mmol) and acetic acid (0.19 mL, 3.31 mmol) in THF (10 mL) was stirred at 60° C. for 10 min. Sodium triacetoxyborohydride (1.051 g, 4.96 mmol) was then added and the mixture was stirred at 60° C. for 24 h. The reaction was purified by silica-gel chromatography, eluting with 0-100% EtOAc in isohexane, then re-purified by silica-gel chromatography, eluting with 0-4% MeOH in DCM, to give the title compound 3E (206 mg, 28%). LC-MS (Method 1): Rt=1.01 min, m/z=453.3 [M($^{79}$Br)+H]$^+$.

Step 5: tert-butyl 4-((8-amino-1-(4-(((2-chlorophenyl)methyl)sulfonamido)-3-fluorophenyl)-3-isopropylimidazo[1,5-a]pyrazin-5-yl)methyl)piperazine-1-carboxylate 3F The title compound 3F was prepared using a similar method to that described for Example 169, step 3 using tert-butyl 4-((8-amino-1-bromo-3-isopropylimidazo[1,5-a]pyrazin-5-yl)methyl)piperazine-1-carboxylate 3E (100 mg, 0.221 mmol) to give the product 3F (124 mg, 84%). LC-MS (Method 1): Rt=1.17 min, m/z=672.5 [M($^{35}$Cl)+H]$^+$.

Step 6: N-(4-(8-amino-3-isopropyl-5-(piperazin-1-ylmethyl)imidazo[1,5-a]pyrazin-1-yl)-2-fluorophenyl)-1-(2-chlorophenyl)methanesulfonamide 3G A solution of tert-butyl 4-((8-amino-1-(4-(((2-chlorophenyl)methyl)sulfonamido)-3-fluorophenyl)-3-isopropylimidazo[1,5-a]pyrazin-5-yl)methyl)piperazine-1-carboxylate 3F (124 mg, 0.184 mmol) in methanol (3 mL) and 4 N HCl in 1,4-dioxane (1 mL, 4.0 mmol) was stirred at RT for 1.5 h. The solvents were concentrated in vacuo and the residue was dissolved in methanol and passed down an SCX-2 cartridge, eluting with 2 N NH$_3$ in MeOH. The residue was purified by MDAP (Method B) and the product was again passed down an SCX-2 cartridge, eluting with 2 N NH$_3$ in MeOH, to provide the title compound 3F (45 mg, 43%). QC LC-MS (Method 3): Rt=2.50 min, m/z=572.3 [M($^{35}$Cl)+H]$^+$.

The following examples were prepared using an analogous method to Example 36:

Example 12: 3-{4-[8-amino-3-methyl-5-(piperazin-1-ylmethyl)imidazo[1,5-a]pyrazin-1-yl]naphthalen-1-yl}-1-[3-(trifluoromethyl)phenyl]urea Example 13: 3-(4-{8-amino-5-[(4-aminopiperidin-1-yl)methyl]-3-methylimidazo[1,5-a]pyrazin-1-yl}naphthalen-1-yl)-1-[3-(trifluoromethyl)phenyl]urea Example 14: 3-[4-(8-amino-3-methyl-5-{[(piperidin-4-yl)amino]methyl}imidazo[1,5-a]pyrazin-1-yl)naphthalen-1-yl]-1-[3-(trifluoromethyl)phenyl]urea Example 15: 3-[4-(8-amino-5-{[(3R)-3-aminopiperidin-1-yl]methyl}-3-methylimidazo[1,5-a]pyrazin-1-yl)naphthalen-1-yl]-1-[3-(trifluoromethyl)phenyl]urea Example 16: 3-[4-(8-amino-5-{[(3S)-3-aminopiperidin-1-yl]methyl}-3-methylimidazo[1,5-a]pyrazin-1-yl)naphthalen-1-yl]-1-[3-(trifluoromethyl)phenyl]urea Example 17: 3-[4-(8-amino-3-methyl-5-{[(piperidin-3-yl)amino]methyl}imidazo[1,5-a]pyrazin-1-yl)naphthalen-1-yl]-1-[3-(trifluoromethyl)phenyl]urea Example 18: 3-{4-[8-amino-3-methyl-5-({[(3S)-piperidin-3-yl]amino}methyl)imidazo[1,5-a]pyrazin-1-yl]naphthalen-1-yl}-1-[3-(trifluoromethyl)phenyl]urea Example 19: 3-(4-{8-amino-3-methyl-5-[(4-methylpiperazin-1-yl)methyl]imidazo[1,5-a]pyrazin-1-yl}naphthalen-1-yl)-1-[3-(trifluoromethyl)phenyl]urea Example 20: 3-{4-[8-amino-3-ethyl-5-(piperazin-1-ylmethyl)imidazo[1,5-a]pyrazin-1-yl]naphthalen-1-yl}-1-[3-(trifluoromethyl)phenyl]urea Example 21: 3-{4-[8-amino-5-(piperazin-1-ylmethyl)-3-(propan-2-yl)imidazo[1,5-a]pyrazin-1-yl]naphthalen-1-yl}-1-[3-(trifluoromethyl)phenyl]urea Example 22: 3-(4-{8-amino-3-ethyl-5-[(4-methylpiperazin-1-yl)methyl]imidazo[1,5-a]pyrazin-1-yl}naphthalen-1-yl)-1-[3-(trifluoromethyl)phenyl]urea Example 23: 3-[4-(8-amino-3-methyl-5-{[4-(methylamino)piperidin-1-yl]methyl}imidazo[1,5-a]pyrazin-1-yl)naphthalen-1-yl]-1-[3-(trifluoromethyl)phenyl]urea Example 24: 3-[4-(8-amino-3-methyl-5-{[(3R)-3-methylpiperazin-1-yl]methyl}imidazo[1,5-a]pyrazin-1-yl)naphthalen-1-yl]-1-[3-(trifluoromethyl)phenyl]urea Example 25: 3-[4-(8-amino-3-methyl-5-{[(3S)-3-methylpiperazin-1-yl]methyl}imidazo[1,5-a]pyrazin-1-yl)naphthalen-1-yl]-1-[3-(trifluoromethyl)phenyl]urea Example 26: 3-[4-(8-amino-5-{[(3R,5S)-3,5-dimethylpiperazin-1-yl]methyl}-3-methylimidazo[1,5-a]pyrazin-1-yl)naphthalen-1-yl]-1-[3-(trifluoromethyl)phenyl]urea Example 27: 3-[4-(8-amino-3-ethyl-5-{[(3R)-3-methylpiperazin-1-yl]methyl}imidazo[1,5-a]pyrazin-1-yl)naphthalen-1-yl]-1-[3-(trifluoromethyl)phenyl]urea Example 28: 3-[4-(8-amino-3-ethyl-5-{[(3S)-3-methylpiperazin-1-yl]methyl}imidazo[1,5-a]pyrazin-1-yl)naphthalen-1-yl]-1-[3-(trifluoromethyl)phenyl]urea Example 29: 3-{4-[8-amino-5-(1,4-diazepan-1-ylmethyl)-3-methylimidazo[1,5-a]pyrazin-1-yl]naphthalen-1-yl}-1-[3-(trifluoromethyl)phenyl]urea Example 30: 3-[4-(8-amino-5-{2,5-diazabicyclo[2.2.1]heptan-2-ylmethyl}-3-methylimidazo[1,5-a]pyrazin-1-yl)naphthalen-1-yl]-1-[3-(trifluoromethyl)phenyl]urea Example 31: 3-[4-(8-amino-3-methyl-5-{octahydropyrrolo[3,4-c]pyrrol-2-ylmethyl}imidazo[1,5-a]pyrazin-1-yl)naphthalen-1-yl]-1-[3-(trifluoromethyl)phenyl]urea Example 32: 3-{4-[8-amino-3-methyl-5-(piperazin-1-ylmethyl)imidazo[1,5-a]pyrazin-1-yl]naphthalen-1-yl}-1-(3-fluorophenyl)urea Example 33: 3-{4-[8-amino-3-methyl-5-(piperazin-1-ylmethyl)imidazo[1,5-a]pyrazin-1-yl]naphthalen-1-yl}-1-(3-methylphenyl)urea Example 34: 3-{4-[8-amino-3-methyl-5-(piperazin-1-ylmethyl)imidazo[1,5-a]pyrazin-1-yl]-3-fluorophenyl}-1-[3-(trifluoromethyl)phenyl]urea Example 35: 3-{4-[8-amino-3-ethyl-5-(piperazin-1-ylmethyl)imidazo[1,5-a]pyrazin-1-yl]-3-fluorophenyl}-1-[3-(trifluoromethyl)phenyl]urea Example 37: 3-isopropyl-1-(4-((7-methyl-1H-benzo[d]imidazol-2-yl)methyl)naphthalen-1-yl)-5-(piperazin-1-ylmethyl)imidazo[1,5-a]pyrazin-8-amine Example 38: 2-{4-[8-amino-3-methyl-1-(piperazin-1-ylmethyl)imidazo[1,5-a]pyrazin-1-yl]naphthalen-1-yl}-N-[3-(trifluoromethyl)phenyl]acetamide Example 204: 1-[(8-amino-1-{4-[(4-methyl-1H-1,3-benzodiazol-2-yl)methyl]naphthalen-1-yl}-3-(propan-2-yl)imidazo[1,5-a]pyrazin-5-yl)methyl]piperidin-4-amine Example 205: (3S)-1-[(8-amino-1-{4-[(4-methyl-1H-1,3-benzodiazol-2-yl)methyl]naphthalen-1-yl}-3-(propan-2-yl)imidazo[1,5-a]pyrazin-5-yl)methyl]piperidin-3-amine

TABLE 1

| Ex. | R' | R² | X | R¹ | LCMS m/z (M + H) |
|---|---|---|---|---|---|
| 12 | piperazinyl (N-linked, NH) | CH₃ | 2,3-(C₄H₄) | -NH-C(O)-NH-C₆H₄-3-CF₃ | 574.7 |
| 13 | 4-aminopiperidin-1-yl | CH₃ | 2,3-(C₄H₄) | -NH-C(O)-NH-C₆H₄-3-CF₃ | 589.4 |
| 14 | piperidin-4-ylamino | CH₃ | 2,3-(C₄H₄) | -NH-C(O)-NH-C₆H₄-3-CF₃ | 589.3 |
| 15 | (3S)-3-aminopiperidin-1-yl | CH₃ | 2,3-(C₄H₄) | -NH-C(O)-NH-C₆H₄-3-CF₃ | 589.4 |
| 16 | (3R)-3-aminopiperidin-1-yl | CH₃ | 2,3-(C₄H₄) | -NH-C(O)-NH-C₆H₄-3-CF₃ | 589.3 |
| 17 | (3S)-piperidin-3-ylamino | CH₃ | 2,3-(C₄H₄) | -NH-C(O)-NH-C₆H₄-3-CF₃ | 589.3 |
| 18 | (3R)-piperidin-3-ylamino | CH₃ | 2,3-(C₄H₄) | -NH-C(O)-NH-C₆H₄-3-CF₃ | 589.4 |
| 19 | 4-methylpiperazin-1-yl | CH₃ | 2,3-(C₄H₄) | -NH-C(O)-NH-C₆H₄-3-CF₃ | 589.1 |

TABLE 1-continued

| Ex. | R' | R² | X | R¹ | LCMS m/z (M + H) |
|---|---|---|---|---|---|
| 20 | piperazin-1-yl | CH₂CH₃ | 2,3-(C₄H₄) | 3-(CF₃)phenyl urea | 589.3 |
| 21 | piperazin-1-yl | CH(CH₃)₂ | 2,3-(C₄H₄) | 3-(CF₃)phenyl urea | 603.5 |
| 22 | 4-methylpiperazin-1-yl | CH₂CH₃ | 2,3-(C₄H₄) | 3-(CF₃)phenyl urea | 603.6 |
| 23 | 4-(methylamino)piperidin-1-yl | CH₃ | 2,3-(C₄H₄) | 3-(CF₃)phenyl urea | 603.6 |
| 24 | (3S)-3-methylpiperazin-1-yl | CH₃ | 2,3-(C₄H₄) | 3-(CF₃)phenyl urea | 589.2 |
| 25 | (3R)-3-methylpiperazin-1-yl | CH₃ | 2,3-(C₄H₄) | 3-(CF₃)phenyl urea | 589.3 |
| 26 | 3,5-dimethylpiperazin-1-yl | CH₃ | 2,3-(C₄H₄) | 3-(CF₃)phenyl urea | 603.1 |
| 27 | 3-methylpiperazin-1-yl | CH₂CH₃ | 2,3-(C₄H₄) | 3-(CF₃)phenyl urea | 602.8 |

TABLE 1-continued

| Ex. | R' | R² | X | R¹ | LCMS m/z (M + H) |
|---|---|---|---|---|---|
| 28 | (S)-3-methylpiperazin-1-yl | CH₂CH₃ | 2,3-(C₄H₄) | NHC(O)NH-(3-CF₃-phenyl) | 603.3 |
| 29 | 1,4-diazepan-1-yl | CH₃ | 2,3-(C₄H₄) | NHC(O)NH-(3-CF₃-phenyl) | 589.4 |
| 30 | 2,5-diazabicyclo[2.2.1]heptan-2-yl | CH₃ | 2,3-(C₄H₄) | NHC(O)NH-(3-CF₃-phenyl) | 586.9 |
| 31 | octahydropyrrolo[3,4-b]pyrrol-5-yl | CH₃ | 2,3-(C₄H₄) | NHC(O)NH-(3-CF₃-phenyl) | 600.6 |
| 32 | piperazin-1-yl | CH₃ | 3-F | NHC(O)NH-(3-CF₃-phenyl) | 525.6 |
| 33 | piperazin-1-yl | CH₃ | 2,3-(C₄H₄) | NHC(O)NH-(3-CF₃-phenyl) | 521.6 |
| 34 | piperazin-1-yl | CH₃ | 3-F | NHC(O)NH-(3-CF₃-phenyl) | 543.0 |
| 35 | piperazin-1-yl | CH₂CH₃ | 3-F | NHC(O)NH-(3-CF₃-phenyl) | 557.0 |

TABLE 1-continued

| Ex. | R' | R² | X | R¹ | LCMS m/z (M + H) |
|---|---|---|---|---|---|
| 36 | piperazin-1-yl (attached via N) | CH(CH₃)₂ | 2-F | -NH-S(O)₂-CH₂-(2-Cl-phenyl) | 572.3 |
| 37 | piperazin-1-yl | CH(CH₃)₂ | 2,3-(C₄H₄) | -CH₂-(7-methyl-1H-benzimidazol-2-yl) | 545.5 |
| 38 | piperazin-1-yl | CH₃ | 2,3-(C₄H₄) | -NH-C(O)-NH-(3-CF₃-phenyl) | 575.6 |
| 204 | 4-aminopiperidin-1-yl | CH(CH₃)₂ | 2,3-(C₄H₄) | -CH₂-(7-methyl-1H-benzimidazol-2-yl) | 559.4 |
| 205 | (3R)-3-aminopiperidin-1-yl | CH(CH₃)₂ | 2,3-(C₄H₄) | -CH₂-(7-methyl-1H-benzimidazol-2-yl) | 559.4 |

Compounds in another aspect of this invention can be made using the chemistry outlined in Scheme 4. Pd(0)-catalyzed coupling of 8-chloro-5-iodo-3-methyl-imidazo[1,5-a]pyrazine 4A with a vinyl or aryl boronate provides the C-5 substituted vinyl analog 4B. Iodination and then treatment with ammonium hydroxide gives 4C which is subject to a second Pd(O)-catalyzed coupling with an aryl boronate to give 4 D. Deprotection with TFA affords the vinyl analog 4F which can be acetylated to yield 4G. Alternatively, reaction of 4 D with triethylsilane in TFA leads to the reduced analog 4E.

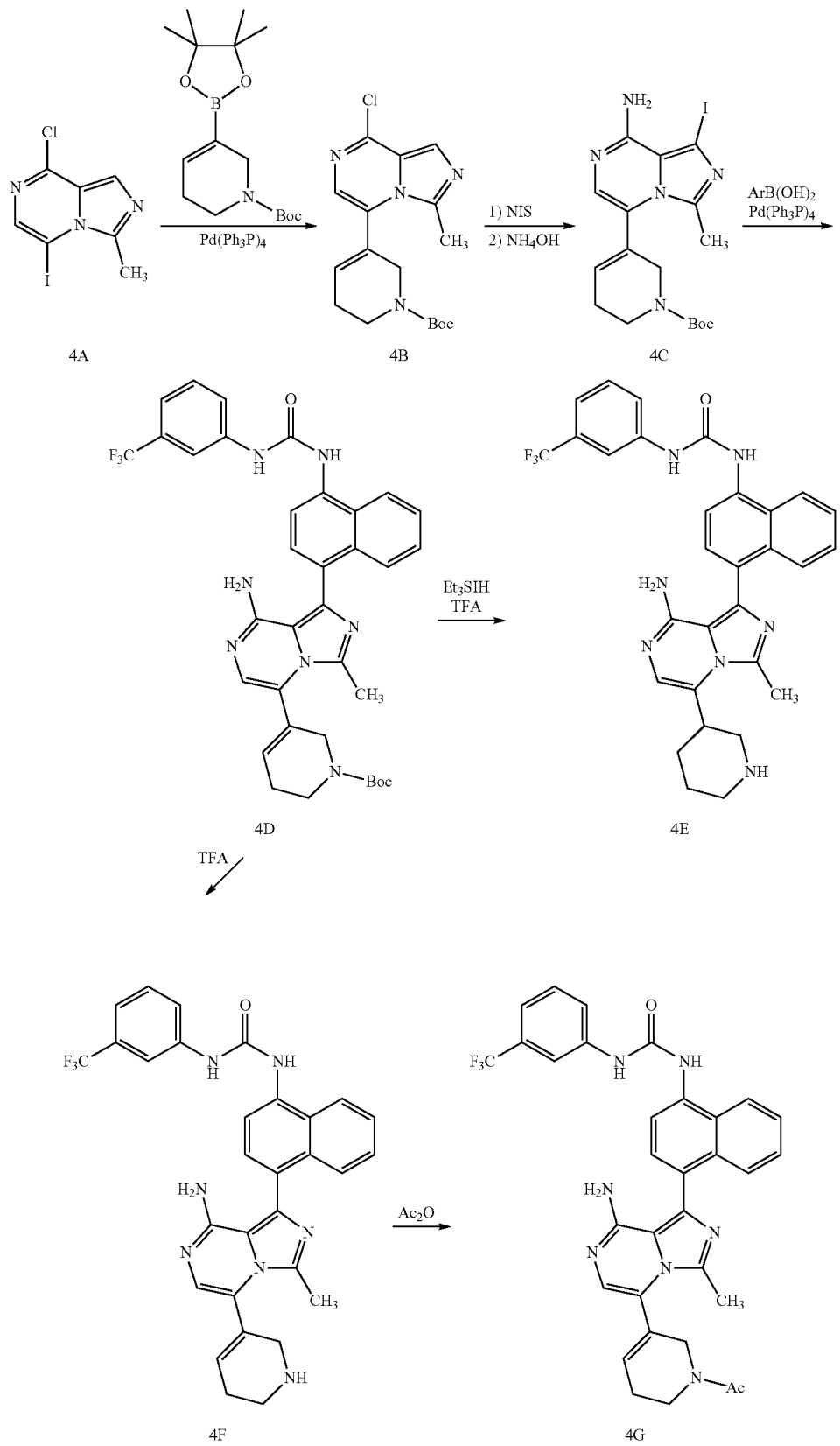
Scheme 4

Example 39. 3-{4-[8-amino-3-methyl-5-(1,2,5,6-tetrahydropyridin-3-yl)imidazo[1,5-a]pyrazin-1-yl]naphthalen-1-yl}-1-[3-(trifluoromethyl)phenyl]urea 4F Step 1: 8-Chloro-5-iodo-3-methyl-imidazo[1,5-a]pyrazine 4A (760 mg, 2.59 mmol), tert-butyl 5-(4,4,5,5-tetramethyl-1,3,2-dioxaborolan-2-yl)-3,6-dihydropyridine (2H)-carboxylate (800 mg, 2.59 mmol) and $Cs_2CO_3$ (2.50 g, 7.77 mmol) were suspended in DME (120 mL) and $H_2O$ (30 mL). $Pd(PPh_3)_4$ (150 mg) was added. The mixture was heated to 60° C. for 0.5 h in microwave. The desired compound 8-chloro-3-methylimidazo[1,5-a]pyrazine-5-N-Boc-(1,2,5,6-tetrahydropyridine) 4B (500 mg, 55%) was purified through column chromatography.

Step 2: 8-chloro-3-methylimidazo[1,5-a]pyrazine-5-N-Boc-(1,2,5,6-tetrahydropyridine) 4B (1.3 g, 3.73 mmol) was dissolved in DMF (5 mL) and NIS (2 eq.) in DMF was added into the solution. The mixture was heated to 55° C. overnight. The desired compound was purified through column chromatography, then was dissolved in 1,4-dioxane, and ammonia was added into the solution. The reaction mixture was irradiated by microwave at 100° C. for 2 h. Purification via flash chromatography yielded 610 mg overall (36%) of 8-amino-3-iodo-imidazo[1,5-a]pyrazine-5-N-Boc-(1,2,5,6-tetrahydropyridine) 4C.

Step 3: 8-amino-3-iodo-imidazo[1,5-a]pyrazine-5-N-Boc-(1,2,5,6-tetrahydropyridine) (610 mg, 1.34 mmol) 4C, 1-(4-(4,4,5,5-tetramethyl-1,3,2-dioxaborolan-2-yl)naphthalene-1-yl)-3-(3-(trifluoromethyl)phenyl)urea (1.0 eq.) and $Cs_2CO_3$ (4 eq.) were suspended in DME (1 mL) and $H_2O$ (0.25 mL). $Pd(PPh_3)_4$ (0.05. eq) was added. The mixture was heated to 100° C. for 60 minutes in a microwave. After cooling, the mixture was filtered, and the filtrate was concentrated to dryness. The residue was purified by flash column chromatography on silica gel to afford 3-{4-[8-amino-3-methyl-5-(N-Boc-(1,2,5,6-tetrahydropyridine)-imidazo[1,5-a]pyrazin-1-yl]naphthalen-1-yl}-1-[3-(trifluoromethyl)phenyl]urea (250 mg, 29%) 4 D as a solid, 200 mg of which was dissolved in DCM and TFA, and the mixture was stirred for 3 h. The solvent was removed and the residue was neutralized with saturated $NaHCO_3$. The desired compound 4F was purified through C-18 column chromatography to provide 80 mg of final product 3-{4-[8-amino-3-methyl-5-(1,2,5,6-tetrahydropyridin-3-yl)imidazo[1,5-a]pyrazin-1-yl]naphthalen-1-yl}-1-[3-(trifluoromethyl)phenyl]urea, ES-LCMS m/z 558.5 (M+H).

Example 40: 3-{4-[8-amino-3-methyl-5-(piperidin-3-yl)imidazo[1,5-a]pyrazin-1-yl]naphthalen-1-yl}-1-[3-(trifluoromethyl)phenyl]urea 4E 3-{4-[8-amino-3-methyl-5-(N-Boc-(1,2,5,6-tetrahydropyridine)-imidazo[1,5-a]pyrazin-1-yl]naphthalen-1-yl}-1-[3-(trifluoromethyl)phenyl]urea 4 D (280 mg) was dissolved in TFA, and triethylsilane (10 eq.) was added. The mixture was stirred at RT for 2 h, concentrated and purified to provide 50 mg of the title compound 4E, ES-LCMS m/z 560.7 (M+H).

Example 43: 3-{4-[5-(1-acetyl-1,2,5,6-tetrahydropyridin-3-yl)-8-amino-3-methylimidazo[1,5-a]pyrazin-1-yl]naphthalen-1-yl}-1-[3-(trifluoromethyl)phenyl]urea 4G 3-{4-[8-amino-3-methyl-5-(1,2,5,6-tetrahydropyridin-3-yl)imidazo[1,5-a]pyrazin-1-yl]naphthalen-1-yl}-1-[3-(trifluoromethyl)phenyl]urea 4F (80 mg) and 18-crown-6 (2.0 eq.) were dissolved in a 0.5 M $Ac_2O$ in DCM solution (4 mL) at 0° C. TEA (1.5 eq.) was added and the reaction mixture was stirred for 1 h. Purification yielded 32 mg of desired product 4G, ES-LCMS m/z 600.6 (M+H).

The below examples were made using similar procedures.

Example 41: 3-{4-[8-amino-3-methyl-5-(1,2,3,6-tetrahydropyridin-4-yl)imidazo[1,5-a]pyrazin-1-yl]naphthalen-1-yl}-1-[3-(trifluoromethyl)phenyl]urea, ES-LCMS m/z 558.7 (M+H).

Example 42: 3-{4-[8-amino-3-methyl-5-(1,2,3,6-tetrahydropyridin-4-yl)imidazo[1,5-a]pyrazin-1-yl]-3-fluorophenyl}-1-[3-(trifluoromethyl)phenyl]urea, ES-LCMS m/z 526.5 (M+H).

Example 44: 3-{4-[5-(1-acetylpiperidin-3-yl)-8-amino-3-methylimidazo[1,5-a]pyrazin-1-yl]naphthalen-1-yl}-1-[3-(trifluoromethyl)phenyl]urea, ES-LCMS m/z 602.6 (M+H).

Example 45: 3-{4-[5-(1-acetyl-1,2,3,6-tetrahydropyridin-4-yl)-8-amino-3-methylimidazo[1,5-a]pyrazin-1-yl]-3-fluorophenyl}-1-[3-(trifluoromethyl)phenyl]urea, ES-LCMS m/z 568.6 (M+H).

Example 46: 3-{4-[8-amino-5-(cyclohex-1-en-1-yl)-3-methylimidazo[1,5-a]pyrazin-1-yl]naphthalen-1-yl}-1-[3-(trifluoromethyl)phenyl]urea, ES-LCMS m/z 557.6 (M+H).

Example 47: 3-{4-[8-amino-3-methyl-5-(1-methyl-1,2,3,6-tetrahydropyridin-4-yl)imidazo[1,5-a]pyrazin-1-yl]naphthalen-1-yl}-1-[3-(trifluoromethyl)phenyl]urea, ES-LCMS m/z 571.2 (M+H).

Example 48: 3-{4-[8-amino-3-methyl-5-(pyridin-3-yl)imidazo[1,5-a]pyrazin-1-yl]naphthalen-1-yl}-1-[3-(trifluoromethyl)phenyl]urea, ES-LCMS m/z 553.7 (M+H).

Example 49: 3-(4-{8-amino-3-methyl-5-[1-(prop-2-enoyl)-1,2,3,6-tetrahydropyridin-4-yl]imidazo[1,5-a]pyrazin-1-yl}naphthalen-1-yl)-1-[3-(trifluoromethyl)phenyl]urea, ES-LCMS m/z 612.3 (M+H).

Example 50: 3-{4-[8-amino-5-(4-aminophenyl)-3-methylimidazo[1,5-a]pyrazin-1-yl]naphthalen-1-yl}-1-[3-(trifluoromethyl)phenyl]urea, ES-LCMS m/z 568.5 (M+H).

Example 51: 3-{4-[8-amino-3-methyl-5-(1-methyl-1H-pyrazol-4-yl)imidazo[1,5-a]pyrazin-1-yl]naphthalen-1-yl}-1-[3-(trifluoromethyl)phenyl]urea, ES-LCMS m/z 557.3 (M+H).

Example 52: 3-{4-[8-amino-5-(1,5-dimethyl-1H-pyrazol-4-yl)-3-methylimidazo[1,5-a]pyrazin-1-yl]naphthalen-1-yl}-1-[3-(trifluoromethyl)phenyl]urea, ES-LCMS m/z 569.3 (ES-).

Example 53: 3-{4-[8-amino-5-(1,3-dimethyl-1H-pyrazol-4-yl)-3-methylimidazo[1,5-a]pyrazin-1-yl]naphthalen-1-yl}-1-[3-(trifluoromethyl)phenyl]urea, ES-LCMS m/z 570.7 (M+H).

Example 54: 3-(4-{8-amino-3-methyl-5-[1-(piperidin-4-yl)-1H-pyrazol-4-yl]imidazo[1,5-a]pyrazin-1-yl}naphthalen-1-yl)-1-[3-(trifluoromethyl)phenyl]urea, ES-LCMS m/z 625.7 (M+H).

Example 55: 3-{4-[8-amino-3-methyl-5-(1,2,3,4-tetrahydroisoquinolin-5-yl)imidazo[1,5-a]pyrazin-1-yl]naphthalen-1-yl}-1-[3-(trifluoromethyl)phenyl]urea, ES-LCMS m/z 608.7 (M+H).

Example 56: 3-{4-[8-amino-5-(2-aminopyridin-4-yl)-3-methylimidazo[1,5-a]pyrazin-1-yl]naphthalen-1-yl}-1-[3-(trifluoromethyl)phenyl]urea, ES-LCMS m/z 569.2 (M+H).

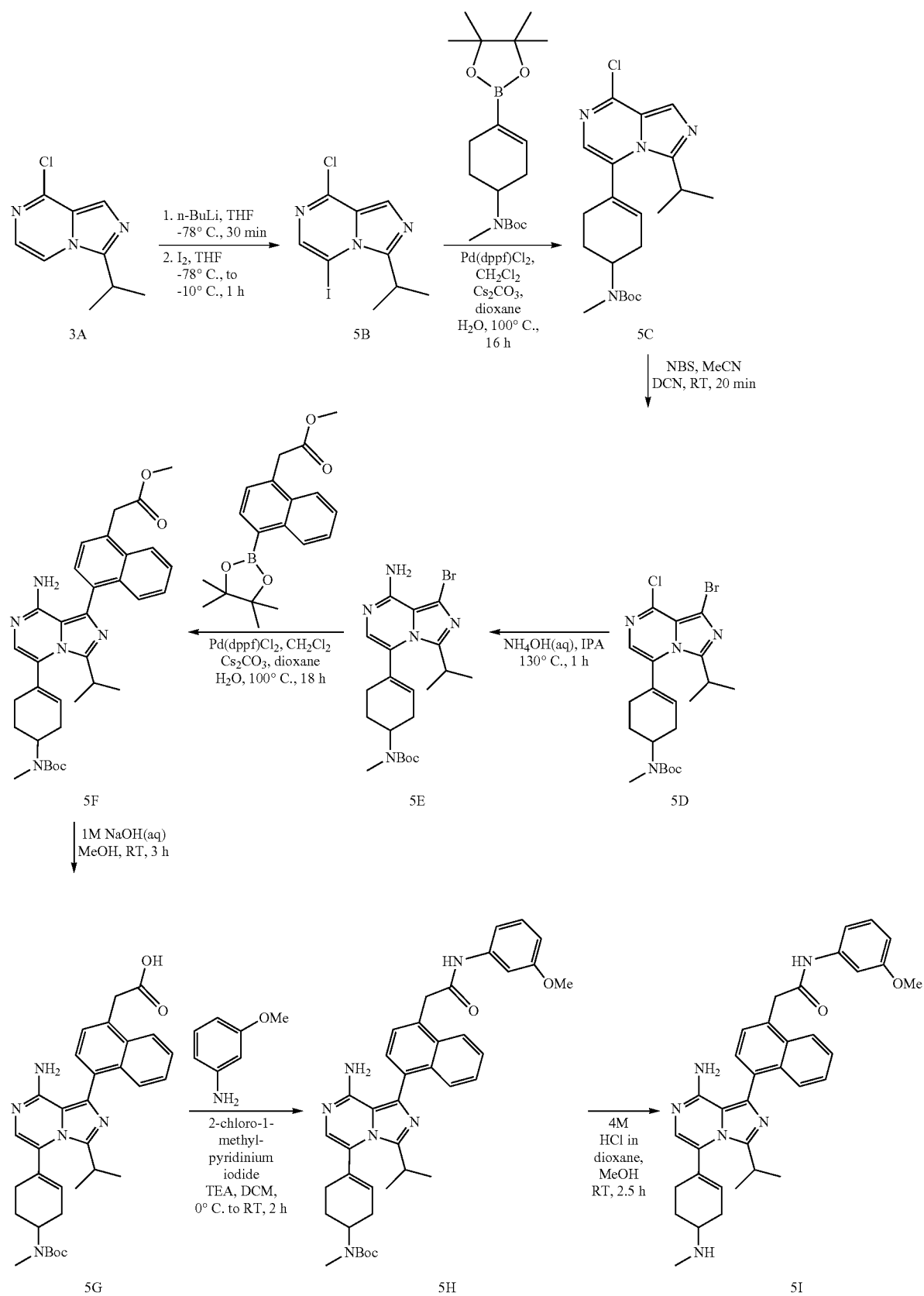

Additional compounds of the invention can be made according to the chemistry outlined in Scheme 5. Treatment of 8-chloro-3-isopropylimidazo[1,5-a]pyrazine 3A with n-butyllithium followed by quenching with iodine gives iodo-intermediate 5B, which can undergo Pd(0)-catalyzed coupling with vinyl or aryl boronates to give a coupling product such as 5C. Bromination and reaction with ammonium hydroxide gives 5E which can undergo another Pd(0)-catalyzed coupling with aryl boronates to give 5F. Hydrolysis of the ester furnishes the acid 5G which can be coupled to a variety of amines to form amides such as 5H. Acid deprotection affords the final product 5I.

Example 71: 2-(4-(8-amino-3-isopropyl-5-(4-(methylamino)cyclohex-1-en-1-yl)imidazo[1,5-a]pyrazin-1-yl)naphthalen-1-yl)-N-(3-methoxyphenyl)acetamide 5I Step 1: 8-Chloro-5-iodo-3-isopropylimidazo[1,5-a]pyrazine 5B To a stirred solution of 8-chloro-3-isopropylimidazo[1,5-a]pyrazine (31 g, 158.5 mmol) in dry THF (300 mL) at −78° C. under nitrogen was added n-butyllithium (2.5 M in hexanes, 82.4 mL, 206 mmol), keeping the internal temperature below −65° C. After stirring for 30 min a solution of iodine (56.3 g, 221.8 mmol) in THF (50 mL) was added dropwise over 10 min keeping the internal temperature below −65° C. during addition. The resulting suspension was stirred for 1 hour whilst warming to −10° C. then the reaction mixture was quenched by the addition of saturated aqueous $NH_4Cl$ and extracted with 2-methyltetrahydrofuran (×3). The combined organic extracts were washed with water and brine, dried ($Na_2SO_4$), filtered and concentrated in vacuo. The residue was purified by passage through a silica-gel pad, eluting with 0-20% EtOAc in DCM to give an orange solid, which was triturated with $Et_2O$ to give the title compound 5B as a yellow solid (41.2 g, 81%). LC-MS: Rt=1.29 min, m/z=322.0 [M+H]$^+$ Step 2: tert-Butyl (4-(8-chloro-3-isopropylimidazo[1,5-a]pyrazin-5-yl)cyclohex-3-en-1-yl) (methyl)carbamate 5C A mixture of 8-chloro-5-iodo-3-isopropylimidazo[1,5-a]pyrazine 5B 32.5 g, 101.1 mmol), tert-butyl methyl(4-(4,4,5,5-tetramethyl-1,3,2-dioxaborolan-2-yl) cyclohex-3-en-1-yl)carbamate (35.8 g, 106.15 mmol), $PdCl_2$(dppf).DCM (8.3 g, 10.1 mmol) and cesium carbonate (65.9 g, 202.2 mmol) in a mixture of dioxane (500 mL) and water (100 mL) was purged with argon with sonication prior to being heated to 100° C. for 16 h. The reaction mixture was diluted with water and extracted with EtOAc (×2) and the combined organic extract was washed with brine prior to drying ($MgSO_4$), filtering and concentrating in vacuo. The resultant residue was purified by silica-gel chromatography, eluting with 0-50% EtOAc in isohexane to give a solid, which was triturated with $Et_2O$ to provide the title compound 5C as yellow solid (22.1 g, 54%). LC-MS: Rt=1.55 min, m/z=405.4 [M+H]$^+$.

Step 3: tert-Butyl (4-(1-bromo-8-chloro-3-isopropylimidazo[1,5-a]pyrazin-5-yl)cyclohex-3-en-1-yl) (methyl)carbamate 5 D To a stirred suspension of tert-butyl (4-(8-chloro-3-isopropylimidazo[1,5-a]pyrazin-5-yl)cyclohex-3-en-1-yl) (methyl)carbamate 5C (22.1 g, 54.58 mmol) in MeCN (200 mL) was added NBS (10.69 g, 60.03 mmol). After 15 min most solids had dissolved before a fine precipitate was evolved. DCM (20 mL) was added to aid solubility and after a further 5 min the reaction was complete. The reaction mixture was concentrated in vacuo and the resultant residue triturated with water and the solid collected by filtration and dried in vacuo to give the title compound 5D, which was used without further purification (24.8 g, 94%). LC-MS: Rt=1.69 min, m/z=483.3 [M($^{79}$Br)+H]$^+$.

Step 4: tert-Butyl (4-(8-amino-1-bromo-3-isopropylimidazo[1,5-a]pyrazin-5-yl)cyclohex-3-en-1-yl) (methyl)carbamate 5E The reaction was split between 9 microwave vials: A suspension of tert-butyl (4-(1-bromo-8-chloro-3-isopropylimidazo[1,5-a]pyrazin-5-yl)cyclohex-3-en-1-yl)(methyl) carbamate 5 D (24.8 g, 51.2 mmol) in [1:1] IPA: ammonia (180 mL) was heated under microwave irradiation at 130° C. for 1 h. The combined reaction mixture was diluted with water and extracted with EtOAc (×2) and the combined organic extract was washed with brine prior to drying ($MgSO_4$), filtering and concentrating in vacuo. The resultant residue was triturated with $Et_2O$ to provide the title compound 5E as buff coloured solid (18 g, 76%). LC-MS: Rt=1.01 min, m/z=464.3 [M($^{79}$Br)+H]$^+$ Step 5: Methyl 2-(4-(8-amino-5-(4-((tert-butoxycarbonyl)(methyl)amino)cyclohex-1-en-1-yl)-3-isopropylimidazo[1,5-a]pyrazin-1-yl)naphthalen-1-yl)acetate 5F A solution of tert-butyl (4-(1-bromo-8-chloro-3-isopropylimidazo[1,5-a]pyrazin-5-yl)cyclohex-3-en-1-yl)(methyl) carbamate 5E (2.4 g, 5.2 mmol), methyl 2-(4-(4,4,5,5-tetramethyl-1,3,2-dioxaborolan-2-yl)naphthalen-1-yl) acetate (1.70 g, 5.2 mmol), $PdCl_2$(dppf).DCM (378 mg, 0.52 mmol) and cesium carbonate (2.5 g, 7.7 mmol) in a mixture of dioxane (15 mL) and water (2.9 mL) was purged with nitrogen prior to being heated to 100° C. for 18 h. The reaction mixture was concentrated in vacuo. The resultant residue was purified by silica-gel chromatography, eluting with 0-100% EtOAc in isohexane to give the desired product 5F (1.9 g, 63%). LC-MS: Rt=1.29 min, m/z=584.3 [M+H]$^+$ Step 6: 2-(4-(8-Amino-5-(4-((tert-butoxycarbonyl) (methyl)amino)cyclohex-1-en-1-yl)-3-isopropylimidazo[1,5-a]pyrazin-1-yl)naphthalen-1-yl)acetic acid 5G To a stirred solution of methyl 2-(4-(8-amino-5-(4-((tert-butoxycarbonyl) (methyl) amino)cyclohex-1-en-1-yl)-3-isopropylimidazo[1,5-a]pyrazin-1-yl)naphthalen-1-yl) acetate 5F (1.9 g, 3.2 mmol) in MeOH (15 mL) was added 1 M aqueous NaOH (8 mL) and the resulting mixture was sonicated to help dissolution. After 3 h the reaction was concentrated in vacuo and extracted with EtOAc (×3) prior to drying ($MgSO_4$), filtering and concentrating in vacuo to give the title compound 5G as a brown solid (1.5 g, 82%). LC-MS: Rt=1.24 min, m/z=570.3 [M+H]$^+$.

Step 7: tert-Butyl (4-(8-amino-3-isopropyl-1-(4-(2-((3-methoxyphenyl)amino)-2-oxoethyl)naphthalen-1-yl)imidazo[1,5-a]pyrazin-5-yl)cyclohex-3-en-1-yl) (methyl)carbamate 5H To a solution of 2-(4-(8-amino-5-(4-((tert-butoxycarbonyl)(methyl)amino)cyclohex-1-en-1-yl)-3-isopropylimididazo[1,5-a]pyrazin-1-yl)naphthalen-1-yl)acetic acid 5G (115 mg, 0.20 mmol) in DCM (3.5 mL) at 0° C. was added 2-chloro-1-methylpyridinium iodide (77 mg, 0.30 mmol), TEA (0.14 mL, 1.00 mmol), then 3-methoxyaniline (68 µL, 0.61 mmol). The resulting solution was allowed to warm to RT and stirred for 2 h. 1 M aqueous HCl was added and the mixture was extracted with DCM (2×). The combined organic extracts were concentrated in vacuo and the residue was purified by silica-gel chromatography, eluting with 0-100% EtOAc/hexane to give the title compound 5H (80 mg, 59%). LC-MS: Rt=3.22 min, m/z=675.3 [M+H]$^+$.

Step 8: 2-(4-(8-amino-3-isopropyl-5-(4-(methyl-amino)cyclohex-1-en-1-yl)imidazo[1,5-a]pyrazin-1-yl)naphthalen-1-yl)-N-(3-methoxyphenyl)acetamide (Example 71) 5I To a solution of tert-butyl (4-(8-amino-3-isopropyl-1-(4-(2-((3-methoxyphenyl)amino)-2-oxoethyl)naphthalen-1-yl)imidazo[1,5-a]pyrazin-5-yl)cyclohex-3-en-1-yl)(methyl)carbamate 5H (80 mg, 0.12 mmol) in methanol (4 mL) was added 4 M HCl in 1,4-dioxane (1 mL) and the resulting solution was stirred at RT for 2.5 h. The solvents were concentrated in vacuo and the residue was passed down an SCX-2 cartridge (5 g). The basic fractions were concentrated in vacuo and the residue was purified by MDAP to provide the title compound (42 mg, 62%). QC LC-MS (Method 2): Rt=3.13 min, m/z=575.4 [M+H]$^+$.

The following examples in Table 2 were prepared using an analogous method to Example 71. Other central linkers were made by similar methods, replacing the 4-bromonaphthylacetate moiety with appropriate 5-bromonaphthylacetates or by substituted 4-bromophenylacetates.

TABLE 2

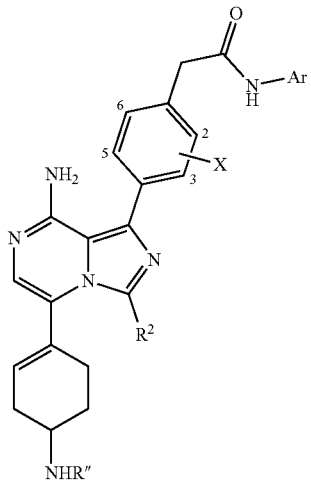

| Ex. | R" | R$^2$ | X | Ar | LCMS m/z (M + H) | HPLC Rt (min)/Method |
|---|---|---|---|---|---|---|
| 57 | H | CH$_3$ | 2,3-(C$_4$H$_4$) | 3-CF$_3$—Ph | 571.2 | 2.57/1 |
| 58 | CH$_3$ | CH$_2$CH$_3$ | 2,3-(C$_4$H$_4$) | 3-CF$_3$—Ph | 599.5 | 7.3/1 |
| 59 | CH$_3$ | CH(CH$_3$)$_2$ | 2,3-(C$_4$H$_4$) | 3-CF$_3$—Ph | 613.3 | 2.66/1 |
| 60 | CH$_3$ | CH$_3$ | 2,3-(C$_4$H$_4$) | 3-CF$_3$—Ph | 585.7 | 7.25/1 |
| 61 | CH$_3$ | CH$_3$ | 3-F | 3-CF$_3$—Ph | 553.7 | 5.04/1 |
| 62 | CH$_3$ | CH(CH$_3$)$_2$ | 2,3-(C$_4$H$_4$) | Ph | 545.4 | 2.99/2 |
| 63 | CH$_3$ | CH(CH$_3$)$_2$ | 3-F | 3-F—Ph | 531.4 | 2.94/2 |
| 64 | CH$_3$ | CH(CH$_3$)$_2$ | 2,3-(C$_4$H$_4$) | 3-F—Ph | 563.5 | 3.07/2 |
| 65 | CH$_3$ | CH(CH$_3$)$_2$ | 2,3-(C$_4$H$_4$) | 3-F-5-CH$_3$O—Ph | 593.5 | 3.00/2 |
| 66 | CH$_3$ | CH(CH$_3$)$_2$ | 3-F | Ph | 513.3 | 2.58/1 |
| 67 | CH$_3$ | CH(CH$_3$)$_2$ | 2,3-(C$_4$H$_4$) | 3-F-5-CN—Ph | 588.5 | 2.98/2 |
| 68 | CH$_3$ | CH(CH$_3$)$_2$ | 2,3-(C$_4$H$_4$) | 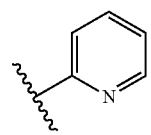 [SMILES: *c1ccccn1] | 546.4 | 2.96/2 |
| 69 | CH$_3$ | CH(CH$_3$)$_2$ | 2,3-(C$_4$H$_4$) | 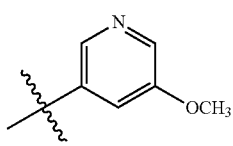 [SMILES: *c1cncc(OC)c1] | 576.4 | 2.87/2 |

TABLE 2-continued

| | | | | | | |
|---|---|---|---|---|---|---|
| 70 | CH$_3$ | CH(CH$_3$)$_2$ | 2,3-(C$_4$H$_4$) | 3-CN—Ph | 570.4 | 3.10/2 |
| 72 | CH$_3$ | CH(CH$_3$)$_2$ | 2,3-(C$_4$H$_4$) | 2-pyridyl | 546.4 | 2.82/2 |
| 73 | CH$_3$ | CH(CH$_3$)$_2$ | 2,3-(C$_4$H$_4$) | pyrazinyl | 547.4 | 2.49/1 |
| 74 | CH$_3$ | CH(CH$_3$)$_2$ | 2,3-(C$_4$H$_4$) | thiazolyl | 552.4 | 2.32/1 |
| 75 | CH$_3$ | CH(CH$_3$)$_2$ | 2,3-(C$_4$H$_4$) | N-methylbenzimidazolyl | 599.6 | 2.20/1 |
| 76 | CH$_3$ | CH(CH$_3$)$_2$ | 2,3-(C$_4$H$_4$) | 2,2-difluorobenzodioxolyl | 625.3 | 2.64/1 |
| 77 | CH$_3$ | CH(CH$_3$)$_2$ | 2,3-(C$_4$H$_4$) | N-methylpyrazolyl | 549.3 | 2.29/1 |
| 78 | CH$_3$ | CH(CH$_3$)$_2$ | 2,3-(C$_4$H$_4$) | 3,4-(OCH$_3$)$_2$-Ph | 605.6 | 2.44/1 |
| 79 | CH$_3$ | CH(CH$_3$)$_2$ | 2,3-(C$_4$H$_4$) | pyrimidinyl | 547.3 | 2.28/1 |
| 80 | CH$_3$ | CH(CH$_3$)$_2$ | 2,3-(C$_4$H$_4$) | 5-F-pyridin-3-yl | 564.4 | 2.40/1 |

TABLE 2-continued

| Ex. | R" | R² | Ar | LCMS m/z (M + H) | HPLC Rt (min)/Method |
|---|---|---|---|---|---|
| 81 | CH₃ | CH(CH₃)₂ | 3-fluorophenyl | 563.5 | 2.94/2 |
| 82 | CH₃ | CH(CH₃)₂ | phenyl | 545.3 | 2.87/2 |

Example 57: 2-(4-(8-amino-5-(4-aminocyclohex-1-en-1-yl)-3-methylimidazo[1,5-a]pyrazin-1-yl)naphthalen-1-yl)-N-(3-(trifluoromethyl)phenyl)acetamide Example 58: 2-(4-{8-amino-3-ethyl-5-[4-(methylamino)cyclohex-1-en-1-yl]imidazo[1,5-a]pyrazin-1-yl}naphthalen-1-yl)-N-[3-(trifluoromethyl)phenyl]acetamide Example 59: 2-(4-{8-amino-5-[4-(methylamino)cyclohex-1-en-1-yl]-3-(propan-2-yl)imidazo[1,5-a]pyrazin-1-yl}naphthalen-1-yl)-N-[3-(trifluoromethyl)phenyl]acetamide Example 60: 2-(4-{8-amino-3-methyl-5-[4-(methylamino)cyclohex-1-en-1-yl]imidazo[1,5-a]pyrazin-1-yl}naphthalen-1-yl)-N-[3-(trifluoromethyl)phenyl]acetamide Example 61: 2-(4-{8-amino-3-methyl-5-[4-(methylamino)cyclohex-1-en-1-yl]imidazo[1,5-a]pyrazin-1-yl}-3-fluorophenyl)-N-[3-(trifluoromethyl)phenyl]acetamide Example 62: 2-(4-(8-amino-3-isopropyl-5-(4-(methylamino)cyclohex-1-en-1-yl)imidazo[1,5-a]pyrazin-1-yl)naphthalen-1-yl)-N-phenylacetamide Example 63: 2-(4-(8-amino-3-isopropyl-5-(4-(methylamino)cyclohex-1-en-1-yl)imidazo[1,5-a]pyrazin-1-yl)-3-fluorophenyl)-N-(3-fluorophenyl)acetamide Example 64: 2-(4-(8-amino-3-isopropyl-5-(4-(methylamino)cyclohex-1-en-1-yl)imidazo[1,5-a]pyrazin-1-yl)naphthalen-1-yl)-N-(3-fluorophenyl)acetamide Example 65: 2-(4-(8-amino-3-isopropyl-5-(4-(methylamino)cyclohex-1-en-1-yl)imidazo[1,5-a]pyrazin-1-yl)naphthalen-1-yl)-N-(3-fluoro-5-methoxyphenyl)acetamide Example 66: 2-(4-(8-amino-3-isopropyl-5-(4-(methylamino)cyclohex-1-en-1-yl)imidazo[1,5-a]pyrazin-1-yl)-3-fluorophenyl)-N-phenylacetamide Example 67: 2-(4-(8-amino-3-isopropyl-5-(4-(methylamino)cyclohex-1-en-1-yl)imidazo[1,5-a]pyrazin-1-yl)naphthalen-1-yl)-N-(3-cyano-5-fluorophenyl)acetamide Example 68: 2-(4-(8-amino-3-isopropyl-5-(4-(methylamino)cyclohex-1-en-1-yl)imidazo[1,5-a]pyrazin-1-yl)naphthalen-1-yl)-N-(pyridin-2-yl)acetamide Example 69: 2-(4-(8-amino-3-isopropyl-5-(4-(methylamino)cyclohex-1-en-1-yl)imidazo[1,5-a]pyrazin-1-yl)naphthalen-1-yl)-N-(5-methoxypyridin-3-yl)acetamide Example 70: 2-(4-(8-amino-3-isopropyl-5-(4-(methylamino)cyclohex-1-en-1-yl)imidazo[1,5-a]pyrazin-1-yl)naphthalen-1-yl)-N-(3-cyanophenyl)acetamide Example 72: 2-(4-(8-amino-3-isopropyl-5-(4-(methylamino)cyclohex-1-en-1-yl)imidazo[1,5-a]pyrazin-1-yl)naphthalen-1-yl)-N-(pyridin-3-yl)acetamide Example 73: 2-(4-(8-amino-3-isopropyl-5-(4-(methylamino)cyclohex-1-en-1-yl)imidazo[1,5-a]pyrazin-1-yl)naphthalen-1-yl)-N-(pyrazin-2-yl)acetamide Example 74: 2-(4-(8-amino-3-isopropyl-5-(4-(methylamino)cyclohex-1-en-1-yl)imidazo[1,5-a]pyrazin-1-yl)naphthalen-1-yl)-N-(thiazol-5-yl)acetamide Example 75: 2-(4-(8-amino-3-isopropyl-5-(4-(methylamino)cyclohex-1-en-1-yl)imidazo[1,5-a]pyrazin-1-yl)naphthalen-1-yl)-N-(1-methyl-1H-benzo[d]imidazol-5-yl)acetamide Example 76: 2-(4-(8-amino-3-isopropyl-5-(4-(methylamino)cyclohex-1-en-1-yl)imidazo[1,5-a]pyrazin-1-yl)naphthalen-1-yl)-N-(2,2-difluorobenzo[d][1,3]dioxol-5-yl)acetamide Example 77: 2-(4-(8-amino-3-isopropyl-5-(4-(methylamino)cyclohex-1-en-1-yl)imidazo[1,5-a]pyrazin-1-yl)naphthalen-1-yl)-N-(1-methyl-1H-pyrazol-4-yl)acetamide Example 78: 2-(4-(8-amino-3-isopropyl-5-(4-(methylamino)cyclohex-1-en-1-yl)imidazo[1,5-a]pyrazin-1-yl)naphthalen-1-yl)-N-(3,4-dimethoxyphenyl)acetamide Example 79: 2-(4-(8-amino-3-isopropyl-5-(4-(methylamino)cyclohex-1-en-1-yl)imidazo[1,5-a]pyrazin-1-yl)naphthalen-1-yl)-N-(pyrimidin-5-yl)acetamide Example 80: 2-(4-(8-amino-3-isopropyl-5-(4-(methylamino)cyclohex-1-en-1-yl)imidazo[1,5-a]pyrazin-1-yl)naphthalen-1-yl)-N-(5-fluoropyridin-3-yl)acetamide Example 81: 2-(5-(8-amino-3-isopropyl-5-(4-(methylamino)cyclohex-1-en-1-yl)imidazo[1,5-a]pyrazin-1-yl)naphthalen-1-yl)-N-(3-fluorophenyl)acetamide Example 82: 2-(5-(8-amino-3-isopropyl-5-(4-(methylamino)cyclohex-1-en-1-yl)imidazo[1,5-a]pyrazin-1-yl)naphthalen-1-yl)-N-phenylacetamide Scheme 6

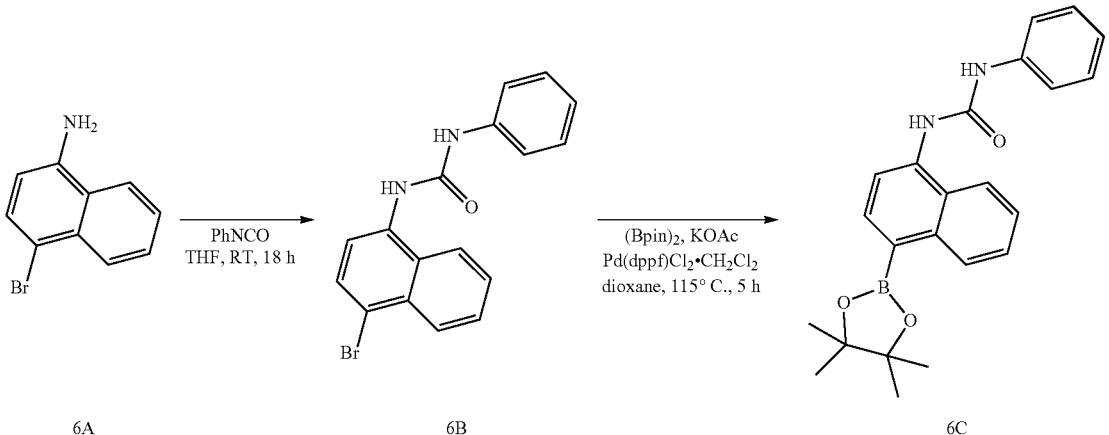

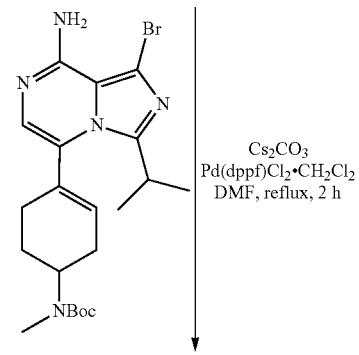

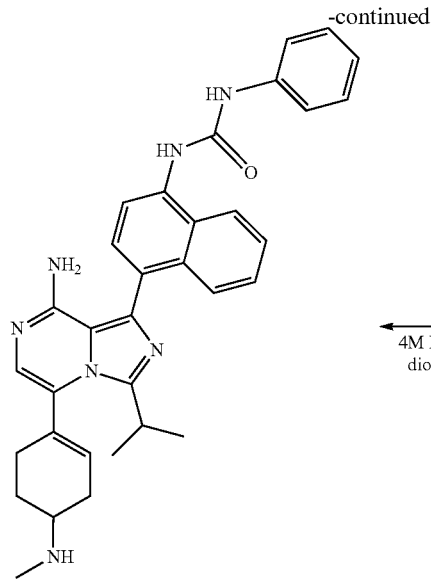

6E

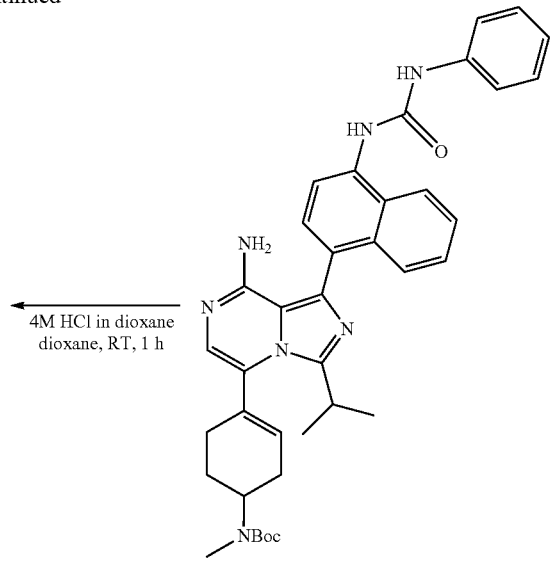

6D

Another set of compounds in this invention can be made according to the chemistry outlined in Scheme 6. Treatment of 4-bromonaphthalen-1-amine 6A with an isocyanate such as phenyl isocyanate gives the urea intermediate 6B, which can be converted to the boronate 6C using standard conditions. 6C undergoes Pd(0)-catalyzed coupling with a heterocyclic bromide as before to give a coupling product such as 6 D. Acid deprotection affords the final product 6E.

Example 121: 1-(4-(8-Amino-3-isopropyl-5-(4-(methylamino)cyclohex-1-en-1-yl)imidazo[1,5-a]pyrazin-1-yl)naphthalen-1-yl)-3-phenylurea 6E Step 1: 1-(4-Bromonaphthalen-1-yl)-3-phenylurea 6B To a solution of 4-bromonaphthalen-1-amine (5.0 g, 22.5 mmol) in THF (50 mL) was added phenyl isocyanate (2.57 mL, 23.6 mmol) and the resultant mixture was stirred at RT for 18 h. The reaction mixture was diluted with Et$_2$O and the solid precipitate collected by filtration to give the title compound 6B as a tan coloured solid (7.4 g, 96%). QC LC-MS (Method 1): Rt=3.88 min, m/z=341.1 [M($^{79}$Br)+H]$^+$.

Step 2: 1-Phenyl-3-(4-(4,4,5,5-tetramethyl-1,3,2-dioxaborolan-2-yl)naphthalen-1-yl)urea 6C A stirred mixture of 1-(4-bromonaphthalen-1-yl)-3-phenylurea 6B (2.50 g, 7.33 mmol), bis(pinacolato)diboron (1.87 g, 8.06 mmol), PdCl$_2$(dppf).DCM (0.27 g, 0.40 mmol) and potassium acetate (1.31 g, 14.7 mmol) in 1,4-dioxane (40 mL, purged with nitrogen for 10 min before use) was heated at 115° C. for 5 h. The reaction mixture was concentrated in vacuo then partitioned between EtOAc and water. The organic layer was dried (MgSO$_4$), filtered, and concentrated in vacuo. The residue was purified by silica-gel chromatography, eluting with 0-100% EtOAc in isohexane to give the title compound 6C as a solid (2.27 g, 80%). LC-MS: Rt=1.72 min, m/z=389.2 [M+H]$^+$. $^1$H NMR (400 MHz, DMSO-d$_6$) δ 9.21 (s, 1H), 8.99 (s, 1H), 8.82-8.75 (m, 1H), 8.25-8.20 (m, 2H), 8.03-8.00 (m, 1H), 7.68-7.54 (m, 4H), 7.40-7.35 (m, 2H), 7.08-7.04 (m, 1H), 1.43 (s, 12H).

Step 3: tert-Butyl (4-(8-amino-3-isopropyl-1-(4-(3-phenylureido)naphthalen-1-yl)imidazo[1,5-a]pyrazin-5-yl)cyclohex-3-en-1-yl)(methyl)carbamate 6 D To a stirred solution of tert-butyl (4-(8-amino-1-bromo-3-isopropylimidazo[1,5-a]pyrazin-5-yl)cyclohex-3-en-1-yl)(methyl)carbamate 5E (100 mg, 0.22 mmol), 1-phenyl-3-(4-(4,4,5,5-tetramethyl-1,3,2-dioxaborolan-2-yl)naphthalen-1-yl) urea 6C (92 mg, 0.24 mmol), PdCl$_2$(dppf).DCM (9 mg, 0.01 mmol) and cesium carbonate (211 mg, 0.65 mmol) in DME (3 mL) was purged with nitrogen prior to being heated to reflux for 2 h. The reaction mixture was diluted with EtOAc and washed with water prior to drying (MgSO$_4$), filtering and concentrating in vacuo. The residue was purified by silica-gel chromatography, eluting with 0-100% EtOAc in isohexane to give the title compound 6D as a yellow/green solid (80 mg, 56%). LC-MS Rt=1.31 min, m/z=646.4 [M+H]$^+$.

Step 4: 1-(4-(8-Amino-3-isopropyl-5-(4-(methylamino)cyclohex-1-en-1-yl)imidazo[1,5-a]pyrazin-1-yl)naphthalen-1-yl)-3-phenylurea (Example 121) 6E To a stirred solution of tert-butyl (4-(8-amino-3-isopropyl-1-(4-(3-phenylureido)naphthalen-1-yl)imidazo[1,5-a]pyrazin-5-yl)cyclohex-3-en-1-yl)(methyl)carbamate 6 D (80 mg, 0.12 mmol) in dioxane (2 mL) was added dropwise 4 M HCl in dioxane (1 mL) and the reaction mixture stirred at RT for 1 h. The reaction mixture was diluted with EtOAc and the resultant mixture stirred with saturated aqueous NaHCO$_3$. The organic layer was collected and concentrated in vacuo and the residue was purified by MDAP to give the title compound 6E as a yellow solid, (22 mg, 34%). QC LC-MS (Method 1): Rt=2.48 min, m/z=546.5 [M+H]$^+$.

The following examples in Table 3 were prepared using an analogous method to Example 121. Other central linkers were made by similar methods by replacing 4-bromonaphthalen-1-amine by 5-bromonaphthylamines, 5-bromoisoquinoline or substituted 4-bromoanilines.

TABLE 3

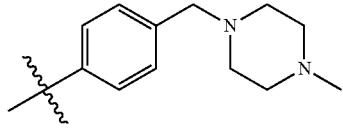 [SMILES: *c1ccc(CN2CCN(C)CC2)cc1]

| Ex. | R'' | R² | X | Ar | LCMS m/z (M + H) |
|---|---|---|---|---|---|
| 83 | H | CH₃ | 2,3-(C₄H₄) | 3-CF₃—Ph | 572.4 |
| 84 | CH₃ | CH₃ | 2,3-(C₄H₄) | 3-CF₃—Ph | 586.7 |
| 85 | H | CH₂CH₃ | 2,3-(C₄H₄) | 3-CF₃—Ph | 586.4 |
| 86 | H | CH(CH₃)₂ | 2,3-(C₄H₄) | 3-CF₃—Ph | 599.8 |
| 87 | H | CH₃ | 2,3-(C₄H₄) | Ph | 503.0 (ES−) |
| 88 | H | CH₃ | 2,3-(C₄H₄) | 3-5-(CF₃)₂—Ph | 641.5 |
| 89 | H | CH₃ | 2,3-(C₄H₄) | 3-5-(CH₃)₂—Ph | 532.6 |
| 90 | H | CH₃ | 2,3-(C₄H₄) | 3-CF₃-4-Cl—Ph | 606.4 |
| 91 | H | CH₃ | 2,3-(C₄H₄) | CH₂Ph | 518.2 |
| 92 | H | CH₃ | 2,3-(C₄H₄) | CH₂(4-CH₃—Ph) | 532.6 |
| 93 | H | CH₃ | 2,3-(C₄H₄) | 3-CF₃-6-Cl—Ph | 606.1 |
| 94 | H | CH₃ | 2,3-(C₄H₄) | 3-Cl-2-OCH₃—Ph | 568.5 |
| 95 | H | CH₃ | 2,3-(C₄H₄) | 3-CH₃-2-OCH₃—Ph | 548.2 |
| 96 | H | CH₃ | 2,3-(C₄H₄) | 3-Cl-5-CH₃—Ph | 552.6 |
| 97 | H | CH₃ | 2,3-(C₄H₄) | 3-F—Ph | 519.7 (ES−) |
| 98 | H | CH₃ | 2,3-(C₄H₄) | 3-CH₃—Ph | 518.2 |
| 99 | H | CH₃ | 2,3-(C₄H₄) | 2-OCH₃—Ph | 534.6 |
| 100 | H | CH₃ | 2,3-(C₄H₄) | 4-CF₃—Ph | 570.3 (ES−) |
| 101 | Ac | CH₃ | 2,3-(C₄H₄) | 2-CF₃—Ph | 614.5 |
| 102 | H | CH₃ | 2,3-(C₄H₄) | 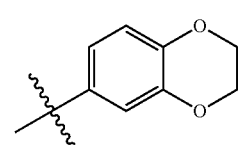 [SMILES: *c1ccc2c(c1)OCCO2] | 616.6 |
| 103 | H | CH₃ | 2,3-(C₄H₄) | 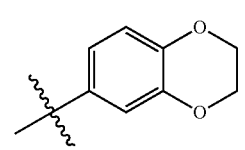 [SMILES: *c1ccc2c(c1)OCCO2] | 562.5 |
| 104 | H | CH₃ | 3-F | 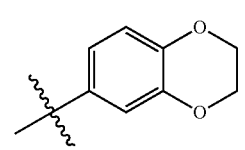 [SMILES: *c1ccc2c(c1)OCCO2] | 530.5 |

TABLE 3-continued

| | | | | | |
|---|---|---|---|---|---|
| 105 | H | CH₃ | 3-F | 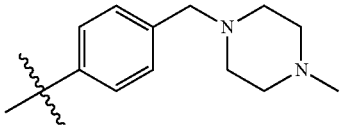 [SMILES: *c1ccc(CN2CCN(C)CC2)cc1] | 584.6 |
| 106 | CH₃ | CH₂CH₃ | 2,3-(C₄H₄) | 3-CF₃—Ph | 600.1 |
| 107 | CH₃ | CH(CH₃)₂ | 2,3-(C₄H₄) | 3-CF₃—Ph | 614.4 |
| 108 | CH₃ | CH₂CH₃ | 3-F | 3-CF₃—Ph | 568.6 |
| 109 | CH₃ | CH(CH₃)₂ | 3-F | 3-CF₃—Ph | 582.6 |
| 110 | CH₃ | CH₃ | 3-F | 3-CF₃—Ph | 554.7 |
| 111 | CH₃ | CH₃ | 3-CH₃ | 3-CF₃—Ph | 550.6 |
| 112 | CH₃ | CH₃ | 2-CH₃ | 3-CF₃—Ph | 550.6 |
| 113 | CH₃ | CH₃ | 3-F,6-CH₃ | 3-CF₃—Ph | 568.5 |
| 114 | CH₃ | CH₃ | 3-F,6-OCH₃ | 3-CF₃—Ph | 584.2 |
| 115 | CH₃ | CH₃ | 2,3-(C₄H₄) | 3-CH₃—Ph | 532.4 |
| 116 | CH₃ | CH₃ | 2,3-(C₄H₄) | 3-F—Ph | 536.7 |
| 117 | CH₃ | CH₂CH₃ | 2,3-(C₄H₄) | 3-F | 550.6 |
| 118 | CH₃ | CH₂CH₃ | 2,3-(C₄H₄) | 3-CH₃ | 546.8 |
| 119 | CH₃ | CH(CH₃)₂ | 2,3-(C₄H₄) | 3-CH₃ | 560.8 |
| 120 | CH₃ | CH(CH₃)₂ | 2,3-(C₄H₄) | 3-F | 564.7 |
| 122 | CH₃ | CH(CH₃)₂ | 2,3-(C₄H₄) | 3-pyridyl | 547.5 |
| 125 | CH₃ | CH(CH₃)₂ | 3-F | 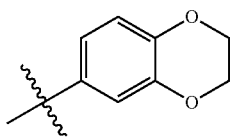 [SMILES: *c1ccc2c(c1)OCCO2] | 572.3 |
| 126 | CH₃ | CH₂CH₃ | 3-F | 3-F—Ph | 518.4 |
| 129 | CH₃ | CH(CH₃)₂ | 3-F | 3-F—Ph | 532.4 |
| 130 | CH₃ | CH(CH₃)₂ | 3-F | Ph | 514.4 |
| 131 | CH₃ | CH(CH₃)₂ | 2,3-(C₄H₄) | 2-pyridyl | 547.5 |
| 132 | CH₃ | CH(CH₃)₂ | 3-OCH₃ | 3-F—Ph | 544.5 |
| 133 | CH₃ | CH(CH₃)₂ | 2-F | Ph | 514.5 |
| 134 | CH₃ | CH(CH₃)₂ | 2-F | 3-F—Ph | 532.4 |
| 135 | CH₃ | CH(CH₃)₂ | H | 3-pyridyl | 497.4 |
| 136 | CH₃ | CH(CH₃)₂ | 2,3-(C₄H₄) | 3-F,5-CN—Ph | 589.4 |
| 138 | CH₃ | CH(CH₃)₂ | 3-F | 3-pyridyl | 515.3 |
| 139 | CH₃ | CH(CH₃)₂ | 2,3-(C₄H₄) | CH₂—Ph | 560.4 |
| 140 | CH₃ | CH(CH₃)₂ | 2,3-(C₄H₄) | 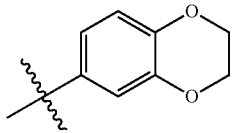 [SMILES: *c1ccc2c(c1)OCCO2] | 604.4 |
| 141 | CH₃ | CH(CH₃)₂ | 2,3-(C₄H₄) | 3-OCH₃—Ph | 576.4 |
| 142 | CH₃ | CH(CH₃)₂ | 2,3-(C₄H₄) | 3-CN—Ph | 571.4 |
| 143 | CH₃ | CH(CH₃)₂ | 2,3-(C₄H₄) | 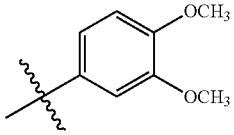 [SMILES: *c1ccc(OC)c(OC)c1] | 606.3 |
| 144 | CH₃ | CH(CH₃)₂ | 2,3-(C₄H₄) | 4-pyridyl | 547.4 |
| 145 | CH₃ | CH(CH₃)₂ | 2,3-(C₄H₄) | 4-F—Ph | 564.4 |
| 146 | CH₃ | CH(CH₃)₂ | 2,3-(C₄H₄) | 3-F,5-CH₃O—Ph | 562.3 |
| 147 | CH₃ | CH₃ | 2,3-(C₄H₄) | 3-pyridyl | 519.3 |
| 148 | CH₃ | CH(CH₃)₂ | 3-F | 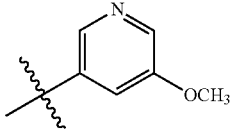 [SMILES: *c1cncc(OC)c1] | 545.3 |

TABLE 3-continued
| Ex. | R" | R² | | Y | LCMS m/z (M + H) |
|---|---|---|---|---|---|
| 149 | CH₃ | CH(CH₃)₂ | 3-F | 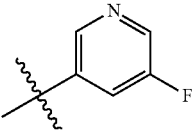 [SMILES: *c1cncc(F)c1] | 533.3 |
| 150 | CH₃ | CH(CH₃)₂ | 2,3-(C₄H₄) | 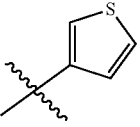 [SMILES: *c1ccsc1] | 552.4 |
| 151 | CH₃ | CH(CH₃)₂ | 2,3-(C₄H₄) | 3,5-Di-F—Ph | 582.4 |
| 152 | CH₃ | CH(CH₃)₂ | 2,3-(C₄H₄) | 2-F—Ph | 564.5 |
| 153 | CH₃ | CH(CH₃)₂ | 3-CH₃ | 3-pyridyl | 511.3 |
| 154 | CH₃ | CH(CH₃)₂ | 3-Cl | 3-pyridyl | 529.3 |
| 155 | CH₃ | CH(CH₃)₂ | 2,3-(C₄H₄) | Ph | 531.4 |
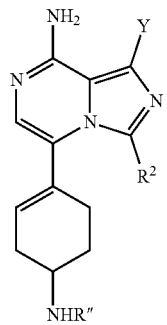
| Ex. | R" | R² | Y | LCMS m/z (M + H) |
|---|---|---|---|---|
| 123 | CH₃ | CH(CH₃)₂ | 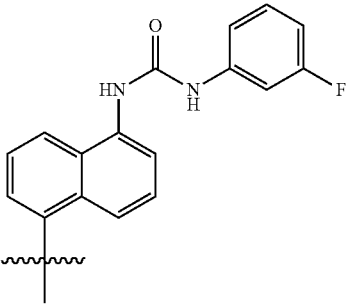 [SMILES: *c1cccc2c(NC(=O)Nc3cccc(F)c3)cccc12] | 564.5 |
| 124 | CH₃ | CH(CH₃)₂ | 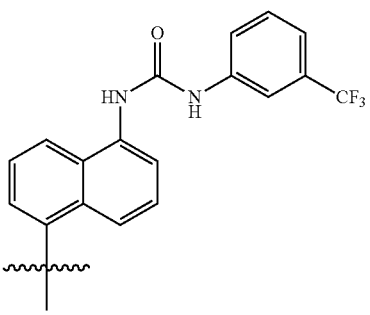 [SMILES: *c1cccc2c(NC(=O)Nc3cccc(C(F)(F)F)c3)cccc12] | 614.3 |

TABLE 3-continued

| 127 | CH₃ | CH(CH₃)₂ | 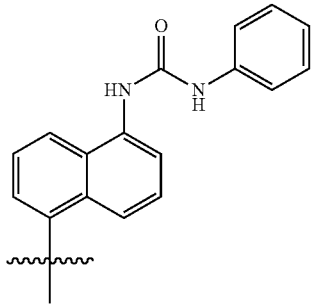 [SMILES: *c1cccc2c(NC(=O)Nc3ccccc3)cccc12] | 546.3 |
| 128 | CH₃ | CH(CH₃)₂ | 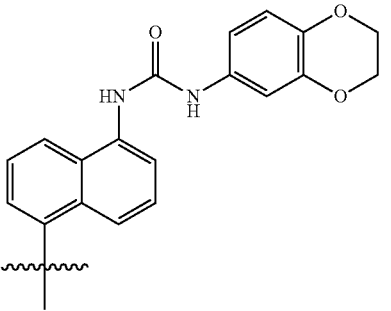 [SMILES: *c1cccc2c(NC(=O)Nc3ccc4c(c3)OCCO4)cccc12] | 604.3 |
| 137 | CH₃ | CH(CH₃)₂ | 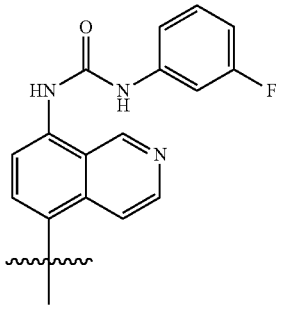 [SMILES: *c1ccc(NC(=O)Nc2cccc(F)c2)c2cnccc12] | 565.4 |

Example 83: 3-{4-[8-amino-5-(4-aminocyclohex-1-en-1-yl)-3-methylimidazo[1,5-a]pyrazin-1-yl]naphthalen-1-yl}-1-[3-(trifluoromethyl)phenyl]urea Example 84: 3-(4-{8-amino-3-methyl-5-[4-(methylamino)cyclohex-1-en-1-yl]imidazo[1,5-a]pyrazin-1-yl}naphthalen-1-yl)-1-[3-(trifluoromethyl)phenyl]urea Example 85: 1-(4-(8-amino-5-(4-aminocyclohex-1-en-1-yl)-3-ethylimidazo[1,5-a]pyrazin-1-yl)naphthalen-1-yl)-3-(3-(trifluoromethyl)phenyl)urea Example 86: 3-{4-[8-amino-5-(4-aminocyclohex-1-en-1-yl)-3-(propan-2-yl)imidazo[1,5-a]pyrazin-1-yl]naphthalen-1-yl}-1-[3-(trifluoromethyl)phenyl]urea Example 87: 1-(4-(8-amino-5-(4-aminocyclohex-1-en-1-yl)-3-methylimidazo[1,5-a]pyrazin-1-yl)naphthalen-1-yl)-3-phenylurea Example 88: 3-{4-[8-amino-5-(4-aminocyclohex-1-en-1-yl)-3-methylimidazo[1,5-a]pyrazin-1-yl]naphthalen-1-yl}-1-[3,5-bis(trifluoromethyl)phenyl]urea Example 89: 3-{4-[8-amino-5-(4-aminocyclohex-1-en-1-yl)-3-methylimidazo[1,5-a]pyrazin-1-yl]naphthalen-1-yl}-1-(3,5-dimethylphenyl)urea Example 90: 3-{4-[8-amino-5-(4-aminocyclohex-1-en-1-yl)-3-methylimidazo[1,5-a]pyrazin-1-yl]naphthalen-1-yl}-1-[4-chloro-3-(trifluoromethyl)phenyl]urea Example 91: 1-(4-(8-amino-5-(4-aminocyclohex-1-en-1-yl)-3-methylimidazo[1,5-a]pyrazin-1-yl)naphthalen-1-yl)-3-benzylurea Example 92: 3-{4-[8-amino-5-(4-aminocyclohex-1-en-1-yl)-3-methylimidazo[1,5-a]pyrazin-1-yl]naphthalen-1-yl}-1-[(4-methylphenyl)methyl]urea Example 93: 1-(4-(8-amino-5-(4-aminocyclohex-1-en-1-yl)-3-methylimidazo[1,5-a]pyrazin-1-yl)naphthalen-1-yl)-3-(2-chloro-5-(trifluoromethyl)phenyl)urea Example 94: 1-{4-[8-amino-5-(4-aminocyclohex-1-en-1-yl)-3-methylimidazo[1,5-a]pyrazin-1-yl]naphthalen-1-yl}-3-(5-chloro-2-methoxyphenyl)urea Example 95: 1-{4-[8-amino-5-(4-aminocyclohex-1-en-1-yl)-3-methylimidazo[1,5-a]pyrazin-1-yl]naphthalen-1-yl}-3-(2-methoxy-5-methylphenyl)urea Example 96: 3-{4-[8-amino-5-(4-aminocyclohex-1-en-1-yl)-3-methylimidazo[1,5-a]pyrazin-1-yl]naphthalen-1-yl}-1-(5-chloro-2-methylphenyl)urea Example 97: 3-{4-[8-amino-5-(4-aminocyclohex-1-en-1-yl)-3-methylimidazo[1,5-a]pyrazin-1-yl]naphthalen-1-yl}-1-(3-fluorophenyl)urea Example 98: 1-(4-(8-amino-5-(4-aminocyclohex-1-en-1-yl)-3-methylimidazo[1,5-a]pyrazin-1-yl)naphthalen-1-yl)-3-(m-tolyl)urea Example 99: 1-{4-[8-amino-5-(4-aminocyclohex-1-en-1-yl)-3-methylimidazo[1,5-a]pyrazin-1-yl]naphthalen-1-yl}-3-(2-methoxyphenyl)urea Example 100: 3-{4-[8-amino-5-(4-aminocyclohex-1-en-1-yl)-3-methylimidazo[1,5-a]pyrazin-1-yl]naphthalen-1-yl}-1-[4-(trifluoromethyl)phenyl]urea Example 101: N-(4-{8-amino-3-methyl-1-[4-({[3-(trifluoromethyl)phenyl]carbamoyl}amino)naphthalen-1-yl]imidazo[1,5-a]pyrazin-5-yl}cyclohex-3-en-1-yl)acetamide Example 102: 1-{4-[8-amino-5-(4-aminocyclohex-1-en-1-yl)-3-methylimidazo[1,5-a]pyrazin-1-yl]naphthalen-1-yl}-3-{4-[(4-methylpiperazin-1-yl)methyl]phenyl}urea Example 103: 3-{4-[8-amino-5-(4-aminocyclohex-1-en-1-yl)-3-methylimidazo[1,5-a]pyrazin-1-yl]naphthalen-1-yl}-1-(2,3-dihydro-1,4-benzodioxin-6-yl)urea Example 104: 3-{4-[8-amino-5-(4-aminocyclohex-1-en-1-yl)-3-methylimidazo[1,5-a]pyrazin-1-yl]-3-fluorophenyl}-1-(2,3-dihydro-1,4-benzodioxin-6-yl)urea Example 105: 1-{4-[8-amino-5-(4-aminocyclohex-1-en-1-yl)-3-methylimidazo[1,5-a]pyrazin-1-yl]-3-fluorophenyl}-3-{4-[(4-methylpiperazin-1-yl)methyl]phenyl}urea Example 106: 3-(4-{8-amino-3-ethyl-5-[4-(methylamino)cyclohex-1-en-1-yl]imidazo[1,5-a]pyrazin-1-yl}naphthalen-1-yl)-1-[3-(trifluoromethyl)phenyl]urea Example 107: 1-(4-(8-amino-3-isopropyl-5-(4-(methylamino)cyclohex-1-en-1-yl)imidazo[1,5-a]pyrazin-1-yl)naphthalen-1-yl)-3-(3-(trifluoromethyl)phenyl)urea Example 108: 3-(4-{8-amino-3-ethyl-5-[4-(methylamino)cyclohex-1-en-1-yl]imidazo[1,5-a]pyrazin-1-yl}-3-fluorophenyl)-1-[3-(trifluoromethyl)phenyl]urea Example 109: 3-(4-{8-amino-5-[4-(methylamino)cyclohex-1-en-1-yl]-3-(propan-2-yl)imidazo[1,5-a]pyrazin-1-yl}-3-fluorophenyl)-1-[3-(trifluoromethyl)phenyl]urea Example 110: 3-(4-{8-amino-3-methyl-5-[4-(methylamino)cyclohex-1-en-1-yl]imidazo[1,5-a]pyrazin-1-yl}-3-fluorophenyl)-1-[3-(trifluoromethyl)phenyl]urea Example 111: 3-(4-{8-amino-3-methyl-5-[4-(methylamino)cyclohex-1-en-1-yl]imidazo[1,5-a]pyrazin-1-yl}-3-methylphenyl)-1-[3-(trifluoromethyl)phenyl]urea Example 112: 3-(4-{8-amino-3-methyl-5-[4-(methylamino)cyclohex-1-en-1-yl]imidazo[1,5-a]pyrazin-1-yl}-2-methylphenyl)-1-[3-(trifluoromethyl)phenyl]urea Example 113: 3-(4-{8-amino-3-methyl-5-[4-(methylamino)cyclohex-1-en-1-yl]imidazo[1,5-a]pyrazin-1-yl}-5-fluoro-2-methylphenyl)-1-[3-(trifluoromethyl)phenyl]urea Example 114: 3-(4-{8-amino-3-methyl-5-[4-(methylamino)cyclohex-1-en-1-yl]imidazo[1,5-a]pyrazin-1-yl}-5-fluoro-2-methoxyphenyl)-1-[3-(trifluoromethyl)phenyl]urea Example 115: 3-(4-{8-amino-3-methyl-5-[4-(methylamino)cyclohex-1-en-1-yl]imidazo[1,5-a]pyrazin-1-yl}naphthalen-1-yl)-1-(3-methylphenyl)urea Example 116: 3-(4-{8-amino-3-methyl-5-[4-(methylamino)cyclohex-1-en-1-yl]imidazo[1,5-a]pyrazin-1-yl}naphthalen-1-yl)-1-(3-fluorophenyl)urea Example 117: 3-(4-{8-amino-3-ethyl-5-[4-(methylamino)cyclohex-1-en-1-yl]imidazo[1,5-a]pyrazin-1-yl}naphthalen-1-yl)-1-(3-fluorophenyl)urea Example 118: 3-(4-{8-amino-3-ethyl-5-[4-(methylamino)cyclohex-1-en-1-yl]imidazo[1,5-a]pyrazin-1-yl}naphthalen-1-yl)-1-(3-methylphenyl)urea Example 119: 3-(4-{8-amino-5-[4-(methylamino)cyclohex-1-en-1-yl]-3-(propan-2-yl)imidazo[1,5-a]pyrazin-1-yl}naphthalen-1-yl)-1-(3-methylphenyl)urea Example 120: 3-(4-{8-amino-5-[4-(methylamino)cyclohex-1-en-1-yl]-3-(propan-2-yl)imidazo[1,5-a]pyrazin-1-yl}naphthalen-1-yl)-1-(3-fluorophenyl)urea Example 122: 1-(4-(8-amino-3-isopropyl-5-(4-(methylamino)cyclohex-1-en-1-yl)imidazo[1,5-a]pyrazin-1-yl)naphthalen-1-yl)-3-(pyridin-3-yl)urea Example 123: 1-(5-(8-amino-3-isopropyl-5-(4-(methylamino)cyclohex-1-en-1-yl)imidazo[1,5-a]pyrazin-1-yl)naphthalen-1-yl)-3-(3-fluorophenyl)urea Example 124: 1-(5-(8-amino-3-isopropyl-5-(4-(methylamino)cyclohex-1-en-1-yl)imidazo[1,5-a]pyrazin-1-yl)naphthalen-1-yl)-3-(3-(trifluoromethyl)phenyl)urea Example 125: 1-(4-(8-amino-3-isopropyl-5-(4-(methylamino)cyclohex-1-en-1-yl)imidazo[1,5-a]pyrazin-1-yl)-3-fluorophenyl)-3-(2,3-dihydrobenzo[b][1,4]dioxin-6-yl)urea Example 126: 1-(4-(8-amino-3-ethyl-5-(4-(methylamino)cyclohex-1-en-1-yl)imidazo[1,5-a]pyrazin-1-yl)-3-fluorophenyl)-3-(3-fluorophenyl)urea Example 127: 1-(5-(8-amino-3-isopropyl-5-(4-(methylamino)cyclohex-1-en-1-yl)imidazo[1,5-a]pyrazin-1-yl)naphthalen-1-yl)-3-phenylurea Example 128: 1-(5-(8-amino-3-isopropyl-5-(4-(methylamino)cyclohex-1-en-1-yl)imidazo[1,5-a]pyrazin-1-yl)naphthalen-1-yl)-3-(2,3-dihydrobenzo[b][1,4]dioxin-6-yl)urea Example 129: 1-(4-(8-amino-3-isopropyl-5-(4-(methylamino)cyclohex-1-en-1-yl)imidazo[1,5-a]pyrazin-1-yl)-3-fluorophenyl)-3-(3-fluorophenyl)urea Example 130: 1-(4-(8-amino-3-isopropyl-5-(4-(methylamino)cyclohex-1-en-1-yl)imidazo[1,5-a]pyrazin-1-yl)-3-fluorophenyl)-3-phenylurea Example 131: 1-(4-(8-amino-3-isopropyl-5-(4-(methylamino)cyclohex-1-en-1-yl)imidazo[1,5-a]pyrazin-1-yl)naphthalen-1-yl)-3-(pyridin-2-yl)urea Example 132: 1-(4-(8-amino-3-isopropyl-5-(4-(methylamino)cyclohex-1-en-1-yl)imidazo[1,5-a]pyrazin-1-yl)-3-methoxyphenyl)-3-(3-fluorophenyl)urea Example 133: 1-(4-(8-amino-3-isopropyl-5-(4-(methylamino)cyclohex-1-en-1-yl)imidazo[1,5-a]pyrazin-1-yl)-2-fluorophenyl)-3-phenylurea Example 134: 1-(4-(8-amino-3-isopropyl-5-(4-(methylamino)cyclohex-1-en-1-yl)imidazo[1,5-a]pyrazin-1-yl)-2-fluorophenyl)-3-(3-fluorophenyl)urea Example 135: 1-(4-(8-amino-3-isopropyl-5-(4-(methylamino)cyclohex-1-en-1-yl)imidazo[1,5-a]pyrazin-1-yl)phenyl)-3-(pyridin-3-yl)urea Example 136: 1-(4-(8-amino-3-isopropyl-5-(4-(methylamino)cyclohex-1-en-1-yl)imidazo[1,5-a]pyrazin-1-yl)naphthalen-1-yl)-3-(3-cyano-5-fluorophenyl)urea Example 137: 1-(5-(8-amino-3-isopropyl-5-(4-(methylamino)cyclohex-1-en-1-yl)imidazo[1,5-a]pyrazin-1-yl)isoquinolin-8-yl)-3-(3-fluorophenyl)urea Example 138: 1-(4-(8-amino-3-isopropyl-5-(4-(methylamino)cyclohex-1-en-1-yl)imidazo[1,5-a]pyrazin-1-yl)-3-fluorophenyl)-3-(pyridin-3-yl)urea Example 139: 1-(4-(8-amino-3-isopropyl-5-(4-(methylamino)cyclohex-1-en-1-yl)imidazo[1,5-a]pyrazin-1-yl)naphthalen-1-yl)-3-benzylurea Example 140: 1-(4-(8-amino-3-isopropyl-5-(4-(methylamino)cyclohex-1-en-1-yl)imidazo[1,5-a]pyrazin-1-yl)naphthalen-1-yl)-3-(2,3-dihydrobenzo[b][1,4]dioxin-6-yl)urea Example 141: 1-(4-(8-amino-3-isopropyl-5-(4-(methylamino)cyclohex-1-en-1-yl)imidazo[1,5-a]pyrazin-1-yl)naphthalen-1-yl)-3-(3-methoxyphenyl)urea Example 142: 1-(4-(8-amino-3-isopropyl-5-(4-(methylamino)cyclohex-1-en-1-yl)imidazo[1,5-a]pyrazin-1-yl)naphthalen-1-yl)-3-(3-cyanophenyl)urea Example 143: 1-(4-(8-amino-3-isopropyl-5-(4-(methylamino)cyclohex-1-en-1-yl)imidazo[1,5-a]pyrazin-1-yl)naphthalen-1-yl)-3-(3,4-dimethoxyphenyl)urea Example 144: 1-(4-(8-amino-3-isopropyl-5-(4-(methylamino)cyclohex-1-en-1-yl)imidazo[1,5-a]pyrazin-1-yl)naphthalen-1-yl)-3-(pyridin-4-yl)urea Example 145: 1-(4-(8-amino-3-isopropyl-5-(4-(methylamino)cyclohex-1-en-1-yl)imidazo[1,5-a]pyrazin-1-yl)naphthalen-1-yl)-3-(4-fluorophenyl)urea Example 146: 1-(4-(8-amino-3-isopropyl-5-(4-(methylamino)cyclohex-1-en-1-yl)imidazo[1,5-a]pyrazin-1-yl)-3-fluorophenyl)-3-(3-fluoro-5-methoxyphenyl)urea Example 147: 1-(4-(8-amino-3-methyl-5-(4-(methylamino)cyclohex-1-en-1-yl)imidazo[1,5-a]pyrazin-1-yl)naphthalen-1-yl)-3-(pyridin-3-yl)urea Example 148: 1-(4-(8-amino-3-isopropyl-5-(4-(methylamino)cyclohex-1-en-1-yl)imidazo[1,5-a]pyrazin-1-yl)-3-fluorophenyl)-3-(5-methoxypyridin-3-yl)urea Example 149: 1-(4-(8-amino-3-isopropyl-5-(4-(methylamino)cyclohex-1-en-1-yl)imidazo[1,5-a]pyrazin-1-yl)-3-fluorophenyl)-3-(5-fluoropyridin-3-yl)urea Example 150: 1-(4-(8-amino-3-isopropyl-5-(4-(methylamino)cyclohex-1-en-1-yl)imidazo[1,5-a]pyrazin-1-yl)naphthalen-1-yl)-3-(thiophen-3-yl)urea Example 151: 1-(4-(8-amino-3-isopropyl-5-(4-(methylamino)cyclohex-1-en-1-yl)imidazo[1,5-a]pyrazin-1-yl)naphthalen-1-yl)-3-(3,5-difluorophenyl)urea Example 152: 1-(4-(8-amino-3-isopropyl-5-(4-(methylamino)cyclohex-1-en-1-yl)imidazo[1,5-a]pyrazin-1-yl)naphthalen-1-yl)-3-(2-fluorophenyl)urea Example 153: 1-(4-(8-amino-3-isopropyl-5-(4-(methylamino)cyclohex-1-en-1-yl)imidazo[1,5-a]pyrazin-1-yl)-3-methylphenyl)-3-(pyridin-3-yl)urea Example 154: 1-(4-(8-amino-3-isopropyl-5-(4-(methylamino)cyclohex-1-en-1-yl)imidazo[1,5-a]pyrazin-1-yl)-3-chlorophenyl)-3-(pyridin-3-yl)urea Example 155: 1-(4-(3-isopropyl-5-(4-(methylamino)cyclohex-1-en-1-yl)imidazo[1,5-a]pyrazin-1-yl)naphthalen-1-yl)-3-phenylurea

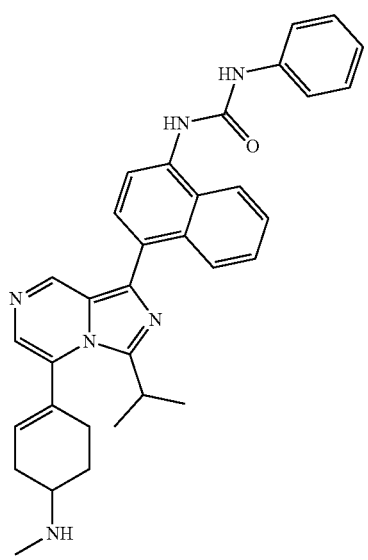 [SMILES: CNC1CC=C(c2cncc3c(-c4ccc(NC(=O)Nc5ccccc5)c5ccccc45)nc(C(C)C)n23)CC1]

Step 1: tert-Butyl (4-(1-bromo-3-isopropylimidazo[1,5-a]pyrazin-5-yl)cyclohex-3-en-1-yl)(methyl)carbamate To a solution of tert-butyl (4-(8-amino-1-bromo-3-isopropylimidazo[1,5-a]pyrazin-5-yl)cyclohex-3-en-1-yl)(methyl)carbamate 5E (0.30 g, 0.648 mmol) in THF (6 mL) in two reaction tubes was added tert-butyl nitrite (0.31 mL, 2.57 mmol) and the mixture was heated at 60° C. for 30 min. The mixture was cooled to RT and concentrated in vacuo. The residue was purified by silica-gel chromatography, eluting with 0-100% EtOAc in isohexane to provide the title compound (0.22 g, 76%). LC-MS: Rt=1.70 min, m/z=449.2 [M($^{79}$Br)+H]$^+$.

Step 2: tert-Butyl (4-(3-isopropyl-1-(4-(3-phenylureido)naphthalen-1-yl)imidazo[1,5-a]pyrazin-5-yl)cyclohex-3-en-1-yl)(methyl)carbamate A mixture of tert-butyl (4-(1-bromo-3-isopropylimidazo[1,5-a]pyrazin-5-yl)cyclohex-3-en-1-yl)(methyl)carbamate (Example 155, Step 1) (0.21 g, 0.47 mmol), 1-phenyl-3-(4-(4,4,5,5-tetramethyl-1,3,2-dioxaborolan-2-yl)naphthalen-1-yl) urea 6C (0.20 g, 0.52 mmol) and cesium carbonate (0.5038 g, 1.55 mmol) in DME (4.5 mL) and water (1.15 mL) was purged with nitrogen for 2 min then PdCl$_2$(dppf).DCM (19.1 mg, 0.023 mmol) was added. The mixture was purged for a further 30 sec then heated at 90° C. overnight. The reaction mixture was partitioned between EtOAc and brine. The aqueous layer was extracted further with EtOAc (2×) and the combined organic extracts were dried (MgSO$_4$), filtered and concentrated in vacuo. The residue was purified by silica-gel chromatography, eluting with 0-100% EtOAc in isohexane to give the title compound (0.1021 g, 35%). LC-MS: Rt=1.61 min, m/z=631.4 [M+H]$^+$.

Step 3: 1-(4-(3-isopropyl-5-(4-(methylamino)cyclohex-1-en-1-yl)imidazo[1,5-a]pyrazin-1-yl)naphthalen-1-yl)-3-phenylurea (Example 155)

The title compound was prepared from tert-butyl (4-(3-isopropyl-1-(4-(3-phenylureido)naphthalen-1-yl)imidazo[1,5-a]pyrazin-5-yl)cyclohex-3-en-1-yl)(methyl)carbamate (Example 155, Step 2) (100 mg, 0.16 mmol) using a similar method to that described for Example 121, Step 4 to give the product as a yellow-orange solid (12 mg, 14%). QC LC-MS (Method 1): Rt=2.65 min, m/z=531.4 [M+H]$^+$.

Another set of compounds in this invention can be made according to the chemistry outlined in Scheme 7. Treatment of 2-(4-bromonaphthalen-1-yl)acetic acid 7A with a phenylene diamine such as 2,3-diaminotoluene gives the amide intermediate 7B, which can be converted to the benzimidazole 7C using standard conditions. 7C can be converted to the boronate 7 D which undergoes Pd(0)-catalyzed coupling with a heterocyclic bromide as before to give a coupling product such as 7E. Acid deprotection affords the final product 7F.

Scheme 7

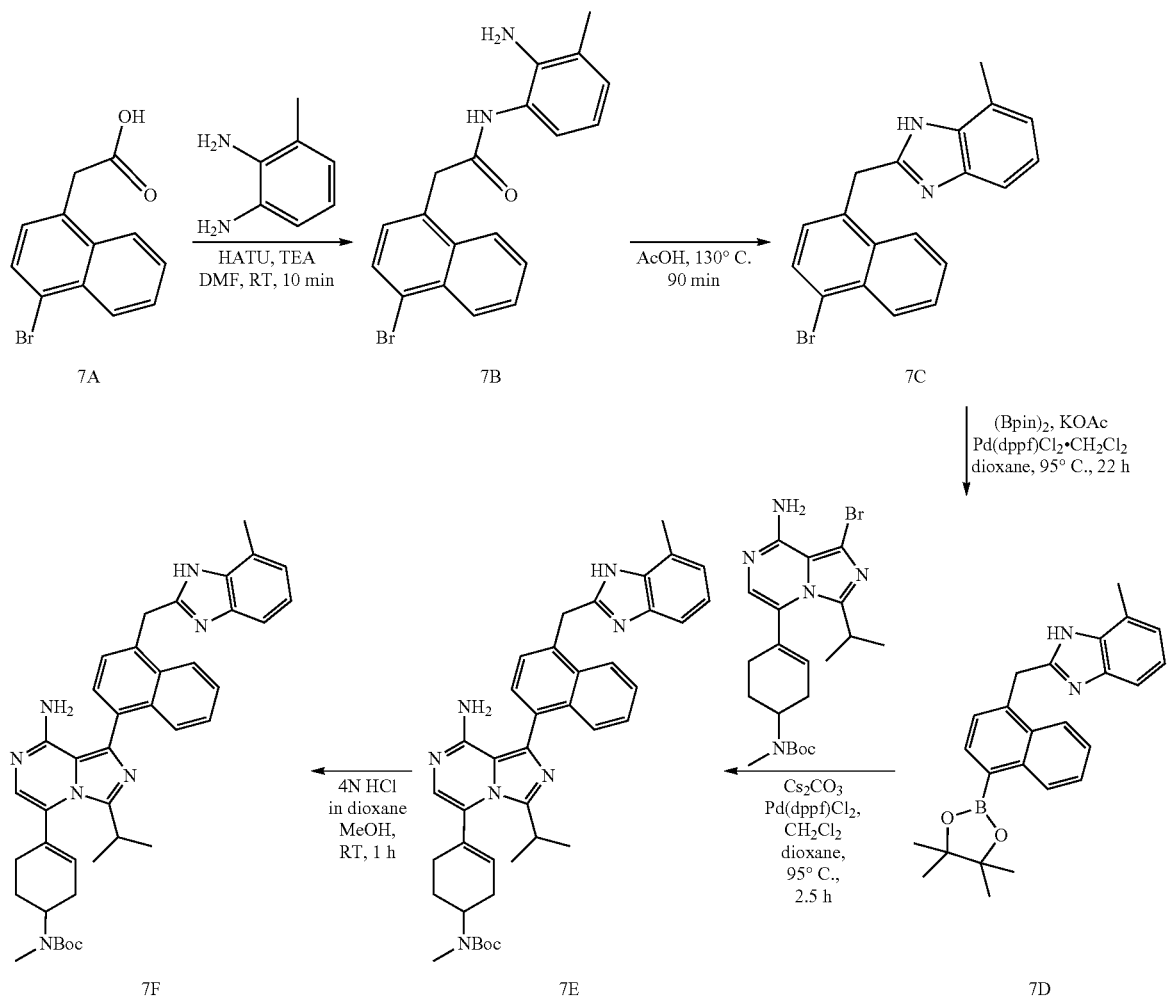

Example 156: 3-Isopropyl-1-(4-((7-methyl-1H-benzo[d]imidazol-2-yl)methyl)naphthalen-1-yl)-5-(4-(methylamino)cyclohex-1-en-1-yl)imidazo[1,5-a]pyrazin-8-amine 7F Step 1: N-(2-Amino-3-methylphenyl)-2-(4-bromonaphthalen-1-yl)acetamide 7B To a solution of 2-(4-bromonaphthalen-1-yl)acetic acid (5.00 g, 18.9 mmol), 2,3-diaminotoluene (3.46 g, 28.3 mmol) and TEA (5.3 mL, 37.7 mmol) in DMF (75 mL) was added HATU (7.89 g, 20.8 mmol) and the resulting solution was stirred at RT for 10 min. The mixture was poured into water (750 mL) and the resulting solid was collected by filtration, washed with water and dried under vacuum overnight. The solid was then washed with Et$_2$O-MeCN (3:1) and dried under vacuum at 40° C. to provide the title compound 7B as a tan solid (6.39 g, 92%). LC-MS (Method 1): Rt=1.85 and 1.95 min, m/z=369.1 [M($^{79}$Br)+H]$^+$.

Step 2: 2-((4-Bromonaphthalen-1-yl)methyl)-7-methyl-1H-benzo[d]imidazole 7C

A solution of N-(2-amino-3-methylphenyl)-2-(4-bromonaphthalen-1-yl)acetamide 7B (6.39 g, 17.3 mmol) in glacial acetic acid (100 mL) was heated at 130° C. for 90 min. After allowing to cool to RT, the solvent was concentrated in vacuo and the residue was taken up in EtOAc and washed with 1 N NaOH (×2), then brine, dried (Na$_2$SO$_4$), filtered, and concentrated in vacuo. The resulting solid was triturated with water, collected by filtration, washed with water and dried under vacuum at 40° C. to give the title compound 7C as a tan solid (5.86 g, 96%). LC-MS (Method 1): Rt=1.36 min, m/z=351.0 [M($^{79}$Br)+H]$^+$.

Step 3: 7-Methyl-2-((4-(4,4,5,5-tetramethyl-1,3,2-dioxaborolan-2-yl)naphthalen-1-yl)methyl)-1H-benzo[d]imidazole 7 D A mixture of 2-((4-bromonaphthalen-1-yl)methyl)-7-methyl-1H-benzo[d]imidazole 7C (5.86 g, 16.7 mmol), bis(pinacolato)diboron (6.35 g, 25.0 mmol), PdCl$_2$(dppf).DCM (680 mg, 0.84 mmol) and potassium acetate (4.09 g, 41.7 mmol) in dioxane (150 mL) was purged with argon for 10 min then heated at 95° C. for 22 h. After allowing to cool to RT, the solvent was concentrated in vacuo and the residue was diluted with EtOAc, washed with water then brine, dried (Na$_2$SO$_4$), filtered, and concentrated in vacuo. The residue was purified by silica-gel chromatography, eluting with 25% EtOAc in isohexane. The residue was taken up in a minimal volume of EtOAc and a solid was precipitated by adding isohexane. The solid was collected by filtration, washed with isohexane and dried under vacuum at 45° C. to give the title compound 7D as a tan solid, (5.08 g, 76%). LC-MS (Method 1): Rt=1.54 min, m/z=399.2 [M+H]$^+$.

Step 4: tert-Butyl (4-(8-amino-3-isopropyl-1-(4-((7-methyl-1H-benzo[d]imidazol-2-yl)methyl)naphthalen-1-yl)imidazo[1,5-a]pyrazin-5-yl)cyclohex-3-en-1-yl)(methyl)carbamate 7E A mixture of tert-butyl (4-(8-amino-1-bromo-3-isopropylimidazo[1,5-a]pyrazin-5-yl)cyclohex-3-en-1-yl)(methyl) carbamate 5E (5.08 g, 10.9 mmol), 7-methyl-2-((4-(4,4,5,5-tetramethyl-1,3,2-dioxaborolan-2-yl)naphthalen-1-yl) methyl)-1H-benzo[d]imidazole 7 D (5.66 g, 14.2 mmol), PdCl$_2$(dppf).DCM (0.89 g, 1.09 mmol) and cesium carbonate (10.68 g, 32.8 mmol) in 1,4-dioxane (100 mL) was purged with argon for 10 min, then heated at 95° C. for 2.5 h. The reaction mixture was allowed to cool to RT, diluted with EtOAc (200 mL) and washed with water, then brine, dried (Na$_2$SO4), filtered and concentrated in vacuo. The residue was purified by silica-gel chromatography, eluting with 0-10% 2 N NH$_3$ in MeOH/DCM, then re-purified by silica-gel chromatography, eluting with 0-15% MeOH/ EtOAc, to provide the title compound 7E as an orange solid (5.35 g, 75%). LC-MS (Method 1): Rt=1.33 min, m/z=656.4 [M+H]$^+$.

Step 5: 3-Isopropyl-1-(4-((7-methyl-1H-benzo[d] imidazol-2-yl)methyl)naphthalen-1-yl)-5-(4-(methylamino)cyclohex-1-en-1-yl)imidazo[1,5-a]pyrazin-8-amine (Example 156) 7F To a mixture of tert-butyl (4-(8-amino-3-isopropyl-1-(4-((7-methyl-1H-benzo[d]imidazol-2-yl)methyl)naphthalen-1-yl)imidazo[1,5-a]pyrazin-5-yl)cyclohex-3-en-1-yl) (methyl)carbamate 7E (5.35 g, 8.16 mmol) in methanol (20 mL) was added 4 N HCl in 1,4-dioxane (20.4 mL, 81.6 mmol) and the resulting solution was stirred at RT for 60 min, during which time a solid precipitated. The solvent was concentrated in vacuo and the residue was dissolved in a minimal amount of water, filtered, and then dropped into aqueous ammonia solution (800 mL). The solid was collected by filtration, washed with water and dried under vacuum at 45° C. to provide the title compound 7F (4.47 g, 99%). QC LC-MS (Method 3) Rt=2.01 min, m/z=556.3 [M+H]$^+$.

The following examples in Table 4 were prepared using an analogous method to Example 156. Other central linkers were made by similar methods by replacing 4-bromonaphthylacetic acid with 5-bromonaphthylacetic acids or by substituted 4-bromophenylacetic acids.

TABLE 4

| Ex. | R''' | R$^2$ | X | Ar | LCMS m/z (M + H) | HPLC Rt (min)/Method |
|---|---|---|---|---|---|---|
| 157 | NHCH$_3$ | CH$_3$ | 2,3-(C$_4$H$_4$) | benzimidazol-2-yl | 514.5 | 2.69/2 |
| 158 | NHCH$_3$ | CH(CH$_3$)$_2$ | 3-F | benzimidazol-2-yl | 510.5 | 2.74/2 |
| 159 | NHCH$_3$ | CH(CH$_3$)$_2$ | 2,3-(C$_4$H$_4$) | benzimidazol-2-yl | 542.3 | 2.39/1 |

TABLE 4-continued
| | | | | | | |
|---|---|---|---|---|---|---|
| 161 | NHCH$_3$ | CH(CH$_3$)$_2$ | 2,3-(C$_4$H$_4$) | 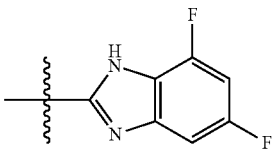 [SMILES: *c1nc2cc(F)cc(F)c2[nH]1] | 578.3 | 2.46/1 |
| 162 | NHCH$_3$ | CH(CH$_3$)$_2$ | 2,3-(C$_4$H$_4$) | 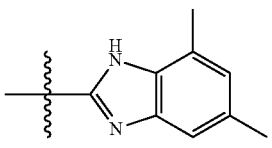 [SMILES: *c1nc2cc(C)cc(C)c2[nH]1] | 570.3 | 2.32/1 |
| 163 | NHCH$_3$ | CH(CH$_3$)$_2$ | 2,3-(C$_4$H$_4$) | 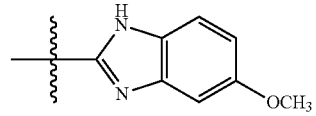 [SMILES: *c1nc2cc(OC)ccc2[nH]1] | 572.3 | 1.97/3 |
| 164 | NHCH$_3$ | CH(CH$_3$)$_2$ | 2,3-(C$_4$H$_4$) | 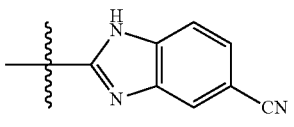 [SMILES: *c1nc2cc(C#N)ccc2[nH]1] | 567.3 | 2.33/3 |
| 165 | NHCH$_3$ | CH(CH$_3$)$_2$ | 2,3-(C$_4$H$_4$) | 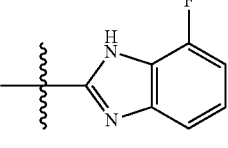 | 560.3 | 2.28/3 |
| 166 | NHCH$_3$ | CH(CH$_3$)$_2$ | 2,3-(C$_4$H$_4$) | 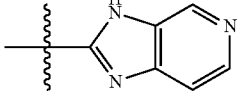 | 543.3 | 1.67/3 |
| 167 | NHCH$_3$ | CH(CH$_3$)$_2$ | 2,3-(C$_4$H$_4$) | 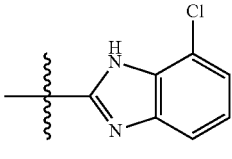 [SMILES: *c1nc2cccc(Cl)c2[nH]1] | 576.3 | 2.46/3 |
| 168 | NHCH$_3$ | CH(CH$_3$)$_2$ | 2,3-(C$_4$H$_4$) | 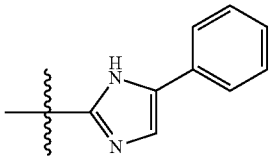 [SMILES: *c1ncc(-c2ccccc2)[nH]1] | 568.3 | 2.26/1 |
| 206 | NHCH$_3$ | CH(CH$_3$)$_2$ | 2,3-(C$_4$H$_4$) | 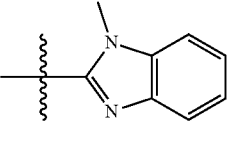 [SMILES: *c1nc2ccccc2n1C] | 556.5 | 1.98/3 |
| 207 | OH | CH(CH$_3$)$_2$ | 2,3-(C$_4$H$_4$) | 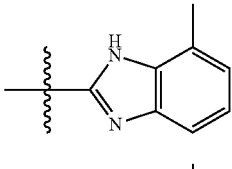 | 543.3 | 2.53/3 |
| 208 | N(CH$_3$)$_2$ | CH(CH$_3$)$_2$ | 2,3-(C$_4$H$_4$) | 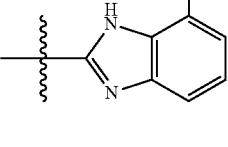 | 570.3 | 2.00/3 |

TABLE 4-continued

| | | | | | | |
|---|---|---|---|---|---|---|
| 209 | N(CH₃)—CH₂CHF₂ | CH(CH₃)₂ | 2,3-(C₄H₄) | benzimidazole | 620.4 | 2.29/3 |
| 210 | NH₂ | CH(CH₃)₂ | 2,3-(C₄H₄) | benzimidazole | 542.3 | 1.97/3 |
| 211 | N(CH₃)—CH₂CF₃ | CH(CH₃)₂ | 2,3-(C₄H₄) | benzimidazole | 638.4 | 3.21/3 |
| 212 | NH—CH₂CHF₂ | CH(CH₃)₂ | 2,3-(C₄H₄) | benzimidazole | 606.4 | 2.08/3 |
| 213 | NH—CH₂CH₂F | CH(CH₃)₂ | 2,3-(C₄H₄) | benzimidazole | 588.4 | 2.02/3 |
| 214 | NH—CH₂CF₃ | CH(CH₃)₂ | 2,3-(C₄H₄) | benzimidazole | 624.4 | 2.68/3 |
| 215 | N(CH₃)—CH₂CH₂F | CH(CH₃)₂ | 2,3-(C₄H₄) | benzimidazole | 602.4 | 2.06/3 |
| 216 | N(CH₃)—CH₂CH₂—CF₃ | CH(CH₃)₂ | 2,3-(C₄H₄) | benzimidazole | 652.4 | 2.28/3 |
| 217 | NH—CH₂CH₂—CONMe₂ | CH(CH₃)₂ | 2,3-(C₄H₄) | benzimidazole | 641.4 | 2.23/3 |

TABLE 4-continued

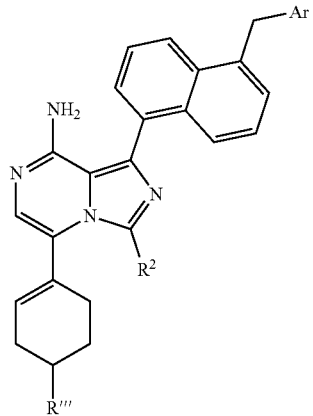

| Ex. | R''' | R² | Ar | LCMS m/z (M + H) | HPLC Rt (min)/Method |
|---|---|---|---|---|---|
| 160 | NHCH₃ | CH(CH₃)₂ | (1H-benzo[d]imidazol-2-yl) | 542.4 | 2.19/1 |

Example 157: 1-(4-((1H-benzo[d]imidazol-2-yl)methyl)naphthalen-1-yl)-3-methyl-5-(4-(methylamino)cyclohex-1-en-1-yl)imidazo[1,5-a]pyrazin-8-amine Example 158: 1-(4-((1H-benzo[d]imidazol-2-yl)methyl)-2-fluorophenyl)-3-isopropyl-5-(4-(methylamino)cyclohex-1-en-1-yl)imidazo[1,5-a]pyrazin-8-amine Example 159: 1-(4-((1H-benzo[d]imidazol-2-yl)methyl)naphthalen-1-yl)-3-isopropyl-5-(4-(methylamino)cyclohex-1-en-1-yl)imidazo[1,5-a]pyrazin-8-amine Example 160: 1-(5-((1H-benzo[d]imidazol-2-yl)methyl)naphthalen-1-yl)-3-isopropyl-5-(4-(methylamino)cyclohex-1-en-1-yl)imidazo[1,5-a]pyrazin-8-amine Example 161: 1-(4-((4,6-difluoro-1H-benzo[d]imidazol-2-yl)methyl)naphthalen-1-yl)-3-isopropyl-5-(4-(methylamino)cyclohex-1-en-1-yl)imidazo[1,5-a]pyrazin-8-amine Example 162: 1-(4-((4,6-dimethyl-1H-benzo[d]imidazol-2-yl)methyl)naphthalen-1-yl)-3-isopropyl-5-(4-(methylamino)cyclohex-1-en-1-yl)imidazo[1,5-a]pyrazin-8-amine Example 163: 3-isopropyl-1-(4-((5-methoxy-1H-benzo[d]imidazol-2-yl)methyl)naphthalen-1-yl)-5-(4-(methylamino)cyclohex-1-en-1-yl)imidazo[1,5-a]pyrazin-8-amine Example 164: 2-((4-(8-amino-3-isopropyl-5-(4-(methylamino)cyclohex-1-en-1-yl)imidazo[1,5-a]pyrazin-1-yl)naphthalen-1-yl)methyl)-1H-benzo[d]imidazole-5-carbonitrile Example 165: 1-(4-((7-fluoro-1H-benzo[d]imidazol-2-yl)methyl)naphthalen-1-yl)-3-isopropyl-5-(4-(methylamino)cyclohex-1-en-1-yl)imidazo[1,5-a]pyrazin-8-amine Example 166: 1-(4-((1H-imidazo[4,5-c]pyridin-2-yl)methyl)naphthalen-1-yl)-3-isopropyl-5-(4-(methylamino)cyclohex-1-en-1-yl)imidazo[1,5-a]pyrazin-8-amine Example 167: 1-(4-((7-chloro-1H-benzo[d]imidazol-2-yl)methyl)naphthalen-1-yl)-3-isopropyl-5-(4-(methylamino)cyclohex-1-en-1-yl)imidazo[1,5-a]pyrazin-8-amine Example 168: 3-Isopropyl-5-(4-(methylamino)cyclohex-1-en-1-yl)-1-(4-((5-phenyl-1H-imidazol-2-yl)methyl)naphthalen-1-yl)imidazo[1,5-a]pyrazin-8-amine

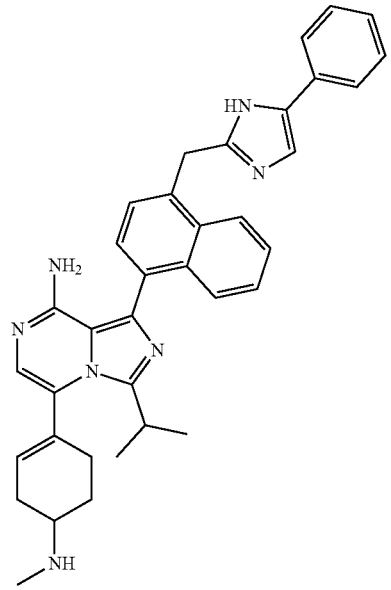 [SMILES: CNC1CC=C(c2cnc(N)c3c(-c4ccc(Cc5ncc(-c6ccccc6)[nH]5)c5ccccc45)nc(C(C)C)n23)CC1]

Step 1: 2-((4-Bromonaphthalen-1-yl)methyl)-5-phenyl-1H-imidazole

A solution 2-(4-bromonaphthalen-1-yl)acetic acid (250 mg, 0.94 mmol) in methanol (7 mL) was added cesium carbonate (153.6 mg, 0.47 mmol) and the mixture was stirred at RT for 1 h. The solvent was concentrated in vacuo and the residue was suspended in DMF (5 mL). 2-Bromo-1-phenylethan-1-one (197.1 mg, 0.99 mmol) was added and the mixture was stirred at RT for 1 h. The solvent was concentrated in vacuo and the residue was suspended in EtOAc, filtered from inorganic salts, dried (Na₂SO₄), filtered and concentrated in vacuo. The residue was dissolved in xylene (7.5 mL), ammonium acetate (1.454 g, 18.9 mmol)

was added, and the mixture was heated at reflux for 16 h. The mixture was cooled, diluted with EtOAc, washed successively with water, aqueous NaHCO$_3$ solution and brine, dried (Na$_2$SO$_4$) and concentrated in vacuo. The residue was purified on an SCX cartridge, eluting with 10% 4 M NH$_3$ in MeOH/DCM to give the title compound as a yellow foam (296 mg, 86%). LC-MS: Rt 1.23=min, m/z=363.0 [M($^{79}$Br)+H]$^+$.

Step 2: tert-Butyl (4-(8-amino-3-isopropyl-1-(4-((5-phenyl-1H-imidazol-2-yl)methyl) naphthalen-1-yl) imidazo[1,5-a]pyrazin-5-yl)cyclohex-3-en-1-yl) (methyl)carbamate To a mixture of 2-((4-bromonaphthalen-1-yl)methyl)-5-phenyl-1H-imidazole (Example 168, Step 1) (129.0 mg, 0.355 mmol), potassium acetate (95 mg, 0.97 mmol) and bis(neopentylglycolato)diboron (109 mg, 0.48 mmol) in DMF (2.5 mL, previously purged with nitrogen for 10 min) was added Pd(dppf)Cl$_2$ (24 mg, 0.032 mmol) and the mixture was purged with nitrogen for 10 sec, then heated at 80° C. for 2 h. The mixture was allowed to cool to RT and tert-butyl (4-(8-amino-1-bromo-3-isopropylimidazo[1,5-a]pyrazin-5-yl)cyclohex-3-en-1-yl)(methyl)carbamate 5E (150 mg, 0.32 mmol) was added, followed by aqueous cesium carbonate solution (3.7 M, 0.19 mL, 0.70 mmol) and Pd(dppf)C$_{12}$ (23.6 mg, 0.032 mmol). The mixture was flushed with nitrogen and heated at 90° C. overnight. The mixture was diluted with EtOAc and washed with water then brine, dried (MgSO$_4$), filtered, and concentrated in vacuo. The residue was purified by silica-gel chromatography, eluting with 0-100% EtOAc in isohexane, to provide the title compound as a brown oil (176 mg, 74%). LC-MS: Rt=1.23 min, m/z=668.4 [M+H]$^+$.

Step 3: 3-Isopropyl-5-(4-(methylamino)cyclohex-1-en-1-yl)-1-(4-((5-phenyl-1H-imidazol-2-yl)methyl) naphthalen-1-yl)imidazo[1,5-a]pyrazin-8-amine This was prepared from tert-Butyl (4-(8-amino-3-isopropyl-1-(4-((5-phenyl-1H-imidazol-2-yl)methyl)naphthalen-1-yl)imidazo[1,5-a]pyrazin-5-yl)cyclohex-3-en-1-yl) (methyl)carbamate (176 mg, 0.264 mmol) using a similar method to that described for 6E. This was purified by MDAP then by SFC (LUX CELLULOSE-4 40-60% EtOH+0.1% DEA) to provide the two enantiomers of the title compound as off-white solids (48 mg, 32%). Isomer A: 25 mg; QC LC-MS (Method 1): Rt=2.26 min, m/z=568.3 [M+H]$^+$; SFC Analysis (LUX CELLULOSE-4 40% EtOH+0.1% DEA) Rt=6.22 min ee=100%. Isomer B: 23 mg; QC LC-MS (Method 1): Rt=2.26 min, m/z=568.3 [M+H]$^+$; SFC Analysis (LUX CELLULOSE-4 40% EtOH+0.1% DEA) Rt=7.65 min; ee=94.9%.

Example 206: 1-{4-[(1-methyl-1H-1,3-benzodiazol-2-yl)methyl]naphthalen-1-yl}-5-[4-(methylamino)cyclohex-1-en-1-yl]-3-(propan-2-yl)imidazo[1,5-a]pyrazin-8-amine Example 207: 4-(8-amino-1-{4-[(4-methyl-1H-1,3-benzodiazol-2-yl)methyl]naphthalen-1-yl}-3-(propan-2-yl)imidazo[1,5-a]pyrazin-5-yl)cyclohex-3-en-1-ol Example 208: 5-[4-(dimethylamino)cyclohex-1-en-1-yl]-1-{4-[(1-methyl-1H-1,3-benzodiazol-2-yl)methyl]naphthalen-1-yl}-3-(propan-2-yl)imidazo[1,5-a]pyrazin-8-amine Example 209: 5-{4-[(2,2-difluoroethyl)(methyl)amino]cyclohex-1-en-1-yl}-1-{4-[(4-methyl-1H-1,3-benzodiazol-2-yl)methyl]naphthalen-1-yl}-3-(propan-2-yl)imidazo[1,5-a]pyrazin-8-amine Example 210:5-(4-aminocyclohex-1-en-1-yl)-1-{4-[(4-methyl-1H-1,3-benzodiazol-2-yl)methyl]naphthalen-1-yl}-3-(propan-2-yl)imidazo[1,5-a]pyrazin-8-amine Example 211:5-{4-[methyl(2,2,2-trifluoroethyl)amino]cyclohex-1-en-1-yl}-1-{4-[(4-methyl-1H-1,3-benzodiazol-2-yl)methyl]naphthalen-1-yl}-3-(propan-2-yl)imidazo[1,5-a]pyrazin-8-amine Example 212:5-{4-[(2,2-difluoroethyl)amino]cyclohex-1-en-1-yl}-1-{4-[(4-methyl-1H-1,3-benzodiazol-2-yl)methyl]naphthalen-1-yl}-3-(propan-2-yl)imidazo[1,5-a]pyrazin-8-amine Example 213:5-{4-[(2-fluoroethyl)amino]cyclohex-1-en-1-yl}-1-{4-[(4-methyl-1H-1,3-benzodiazol-2-yl)methyl]naphthalen-1-yl}-3-(propan-2-yl)imidazo[1,5-a]pyrazin-8-amine Example 214:1-{4-[(4-methyl-1H-1,3-benzodiazol-2-yl)methyl]naphthalen-1-yl}-3-(propan-2-yl)-5-{4-[(2,2,2-trifluoroethyl)amino]cyclohex-1-en-1-yl}imidazo[1,5-a]pyrazin-8-amine Example 215:5-{4-[(2-fluoroethyl)(methyl)amino]cyclohex-1-en-1-yl}-1-{4-[(4-methyl-1H-1,3-benzodiazol-2-yl)methyl]naphthalen-1-yl}-3-(propan-2-yl)imidazo[1,5-a]pyrazin-8-amine Example 216:5-{4-[methyl(3,3,3-trifluoropropyl)amino]cyclohex-1-en-1-yl}-1-{4-[(4-methyl-1H-1,3-benzodiazol-2-yl)methyl]naphthalen-1-yl}-3-(propan-2-yl)imidazo[1,5-a]pyrazin-8-amine Example 217:3-((4-(8-amino-3-isopropyl-1-(4-((7-methyl-1H-benzo[d]imidazol-2-yl)methyl)naphthalen-1-yl)imidazo[1,5-a]pyrazin-5-yl)cyclohex-3-en-1-yl)amino)-N,N-dimethylpropanamide Additional compounds of the invention can be made according to the chemistry outlined in Scheme 8. Treatment of 4-bromo-2-fluoroaniline 8A with a sulfonyl chloride such as (2-chlorophenyl)methanesulfonyl chloride gives the sulfonamide intermediate 8B, which can be converted to the boronate 8C which then undergoes Pd(0)-catalyzed coupling with a heteroaromatic bromide as before to give a coupling product such as 8 D. Acid deprotection affords the final product 8E.

Scheme 8
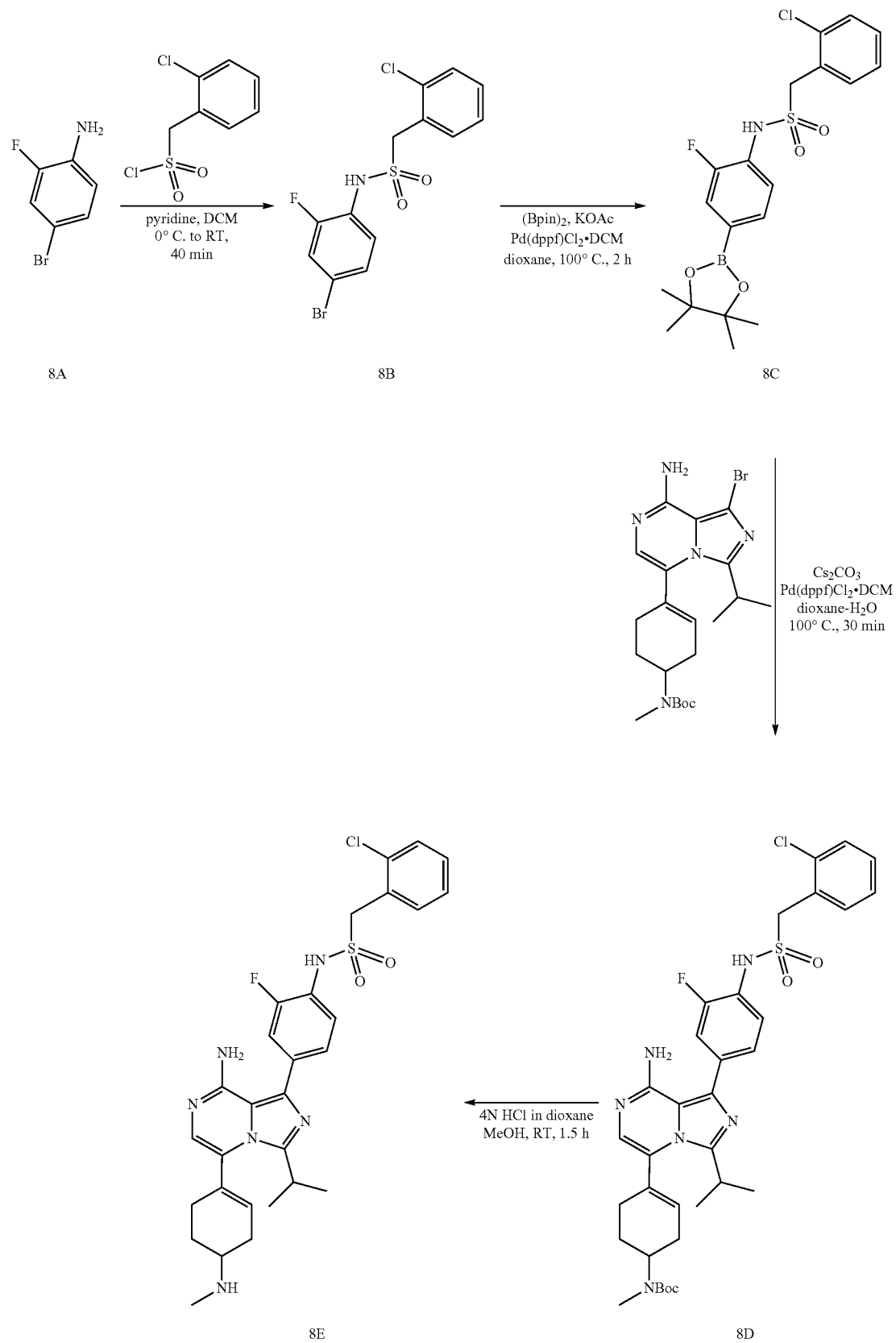

Example 169: N-(4-(8-Amino-3-isopropyl-5-(4-(methylamino)cyclohex-1-en-1-yl)imidazo[1,5-a]pyrazin-1-yl)-2-fluorophenyl)-1-(2-chlorophenyl)methanesulfonamide 8E

Step 1: N-(4-Bromo-2-fluorophenyl)-1-(2-chlorophenyl)methanesulfonamide 8B

To an ice-cold solution of 4-bromo-2-fluoroaniline (3.52 g, 18.5 mmol) in DCM (100 mL) was added pyridine (4.5 mL, 55.5 mmol), then (2-chlorophenyl)methanesulfonyl chloride (5.00 g, 22.2 mmol). The mixture was stirred at 0° C. for 30 min, then at RT for 10 min. The mixture was diluted with 1 N HCl and extracted with DCM. The combined organic extracts were washed with brine, dried (MgSO$_4$) and concentrated in vacuo to give the title compound 8B (7.46 g, 89%). LC-MS (Method 1): Rt=1.44 min, m/z=376.0 [M($^{79}$Br$^{35}$C)—H]$^-$.

Step 2: 1-(2-Chlorophenyl)-N-(2-fluoro-4-(4,4,5,5-tetramethyl-1,3,2-dioxaborolan-2-yl)phenyl)methanesulfonamide 8C A mixture of N-(4-bromo-2-fluorophenyl)-1-(2-chlorophenyl)methanesulfonamide (8B (7.46 g, 19.7 mmol), bis(pinacolato)diboron (6.00 g, 23.6 mmol), PdCl$_2$(dppf).DCM (0.80 g, 0.99 mmol) and potassium acetate (4.83 g, 49.3 mmol) in dioxane (100 mL) was purged with argon under sonication then heated at 100° C. for 2 h. After allowing to cool to RT, the mixture was diluted with water and extracted with EtOAc. The combined organic extracts were washed with brine, dried (MgSO$_4$), filtered, and concentrated in vacuo. The residue was purified by silica-gel chromatography, eluting with 0-50% EtOAc in isohexane. The oily residue was triturated with isohexane and collected by filtration to give the title compound 8C as an off-white solid (6.28 g, 75%). LC-MS (Method 1): Rt=1.56 min, m/z=424.2 [M($^{35}$Cl)—H]$^-$.

Step 3: tert-Butyl (4-(8-amino-1-(4-(((2-chlorophenyl)methyl)sulfonamido)-3-fluorophenyl)-3-isopropylimidazo[1,5-a]pyrazin-5-yl)cyclohex-3-en-1-yl)(methyl)carbamate 8 D A mixture of tert-butyl (4-(8-amino-1-bromo-3-isopropylimidazo[1,5-a]pyrazin-5-yl)cyclohex-3-en-1-yl)(methyl)carbamate 5E (2.00 g, 4.31 mmol), 1-(2-chlorophenyl)-N-(2-fluoro-4-(4,4,5,5-tetramethyl-1,3,2-dioxaborolan-2-yl)phenyl)methanesulfonamide 8C (2.02 g, 4.74 mmol), PdCl$_2$(dppf).DCM (0.35 g, 0.43 mmol) and cesium carbonate (2.81 g, 8.61 mmol) in 1,4-dioxane (40 mL) and water (10 mL) was purged with argon with sonication, then heated at 100° C. for 30 min. After allowing to cool to RT, the mixture was diluted with water and extracted with EtOAc. The combined organic extracts were washed with brine, dried (MgSO$_4$), filtered, and concentrated in vacuo. The residue was purified by silica-gel chromatography, eluting with 0-5% MeOH in DCM to give the title compound 8D (2.97 g, 100%). LC-MS (Method 1): Rt=1.18 min, m/z=683.5 [M($^{35}$Cl)+H]$^+$.

Step 4: N-(4-(8-Amino-3-isopropyl-5-(4-(methylamino)cyclohex-1-en-1-yl)imidazo[1,5-a]pyrazin-1-yl)-2-fluorophenyl)-1-(2-chlorophenyl)methanesulfonamide (Example 169)$_8$E To a solution of tert-butyl (4-(8-amino-1-(4-(((2-chlorophenyl)methyl)sulfonamido)-3-fluorophenyl)-3-isopropylimidazo[1,5-a]pyrazin-5-yl)cyclohex-3-en-1-yl)(methyl)carbamate 8 D (5.40 g, 7.90 mmol) in 1,4-dioxane (20 mL) was added 4 N HCl in 1,4-dioxane (20 mL, 80 mmol), causing a gummy solid to precipitate. Methanol (20 mL) was added to aid dissolution and the mixture was stirred for 1.5 h. The solvents were evaporated in vacuo and the residue was dissolved in water (20 mL) and added dropwise to a rapidly stirred solution of aqueous ammonia (30%). The resulting solid was collected by filtration to give the title compound 8E (4.11 g, 89%). QC LC-MS (Method 3): Rt=2.55 min, m/z=583.4 [M($^{35}$Cl)+H]$^+$.

The following examples in Table 5 were prepared using an analogous method to Example 169. Other central linkers were made using similar methods by replacing 4-bromo-2-fluoroaniline by appropriately substituted 4-bromoanilines or bromonaphthylamines.

TABLE 5

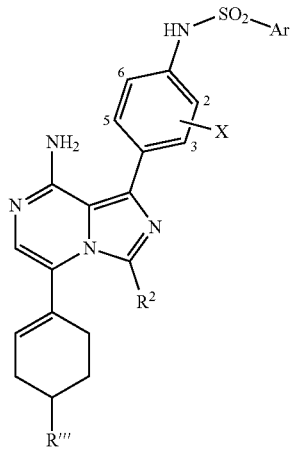

| Ex. | R''' | R$^2$ | X | Ar | LCMS m/z (M + H) | HPLC Rt (min)/Method |
|---|---|---|---|---|---|---|
| 170 | NHCH$_3$ | CH$_3$ | 2,3-(C$_4$H$_4$) | 2-Cl—Ph | 573.4 | 2.51/1 |
| 171 | NHCH$_3$ | CH(CH$_3$)$_2$ | 3-F | Ph | 535.3 | 2.43/1 |
| 172 | NHCH$_3$ | CH(CH$_3$)$_2$ | 3-F | 3-F—Ph | 542.3 | 2.39/1 |
| 173 | NHCH$_3$ | CH(CH$_3$)$_2$ | 2,3-(C$_4$H$_4$) | CH$_2$-(2-Cl—Ph) | 615.4 | 2.91/2 |

TABLE 5-continued

| | | | | | | |
|---|---|---|---|---|---|---|
| 174 | NHCH₃ | CH(CH₃)₂ | 3-F-Ph | 2-Cl—Ph | 569.3 | 2.66/2 |
| 176 | NHCH₃ | CH(CH₃)₂ | 2,3-(C₄H₄) | 3-F—Ph | 585.4 | 2.53/1 |
| 177 | NHCH₃ | CH(CH₃)₂ | 2,3-(C₄H₄) | 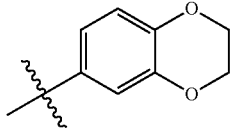 [SMILES: *c1ccc2c(c1)OCCO2] | 625.3 | 2.77/2 |
| 178 | NHCH₃ | CH(CH₃)₂ | 3-F | 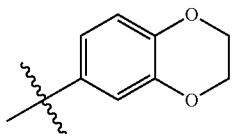 [SMILES: *c1ccc2c(c1)OCCO2] | 593.4 | 2.65/2 |
| 179 | NHCH₃ | CH(CH₃)₂ | 2-F | 2-Cl—Ph | 569.4 | 2.53/1 |
| 180 | NHCH₃ | CH(CH₃)₂ | 3-F | CH₂-(2-Cl—Ph) | 583.4 | 2.48/1 |
| 181 | NHCH₃ | CH(CH₃)₂ | 2,3-(C₄H₄) | 2-Cl—Ph | 601.4 | 2.57/1 |
| 182 | NHCH₃ | CH(CH₃)₂ | 2,3-(C₄H₄) | CH₂-(3-F—Ph) | 599.4 | 2.49/1 |
| 183 | NHCH₃ | CH(CH₃)₂ | 3-F | CH₂—Ph | 549.3 | 2.41/1 |
| 184 | NHCH₃ | CH(CH₃)₂ | 2,3-(C₄H₄) | 2,5-F₂—Ph | 603.5 | 2.48/1 |
| 185 | NHCH₃ | CH(CH₃)₂ | 2,3-(C₄H₄) | 2-F,5-CH₃—Ph | 599.3 | 2.79/2 |
| 186 | NHCH₃ | CH(CH₃)₂ | 2,3-(C₄H₄) | 2-Cl,5-F—Ph | 619.2 | 2.69/2 |
| 187 | NHCH₃ | CH(CH₃)₂ | 2,3-(C₄H₄) | CH₂-(2-F—Ph) | 599.3 | 2.54/3 |
| 188 | NHCH₃ | CH(CH₃)₂ | 2,3-(C₄H₄) | CH₂-(2,5-F₂—Ph) | 617.2 | 2.59/3 |
| 189 | NHCH₃ | CH(CH₃)₂ | 3-F | CH₂-(2-F—Ph) | 567.2 | 2.41/3 |
| 190 | NHCH₃ | CH(CH₃)₂ | 3-F | CH₂-(2,5-F₂—Ph) | 585.2 | 2.47/3 |
| 191 | NHCH₃ | CH(CH₃)₂ | 3-F | CH₂-(3,5-F₂—Ph) | 585.2 | 2.53/3 |
| 192 | NHCH₃ | CH(CH₃)₂ | 2,3-(C₄H₄) | 2-F,5-CF₃—Ph | 653.3 | 2.83/3 |
| 193 | NHCH₃ | CH(CH₃)₂ | 2,3-(C₄H₄) | 3-CF₃—Ph | 635.4 | 2.81/3 |
| 194 | NHCH₃ | CH(CH₃)₂ | 3-F | 3-CF₃—Ph | 603.3 | 2.74/3 |
| 195 | NHCH₃ | CH(CH₃)₂ | 3-F | 2,5-Cl₂—Ph | 603.2 | 2.72/3 |
| 196 | NHCH₃ | CH(CH₃)₂ | 3,6-F₂ | CH₂-(2-Cl—Ph) | 601.3 | 2.59/3 |
| 197 | NHCH₃ | CH(CH₃)₂ | 2,3-F₂ | CH₂-(2-Cl—Ph) | 601.3 | 2.56/3 |
| 198 | NHCH₃ | CH(CH₃)₂ | 3-F | CH₂-(3-pyridyl) | 550.2 | 1.83/3 |
| 199 | NHCH₃ | CH(CH₃)₂ | 2,3-(C₄H₄) | CH₂-(3-pyridyl) | 582.2 | 1.9/3 |
| 200 | NHCH₃ | CH(CH₃)₂ | 2,3-(C₄H₄) | 3-CH₃O—Ph | 611.2 | 2.53/3 |
| 201 | NHCH₃ | CH(CH₃)₂ | 3-F | CH₂-(3-CH₃O—Ph) | 579.3 | 2.42/3 |
| 202 | NHCH₃ | CH(CH₃)₂ | 2,3-(C₄H₄) | CH₂-(3,5-F₂—Ph) | 617.2 | 2.65/3 |
| 218 | NHCH₃ | CH(CH₃)₂ | 2-F | 2-F,5-CH₃—Ph | 567.2 | 2.50/3 |
| 219 | NHCH₃ | CH(CH₃)₂ | 2,3-(C₄H₄) | 2-Cl,5-CH₃—Ph | 615.3 | 2.81/3 |
| 220 | NHCH₂CH₂F | CH(CH₃)₂ | 2-F | CH₂-(2-Cl—Ph) | 615.3 | 2.72/3 |
| 223 | NHCH₂CH₂F | CH(CH₃)₂ | 2-F | 2-Cl—Ph | 601.3 | 2.66/3 |
| 224 | OH | CH(CH₃)₂ | 2-F | CH₂-(2-Cl—Ph) | 570.3 | 3.22/3 |
| 225 | OH | CH(CH₃)₂ | 2-F | 2-Cl—Ph | 556.3 | 3.36/3 |
| 226 | NHCH₂CHF₂ | CH(CH₃)₂ | 2-F | 2-Cl—Ph | 619.3 | 2.72/3 |
| 227 | 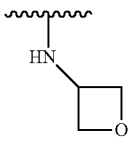 | CH(CH₃)₂ | 2-F | CH₂-(2-Cl—Ph) | 625.3 | 2.64/3 |
| 228 | NHCH₂CH₂F | CH(CH₃)₂ | 2,5-F₂ | 2-Cl—Ph | 619.3 | 2.46/4 |
| 229 | NHCH₂CH₂F | CH(CH₃)₂ | 2-F | 2-F—Ph | 585.4 | 2.81/5 |
| 230 | NMeCH₂CH₂F | CH(CH₃)₂ | 2-F | 2-Cl—Ph | 615.2 | 2.65/3 |
| 231 | NHCH₂CH₂F | CH₃ | 2-F | 2-Cl—Ph | 573.2 | 2.34/3 |
| 232 | 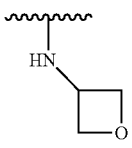 | CH(CH₃)₂ | 2-F | 2-Cl—Ph | 611.4 | 2.68/3 |

TABLE 5-continued

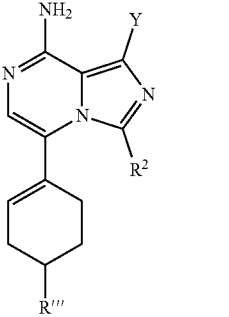

| Ex. | R''' | R² | Y | LCMS m/z (M + H) | HPLC Rt (min)/Method |
|---|---|---|---|---|---|
| 175 | NHCH₃ | CH(CH₃)₂ | 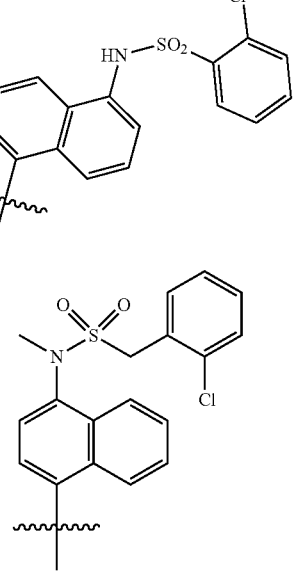 | 601.4 | 2.83/2 |
| 203 | NHCH₃ | CH(CH₃)₂ | | 629.3 | 2.88/3 |

Example 170: N-(4-(8-amino-3-methyl-5-(4-(methylamino)cyclohex-1-en-1-yl)imidazo[1,5-a]pyrazin-1-yl)naphthalen-1-yl)-2-chlorobenzenesulfonamide Example 171: N-(4-(8-amino-3-isopropyl-5-(4-(methylamino)cyclohex-1-en-1-yl)imidazo[1,5-a]pyrazin-1-yl)-3-fluorophenyl)benzenesulfonamide Example 172: N-(4-(8-amino-3-isopropyl-5-(4-(methylamino)cyclohex-1-en-1-yl)imidazo[1,5-a]pyrazin-1-yl)-3-fluorophenyl)-3-fluorobenzenesulfonamide Example 173: N-(4-(8-amino-3-isopropyl-5-(4-(methylamino)cyclohex-1-en-1-yl)imidazo[1,5-a]pyrazin-1-yl)naphthalen-1-yl)-1-(2-chlorophenyl)methanesulfonamide Example 174: N-(4-(8-amino-3-isopropyl-5-(4-(methylamino)cyclohex-1-en-1-yl)imidazo[1,5-a]pyrazin-1-yl)-3-fluorophenyl)-2-chlorobenzenesulfonamide Example 175: N-(5-(8-amino-3-isopropyl-5-(4-(methylamino)cyclohex-1-en-1-yl)imidazo[1,5-a]pyrazin-1-yl)naphthalen-1-yl)-2-chlorobenzenesulfonamide Example 176: N-(4-(8-amino-3-isopropyl-5-(4-(methylamino)cyclohex-1-en-1-yl)imidazo[1,5-a]pyrazin-1-yl)naphthalen-1-yl)-3-fluorobenzenesulfonamide Example 177: N-(4-(8-amino-3-isopropyl-5-(4-(methylamino)cyclohex-1-en-1-yl)imidazo[1,5-a]pyrazin-1-yl)naphthalen-1-yl)-2,3-dihydrobenzo[b][1,4]dioxine-6-sulfonamide Example 178: N-(4-(8-amino-3-isopropyl-5-(4-(methylamino)cyclohex-1-en-1-yl)imidazo[1,5-a]pyrazin-1-yl)-3-fluorophenyl)-2,3-dihydrobenzo[b][1,4]dioxine-6-sulfonamide Example 179: N-(4-(8-amino-3-isopropyl-5-(4-(methylamino)cyclohex-1-en-1-yl)imidazo[1,5-a]pyrazin-1-yl)-2-fluorophenyl)-2-chlorobenzenesulfonamide Example 180: N-(4-(8-amino-3-isopropyl-5-(4-(methylamino)cyclohex-1-en-1-yl)imidazo[1,5-a]pyrazin-1-yl)-3-fluorophenyl)-1-(2-chlorophenyl)methanesulfonamide Example 181: N-(4-(8-amino-3-isopropyl-5-(4-(methylamino)cyclohex-1-en-1-yl)imidazo[1,5-a]pyrazin-1-yl)naphthalen-1-yl)-2-chlorobenzenesulfonamide Example 182: N-(4-(8-amino-3-isopropyl-5-(4-(methylamino)cyclohex-1-en-1-yl)imidazo[1,5-a]pyrazin-1-yl)naphthalen-1-yl)-1-(3-fluorophenyl)methanesulfonamide Example 183: N-(4-(8-amino-3-isopropyl-5-(4-(methylamino)cyclohex-1-en-1-yl)imidazo[1,5-a]pyrazin-1-yl)-3-fluorophenyl)-1-phenylmethanesulfonamide Example 184: N-(4-(8-amino-3-isopropyl-5-(4-(methylamino)cyclohex-1-en-1-yl)imidazo[1,5-a]pyrazin-1-yl)naphthalen-1-yl)-2,5-difluorobenzenesulfonamide Example 185: N-(4-(8-amino-3-isopropyl-5-(4-(methylamino)cyclohex-1-en-1-yl)imidazo[1,5-a]pyrazin-1-yl)naphthalen-1-yl)-2-fluoro-5-methylbenzenesulfonamide Example 186: N-(4-(8-amino-3-isopropyl-5-(4-(methylamino)cyclohex-1-en-1-yl)imidazo[1,5-a]pyrazin-1-yl)naphthalen-1-yl)-2-chloro-5-fluorobenzenesulfonamide Example 187: N-(4-(8-amino-3-isopropyl-5-(4-(methylamino)cyclohex-1-en-1-yl)imidazo[1,5-a]pyrazin-1-yl)naphthalen-1-yl)-1-(2-fluorophenyl)methanesulfonamide Example 188: N-(4-(8-amino-3-isopropyl-5-(4-(methylamino)cyclohex-1-en-1-yl)imidazo[1,5-a]pyrazin-1-yl)naphthalen-1-yl)-1-(2,5-difluorophenyl)methanesulfonamide Example 189: N-(4-(8-amino-3-isopropyl-5-(4-(methylamino)cyclohex-1-en-1-yl)imidazo[1,5-a]pyrazin-1-yl)-3-fluorophenyl)-1-(2-fluorophenyl)methanesulfonamide Example 190: N-(4-(8-amino-3-isopropyl-5-(4-(methylamino)cyclohex-1-en-1-yl)imidazo[1,5-a]pyrazin-1-yl)-3-fluorophenyl)-1-(2,5-difluorophenyl)methanesulfonamide Example 191: N-(4-(8-amino-3-isopropyl-5-(4-(methylamino)cyclohex-1-en-1-yl)imidazo[1,5-a]pyrazin-1-yl)-3-fluorophenyl)-1-(3,5-difluorophenyl)methanesulfonamide Example 192: N-(4-(8-amino-3-isopropyl-5-(4-(methylamino)cyclohex-1-en-1-yl)imidazo[1,5-a]pyrazin-1-yl)naphthalen-1-yl)-2-fluoro-5-(trifluoromethyl)benzenesulfonamide Example 193: N-(4-(8-amino-3-isopropyl-5-(4-(methylamino)cyclohex-1-en-1-yl)imidazo[1,5-a]pyrazin-1-yl)naphthalen-1-yl)-3-(trifluoromethyl)benzenesulfonamide Example 194: N-(4-(8-amino-3-isopropyl-5-(4-(methylamino)cyclohex-1-en-1-yl)imidazo[1,5-a]pyrazin-1-yl)-3-fluorophenyl)-3-(trifluoromethyl)benzenesulfonamide Example 195: N-(4-(8-amino-3-isopropyl-5-(4-(methylamino)cyclohex-1-en-1-yl)imidazo[1,5-a]pyrazin-1-yl)-3-fluorophenyl)-2,5-dichlorobenzenesulfonamide Example 196: N-(4-(8-amino-3-isopropyl-5-(4-(methylamino)cyclohex-1-en-1-yl)imidazo[1,5-a]pyrazin-1-yl)-2,5-difluorophenyl)-1-(2-chlorophenyl)methanesulfonamide Example 197: N-(4-(8-amino-3-isopropyl-5-(4-(methylamino)cyclohex-1-en-1-yl)imidazo[1,5-a]pyrazin-1-yl)-2,3-difluorophenyl)-1-(2-chlorophenyl)methanesulfonamide Example 198: N-(4-(8-amino-3-isopropyl-5-(4-(methylamino)cyclohex-1-en-1-yl)imidazo[1,5-a]pyrazin-1-yl)-3-fluorophenyl)-1-(pyridin-3-yl)methanesulfonamide Example 199: N-(4-(8-amino-3-isopropyl-5-(4-(methylamino)cyclohex-1-en-1-yl)imidazo[1,5-a]pyrazin-1-yl)naphthalen-1-yl)-1-(pyridin-3-yl)methanesulfonamide Example 200: N-(4-(8-amino-3-isopropyl-5-(4-(methylamino)cyclohex-1-en-1-yl)imidazo[1,5-a]pyrazin-1-yl)naphthalen-1-yl)-1-(3-methoxyphenyl)methanesulfonamide Example 201: N-(4-(8-amino-3-isopropyl-5-(4-(methylamino)cyclohex-1-en-1-yl)imidazo[1,5-a]pyrazin-1-yl)-3-fluorophenyl)-1-(3-methoxyphenyl)methanesulfonamide Example 202: N-(4-(8-amino-3-isopropyl-5-(4-(methylamino)cyclohex-1-en-1-yl)imidazo[1,5-a]pyrazin-1-yl)naphthalen-1-yl)-1-(3,5-difluorophenyl)methanesulfonamide Example 203: N-(4-(8-amino-3-isopropyl-5-(4-(methylamino)cyclohex-1-en-1-yl)imidazo[1,5-a]pyrazin-1-yl)naphthalen-1-yl)-1-(2-chlorophenyl)-N-methylmethanesulfonamide Example 218: N-(4-{8-amino-5-[4-(methylamino)cyclohex-1-en-1-yl]-3-(propan-2-yl)imidazo[1,5-a]pyrazin-1-yl}-2-fluorophenyl)-2-fluoro-5-methylbenzene-1-sulfonamide Example 219: N-(4-{8-amino-5-[4-(methylamino)cyclohex-1-en-1-yl]-3-(propan-2-yl)imidazo[1,5-a]pyrazin-1-yl}naphthalen-1-yl)-2-chloro-5-methylbenzene-1-sulfonamide Example 220: N-(4-(8-amino-5-(4-((2-fluoroethyl)amino)cyclohex-1-en-1-yl)-3-isopropylimidazo[1,5-a]pyrazin-1-yl)-2-fluorophenyl)-1-(2-chlorophenyl)methanesulfonamide Example 223: N-(4-(8-amino-5-(4-((2-fluoroethyl)amino)cyclohex-1-en-1-yl)-3-isopropylimidazo[1,5-a]pyrazin-1-yl)-2-fluorophenyl)-2-chlorobenzenesulfonamide Example 224: N-(4-(8-amino-5-(4-hydroxycyclohex-1-en-1-yl)-3-isopropylimidazo[1,5-a]pyrazin-1-yl)-2-fluorophenyl)-1-(2-chlorophenyl)methanesulfonamide Example 225: N-(4-(8-amino-5-(4-hydroxycyclohex-1-en-1-yl)-3-isopropylimidazo[1,5-a]pyrazin-1-yl)-2-fluorophenyl)-2-chlorobenzenesulfonamide Example 226: N-(4-(8-amino-5-(4-((2,2-difluoroethyl)amino)cyclohex-1-en-1-yl)-3-isopropylimidazo[1,5-a]pyrazin-1-yl)-2-fluorophenyl)-2-chlorobenzenesulfonamide Example 227: N-(4-(8-amino-3-isopropyl-5-(4-(oxetan-3-ylamino)cyclohex-1-en-1-yl)imidazo[1,5-a]pyrazin-1-yl)-2-fluorophenyl)-1-(2-chlorophenyl)methanesulfonamide Example 228: N-(4-(8-amino-5-(4-((2-fluoroethyl)amino)cyclohex-1-en-1-yl)-3-isopropylimidazo[1,5-a]pyrazin-1-yl)-2,5-difluorophenyl)-2-chlorobenzenesulfonamide Example 229: N-(4-(8-amino-5-(4-((2-fluoroethyl)amino)cyclohex-1-en-1-yl)-3-isopropylimidazo[1,5-a]pyrazin-1-yl)-2-fluorophenyl)-2-fluorobenzenesulfonamide Example 230: N-(4-(8-amino-5-(4-((2-fluoroethyl)(methyl)amino)cyclohex-1-en-1-yl)-3-isopropylimidazo[1,5-a]pyrazin-1-yl)-2-fluorophenyl)-2-chlorobenzenesulfonamide Example 231: N-(4-(8-amino-5-(4-((2-fluoroethyl)amino)cyclohex-1-en-1-yl)-3-methylimidazo[1,5-a]pyrazin-1-yl)-2-fluorophenyl)-2-chlorobenzenesulfonamide Example 232: N-(4-(8-amino-3-isopropyl-5-(4-(oxetan-3-ylamino)cyclohex-1-en-1-yl)imidazo[1,5-a]pyrazin-1-yl)-2-fluorophenyl)-2-chlorobenzenesulfonamide Additional compounds of the invention can be made according to the chemistry outlined in Scheme 9. Coupling of (3-chloropyrazin-2-yl)methanamine 9A with an acid such as 4-Boc-1-piperazineacetic acid gives the amide intermediate 9B, which can be cyclised to the imidazopyrazine 9C. This is then brominated to give 9 D, then treated with ammonia to give 9E, which undergoes Pd(0)-catalyzed coupling with an in situ formed boronate to give a coupling product such as 9F. Acid deprotection affords the final product 9G, which can be subsequently alkylated to give products such as 9H.

Scheme 9
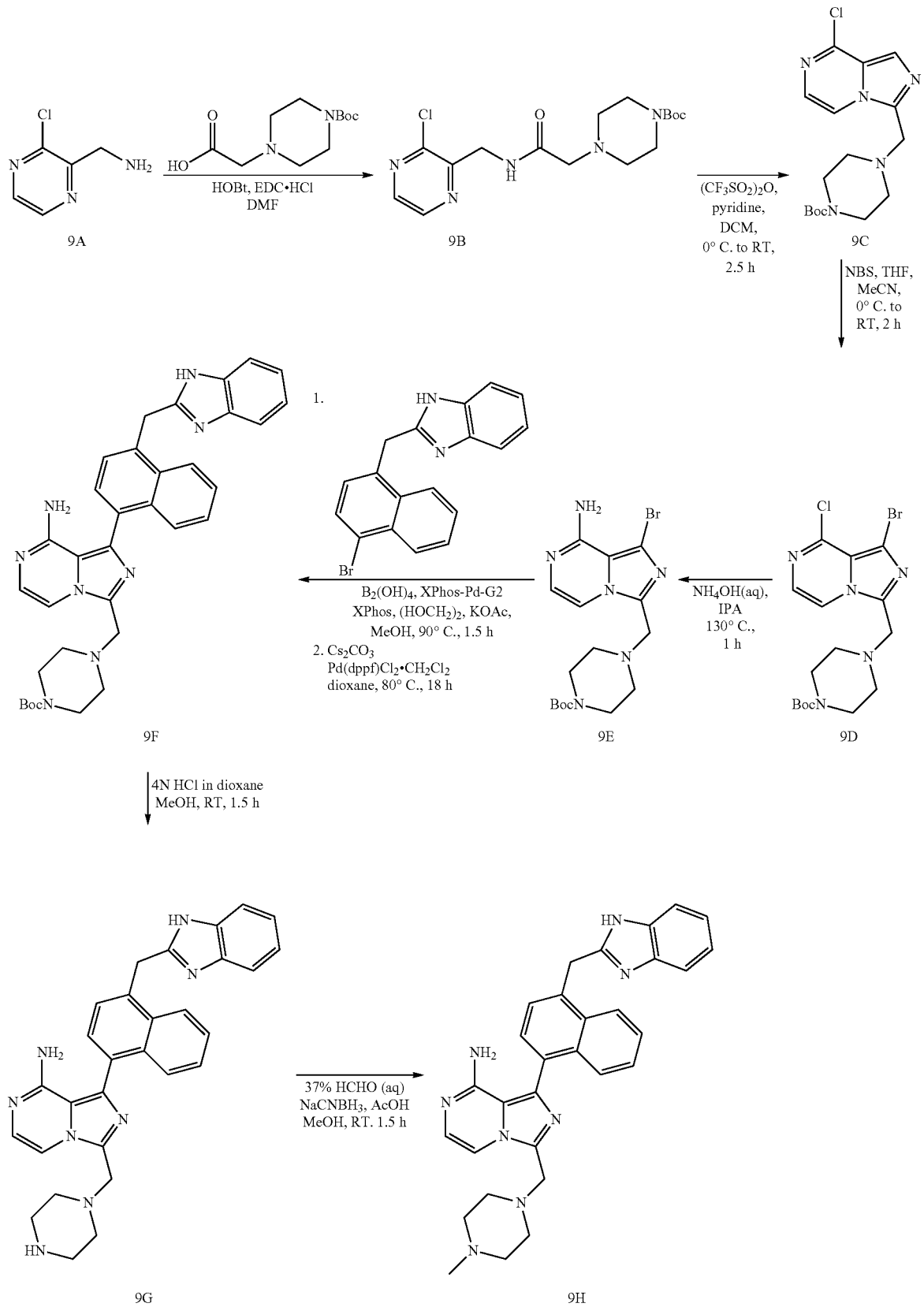

Example 221: 1-(4-((1H-Benzo[d]imidazol-2-yl)methyl)naphthalen-1-yl)-8-chloro-3-(piperazin-1-ylmethyl)imidazo[1,5-a]pyrazine 9G

Step 1: tert-Butyl 4-(2-(((3-chloropyrazin-2-yl)methyl)amino)-2-oxoethyl)piperazine-1-carboxylate 9B A mixture of 4-Boc-1-piperazineacetic acid (2.7 g, 11.1 mmol), HOBT (1.6 g, 12.0 mmol), EDC.HCl (2.3 g, 12.0 mmol) and DIPEA (4.0 mL, 25 mmol)) in DMF (30 mL) was stirred at RT for 5 min before adding (3-chloropyrazin-2-yl)methanamine (1.4 g, 10.0 mmol) and stirring at RT for 18 h. The mixture was partitioned between water and DCM and the combined organic extracts were washed with saturated aqueous NaCl solution, dried (MgSO$_4$), filtered and evaporated in vacuo. The residue was purified by silica gel chromatography, eluting with 0-50% ethyl acetate in hexane. The residue was dissolved in DCM, washed with water twice, then brine and evaporated in vacuo to give the title compound 9B (2.21 g, 67%). $^1$H NMR (400 MHz, CDCl$_3$) δ 8.46 (d, 1H, J=2.4 Hz), 8.33 (m, 1H), 8.28 (br s, 1H), 4.75 (d, 2H, J=5.2 Hz), 3.51 (m, 4H), 3.14 (s, 2H), 2.55 (m, 4H), 1.47 (s, 9H).

Step 2: tert-Butyl 4-((8-chloroimidazo[1,5-a]pyrazin-3-yl)methyl)piperazine-1-carboxylate 9C To a solution of tert-butyl 4-(2-(((3-chloropyrazin-2-yl)methyl)amino)-2-oxoethyl)piperazine-1-carboxylate 9B (2.21 g, 5.98 mmol) in DCM (20 mL) at 0° C. was added pyridine 1.45 mL, 17.9 mmol) then, dropwise over 10 min, trifluoromethanesulfonic anhydride (3.02 mL, 18.0 mmol). The resulting slurry was warmed to RT, adding more DCM (10 mL) to aid stirring, then stirred for 2.5 h. Aqueous NaHCO$_3$ solution was added and the mixture was extracted with DCM twice then EtOAc. The combined organic extracts were washed with brine, dried (MgSO$_4$), filtered and evaporated in vacuo. The residue was purified by silica gel chromatography, eluting with 0-15% methanol in DCM to give the title compound 9C (1.0 g, 86%). LC-MS: Rt=1.11 min, m/z=352.2 [M($^{35}$Cl)+H]$^+$.

Step 3: tert-Butyl 4-((1-bromo-8-chloroimidazo[1,5-a]pyrazin-3-yl)methyl)piperazine-1-carboxylate 9 D To a solution of tert-butyl 4-((8-chloroimidazo[1,5-a]pyrazin-3-yl)methyl)piperazine-1-carboxylate 9C (1.0 g, 2.84 mmol) in THF (7.7 mL) and acetonitrile (18.9 mL) at 0° C. was added NBS (0.6 g, 3.37 mmol). The mixture was allowed to warm to RT and stirred for 2 h. The mixture was concentrated in vacuo and the residue was suspended in DCM and filtered. The filtrate was evaporated in vacuo and purified by silica gel chromatography, eluting with 0-15% methanol in DCM to give the title compound 9D (700 mg, 57%). LC-MS: Rt=1.34 min, m/z=430.1 [M($^{35}$Cl$^{79}$Br)+H]$^+$.

Step 4: tert-Butyl 4-((8-amino-1-bromoimidazo[1,5-a]pyrazin-3-yl)methyl)piperazine-1-carboxylate 9E This was obtained in 64% yield using a similar procedure to that described for 5E, using tert-butyl 4-((1-bromo-8-chloroimidazo[1,5-a]pyrazin-3-yl)methyl)piperazine-1-carboxylate 9 D. LC-MS: Rt=1.14 min, m/z=411.1 [M($^{79}$Br)+H]$^+$.

Step 5: tert-Butyl 4-((1-(4-((1H-benzo[d]imidazol-2-yl)methyl)naphthalen-1-yl)-8-chloroimidazo[1,5-a]pyrazin-3-yl)methyl)piperazine-1-carboxylate 9F A mixture of 2-((4-bromonaphthalen-1-yl)methyl)-1H-benzo[d]imidazole (prepared in a similar manner to that described for 7C (160 mg, 0.47 mmol), tetrahydroxydiboron (128 mg, 1.42 mmol), potassium acetate (140 mg, 1.42 mmol), XPhos Pd G2 (11 mg, 0.01 mmol), ethylene glycol (80 µL, 1.42 mmol) in methanol (4.7 mL) in a reaction tube was purged with nitrogen for 30 min, then heated at 90° C. for 1.5 h. The mixture was filtered through Celite and the filtrate was evaporated in vacuo. The residue was dissolved in 1,4-dioxane (2.4 mL) and tert-butyl 4-((8-amino-1-bromoimidazo[1,5-a]pyrazin-3-yl)methyl)piperazine-1-carboxylate 9E (117 mg, 0.28 mmol), cesium carbonate (3.7 M solution in water, 385 µL, 1.42 mmol) and Pd(dppf)Cl$_2$.DCM (39 mg, 0.05 mmol) was added. The mixture was purged with nitrogen for 30 min, then heated at 80° C. for 18 h. The mixture was concentrated in vacuo and the residue was partitioned between DCM and aqueous NaHCO$_3$ solution. The aqueous layer was extracted twice more with DCM and the combined organic layers were passed through a phase separator and evaporated in vacuo. The residue was purified by silica gel chromatography, eluting with 0-50% ethyl acetate in hexane to give the title compound 9F (99 mg, 59%). LC-MS: Rt=1.16 min, m/z=589.2 [M+H]$^+$.

Step 6: 1-(4-((1H-Benzo[d]imidazol-2-yl)methyl)naphthalen-1-yl)-8-chloro-3-(piperazin-1-ylmethyl)imidazo[1,5-a]pyrazine 9G To a solution of tert-butyl 4-((1-(4-((1H-benzo[d]imidazol-2-yl)methyl)naphthalen-1-yl)-8-chloroimidazo[1,5-a]pyrazin-3-yl)methyl)piperazine-1-carboxylate 9F (99 mg, 0.20 mmol) in methanol (2 mL) was added 4 M HCl in 1,4-dioxane (2 mL) and the resulting solution was stirred at RT for 1.5 h. The solvents were concentrated in vacuo and the residue was passed down an SCX-2 cartridge (5 g). The basic fractions were concentrated in vacuo and the residue was purified by MDAP to provide the title compound 9G (11.6 mg, 14%). QC LC-MS (Method 1): Rt=2.07 min, m/z=489.3 [M+H]$^+$.

Example 222: 1-(4-((1H-benzo[d]imidazol-2-yl)methyl)naphthalen-1-yl)-8-chloro-3-((4-methylpiperazin-1-yl)methyl)imidazo[1,5-a]pyrazine 9H To a solution of 1-(4-((1H-benzo[d]imidazol-2-yl)methyl)naphthalen-1-yl)-8-chloro-3-(piperazin-1-ylmethyl)imidazo[1,5-a]pyrazine (Example 220) 9G (40 mg, 0.082 mmol) in methanol (2 mL) was added formaldehyde (37% solution in water, 0.1 ml, 1.3 mmol) and acetic acid (0.1 mL). The mixture was stirred for 10 min, then sodium cyanoborohydride (8 mg, 0.12 mmol) was added and the mixture was stirred for a further 1.5 h. Water (0.4 mL) was added and the mixture was loaded onto an SCX-2 cartridge (5 g). The cartridge was washed with methanol, then eluted with 1 M ammonia solution in methanol. The basic fractions were concentrated in vacuo and the residue was purified by MDAP to provide the title compound 9H. QC LC-MS (Method 2): Rt=2.71 min, m/z=503.4 [M+H]$^+$.

Example 233: Biochemical Assays to Detect Inhibition of Kinase Activity of IRE1W The kinase reactions were performed in 384 well white ProxiPlate-384 Plus plates (PERKIN Elmer 6008280) using 25 mM MOPS assay buffer with 1 mM dithiothreitol, 25 mM MgCl$_2$, 12.5 mM i-glycerophosphate, 5 mM EGTA, and 50 µg/mL BSA. Test compounds were prepared on the day of assay and dispensed using D300 digital dispenser as a 10-point ½ log dilution series in duplicate, normalised to a final DMSO concentration of 3%. Test compounds were pre-incubated for 30 min at room temperature with 10 nM IRE1α kinase (E31-11G from Signal Chem) in 2.5 µL of assay buffer and the reaction started by addition of 2.5 µL of ATP in assay buffer, to give a final ATP concentration of 100 µM and 5 nM IRE1α kinase. After 4 hours incubation at room temperature the reactions were stopped and the kinase activity determined using the ADP-Glo™ reagent from Promega, according to the manufacturer's instructions. Luminescence was measured on a luminometer (EnVision, PerkinElmer) and IC$_{50}$ values calculated by fitting a sigmoidal curve to percent inhibition of control versus Log$_{10}$ of compound concentration. IRE1α kinase inhibitory activity for each compound is reported in Table 6.

TABLE 6

| Example | IRE1α Kinase IC$_{50}$ (µM) |
|---|---|
| 1 | 0.083 |
| 2 | 1.0 |
| 3 | 2.7 |
| 4 | 0.75 |
| 5 | 1.5 |
| 6 | 2.6 |
| 7 | 0.072 |
| 8 | 1.63 |
| 9 | 0.33 |
| 10 | 10-50 |
| 11 | 0.042 |
| 12 | 0.088 |
| 13 | 0.057 |
| 14 | 1.42 |
| 15 | 0.50 |
| 16 | 0.028 |
| 17 | 0.57 |
| 18 | 0.20 |
| 19 | 0.18 |
| 20 | 0.016 |
| 21 | 0.027 |
| 22 | 0.047 |
| 23 | 0.44 |
| 24 | 0.029 |
| 25 | 0.41 |
| 26 | 1.27 |
| 27 | 0.013 |
| 28 | 0.15 |
| 29 | 0.10 |
| 30 | 0.18 |
| 31 | 0.11 |
| 32 | 0.10 |
| 33 | 0.26 |
| 34 | 0.039 |
| 35 | 0.027 |
| 36 | 0.021 |
| 37 | 0.10 |
| 38 | 0.10 |
| 39 | 0.056 |
| 40 | 0.026 |
| 41 | 0.047 |
| 42 | 0.654 |
| 43 | 0.076 |
| 44 | 0.047 |
| 45 | 0.80 |
| 46 | 1.16 |
| 47 | 0.59 |
| 48 | 50-100 |
| 49 | 0.83 |
| 50 | 0.15 |
| 51 | 0.91 |
| 52 | 0.48 |
| 53 | 0.82 |
| 54 | 0.23 |
| 55 | 1.47 |
| 56 | 0.93 |
| 57 | 0.027 |
| 58 | 0.060 |
| 59 | 0.043 |
| 60 | 0.060 |
| 61 | 10-50 |
| 62 | 0.010 |
| 63 | 0.039 |
| 64 | 0.004 |
| 65 | 0.002 |
| 66 | 0.066 |
| 67 | 0.002 |
| 68 | 0.008 |
| 69 | 0.002 |
| 70 | 0.002 |
| 71 | 0.002 |
| 72 | 0.009 |
| 73 | 0.021 |
| 74 | 0.009 |
| 75 | 0.005 |
| 76 | 0.021 |
| 77 | 0.020 |
| 78 | 0.010 |
| 79 | 0.023 |
| 80 | 0.008 |
| 81 | 0.008 |
| 82 | 0.007 |
| 83 | 0.033 |
| 84 | 0.023 |
| 85 | 0.006 |
| 86 | 0.008 |
| 87 | 0.032 |
| 88 | 0.55 |
| 89 | 0.043 |
| 90 | 0.032 |
| 91 | 0.88 |
| 92 | 0.55 |
| 93 | 0.053 |
| 94 | 0.022 |
| 95 | 0.042 |
| 96 | 0.13 |
| 97 | 0.008 |
| 98 | 0.012 |
| 99 | 0.12 |
| 100 | 0.029 |
| 101 | 0.22 |
| 102 | 0.10 |
| 103 | 0.028 |
| 104 | 0.043 |
| 105 | 0.019 |
| 106 | 0.003 |
| 107 | 0.014 |
| 108 | 0.026 |
| 109 | 0.016 |
| 110 | 0.084 |
| 111 | 0.12 |
| 112 | 0.086 |
| 113 | 0.053 |
| 114 | 10-100 |
| 115 | 0.083 |
| 116 | 0.022 |
| 117 | 0.015 |
| 118 | 0.025 |
| 119 | 0.014 |
| 120 | 0.020 |
| 121 | 0.003 |
| 122 | 0.010 |
| 123 | 0.009 |
| 124 | 0.007 |
| 125 | 0.001 |
| 126 | 0.001 |
| 127 | 0.028 |
| 128 | 0.004 |
| 129 | 0.001 |

TABLE 6-continued

| Example | IRE1α Kinase IC$_{50}$ (μM) |
|---|---|
| 130 | 0.001 |
| 131 | 0.015 |
| 132 | 0.031 |
| 133 | 0.027 |
| 134 | 0.011 |
| 135 | 0.007 |
| 136 | 0.003 |
| 137 | 0.009 |
| 138 | 0.001 |
| 139 | 0.009 |
| 140 | 0.003 |
| 141 | 0.001 |
| 142 | 0.002 |
| 143 | 0.005 |
| 144 | 0.005 |
| 145 | 0.004 |
| 146 | 0.001 |
| 147 | 0.007 |
| 148 | 0.001 |
| 149 | 0.001 |
| 150 | 0.002 |
| 151 | 0.001 |
| 152 | 0.003 |
| 153 | 0.009 |
| 154 | 0.002 |
| 155 | 0.019 |
| 156 | 0.003 |
| 157 | 0.078 |
| 158 | 0.104 |
| 159 | 0.009 |
| 160 | 0.019 |
| 161 | 0.002 |
| 162 | 0.005 |
| 163 | 0.003 |
| 164 | 0.004 |
| 165 | 0.003 |
| 166 | 0.018 |
| 167 | 0.007 |
| 168 | 0.02 |
| 169 | 0.002 |
| 170 | 0.075 |
| 171 | 0.080 |
| 172 | 0.065 |
| 173 | 0.009 |
| 174 | 0.010 |
| 175 | 1-10 |
| 176 | 0.009 |
| 177 | 0.241 |
| 178 | 0.250 |
| 179 | 0.013 |
| 180 | 0.009 |
| 181 | 0.027 |
| 182 | 0.010 |
| 183 | 0.020 |
| 184 | 0.012 |
| 185 | 0.005 |
| 186 | 0.005 |
| 187 | 0.011 |
| 188 | 0.016 |
| 189 | 0.012 |
| 190 | 0.012 |
| 191 | 0.026 |
| 192 | 0.011 |
| 193 | 0.019 |
| 194 | 0.027 |
| 195 | 0.004 |
| 196 | 0.009 |
| 197 | 0.017 |
| 198 | 0.028 |
| 199 | 0.042 |
| 200 | 0.017 |
| 201 | 0.015 |
| 202 | 0.024 |
| 203 | 0.57 |
| 204 | 0.10 |
| 205 | 0.15 |
| 206 | 0.017 |
| 207 | 0.037 |
| 208 | 0.033 |
| 209 | 0.17 |
| 210 | 0.012 |
| 211 | 1-10 |
| 212 | 0.085 |
| 213 | 0.055 |
| 214 | 0.65 |
| 215 | 0.16 |
| 216 | 0.17 |
| 217 | 0.08 |
| 218 | 0.007 |
| 219 | 0.0114 |
| 220 | 0.097 |
| 221 | 0.65 |
| 222 | 0.86 |
| 223 | 0.010 |
| 224 | 0.085 |
| 225 | 0.118 |
| 227 | 0.003 |
| 230 | 0.004 |
| 231 | 0.011 |

Example 234: Pharmacological In Vitro Assays

Biochemical Assay: Inhibition of RNase Activity of IRE1α

The RNase reactions were performed in 384 well black ProxiPlate-384 Plus plates (PERKIN Elmer) using 50 mM Tris assay buffer with 0.5 mM MgCl$_2$, 10 mM KCl, 0.03% Tween, 2 mM DTT and 1% DMSO. Test compounds were prepared on the day of assay and dispensed using D300 digital dispenser as a 10-point ½ log dilution series in duplicate, normalized to a final DMSO concentration of 4%. Test compounds were pre-incubated for 30 min at room temperature with IRE1α kinase (E31-11G from Signal Chem) in 2.5 μL of assay buffer. Then 2.5 μl of assay buffer containing substrate (5' Alexa Fluor 647-rCrArU rGrUrC rCrGrC rArGrC rGrCrArUrG—Iowa Black RQ quencher 3') added, giving a final concentration of enzyme of 0.325 nM and of substrate of 100 nM. After 20 minutes incubation at room temperature the reactions were stopped by added 5 μL of 5M urea, incubated at room temperature for 10 minutes and fluorescence measured on a plate reader (EnVision, PerkinElmer) IC$_{50}$ values calculated by fitting a sigmoidal curve to percent inhibition of control versus compound concentration.

Example 235: Cellular In Vitro Assays

Cellular XBP-1 Splicing Assay

ARPE-19 cells stably expressing XBP-1 (a.a. 1-376) with nano-luciferase gene sequence linked so it is in frame when XBP-1 is spliced, were cultured in F12 media, 10% FBS, 0.044% sodium bicarbonate, 150 μg/ml hygromycin B and seeded for assays at 5,000 cells in 384 well plates in culture media without hygromycin B and incubated at 37° C./5% CO$_2$. After overnight incubation test compounds were added to the cell plate in a 10-point ½ log dilution series in duplicate (final DMSO concentration 0.117%). After further incubation of 30 minutes thapsigargin was added (final concentration 150 nM) and then another 4 hour incubation. A NanoLuc luciferase assay (Promega) was used according to the manufacturer's instructions to detect the luciferase and luminescence measured on a luminometer (EnVision, PerkinElmer). IC$_{50}$ values calculated by fitting a sigmoidal curve to percent inhibition of control of compound concentration.

Cellular Apoptosis Assay

INS-1 cells expressing mIRE-1 were grown in RPMI, 10% FCS, 0.0003% β-mercaptoethanol and 150 µg/mL hygromycin B and for assays seeded at 10,000 cells/well in 384 well plates in media without with hygromycin B. After 24 hours incubation test compounds were added to the plate 10-point ½ log dilution series in duplicate and incubated for 30 minutes. Doxycycline (final concentration 100 nM) was added and plates incubated for a further 72 hours. To determine the proportion of apoptotic cells Hoechst 33342 (final concentration 10 µg/mL) was added, then after 30 minutes incubation cells imaged and analyzed on an InCell high content imager.

TABLE 7

| Example | IRE1α RNase IC$_{50}$ (µM) | Cellular assay IC$_{50}$ (µM) |
| --- | --- | --- |
| 20 | 0.011 | 0.47 |
| 36 | 0.156 | 1.53 |
| 37 | 0.007 | 0.32 |
| 40 | 0.020 | 0.28 |
| 67 | 0.001 | 0.21 |
| 68 | 0.003 | 0.43 |
| 69 | 0.001 | 0.35 |
| 70 | 0.001 | 0.14 |
| 71 | 0.001 | 0.062 |
| 81 | 0.005 | 0.29 |
| 82 | 0.006 | 0.40 |
| 121 | 0.001 | 0.089 |
| 123 | 0.002 | 0.23 |
| 124 | 0.005 | 0.43 |
| 125 | 0.001 | 0.30 |
| 126 | 0.001 | 0.45 |
| 129 | 0.001 | 0.28 |
| 130 | 0.001 | 0.41 |
| 139 | 0.003 | 0.38 |
| 140 | 0.001 | 0.078 |
| 141 | 0.001 | 0.059 |
| 142 | 0.001 | 0.094 |
| 143 | 0.002 | 0.21 |
| 144 | 0.002 | 0.49 |
| 145 | 0.004 | 0.074 |
| 146 | 0.006 | 0.24 |
| 147 | 0.007 | 3.1 |
| 148 | 0.001 | 1.3 |
| 149 | 0.001 | 0.78 |
| 150 | 0.001 | 0.090 |
| 151 | 0.001 | 0.060 |
| 152 | 0.001 | 0.10 |
| 155 | 0.019 | 0.64 |
| 156 | 0.001 | 0.016 |
| 168 | 0.003 | 0.096 |
| 169 | 0.001 | 0.031 |
| 185 | 0.002 | 0.21 |
| 195 | 0.002 | 0.066 |
| 218 | 0.017 | 0.025 |
| 219 | 0.002 | 0.020 |
| 220 | 0.002 | 0.050 |
| 224 | 0.010 | 0.042 |
| 225 | 0.121 | 0.25 |
| 226 | 0.213 | 0.33 |
| 227 | 0.073 | 0.087 |
| 228 | 0.006 | 0.010 |
| 229 | 0.025 | 0.025 |
| 230 | 0.012 | 0.019 |
| 231 | 0.029 | 0.019 |
| 232 | 0.060 | 0.20 |

Cellular assay (IC$_{50}$ data) are for the XBP1 splicing assay or the apoptosis assay The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound of formula (Ia):

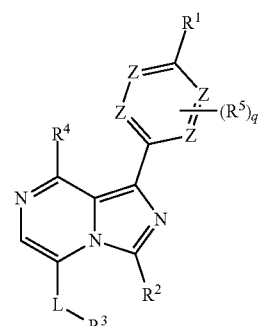

(Ia)

or a pharmaceutically acceptable salt, stereoisomer, or tautomer thereof,
wherein:
$R^1$ is:

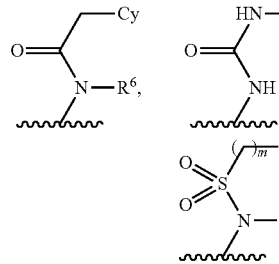

$R^2$ is H, CH$_3$, CHF$_2$, CF$_3$, CH$_2$CH$_3$, CH$_2$CH$_2$CH$_3$, CH(CH$_3$)$_2$, C(CH$_3$)$_3$, or C$_3$-C$_8$ cycloalkyl;
L-R$^3$ is:

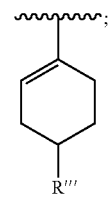

R′″ is NH$_2$, NHC$_1$-C$_6$ alkyl, NH(oxetanyl), N(C$_1$-C$_6$ alkyl)$_2$, OH, or OC$_1$-C$_6$ alkyl, wherein each C$_1$-C$_6$ alkyl is optionally and independently substituted with one or more substituents independently selected from the group consisting of halogen, C(O)NH$_2$, C(O)NHC$_1$-C$_6$ alkyl, C(O)N(C$_1$-C$_6$ alkyl)$_2$, OH, and OC$_1$-C$_6$ alkyl;
$R^4$ is NH$_2$ or NHR$^8$;
each $R^5$ is independently halogen, C$_1$-C$_6$ alkyl, OH, OC$_1$-C$_6$ alkyl, heterocycloalkyl, or phenyl, wherein each $C_1$-$C_6$ alkyl is optionally and independently substituted with one or more substituents independently selected from the group consisting of halogen, CN, $NO_2$, $C(NH)NH_2$, $C(O)C_1$-$C_4$ alkyl, $C(O)NR^aR^a$, $C(O)OH$, $C(O)OC_1$-$C_4$ alkyl, $NR^aR^a$, $NR^aC(O)R^a$, $OR^a$, $OC(O)C_1$-$C_4$ alkyl, =O, $S(O)_2NH_2$, phenyl, 1-methylimidazol-2-yl, pyridin-2-yl, pyridin-3-yl, and pyridin-4-yl, wherein each heterocycloalkyl is optionally and independently substituted with one or more substituents independently selected from the group consisting of halogen, CN, $NO_2$, $C_1$-$C_{10}$ alkyl, $C_1$-$C_6$ perhaloalkyl, benzyl, $C(NH)NH_2$, $C(O)C_1$-$C_4$ alkyl, $C(O)NR^aR^a$, $C(O)OH$, $C(O)OC_1$-$C_4$ alkyl, $NR^aR^a$, $NR^aC(O)R^a$, $OR^a$, $OC(O)C_1$-$C_4$ alkyl, =O, $S(O)_2NH_2$, phenyl, 1-methylimidazol-2-yl, pyridin-2-yl, pyridin-3-yl, and pyridin-4-yl;

wherein each phenyl is optionally and independently substituted with one or more substituents independently selected from the group consisting of halogen, CN, $NO_2$, =O, $C_1$-$C_{10}$ alkyl, $C_1$-$C_6$ perhaloalkyl, $O(C_1$-$C_6$ haloalkyl), $C(O)C_1$-$C_4$ alkyl, $C(O)NR^aR^a$, $C(O)OH$, $C(O)O(C_1$-$C_4$ alkyl), $C(NH)NH_2$, $N(R^a)(R^a)$, $N(R^a)R^aC(=O)R^a$, $OR^a$, $OC(O)C_1$-$C_4$ alkyl, $S(O)_2NH_2$, 1-methylimidazol-2-yl, pyridin-2-yl, pyridin-3-yl, pyridin-4-yl, benzyl, and phenyl, wherein each phenyl substituent is optionally and independently substituted with one or more substituents independently selected from the group consisting of halogen, $C_1$-$C_6$ alkyl, and $OC_1$-$C_6$ alkyl;

$R^6$ is H or $C_1$-$C_6$ alkyl;

wherein the $C_1$-$C_6$ alkyl is optionally substituted with one or more substituents independently selected from the group consisting of halogen, CN, $NO_2$, $C(NH)NH_2$, $C(O)C_1$-$C_4$ alkyl, $C(O)NR^aR^a$, $C(O)OH$, $C(O)OC_1$-$C_4$ alkyl, $NR^aR^a$, $NR^aC(O)R^a$, $OR^a$, $OC(O)C_1$-$C_4$ alkyl, =O, $S(O)_2NH_2$, phenyl, 1-methylimidazol-2-yl, pyridin-2-yl, pyridin-3-yl, and pyridin-4-yl;

wherein each phenyl substituent is optionally and independently substituted with one or more substituents independently selected from the group consisting of halogen, $C_1$-$C_6$ alkyl, and $OC_1$-$C_6$ alkyl;

$R^8$ is $C_1$-$C_3$ alkyl;

wherein the $C_1$-$C_3$ alkyl is optionally substituted with one or more substituents independently selected from the group consisting of halogen, CN, $NO_2$, $C(NH)NH_2$, $C(O)C_1$-$C_4$ alkyl, $C(O)NR^aR^a$, $C(O)OH$, $C(O)OC_1$-$C_4$ alkyl, $NR^aR^a$, $NR^aC(O)R^a$, $OR^a$, $OC(O)C_1$-$C_4$ alkyl, =O, $S(O)_2NH_2$, phenyl, 1-methylimidazol-2-yl, pyridin-2-yl, pyridin-3-yl, and pyridin-4-yl; and wherein each phenyl substituent is optionally and independently selected from the group consisting of halogen, $C_1$-$C_6$ alkyl, and $OC_1$-$C_6$ alkyl;

Cy is $C_3$-$C_{10}$ cycloalkyl, $C_3$-$C_{10}$ cycloalkenyl, $C_3$-$C_{10}$ heterocycloalkyl, $C_3$-$C_{10}$ heterocycloalkenyl, aryl, or heteroaryl;

wherein the $C_3$-$C_{10}$ cycloalkyl, $C_3$-$C_{10}$ cycloalkenyl, $C_3$-$C_{10}$ heterocycloalkyl, $C_3$-$C_{10}$ heterocycloalkenyl, aryl, or heteroaryl is optionally substituted with 'n' independently selected X substituents;

each X is independently halogen, CN, $C_1$-$C_6$ alkyl, $C_1$-$C_6$ haloalkyl, $CH_2$-(4-methylpiperazinyl), OH, $OC_1$-$C_6$ alkyl, aryl, or heteroaryl;

wherein each $C_1$-$C_6$ alkyl is optionally and independently substituted with one or more substituents independently selected from the group consisting of halogen, CN, $NO_2$, $C(NH)NH_2$, $C(O)C_1$-$C_4$ alkyl, $C(O)NR^aR^a$, =O, $C(O)OH$, $C(O)OC_1$-$C_4$ alkyl, $NR^aR^a$, $NR^aC(O)R^a$, $OR^a$, $OC(O)C_1$-$C_4$ alkyl, =O, $S(O)_2NH_2$, phenyl, 1-methylimidazol-2-yl, pyridin-2-yl, pyridin-3-yl, and pyridin-4-yl;

wherein each aryl and heteroaryl is optionally and independently substituted with one or more substituents independently selected from the group consisting of halogen, CN, $NO_2$, $C_1$-$C_{10}$ alkyl, $C_1$-$C_6$ perhaloalkyl, benzyl, $C(NH)NH_2$, $C(O)C_1$-$C_4$ alkyl, $C(O)NR^aR^a$, $C(O)OH$, $C(O)OC_1$-$C_4$ alkyl, $NR^aR^a$, $NR^aC(O)R^a$, $OR^a$, $O(C_1$-$C_6$ haloalkyl), $OC(O)C_1$-$C_4$ alkyl, =O, $S(O)_2NH_2$, phenyl, 1-methylimidazol-2-yl, pyridin-2-yl, pyridin-3-yl, and pyridin-4-yl; and wherein each phenyl substituent is optionally and independently substituted with one or more substituents independently selected from the group consisting of halogen, $C_1$-$C_6$ alkyl, and $OC_1$-$C_6$ alkyl;

each $R^a$ is independently $C_1$-$C_6$ alkyl or $C_3$-$C_8$ cycloalkyl; or two $R^a$, together with the nitrogen atom to which they are bound, independently form a heterocyclyl;

each Z is independently CH;

m is 0, 1, 2, 3, or 4;

n is 1, 2, 3, 4, or 5; and q is 0, 1, 2, 3, or 4.

2. The compound of claim 1, wherein the compound is of formula (Ia"):

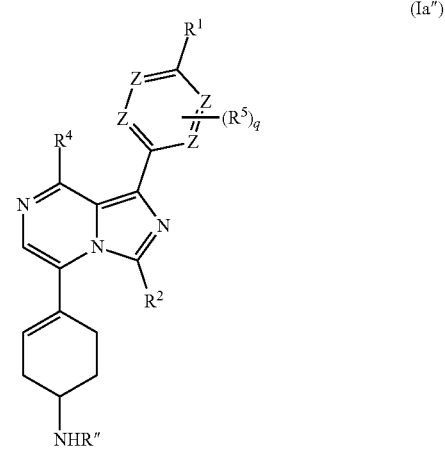

(Ia")

or a pharmaceutically acceptable salt, stereoisomer, or tautomer thereof, wherein:

R" is H or $C_1$-$C_6$ alkyl.

3. The compound of claim 1, wherein the compound is of formula (Ia"):

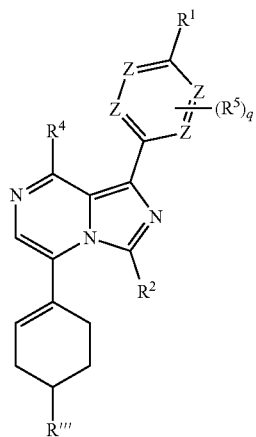

(Ia''')

or a pharmaceutically acceptable salt, stereoisomer, or tautomer thereof,
wherein:
R''' is NH$_2$, NHC$_1$-C$_6$ alkyl, NH(oxetanyl), or N(C$_1$-C$_6$ alkyl)$_2$, wherein each C$_1$-C$_6$ alkyl is optionally and independently substituted with 1 or more substituents independently selected from the group consisting of halogen, C(O)NH$_2$, C(O)NHC$_1$-C$_6$ alkyl, C(O)N(C$_1$-C$_6$ alkyl)$_2$, OH, and OC$_1$-C$_6$ alkyl.

4. The compound of claim 3, or a pharmaceutically acceptable salt, stereoisomer, or tautomer thereof, wherein R''' is NH$_2$, NHCH$_3$, N(CH$_3$)$_2$, NHCH$_2$CH$_2$F, NHCH$_2$CHF$_2$, NHCH$_2$CF$_3$, NHCH$_2$CH$_2$CF$_3$, NHCH$_2$CH$_2$C(O)NH$_2$, NHCH$_2$CH$_2$C(O)NHCH$_3$, NHCH$_2$CH$_2$C(O)N(CH$_3$)$_2$, NH(oxetan-3-yl), N(CH$_3$)CH$_2$CH$_2$F, N(CH$_3$)CH$_2$CHF$_2$, N(CH$_3$)CH$_2$CF$_3$, N(CH$_3$)CH$_2$CH$_2$CF$_3$, N(CH$_3$)CH$_2$CH$_2$C(O)NH$_2$, N(CH$_3$)CH$_2$CH$_2$C(O)NHCH$_3$, N(CH$_3$)CH$_2$CH$_2$C(O)N(CH$_3$)$_2$, or OH.

5. The compound of claim 1, or a pharmaceutically acceptable salt, stereoisomer, or tautomer thereof, wherein R$^1$ is:

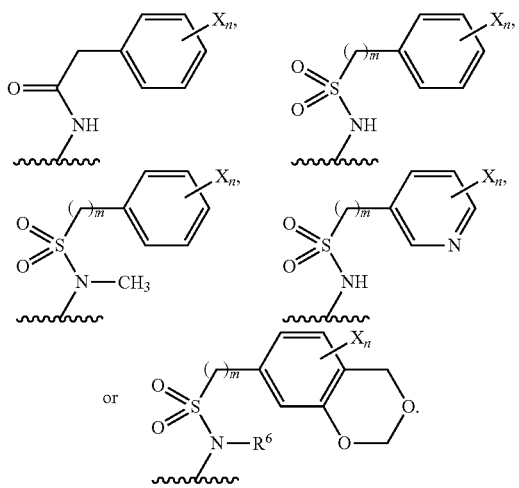

6. The compound of claim 5, or a pharmaceutically acceptable salt, stereoisomer, or tautomer thereof, wherein R$^1$ is:

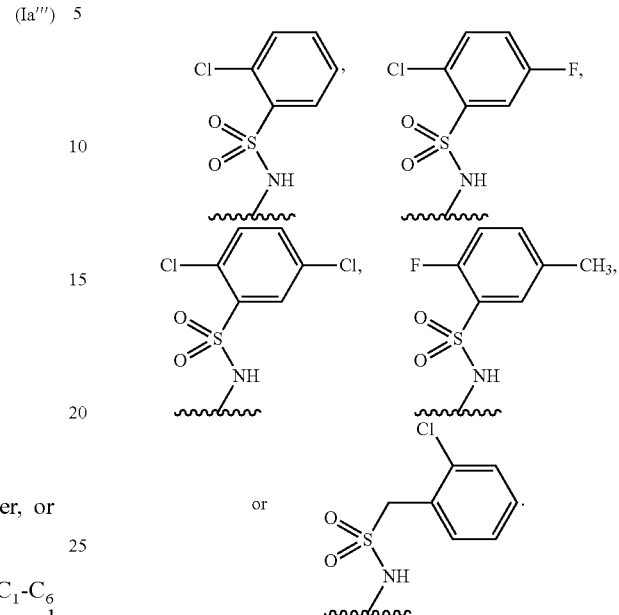

7. The compound of claim 1, or a pharmaceutically acceptable salt, stereoisomer, or tautomer thereof, wherein R$^2$ is CH$_3$, CH$_2$CH$_3$, or CH(CH$_3$)$_2$.

8. The compound of claim 1, or a pharmaceutically acceptable salt, stereoisomer, or tautomer thereof, wherein R$^3$ is:

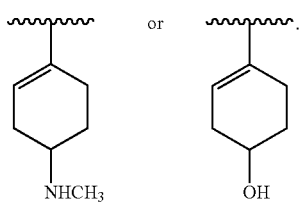 [SMILES: *C1=CCC(NC)CC1 ; *C1=CCC(O)CC1]

9. The compound of claim 8, or a pharmaceutically acceptable salt, stereoisomer, or tautomer thereof, wherein R$^3$ is:

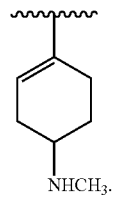 [SMILES: *C1=CCC(NC)CC1]

10. The compound of claim 1, or a pharmaceutically acceptable salt, stereoisomer, or tautomer thereof, wherein R$^4$ is NH$_2$.

11. The compound of claim 1, or a pharmaceutically acceptable salt, stereoisomer, or tautomer thereof, wherein 1, 2, 3, or 4 R$^5$ is F.

12. The compound of claim 1, or a pharmaceutically acceptable salt, stereoisomer, or tautomer thereof, wherein Cy is:

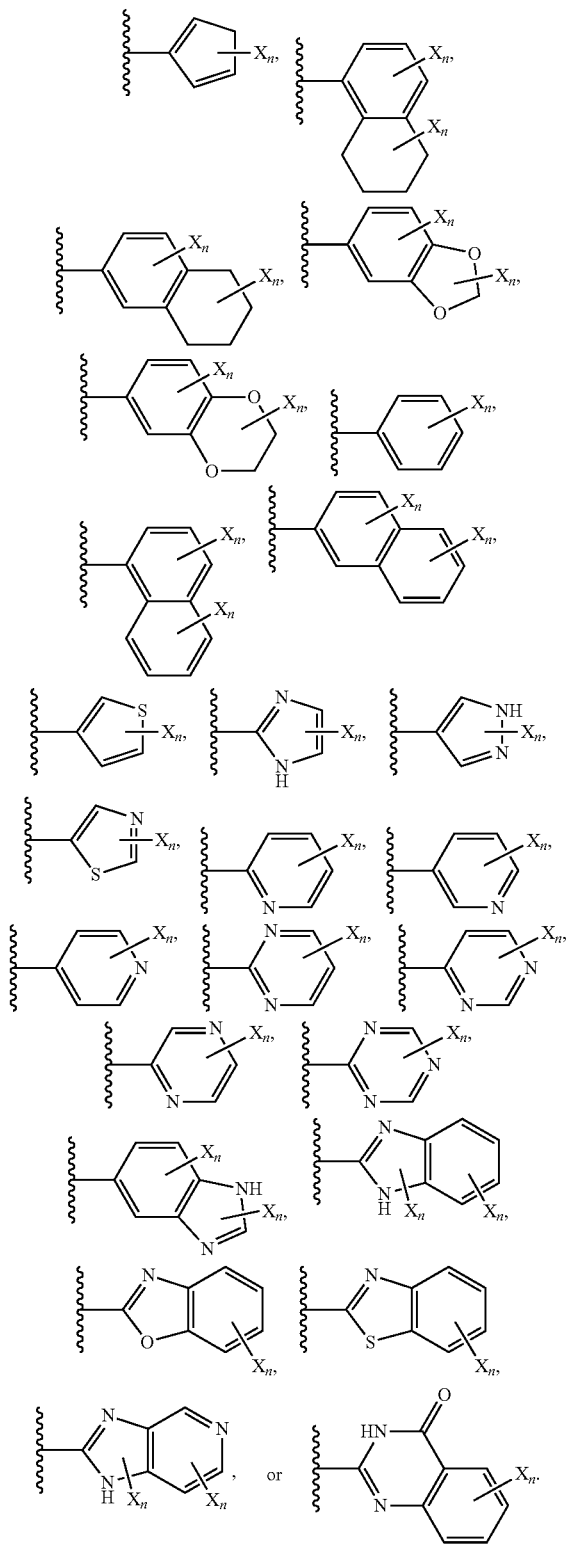

13. A pharmaceutical composition comprising at least one pharmaceutically acceptable carrier and at least one compound of claim 1, or a pharmaceutically acceptable salt, stereoisomer, or tautomer thereof.

14. A method for inhibiting the activity of an inositol requiring enzyme 1 protein, wherein the method comprises contacting the inositol requiring enzyme 1 protein with an effective amount of a compound of claim 1, or a pharmaceutically acceptable salt, stereoisomer, or tautomer thereof.

15. The method of claim 14, wherein the activity of the inositol requiring enzyme 1 protein is selected from the group consisting of kinase activity, oligomerization activity, and ribonuclease activity.

16. The method of claim 14, wherein the inositol requiring enzyme 1 protein is within a cell.

17. The method of claim 16, wherein one of the following applies:
    (a) apoptosis of the cell is prevented; or
    (b) apoptosis of the cell is minimized; or
    (c) the cell is in an organism that has an inositol requiring enzyme 1 alpha-related disease or disorder selected from the group consisting of cancer, a demyelinating disease, diabetes, an eye disease, a fibrotic disease, and a neurodegenerative disease; or
    (d) apoptosis of the cell is prevented and the cell is in an organism that has an inositol requiring enzyme 1 alpha-related disease or disorder selected from the group consisting of cancer, a demyelinating disease, diabetes, an eye disease, a fibrotic disease, and a neurodegenerative disease; or
    (e) apoptosis of the cell is minimized and the cell is in an organism that has an inositol requiring enzyme 1 alpha-related disease or disorder selected from the group consisting of cancer, a demyelinating disease, diabetes, an eye disease, a fibrotic disease, and a neurodegenerative disease.

18. A compound selected from the group consisting of:
3-{4-[8-amino-5-(4-aminocyclohex-1-en-1-yl)-3-methyl-imidazo[1,5-a]pyrazin-1-yl]-3-fluorophenyl}-1-(2,3-dihydro-1,4-benzodioxin-6-yl)urea;
1-{4-[8-amino-5-(4-aminocyclohex-1-en-1-yl)-3-methyl-imidazo[1,5-a]pyrazin-1-yl]-3-fluorophenyl}-3-{4-[(4-methylpiperazin-1-yl)methyl]phenyl}urea;
3-(4-{8-amino-3-ethyl-5-[4-(methylamino)cyclohex-1-en-1-yl]imidazo[1,5-a]pyrazin-1-yl-3-fluorophenyl)-1-[3-(trifluoromethyl)phenyl]urea;
3-(4-{8-amino-5-[4-(methylamino)cyclohex-1-en-1-yl]-3-(propan-2-yl)imidazo[1,5-a]pyrazin-1-yl-3-fluorophenyl)-1-[3-(trifluoromethyl)phenyl]urea;
3-(4-{8-amino-3-methyl-5-[4-(methylamino)cyclohex-1-en-1-yl]imidazo[1,5-a]pyrazin-1-yl}-3-fluorophenyl)-1-[3-(trifluoromethyl)phenyl]urea;
3-(4-{8-amino-3-methyl-5-[4-(methylamino)cyclohex-1-en-1-yl]imidazo[1,5-a]pyrazin-1-yl}-3-methylphenyl)-1-[3-(trifluoromethyl)phenyl]urea;
3-(4-{8-amino-3-methyl-5-[4-(methylamino)cyclohex-1-en-1-yl]imidazo[1,5-a]pyrazin-1-yl}-2-methylphenyl)-1-[3-(trifluoromethyl)phenyl]urea;
3-(4-{8-amino-3-methyl-5-[4-(methylamino)cyclohex-1-en-1-yl]imidazo[1,5-a]pyrazin-1-yl}-5-fluoro-2-methylphenyl)-1-[3-(trifluoromethyl)phenyl]urea;
3-(4-{8-amino-3-methyl-5-[4-(methylamino)cyclohex-1-en-1-yl]imidazo[1,5-a]pyrazin-1-yl}-5-fluoro-2-methoxyphenyl)-1-[3-(trifluoromethyl)phenyl]urea;
1-(4-(8-amino-3-isopropyl-5-(4-(methylamino)cyclohex-1-en-1-yl)imidazo[1,5-a]pyrazin-1-yl)-3-fluorophenyl)-3-(2,3-dihydrobenzo[b][1,4]dioxin-6-yl)urea;

1-(4-(8-amino-3-ethyl-5-(4-(methylamino)cyclohex-1-en-1-yl)imidazo[1,5-a]pyrazin-1-yl)-3-fluorophenyl)-3-(3-fluorophenyl)urea;
1-(4-(8-amino-3-isopropyl-5-(4-(methylamino)cyclohex-1-en-1-yl)imidazo[1,5-a]pyrazin-1-yl)-3-fluorophenyl)-3-(3-fluorophenyl)urea;
1-(4-(8-amino-3-isopropyl-5-(4-(methylamino)cyclohex-1-en-1-yl)imidazo[1,5-a]pyrazin-1-yl)-3-fluorophenyl)-3-phenylurea;
1-(4-(8-amino-3-isopropyl-5-(4-(methylamino)cyclohex-1-en-1-yl)imidazo[1,5-a]pyrazin-1-yl)-3-methoxyphenyl)-3-(3-fluorophenyl)urea;
1-(4-(8-amino-3-isopropyl-5-(4-(methylamino)cyclohex-1-en-1-yl)imidazo[1,5-a]pyrazin-1-yl)-2-fluorophenyl)-3-phenylurea;
1-(4-(8-amino-3-isopropyl-5-(4-(methylamino)cyclohex-1-en-1-yl)imidazo[1,5-a]pyrazin-1-yl)-2-fluorophenyl)-3-(3-fluorophenyl)urea;
1-(4-(8-amino-3-isopropyl-5-(4-(methylamino)cyclohex-1-en-1-yl)imidazo[1,5-a]pyrazin-1-yl)phenyl)-3-(pyridin-3-yl)urea;
1-(4-(8-amino-3-isopropyl-5-(4-(methylamino)cyclohex-1-en-1-yl)imidazo[1,5-a]pyrazin-1-yl)-3-fluorophenyl)-3-(pyridin-3-yl)urea;
1-(4-(8-amino-3-isopropyl-5-(4-(methylamino)cyclohex-1-en-1-yl)imidazo[1,5-a]pyrazin-1-yl)-3-fluorophenyl)-3-(3-fluoro-5-methoxyphenyl)urea;
1-(4-(8-amino-3-isopropyl-5-(4-(methylamino)cyclohex-1-en-1-yl)imidazo[1,5-a]pyrazin-1-yl)-3-fluorophenyl)-3-(5-methoxypyridin-3-yl)urea;
1-(4-(8-amino-3-isopropyl-5-(4-(methylamino)cyclohex-1-en-1-yl)imidazo[1,5-a]pyrazin-1-yl)-3-fluorophenyl)-3-(5-fluoropyridin-3-yl)urea;
1-(4-(8-amino-3-isopropyl-5-(4-(methylamino)cyclohex-1-en-1-yl)imidazo[1,5-a]pyrazin-1-yl)-3-methylphenyl)-3-(pyridin-3-yl)urea;
1-(4-(8-amino-3-isopropyl-5-(4-(methylamino)cyclohex-1-en-1-yl)imidazo[1,5-a]pyrazin-1-yl)-3-chlorophenyl)-3-(pyridin-3-yl)urea;
1-(4-((1H-benzo[d]imidazol-2-yl)methyl)-2-fluorophenyl)-3-isopropyl-5-(4-(methylamino)cyclohex-1-en-1-yl)imidazo[1,5-a]pyrazin-8-amine;
N-(4-(8-Amino-3-isopropyl-5-(4-(methylamino)cyclohex-1-en-1-yl)imidazo[1,5-a]pyrazin-1-yl)-2-fluorophenyl)-1-(2-chlorophenyl)methanesulfonamide;
N-(4-(8-amino-3-isopropyl-5-(4-(methylamino)cyclohex-1-en-1-yl)imidazo[1,5-a]pyrazin-1-yl)-3-fluorophenyl)benzenesulfonamide;
N-(4-(8-amino-3-isopropyl-5-(4-(methylamino)cyclohex-1-en-1-yl)imidazo[1,5-a]pyrazin-1-yl)-3-fluorophenyl)-3-fluorobenzenesulfonamide;
N-(4-(8-amino-3-isopropyl-5-(4-(methylamino)cyclohex-1-en-1-yl)imidazo[1,5-a]pyrazin-1-yl)-3-fluorophenyl)-2-chlorobenzenesulfonamide;
N-(4-(8-amino-3-isopropyl-5-(4-(methylamino)cyclohex-1-en-1-yl)imidazo[1,5-a]pyrazin-1-yl)-3-fluorophenyl)-2,3-dihydrobenzo[b][1,4]dioxine-6-sulfonamide;
N-(4-(8-amino-3-isopropyl-5-(4-(methylamino)cyclohex-1-en-1-yl)imidazo[1,5-a]pyrazin-1-yl)-2-fluorophenyl)-2-chlorobenzenesulfonamide;
N-(4-(8-amino-3-isopropyl-5-(4-(methylamino)cyclohex-1-en-1-yl)imidazo[1,5-a]pyrazin-1-yl)-3-fluorophenyl)-1-(2-chlorophenyl)methanesulfonamide;
N-(4-(8-amino-3-isopropyl-5-(4-(methylamino)cyclohex-1-en-1-yl)imidazo[1,5-a]pyrazin-1-yl)-3-fluorophenyl)-1-phenylmethanesulfonamide;
N-(4-(8-amino-3-isopropyl-5-(4-(methylamino)cyclohex-1-en-1-yl)imidazo[1,5-a]pyrazin-1-yl)-3-fluorophenyl)-1-(2-fluorophenyl)methanesulfonamide;
N-(4-(8-amino-3-isopropyl-5-(4-(methylamino)cyclohex-1-en-1-yl)imidazo[1,5-a]pyrazin-1-yl)-3-fluorophenyl)-1-(2,5-difluorophenyl)methanesulfonamide;
N-(4-(8-amino-3-isopropyl-5-(4-(methylamino)cyclohex-1-en-1-yl)imidazo[1,5-a]pyrazin-1-yl)-3-fluorophenyl)-1-(3,5-difluorophenyl)methanesulfonamide;
N-(4-(8-amino-3-isopropyl-5-(4-(methylamino)cyclohex-1-en-1-yl)imidazo[1,5-a]pyrazin-1-yl)-3-fluorophenyl)-3-(trifluoromethyl)benzenesulfonamide;
N-(4-(8-amino-3-isopropyl-5-(4-(methylamino)cyclohex-1-en-1-yl)imidazo[1,5-a]pyrazin-1-yl)-3-fluorophenyl)-2,5-dichlorobenzenesulfonamide;
N-(4-(8-amino-3-isopropyl-5-(4-(methylamino)cyclohex-1-en-1-yl)imidazo[1,5-a]pyrazin-1-yl)-2,5-difluorophenyl)-1-(2-chlorophenyl)methanesulfonamide;
N-(4-(8-amino-3-isopropyl-5-(4-(methylamino)cyclohex-1-en-1-yl)imidazo[1,5-a]pyrazin-1-yl)-2,3-difluorophenyl)-1-(2-chlorophenyl)methanesulfonamide;
N-(4-(8-amino-3-isopropyl-5-(4-(methylamino)cyclohex-1-en-1-yl)imidazo[1,5-a]pyrazin-1-yl)-3-fluorophenyl)-1-(pyridin-3-yl)methanesulfonamide;
N-(4-(8-amino-3-isopropyl-5-(4-(methylamino)cyclohex-1-en-1-yl)imidazo[1,5-a]pyrazin-1-yl)-3-fluorophenyl)-1-(3-methoxyphenyl)methanesulfonamide;
N-(4-{8-amino-5-[4-(methylamino)cyclohex-1-en-1-yl]-3-(propan-2-yl)imidazo[1,5-a]pyrazin-1-yl}-2-fluorophenyl)-2-fluoro-5-methylbenzene-1-sulfonamide;
N-(4-(8-amino-5-(4-((2-fluoroethyl)amino)cyclohex-1-en-1-yl)-3-isopropylimidazo[1,5-a]pyrazin-1-yl)-2-fluorophenyl)-1-(2-chlorophenyl) methanesulfonamide;
N-(4-(8-amino-5-(4-((2-fluoroethyl)amino)cyclohex-1-en-1-yl)-3-isopropylimidazo[1,5-a]pyrazin-1-yl)-2-fluorophenyl)-2-chlorobenzenesulfonamide;
N-(4-(8-amino-5-(4-hydroxycyclohex-1-en-1-yl)-3-isopropylimidazo[1,5-a]pyrazin-1-yl)-2-fluorophenyl)-1-(2-chlorophenyl)methanesulfonamide;
N-(4-(8-amino-5-(4-hydroxycyclohex-1-en-1-yl)-3-isopropylimidazo[1,5-a]pyrazin-1-yl)-2-fluorophenyl)-2-chlorobenzenesulfonamide;
N-(4-(8-amino-5-(4-((2,2-difluoroethyl)amino)cyclohex-1-en-1-yl)-3-isopropylimidazo[1,5-a]pyrazin-1-yl)-2-fluorophenyl)-2-chlorobenzenesulfonamide;
N-(4-(8-amino-3-isopropyl-5-(4-(oxetan-3-ylamino)cyclohex-1-en-1-yl)imidazo[1,5-a]pyrazin-1-yl)-2-fluorophenyl)-1-(2-chlorophenyl)methanesulfonamide;
N-(4-(8-amino-5-(4-((2-fluoroethyl)amino)cyclohex-1-en-1-yl)-3-isopropylimidazo[1,5-a]pyrazin-1-yl)-2,5-difluorophenyl)-2-chlorobenzenesulfonamide;
N-(4-(8-amino-5-(4-((2-fluoroethyl)amino)cyclohex-1-en-1-yl)-3-isopropylimidazo[1,5-a]pyrazin-1-yl)-2-fluorophenyl)-2-fluorobenzenesulfonamide;
N-(4-(8-amino-5-(4-((2-fluoroethyl)(methyl)amino)cyclohex-1-en-1-yl)-3-isopropylimidazo[1,5-a]pyrazin-1-yl)-2-fluorophenyl)-2-chlorobenzenesulfonamide;
N-(4-(8-amino-5-(4-((2-fluoroethyl)amino)cyclohex-1-en-1-yl)-3-methylimidazo[1,5-a]pyrazin-1-yl)-2-fluorophenyl)-2-chlorobenzenesulfonamide; and
N-(4-(8-amino-3-isopropyl-5-(4-(oxetan-3-ylamino)cyclohex-1-en-1-yl)imidazo[1,5-a]pyrazin-1-yl)-2-fluorophenyl)-2-chlorobenzenesulfonamide;

or a pharmaceutically acceptable salt, stereoisomer, or tautomer thereof.

* * * * *